United States Patent
Reshetnyak et al.

(10) Patent No.: US 9,814,781 B2
(45) Date of Patent: *Nov. 14, 2017

(54) ENVIRONMENTALLY SENSITIVE COMPOSITIONS AND METHODS OF USE THEREOF

(71) Applicants: Rhode Island Council on Postsecondary Education (statutory successor to Rhode Island Board of Governors for Higher Education), Warwick, RI (US); Yale University, New Haven, CT (US)

(72) Inventors: Yana K. Reshetnyak, South Kingstown, RI (US); Oleg A. Andreev, South Kingstown, RI (US); Donald M. Engelman, New Haven, CT (US)

(73) Assignees: Rhode Island Council on Postsecondary Education (Statutory Successor to Rhode Island Board of Governors for Higher Education), Warwick, RI (US); Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/074,581

(22) Filed: Mar. 18, 2016

(65) Prior Publication Data
US 2016/0256560 A1    Sep. 8, 2016

Related U.S. Application Data

(63) Continuation of application No. 13/182,441, filed on Jul. 13, 2011, now Pat. No. 9,289,508.

(60) Provisional application No. 61/363,891, filed on Jul. 13, 2010.

(51) Int. Cl.
| | |
|---|---|
| *A61K 38/04* | (2006.01) |
| *A61K 41/00* | (2006.01) |
| *A61K 49/00* | (2006.01) |
| *A61K 49/08* | (2006.01) |
| *A61K 49/14* | (2006.01) |
| *A61K 51/08* | (2006.01) |
| *A61K 38/12* | (2006.01) |
| *C07K 7/06* | (2006.01) |
| *C07K 14/00* | (2006.01) |
| *A61K 9/127* | (2006.01) |
| *A61K 33/24* | (2006.01) |
| *A61K 48/00* | (2006.01) |
| *C07K 14/705* | (2006.01) |
| *G01N 33/574* | (2006.01) |
| *A61K 47/48* | (2006.01) |

(52) U.S. Cl.
CPC ........ *A61K 47/48276* (2013.01); *A61K 9/127* (2013.01); *A61K 33/24* (2013.01); *A61K 38/04* (2013.01); *A61K 38/12* (2013.01); *A61K 41/0095* (2013.01); *A61K 47/48246* (2013.01); *A61K 48/0033* (2013.01); *A61K 49/0056* (2013.01); *A61K 49/085* (2013.01); *A61K 49/14* (2013.01); *A61K 51/08* (2013.01); *A61K 51/088* (2013.01); *C07K 7/06* (2013.01); *C07K 14/001* (2013.01); *C07K 14/705* (2013.01); *G01N 33/574* (2013.01)

(58) Field of Classification Search
CPC ........ A61K 47/48246; A61K 47/48276; A61K 48/0033; A61K 51/08; A61K 9/127; A61K 33/24; A61K 38/04; A61K 38/12; A61K 41/0095; A61K 49/0056; A61K 49/085; A61K 49/14; A61K 51/088; G01N 33/574; C07K 14/001; C07K 14/705; C07K 7/06
See application file for complete search history.

(56) References Cited

U.S. PATENT DOCUMENTS

| | | | |
|---|---|---|---|
| 5,739,273 A | 4/1998 | Engelman et al. |
| 8,076,451 B2 | 12/2011 | Reshetnyak et al. |
| 8,703,909 B2 | 4/2014 | Reshetnyak et al. |
| 8,846,081 B2 | 9/2014 | Reshetnyak et al. |
| 9,289,508 B2 | 3/2016 | Reshetnyak et al. |
| 2008/0233107 A1 | 9/2008 | Reshetnyak et al. |
| 2015/0086617 A1 | 3/2015 | Reshetnyak et al. |
| 2015/0191508 A1 | 7/2015 | Reshetnyak et al. |

FOREIGN PATENT DOCUMENTS

| | | |
|---|---|---|
| WO | WO-2006078816 A2 | 7/2006 |
| WO | WO-2009079635 A1 | 6/2009 |
| WO | WO-2012021790 A1 | 2/2012 |

OTHER PUBLICATIONS

Engelman DM, et al. FASEB J. 20(4):A457 (No. 318.3). Mar. 6, 2006.*
An et al. "pH-(Low)-Insertion-Peptide (pHLIP) Translocation of Membrane Impermeable Phalloidin Toxin Inhibits Cancer Cell Proliferation." PNAS. 107.47(2010):20246-20250.
Andreev et al. "Mechanism and Uses of a Membrane Peptide That Targets Tumors and Other Acidic Tissues in vivo." PNAS. 104. 19(2007):7893-7898.

(Continued)

*Primary Examiner* — Robert Landsman
(74) *Attorney, Agent, or Firm* — Mintz Levin Cohn Ferris Glovsky and Popeo, P.C.

(57) ABSTRACT

An environmentally sensitive membrane binding polypeptide, pH (low)-sensitive membrane peptide (pHLIP) has improved insertion kinetics balanced with solubility to selectively target acidic tissues.

28 Claims, 134 Drawing Sheets
(115 of 134 Drawing Sheet(s) Filed in Color)

(56) References Cited

OTHER PUBLICATIONS

Andreev et al. "pH (Low) Insertion Peptide (pHLIP) Inserts Across a Lipid Bilayer as a Helix and Exits by a Different Path." *PNAS*. 107.9(2010):4081-4086.
Aroui et al. "Cytotoxicity, Intracellular Distribution and Uptake of Doxorubicin and Doxorubicin Coupled to Cell-Penetrating Peptides in Different Cell Lines: A Comparative Study." *Biochem. Biophys. Res. Comm.* 39.1(2009):419-425.
Bild et al. "Oncogenic Pathway Signatures in Human Cancers as a Guide to Targeted Therapies." *Nature*. 439(2006):353-357.
Blather et al. "Drugs to Enhance the Therapeutic Potency of Anticancer Antibodies, Antibody-Drug Conjugates as Tumor-Activated Prodrugs." Anticancer Agents: Frontiers i Cancer Chemotherapy. Ojima et al., eds. Washington, D.C.: ACS Symposium Series 796. (2001):317338.
Blume et al. "Liposomes for the Sustained Drug Release in vivo." *Biochim. Biophys. Acta.* 1029.1(1990):91-97.
Brambillasca et al. "Transmembrane Topogenesis of a Tail-Anchored Protein is Modulated by Membrane Lipid Composition." *EMBO J.* 24.14(2005):2533-2542.
Brambillasca et al. "Unassisted Translocation of Large Polypeptide Domains Across Phospholipid Bilayers." *J. Cell. Biol.* 175.5(2006):767-777.
Breitz et al. "Clinical Experience With Tc-99m Nofetumomab Merpentan (Verluma) Radioimmunoscintigraphy." *Clin. Nucl. Med.* 22.9(1997):615-620.
Buchsbaum. "Imaging and Therapy of Tumors Induced to Express Somatostatin Receptor by Gene Transfer Using Radiolabeled Peptides and Single Chain Antibody Constructs." *Semin. Nucl. Med.* 34.1(2004):32-46.
Bulmus et al. "A New pH-Responsibe and Glutathione-Reactive, Endosomal Membrane-Distruptive Polymeric Carrier for Intracellular Delivery of Biomolecular Drugs." *J. Control Release.* 93.2(2003):105-120.
Burstein et al. "Decomposition of Protein Tryptophan Fluorescence Spectra Into Log-Normal Components." *Biophys. J.* 81.3(2001):1699-1709.
Carter. "Improving the Efficacy of Antibody-Based Cancer Therapies." *Nat. Rev. Cancer*. 1(2001):118-129.
Clausen et al. "Cerebral Acid-Base Homeostasis After Severe Traumatic Brain Injury." *J. Neurosurg.* 103.4(2005):597-607.
de Bono et al. "ING-1, a Monoclonal Antibody Targeting Ep-CAM in Patients With Advanced Adenocarcinomas." *Clin. Cancer Res.* 10(2004):7555-7565.
Devalapally et al. "Poly(ethylene oxide)-Modified Poly(6-Amino Ester) Nanoparticles as a pH-Sensitive System for Tumor-Targeted Delivery of Hydrophobic Drugs: Part 3." *Cancer Chemother. Pharm.* 59.4(2007):477-484.
Egholm et al. "PNA Hybridizes to Complementary Oligonucleotides Obeying the Watson-Crick Hydrogen-Bonding Rules." *Nature*. 365(1993):566-568.
Fernandez-Escamilla et al. "Prediction of Sequence-Dependent and Mutational Effects on the Aggregation of Peptides and Proteins." *Nat. Biotechnol.* 22.10(2004):1302-1306.
Flach et al. "Location of Structural Transitions in an Isotopically Labeled Lung Surfactant SP-B Peptide by IRRAS." *Biophys. J.* 85(2003):340-349.
Freimark et al. "Targeting of Humanized Antibody D93 to. Sites of Angiogenesis and Tumor Growth by Binding to Multiple Epitopes on Denatured Collagens." *Mol. Immunol.* 44(2007):3741-3750.
Ganta et al. "A Review of Stimuli-Responsive Nanocarriers for Drug and Gene Delivery." *J. Control Release*. 126(2008):187-204.
Gatenby et al. "Acid-Mediated Tumor Invasion: A Multidisciplinary Study." *Cancer Res*. 66.10(2006):5216-5223.
Goldsmith. "Receptor Imaging: Competitive or Complementary to Antibody Imaging?" *Semin. Nucl. Med.* 27.2(1997):85-93.
Graham et al. "A Unique Pathway of Cardiac Myocyte Death Caused by Hypoxia-Acidosis." *J. Exp. Biol.* 207(2004):3189-3200.

Hanke et al. "Protein Biomarkers and Drug Design for Cancer Treatments." *Eur. J. Cancer Prev.* 13(2004):297-305.
Headley. "Necrotizing Soft Tissue Infections: A Primary Care Review." *Am. Fam. Physician*. 68.2(2003):323-328.
Helmlinger et al. "Acid Production in Glycolysis-Impaired Tumors Provides New Insights Into Tumor Metabolism." *Clin. Cancer Res.* 8(2002):1284-1291.
Henry et al. "pH-Responsive Poly(styrene-alt-maleic anhydride) Alkylamide Copolymers for Intracellular Drug Delivery." *Biomacromolecules*. 7.8(2006):2407-2414.
Holloway et al. "*Plasmodium berghei* Infection: Dichloroacetate Improves Survival in Rats With Lactic Acidosis." *Exp. Parasitol.* 80.4(1995):624-632.
Hughes et al. "Use of Carcinoembryonic Antigen Radioimmunodetection and Computed Tomography for Predicting the Resectability of Recurrent Colorectal Cancer." *Ann. Surg.* 226.5(1997):621-631.
Hunt et al. "Spontaneous, pH-Dependent Membrane Insertion of a Transbilayer a-Helix." Biochem. 36.49(1997):15177-15192.
Izumi et al. "Cellular pH Regulators: Potentially Promising Molecular Targets for Cancer Chemotherapy." *Cancer Treat. Rev.* 29.6(2003):541-549.
Janssens et al. "Protein Biomarkers for Breast Cancer Prevention." *Eur. J. Cancer Prev.* 13(2004):307-317.
Jeffrey et al. "Genomics-Based Prognosis and Therapeutic Prediction in Breast Cancer." *J. Natl. Compr. Cancer Netw.* 3.2(2005):291-300.
Kalantar-Zadeh et al. "Metabolic Acidosis and Malnutrition-Inflammation Complex Syndrome in Chronic Renal Failure." *Sem. Dial.* 17.6(2004):455-465.
Kamada et al. "Design of a pH-Sensitive Polymeric Carrier for Drug Release and its Application in Cancer Therapy." *Clin. Cancer Res.* 10.7(2004):2545-2550.
Kennedy et al. "Using Molecular Makers in Sputum for the Early Detection of Lung Cancer: A Review." *Lung Cancer.* 45.S2(2004):S21-S27.
Kobayashi et al. "Aqueous Chromatography Utilizing pH-/Temperature-Responsive Polymer Stationary Phases to Separate Ionic Bioactive Compounds." Anal. Chem. 73.9(2001):20272033.
Krenning et al. "Radiolabelled Somatostatin and Analogue(s) for Peptide Receptor Scinitgraphy and Radionuclide Therapy." *Ann. Oncol.* 10.S2(1999):S23-S29.
Kuyper et al. "Proton Permeation Into Single Vesicle Occurs via a Sequential Two-Step Mechanism and is Heterogeneous." *J. Am. Chem. Soc.* 128.10(2006):3233-3240.
Leake. "Does an Acidic pH Explain Why Low Density Lipoprotein is Oxidised in Atherosclerotic Lesions?" *Atherosclerosis*. 129.2(1997):149-157.
Lian et al. "Trends and Developments in Liposome Dug Delivery Systems." *J. Pharm. Sci*. 90.6(2001):667-680.
Lipinski et al. "Experimental and Computational Approaches to Estimate Solubility and Permeability in Drug Discovery and Development Settings." Adv. Drug Deliv. Rev. 46.13(2001):3-26.
Lister-James et al. "Pharmacokinetic Considerations in the Development of Peptide-Based Imaging Agents." *Q. J. Nucl. Med.* 41(1997):111-118.
Lu et al. "Targeting Serum Antibody for Cancer Diagnosis: A Focus on Colorectal Cancer." *Exp. Opin. Ther. Targets*. 11.2(2007):235-244.
Ma et al. "In Vitro and In Vivo Evaluation of Alexa Fluor 680-Bombesin[7-14]NH2 Peptide Conjugate, a High-Affinity Fluorescent Probe With High Selectivity for the Gastrin-Releasing Peptide Receptor." *Mol. Imaging*. 6.3(2007):171-180.
Martin et al. "(mono[125I]iodo-Tyr10,Met017)-Vasoactive Intestinal Polypeptide." J. Biol. Chem. 261.12(1986):5320-5327.
Mikhail. "The Trauma Triad of Death: Hypothermia, Acidosis, and Coagulopathy." *AACN Clin. Issues*. 10.1(1999):85-94.
Moasser et al. "Targeting the Function of the HER2 Oncogene in Human Cancer Therapeutics." *Oncogene*. 26(2007):6577-6592.
Murelli et al. "Chemical Control Over Immune Recognition: A Class of Antibody-Recruiting Small Molecules That Target Prostate Cancer." J. Am. Chem. Soc. 131.447(2009):1709017092.

(56) References Cited

OTHER PUBLICATIONS

Murthy et al. "Bioinspired pH-Responsive Polymers for the Intracellular Delivery of Biomolecular Drugs." *Bioconj. Chem.* 14.2(2003):412-419.
Murthy et al. "Design and Synthesis of pH-Responsive Polymeric Carriers That Target Uptake and Enhance the Intracellular Delivery of Oligonucleotides." *J. Control. Release.* 89(2003):365-374.
Musial-Siwek et al. "Tuning the Insertion Properties of pHLIP." *Biochim. Biophys. Acta.* 1798.6(2009):1041-1046.
Muxi et al. "Radioimmunoguided Surgery of Colorectal Carcinoma With an 111In-Labelled Anti-TAG72 Monoclonal Antibody." *Nucl. Med. Commun.* 20(1999):123-130.
Na et al. "Adriamycin Loaded Pullulan Acetate/Sulfonamide Conjugate Nanoparticles Responding to Tumor pH: pH-Dependent Cell Interaction, Internalization and Cytotoxicity in vitro." *J. Control. Release.* 87.1-3(2003):3-13.
Nielsen. "Addressing the Challenges of Cellular Delivery and Bioavailability of Peptide Nucleic Acids (PNA)." *Q. Rev. Biophys.* 38.4(2005):345-350.
Osborne et al. "Protein Translocation by the Sec61/SecY Channel." *Annu. Rev. Cell Dev. Biol.*; 21(2005):529-550.
Payne. "Progress in Immunoconjugate Cancer Therapeutics." *Cancer Cells.* 3(2003):207-212.
Polascik et al. "Comparison of Clinical Staging algorithms and 111Indium-Capromab Pendetide Immunoscintigraphy in the Prediction of Lymph Node Involvement in High Risk Prostate Carcinoma Patients." *Cancer.* 85(1999):1586-1592.
Portnoy et al. "Nano-oncology: Drug Delivery, Imaging, and Sensing." *Anal. Bioanal. Chem.* 384.3(2006):620-630.
Rehncrona. "Brain Acidosis." *Ann. Emerg. Med.* 14.8(1985):770-776.
Reshetnyak et al. "A Monomeric Membrane Peptide That Lives in Three Worlds: In Solution, Attached to, and Inserted Across Lipid Bilayers." *Biophys. J.* 93(2007):2363-2372.
Reshetnyak et al. "Energetics of Peptide (pHLIP) Binding to and Folding Across a Lipid Bilayer Membrane." *PNAS.* 105.40(2008):15340-15345.
Reshetnyak et al. "Translocation of Molecules Into Cells by pH-Dependent Insertion of a Transmembrane Helix." *PNAS.* 103.17(2006):6460-6465.
Segala et al. "Accurate Analysis of Tumor Margins Using a Fluorescent pH Low Insertion Peptide (pHLIP)." *Int. J. Mol. Sci.* 10.8(2009):3478-3487.
Sela et al. "Different Roles of D-Amino Acids in Immune Phenomena." *FASEB.* 11(1997):449456.
Shen et al. "The Protein Fluorescence and Structural Toolkit: Database and Programs for the Analysis of Protein Fluorescence and Structural Data." *Proteins.* 71.4(2008):1744-1754.
Siesj6 et al. "Acidosis-Related Damage." Advances in Neurology, vol. 71: Cellular and Molecular Mechanisms of Ischemic Brain Damage. Siesjo et al., eds. Philadelphia: Lippincott-Raven Publishers. (1996):209-233.
Signore et al. "Peptide Radiopharmaceuticals for Diagnosis and Therapy." *Eur. J. Nucl. Med.* 28.10(2001):1555-1565.
Simoes et al. "On the Formulation of pH-Sensitive Liposomes With Long Circulation Times." *Adv. Drug Deliv. Rev.* 56.7(2004):947-965.
Sperotto et al. "Modelling of Proteins in Membranes." *Chem. Phys. Lipids.* 141.1-2(2006):2-29.
Srinivas et al. "Trends in Biomarker Research for Cancer Detection." *Lancet.* 2(2001):698-704.
Stayton et al. "'Smart' Delivery Systems for Biomolecular Therapeutics." *Orthod. Craniofacial Res.* 8(2005):219-225.
Stubbs et al. "Causes and Consequences of Tumour Acidity and Implications for Treatment." *Mol. Med. Today.* 6.1(2000):15-19.
Tang et al. "Dissecting the Membrane Binding and Insertion Kinetics of a pHLIP Peptide." *Biochem.* 47.32(2008):8250-8252.
Thevenin et al. "pHLIP-Mediated Translocation of Membrane-Impermeable Molecules Into Cells." *Chem. Biol.* 16.7(2009):754-762.
Tomlinson et al. "Polyacetal-Doxorubicin Conjugates Designed for pH-Dependent Degradation." *Bioconj. Chem.* 14.6(2003):1096-1106.
Ulbrich et al. "Polymeric Anticancer Drugs With pH-Controlled Activation." *Adv. Drug Deliv. Rev.* 56.7(2004):1023-1050.
van den Berg et al. "X-Ray Structure of a Protein-Conducting Channel." *Nature.* 427(2003):3644.
Wimley et al. "Solvation Energies of Amino Acid Side Chains and Backbone in a Family of Host-Guest Pentapeptides." *Biochem.* 35.16(1996):5109-5124.
Yamamoto et al. "Acidic Extracellular pH-Activated Outwardly Rectifying Chloride Current in Mammalian Cardiac Myocytes." *Am. J. Physiol. Heart Circ. Physiol.* 290(2006):H1905-H1914.
Yao et al. "Calcium and pH Homeostasis in Neurons During Hypoxia and Ischemia." *Cell Calcium.* 36.3-4(2004):247-255.
Ying et al. "Acidosis Potentiates Oxidative Neuronal Death by Multiple Mechanisms." *J. Neurochem.* 73.4(1999):1549-1565.

\* cited by examiner

FIG. 1

| AEQNPIY | WARYADWLFTTPLLLLDLALLV | DADEGT |
|---|---|---|
| Flanking sequence | Membrane-inserting sequence | Flanking sequence |

SEQ ID NO: 2

FIG. 3A
FIG. 3B
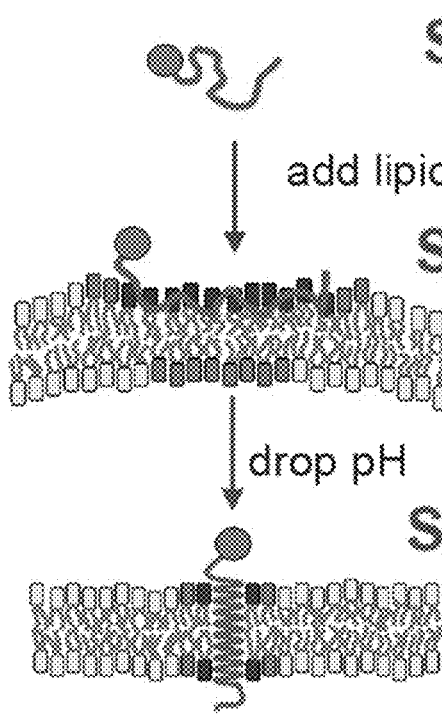
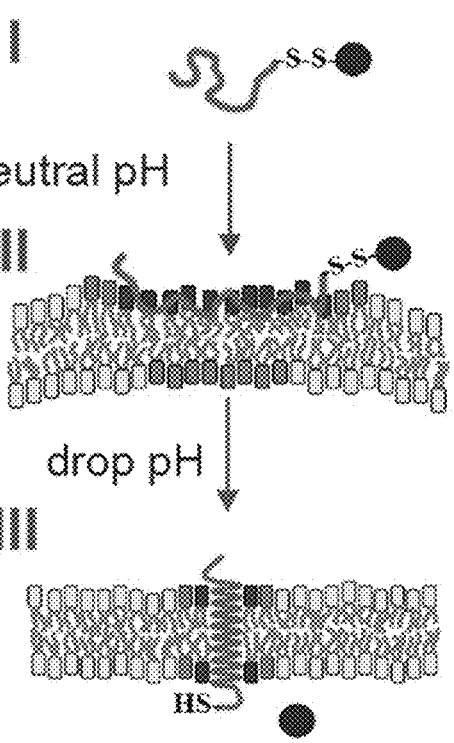

FIG. 10A
pH 6.1
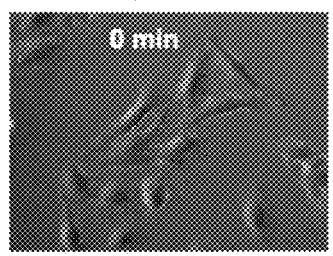
FIG. 10C
pH 7.0
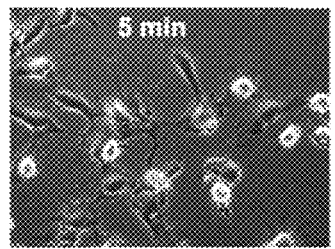
FIG. 10B
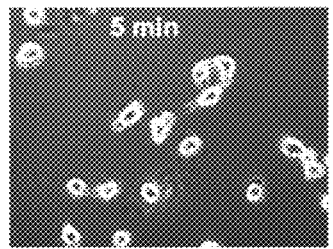
FIG. 10D
FIG. 10E
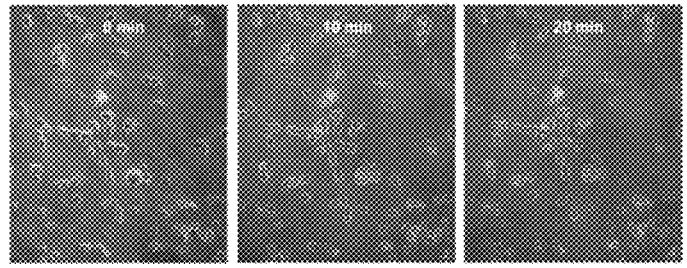

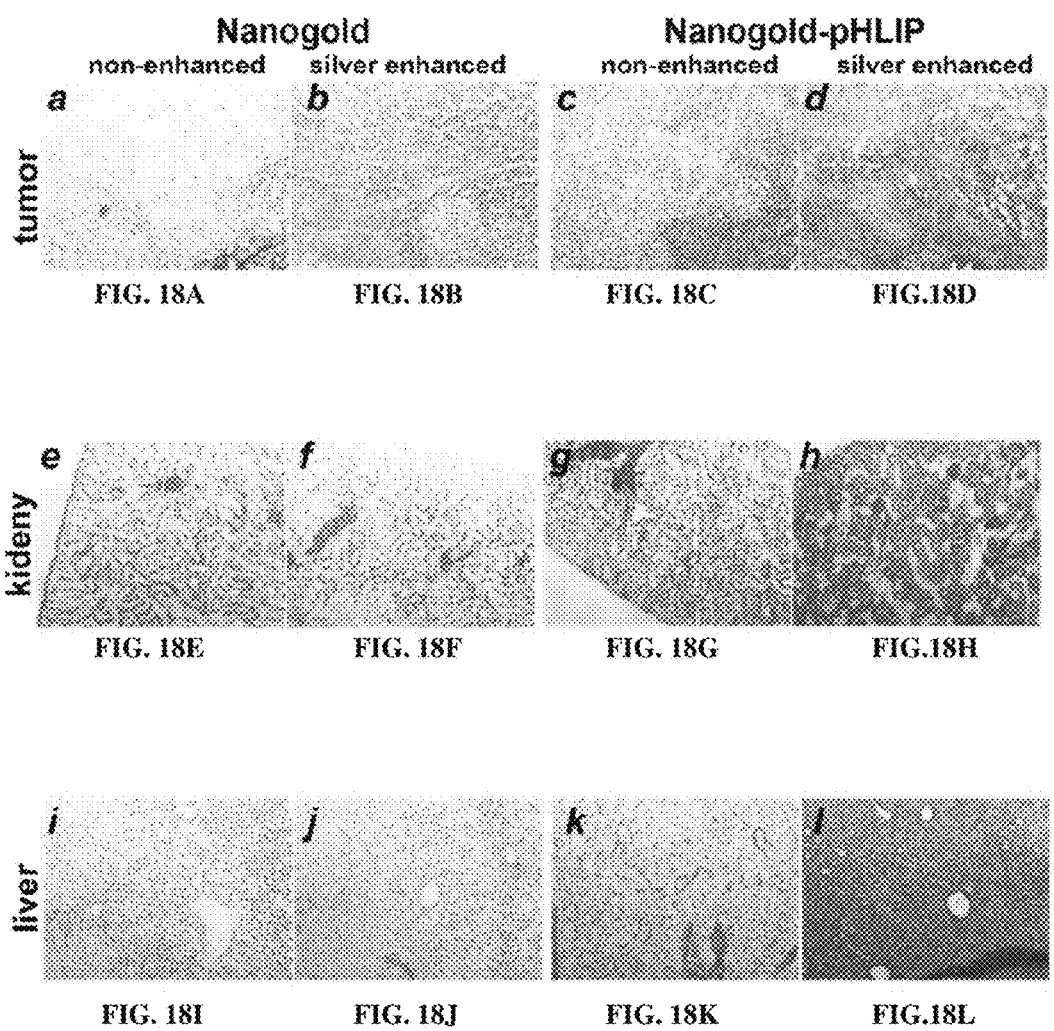

T1 weighted, pre pHLIP

T1 map, pre pHLIP

T1-weighted, 24h post pHLIP

T1 map, 24h post pHLIP

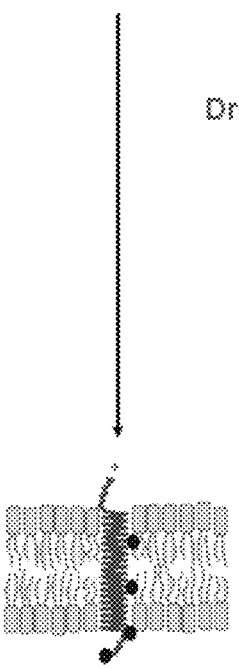

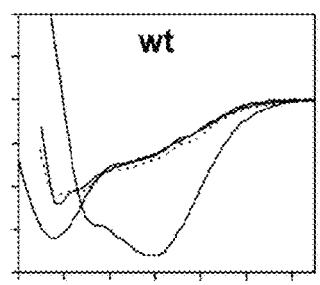
FIG. 38A
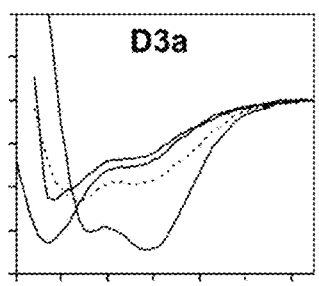
FIG. 38B
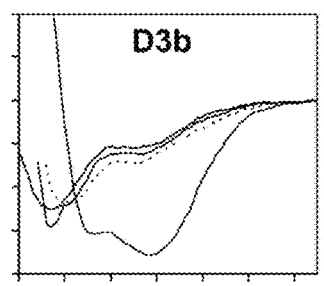
FIG. 38C
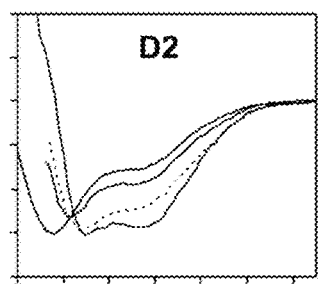
FIG. 38D
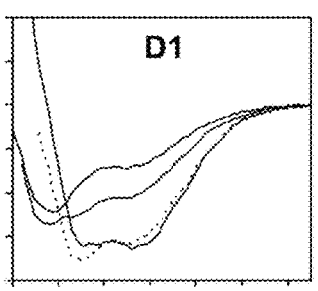
FIG. 38E
FIG. 38F

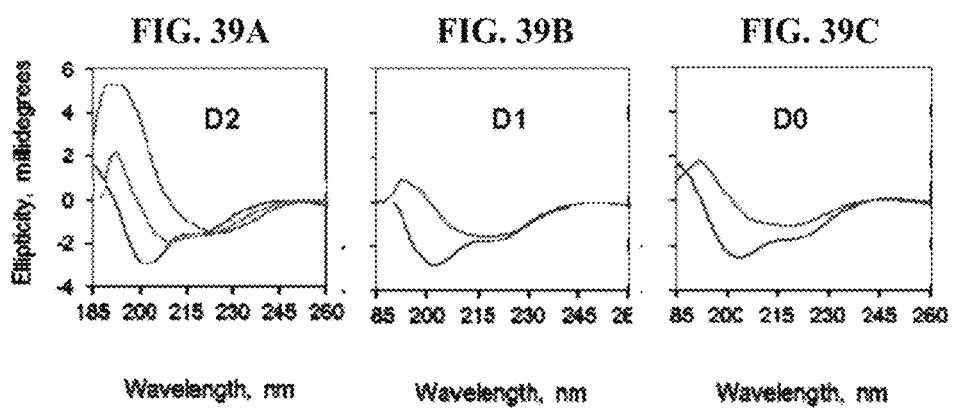

FIG. 41A 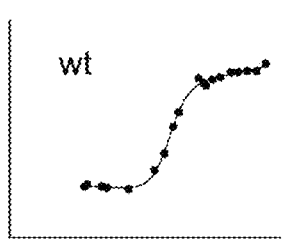 FIG. 41B 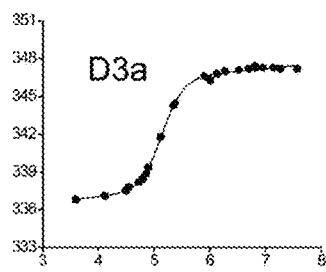 FIG. 41C 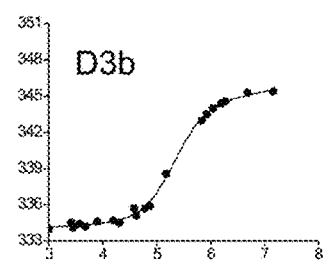
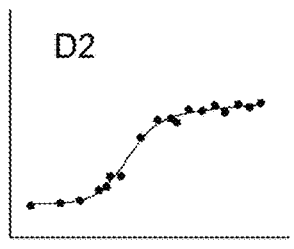 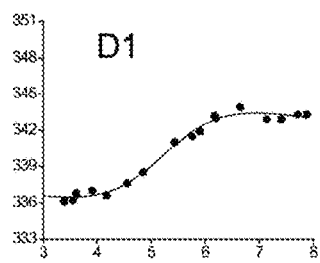 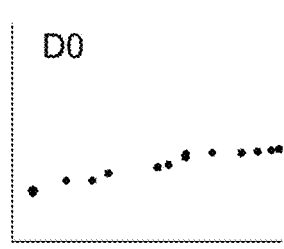
FIG. 41D     FIG. 41E     FIG. 41F

FIG. 45A
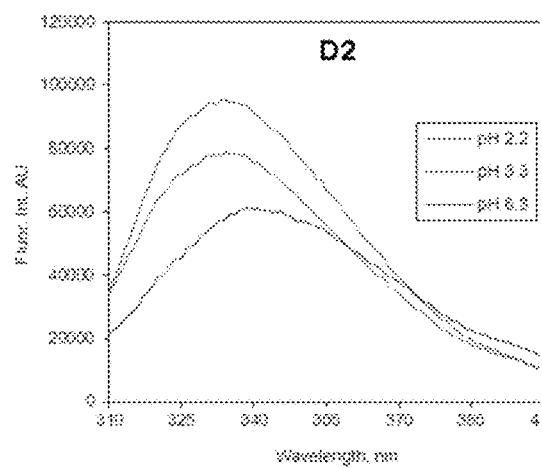
FIG. 45B
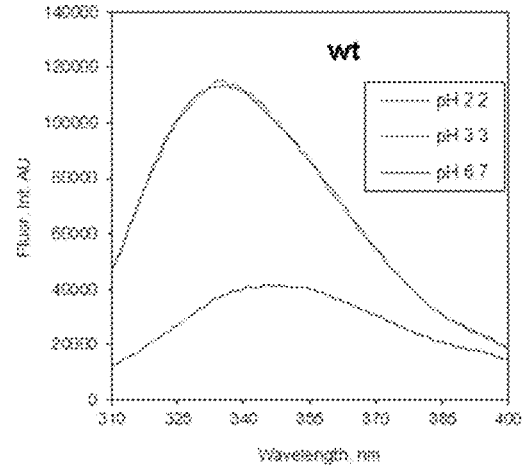
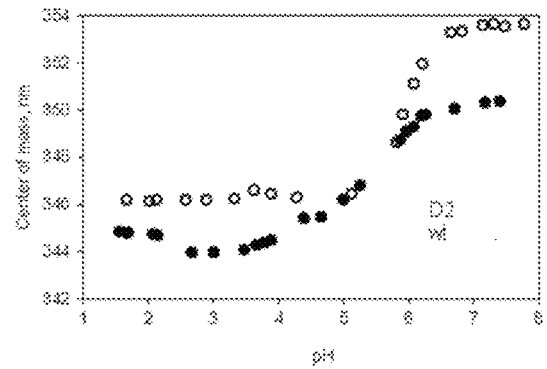
FIG. 45C
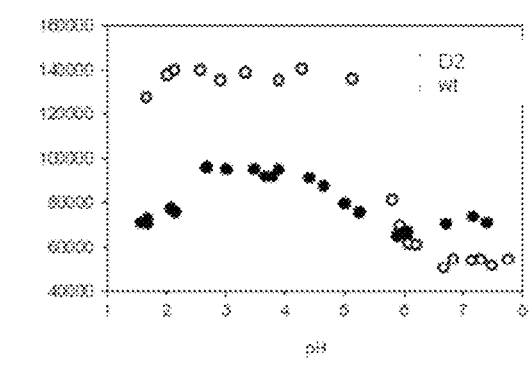
FIG. 45D

FIG. 47A
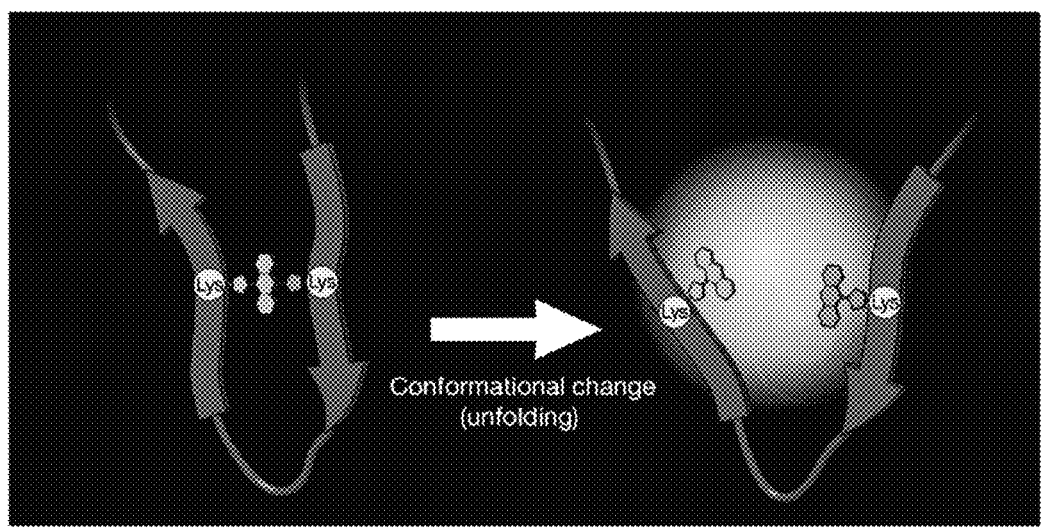
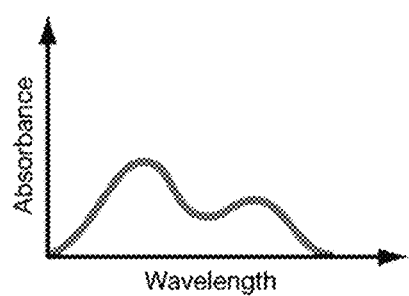
FIG. 47B
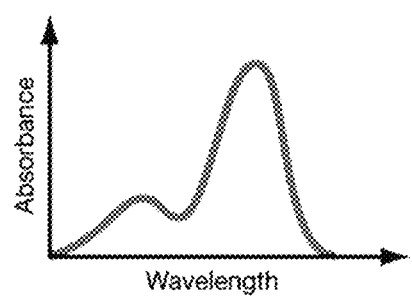
FIG. 47C

IV 20uM 100uL  IV 80uM 100uL

FIG. 60A 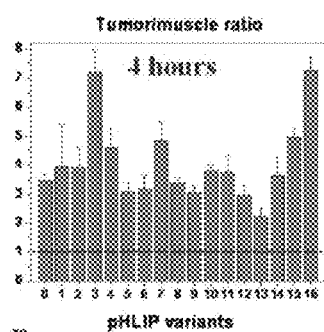 FIG. 60B 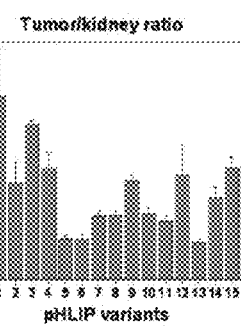 FIG. 60C 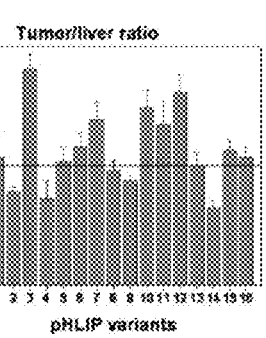
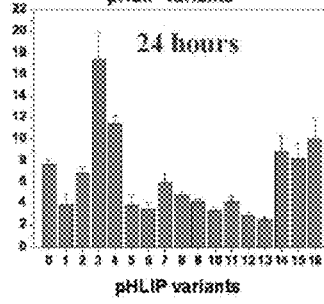 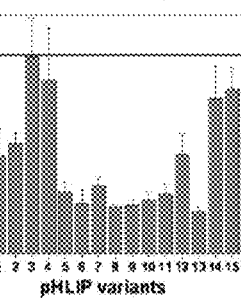 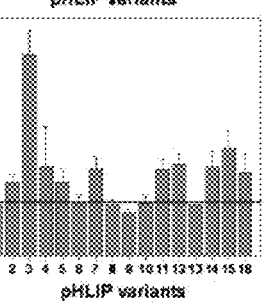
FIG. 60D      FIG. 60E      FIG. 60F

FIG. 67 pHLIP: AEQNPIYWARYADWLFTTPLLLLDLALLVDADEGTCG (38aa)
M1:    AEDQNPYWARYADWLFTTPLLLLDLALLVDCG (32aa)
M2:    AEDQNPYWARYADWLFTTPLLLLLALLVCG (32aa)

FIG. 72A pHLIP-4: AE-QN-PIYWARYADWLFTTPLLLLDLALLV DADEGT-COOH (SEQ ID NO: 240)

pHLIP-2: AEDQN-P- YWARYADWLFTTPLLLLDLALLV D—G—COOH (SEQ ID NO: 241)

pHLIP-1: AEDQNDP- YWARYADWLFTTPLLLLDLALLV —G—COOH (SEQ ID NO: 242)

FIG. 72B pHLIP-W1: AEQNPI YWARYADFLFTPLLLLDLALLV DADET-COOH (SEQ ID NO: 243)

pHLIP-W2: AEQNPI YFARYADWLFTPLLLLDLALLV DADET-COOH (SEQ ID NO: 244)

pHLIP-W3: AEQNPI YFARYADFLFTPLLLLDLALLW DADET-COOH (SEQ ID NO: 245)

FIG. 73

| | pH 8-3.6 | pH 8-5 | pH 8-6 |
|---|---|---|---|
| pHLIP-1 fluorescence | 0.02 s (44.6 – 45.0 s⁻¹ for different pHs) | | |
| | 0.098 s (10.3 s⁻¹) | 0.18 s (5.6 s⁻¹) | 0.2 s (5.0 s⁻¹) |
| pHLIP-1, CD | 0.09 s (11.1 s⁻¹) | | |
| pHLIP-2 fluorescence | 0.08 s (11.3 – 11.4 s⁻¹ for different pHs) | | |
| | 2.8 s (0.36 s⁻¹) | 4.5 s (0.22 s⁻¹) | 13.0 s (0.08 s⁻¹) |
| pHLIP-2 CD | 0.08 s (11.3 – 11.4 s⁻¹ for different pHs) (~85% of signal changes) | | |
| | 2.2 s (0.46 s⁻¹) | 5.0 s (0.20 s⁻¹) | 13.0 s (0.08 s⁻¹) |
| pHLIP-4 fluorescence | 0.09 s (11.1 s⁻¹) (~85% of signal changes) | | |
| | 2.0 s (0.45 s⁻¹) | 3.4 s (0.27 s⁻¹) | 5.0 s (0.18 s⁻¹) |
| | 31.6 s (0.031 s⁻¹) | 101.7 s (0.0097 s⁻¹) | 138 s (0.0072 s⁻¹) |
| pHLIP-4 CD | 0.09 s (11.1 s⁻¹) (~85% of signal changes) | | |
| | 2.0 s (0.45 s⁻¹) | 5.0 s (0.18 s⁻¹) | 5.0 s (0.18 s⁻¹) |
| | 31.6 s (0.031 s⁻¹) | 101.6 s (0.0097 s⁻¹) | 138 s (0.0072 s⁻¹) |

FIG. 74

| | pHLIP-W1 | pHLIP-W2 | pHLIP-W3 |
|---|---|---|---|
| pH 8-3.6 | 0.09 s (11.1 s$^{-1}$) | | |
| | 2.5 s (0.36 s$^{-1}$) | | |
| | 35 s (0.028 s$^{-1}$) | 76 s (0.013 s$^{-1}$) | 71 s (0.014 s$^{-1}$) |
| pH 8-6 | 0.01 s (100 s$^{-1}$) | | |
| | 4 s (0.22 s$^{-1}$) | 2.6 s (0.35 s$^{-1}$) | 6.2 s (0.14 s$^{-1}$) |
| | 200 s (0.005 s$^{-1}$) | | |
| pH 3.6-8 | 0.04 s (22.5 s$^{-1}$) | 0.05 s (18.0 s$^{-1}$) | 0.06 s (14.9 s$^{-1}$) |
| | 0.35 s (2.88 s$^{-1}$) | | |
| pH 3.6-6 | 4.2 s (0.21 s$^{-1}$) | - | - |
| | 54.9 (0.02 s$^{-1}$) | - | - |

FIG. 75 pHLIP-4:   AE-QN-PIYWARYADWLFTTPLLLLDLALLVDADEGCT-COOH (SEQ ID NO: 246)

pHLIP-2:   AEDQN-PIYWARYADWLFTTPLLLLDLALLVDC-G-T-COOH (SEQ ID NO: 247)

pHLIP-2E:  AEDQNDPIYWARYADWLFTTPLLLLELALLVEC-G-T-COOH (SEQ ID NO: 248)

FIG. 76

| Name | Amino Acid Sequence | SEQ ID NO. |
|---|---|---|
| pHLIP-NT | ACEQNPIY WARYADWLFTTPLLLLDLALLVDADEGT | 256 |
| Var1-2D1D | ACEDQNPY WARYADWLFTTPLLLLDLALLV DG | 257 |
| Var2-2D1D | ACEDQNPY WRAYADLFTPLTLLDLLALW DG | 258 |
| Var3-3D | ACDDQNP WRAYLDLLFPTDTLLLDLLW | 259 |
| Var4-3E | ACEEQNP WRAYLELLFPTETLLLELLW | 260 |
| Var5-3Da | ACDDQNP WARYLDWLFPTDTLLLDL | 261 |
| Var6-3Db | CDNNNP WRAYLDLLFPTDTLLLDW | 262 |
| Var7-3E | ACEEQNP WARYLEWLFPTETLLLEL | 263 |
| Var8-3Eb | CEEQQP WAQYLELLFPTETLLLEW | 264 |
| Var9-3Ec | CEEQQP WRAYLELLFPTETLLLEW | 265 |
| Var10-2D | ACEDQNP WARYADWLFPTTLLLLD | 266 |
| Var11-2E | ACEEQNP WARYAEWLFPTTLLLE | 267 |
| Var12-1D | ACEDQNP WARYADLFPTTLAW | 268 |
| Var13-1E | ACEEQNP WARYAELLFPTTLAW | 269 |
| Var14-Rev | Ac-TEDAD VLLALDLLLLPTTFLWDAYRAWYPNQECA-Am | 270 |
| Var15-2N | CDDDDDNPNY WARYANWLFTPLLLLNGALLV EAEET | 271 |
| Var16-2P | CDDDDDNPNY WARYAPWLFTPLLLLPGALLV EAEET | 272 |

| Name | Sequence | | | SEQ ID | Design | | pKa | Findings | Published |
|---|---|---|---|---|---|---|---|---|---|
| | | | | | Biophysical | | | | |
| WT-1 | AEEQNPIY | WARYADWLFTTPLLLLDLLALLV | DADPEGT | SEQ ID NO: 52 | Biophysical | | 6 | Soluble at pH8; reversible insertion | Y |
| WT-2 | AAEQNPIY | WARYADWLFTTPLLLLDLALLV | DADPE_T | SEQ ID NO: 53 | Biophysical | | | | N |
| WT-Cys1 | AAEQNPIY | WARYADWLFTTPLLLLDLALLV | DADPCEGG | SEQ ID NO: 54 | Translocation | | | | N |
| WT-Cys2 | AEQNPIY | WARYADWLFTTPLLLLDLALLV | DADPECT | SEQ ID NO: 55 | Translocation | | | | N |
| WT-Cys3 | GAEQNPIYY | WARYADWLFTTPLLLLLDLALLV | DADSCTES | SEQ ID NO: 56 | Translocation | | | | N |
| Cys-WT2 | ACEQNPIY | WARYADWLFTTPLLLLLDLMALLV | DADPEGT | SEQ ID NO: 57 | Imaging | | | | N |
| Lys-WT | AKEQNPIY | WARYADWLFTTPLLLLLDLKALLV | DADPEGT | SEQ ID NO: 58 | Imaging | | | | N |
| K-WT-C | AKEQNPIY | WARYADWLFTTPLLLLDLALLV | DADCET | SEQ ID NO: 59 | Imaging / Translocation | | | Two cargoes attachment | N |
| P20A | AAEQNPIY | WARYADWLFTTALLLLLDLLALLV | DADEGT | SEQ ID NO: 60 | Biophysical | | | Aggregates | N |
| P20G | AAAEQNPIY | WARYADWLFTTGLLLLDLLALLV | DADEGT | SEQ ID NO: 61 | Imaging | | | Goes the liver | N |
| 1a-Trp | AAEQNPIY | WARYADWLFTTPLLLLDLLALLV | DADE_T | SEQ ID NO: 62 | Biophysical | | | | N |
| 1b-Trp | AAEQNPIY | FARYADWLFTTPLLLLLWLLALLV | DADEGT | SEQ ID NO: 63 | Biophysical | | | | N |
| 1c-Trp | AAEQNPIY | AARYADWLFTTPLLLLDLLALLV | DADE_T | SEQ ID NO: 64 | Biophysical | | | | N |
| Fast-1 | ACEDQNE_Y | WARYADWLFTTVLLLLDLLALLV | DA_ | SEQ ID NO: 65 | Biophysical | | 6.1 | Inserts into membrane 10 times faster than WT | N |
| Cys-Fast1 | ACEEQNP_Y | WARYADWLFTTPLLLLDLLALLV | DA_ | SEQ ID NO: 66 | Imaging | | 6.1 | Inserts into membrane 10 times faster than WT | N |
| Fast1-Cys | AEEQNP_Y | WARYADWLFTTPLLLLDLLALLV | DC_ | SEQ ID NO: 67 | Translocation | | 6.1 | Inserts into membrane 10 times faster than WT | N |
| Fast1-E-Cys | AEEQNP_Y | WEAAEP_LFL_PLLLDLLAGM | DG_ | SEQ ID NO: 68 | Translocation | | 6.6 | Inserts into membrane 10 times faster than WT | N |
| Fast-2 | AAEEQNP_Y | WEAYAE_LFL_PLLLLLDLLAGM | DG_ | SEQ ID NO: 69 | Biophysical | | 5.6 | Inserts into membrane 10 times faster than WT | N |
| Cys-Fast2 | AAEQMP_Y | WFAYAE_LFL_PLLLLDLLYAM | DG_ | SEQ ID NO: 70 | Imaging | | 5.6 | Inserts into membrane 10 times faster than WT | N |
| Fastest | AEEQNP_Y | WARYADWLFTTPLLLLLDLLALLV | | SEQ ID NO: 71 | Biophysical | | 5.4 | Partially helical on the membrane at pH8. Inserts into membrane 10 times faster than WT | N |
| WT-reverse | TEDADVLLALDLLLLPTTFLWDAYRAWYNQECA | | | SEQ ID NO: 72 | Insertion direction | | | | N |

MUTATION; DELETION; INSERTION

Some of these peptides lost main properties of pH-dependent insertion into membrane

FIG. 77I

| Name | Sequence | | Design | pKa | Findings | Comments |
|---|---|---|---|---|---|---|
| WT | GGEQNPIY | WARYADWLFTTPLLLLDLALIV | Biophysical | 6 | Soluble at pH8; reversible membrane insertion | Native sequence |
| Short | AEQNPIY | WARYADWLFTTPL | Biophysical | 4.4 | Fast, pH-dependent membrane insertion | Truncated version of main sequence |
| Short-Cys | AEQNPIY | WARYADWLFTTPCL | Biophysical / translocation | | | |
| Cys-Short | ACEQNPIY | WARYADWLFTTPL | Biophysical | | | |
| Cys-Short-1T | ACEQNPIY | PARYADWLFTTPL | Biophysical | | Does not interact with the membrane as well as other short peptides | |
| Cys-Med-3D | ACDDQNP | WRAYLDLLFFTTYLLLDLL* | Biophysical / imaging | 5.1 | Fast, pH-dependent membrane insertion; fast blood clearance | |
| Cys-Med-3E | ACEEQNP | WRAYLELLFFTETLLLELL* | Biophysical / imaging | 5.3 | Fast, pH-dependent membrane insertion; fast blood clearance | |
| Cys-Short-3D | ACDDQNP | WARYLDWLFFTTYLLLDL | Biophysical / imaging | 4.9 | Fast, pH-dependent membrane insertion; fast blood clearance | |
| Cys-Short-3D | CDDDNP | WRAYLDLLFFTTYLLLD* | Biophysical / imaging | 5.1 | Fast, pH-dependent membrane insertion; fast blood clearance | |
| Cys-Short-3E | ACEEQNP | WARYLEWLFFTETLLLEL | Biophysical / imaging | 5.5 | Fast, pH-dependent membrane insertion; fast blood clearance | |
| Cys-Short-2D | ACEDQNP | WARYADWLFFTTLLLLD | Biophysical / imaging | 5 | Fast, pH-dependent membrane insertion; fast blood clearance | |
| Cys-Short-2E | ACEEQNP | WARYAEWLFFTTLLLLE* | Biophysical / imaging | 5.5 | Fast, pH-dependent membrane insertion; fast blood clearance | |
| Cys-Short-1D | ACEQNP | WARYADLFFTTLA* | Biophysical / imaging | 4.5 | Fast, pH-dependent membrane insertion; fast blood clearance | |
| Cys-Short-1E | ACEQNP | WARYAKLLFFTTL* | Biophysical / imaging | 5.2 | Fast, pH-dependent membrane insertion; fast blood clearance | |
| Short-1D | DEQNP | WARYADLLFFTTL* | Biophysical | 4.5 | Fast, pH-dependent membrane insertion | |

Non of these C-term truncated sequences have been published.

| Denomination | Name | Sequence | | Insertion Reversibility | Insertion pKa | pH 8 Solubility | Notes |
|---|---|---|---|---|---|---|---|
| D25H; D14H; [D insertion position 1; G1/2D; Q4D; G35C] | 2H2 or D2 | DDDEDNPIYWARYADWLFTTPLLLLDGALLVDADEDCT | SEQ ID NO. 88 | Y | 5.1 | Y | Contains D insertion before A1, and deletion of C37, G38 |
| Other variants containing D25H: D14H; L26G; [A1/2D; Q4D; G35C] | | | | | | | |
| D14H; L26G; [G1/2D;Q4D;G35C] | D3b | DDDEDNPIYWARYAWWLFTTPLLLLDGALLVDADEDCT | SEQ ID NO. 89 | N/A | 5.15 | Y | Contains D insertion before A1, and deletion of C37, G38 |
| D25H; D14H; L26G; [G1/2D; Q4D; G35C] | D1 | DDDEDNPIYWARYAWWLFTTPLLLLDGALLVNADEDCT | SEQ ID NO. 90 | N/A | 5.2 | Y | Contains D insertion before A1, and deletion of C37, G38. Yana's same variant (H2N): helical at pH8 on membrane |
| D25H; D14H; L26G; D31N; D33N; [G1/2D; Q4D; G35C] | D0 | DDDEENPIYWARYAWWLFTTPLLLLGGALLVNAMEDCT | SEQ ID NO. 91 | N/A | - | Y | Low percentage insertion. Contains D insertion before A1, and deletion of C37, G38. Yana's same variant (H2N2): helical at pH6 on membrane |
| D25H; L26G; [G1/2D;Q4D;G35C] | 2H3 or D3a | DDDEDNPIYWARYADWLFTTPLLLLDGALLVDADEDCT | SEQ ID NO. 92 | Y | 5.25 | Y | Contains D insertion before A1, and deletion of C37, G38 |

FIG. 77J

| Denomination | Name | Sequence | | Insertion Reversibility | Insertion pKa | pH 8 Solubility | Notes |
|---|---|---|---|---|---|---|---|
| G1A; G2C [G38 deleted] | N-term C-pHLIP or Cys-WT1 (YR) | ACEQNPIYWARYADWLFTTPLLLLDLALLVDADEGTG | SEQ ID NO. 93 | N/A | N/A | N/A | For N-term NBD conjugation / imaging |
| Other variants containing the G1A; G2C [G38 deleted] changes | | | | | | | |
| G1A; G2C [G35/37/38 deleted] | WT-2 | ACEQNPIYWARYADWLFTTPLLLDLALLVDADET | SEQ ID NO. 94 | | | | |
| G1A; G2C [G37/38 deleted] | Cys-WT2 | ACEQNPIYWARYADWLFTTPLLLLDLALLVDADEGT | SEQ ID NO. 95 | N/A | N/A | N/A | For imaging |

FIG. 77K

| Denomination | Name | Sequence | | Insertion Reversibility | Insertion pKa | pH 8 Solubility | Notes |
|---|---|---|---|---|---|---|---|
| D25L; L24D | D25Up | GGEQNPIYWARYADWLFTTPLLLLDLLALLVDADEGTCG | SEQ ID NO. 96 | - | - | N | Aggregates |

Other variants containing the D25Up (D25L; L24D) change

| D25L; L26D | D25Down | GGEQNPIYWARYADWLFTTPLLLLDLLDALLVDADEGTCG | SEQ ID NO. 97 | - | - | N | |

FIG. 77L

| Denomination | Name | Sequence | | Insertion Reversibility | Insertion pKa | pH 8 Solubility | Notes |
|---|---|---|---|---|---|---|---|
| D14W; W15D | D14Down | GGEQNFIYMARYAWDLFTTPLLLDLALLVDADEGTCG | SEQ ID NO. 98 | - | - | N | Aggregates |

Other variants containing the D14Down (D14W; W15D) change

FIG. 77M

| Denomination | Name | Sequence | Insertion Reversibility | Insertion pKa | pH 8 Solubility | Notes |
|---|---|---|---|---|---|---|
| D14E | same | AAEQNPIYWARYADWLFTPLLLLDLALLVDADEGTCG SEQ ID NO. 99 | Y | 6.46 | Y | |

Other variants containing the D14E change

| D14/25E | same | AAEQNPIYWARYADWLFTPLLLLELALLVDADEGTCG SEQ ID NO. 100 | - | - | N | |

FIG. 77N

| Denomination | Name | Sequence | | Insertion Reversibility | Insertion pKa | pH 8 Solubility | Notes |
|---|---|---|---|---|---|---|---|
| D14A; A13D | D14Up | GGEQNPIYWARYADWLFTTPLLLLDLALLVDADEGTCG | SEQ ID NO. 101 | Y | 5.6 | Y | |
| Other variants containing the D14Up (D14A; A13D) change | | | | | | | |
| R11Q; A13D, D14A | R11Q;D14Up | GGEQNPIYWAQYADWLFTTPLLLLDLALLVDADEGTCG | SEQ ID NO. 102 | Y | 5.51 | Y | |
| R11Q,Y12D, A13Y, D14A | R11Q;D14UpUp | GGEQNPIYWAQDYAWLFTTPLLLLDLALLVDADEGTCG | SEQ ID NO. 103 | Y | 5.9 | Y | |
| D14A | same | AAEQNPIYWARYAWLFTTPLLLLDLALLVDADEGTCG | SEQ ID NO. 104 | N | N | - | |

FIG. 77O

| Denomination | Name | Sequence | | Insertion Reversibility | Insertion pKa | pH 8 Solubility | Notes |
|---|---|---|---|---|---|---|---|
| D14/25N | N-pHLIP | ACEQNPIYWARYAWWLFTTPLLLLNLALLVDADEGTG | SEQ ID NO. 105 | N | - | Y | No pH dependent insertion |

Other variants containing the D14/25N change

FIG. 77P

| Denomination | Name | Sequence | | Insertion Reversibi | Inserti on pKa | pH 8 Solubility | Notes |
|---|---|---|---|---|---|---|---|
| D25H; D14H; L26G; D31N; D33N; [G1/2D; Q4D; G35C] | D0 or H2N2 (YR) | DDDEDNPIYWARYAHWLFTTPLLLLHGALLVNANECT | SEQ ID NO. 106 | N/A | - | Y | Low percentage of insertion. Contains D insertion before A1, and deletion of C37, G38. Yana's same variant (H2N2): helical at pH8 on membrane;pKa~5 |
| Other variants containing D25H; D14H; or L26G; D31N; D33N; [A1/2D; Q4D; G35C] | | | | | | | |
| D25H; D14H; L26G; D31N; [G1/2D; Q4D; G35C] | D1 | DDDEDNPIYWARYAHWLFTTPLLLLHGALLVNADECT | SEQ ID NO. 107 | N/A | 5.2 | Y | Contains D insertion before A1, and deletion of C37, G38 |
| D25H; L26G; [G1/2D;Q4D;G35C] | 2H3 or D3a | DDDEDNPIYWARYADWLFTTPLLLLHGALLVDADECT | SEQ ID NO. 108 | Y | 5.25 | Y | Contains D insertion before A1, and deletion of C37, G38 |
| D25H; D14H; L26G; G1/2D; Q4D; G35C] | 2H2 or D2 | DDDEDNPIYWARYAHWLFTTPLLLLHGALLVDADECT | SEQ ID NO. 109 | Y | 5.1 | Y | Contains D insertion before A1, and deletion of C37, G38 |
| D14H; L26G; [G1/2D;Q4D;G35C] | D3b | DDDEDNPIYWARYAHWLFTTPLLLLDGALLVDADECT | SEQ ID NO. 110 | N/A | 5.15 | Y | Contains D insertion before A1, and deletion of C37, G38 |
| D31N;D33N;E34Q | NNQ | GGEQNPIYWARYADWLFTTPLLLLDLALLVNANQGT | SEQ ID NO. 111 | N | - | Y | Slightly aggregates |

FIG. 77Q

| Denomination | Name | Sequence | | Insertion Reversibility | Insertion pKa | pH 8 Solubility | Notes |
|---|---|---|---|---|---|---|---|
| D25E | same | AAEQNPIYWARYADWLFTTPLLLLELALLVDADEGTCG | SEQ ID NO. 112 | - | 6.49 | Y | For biophysical and translocation |
| *Other variants containing D25E* | | | | | | | |
| D14/25E | same | AAEQNPIYWARYAEWLFTTPLLLLELALLVDADEGTCG | SEQ ID NO. 113 | - | - | N | |
| D25E; G37C-(rhodamine); K-(phalloidin) | D25E; pHLIP-KC | AAEQNPIYWARYADWLFTTPLLLLELALLVDADEGTKCG | SEQ ID NO. 114 | N/A | N/A | N/A | Cargo molecules conjugated to C37 and K (inserted after T36) side chains |

FIG. 77R

| Denomination | Name | Sequence | | Insertion Reversibility | Insertion pKa | pH 8 Solubility | Notes |
|---|---|---|---|---|---|---|---|
| R11Q | same | GGEQNPIYWAQYADWLFTTPLLLLDLALLVDADEGTCG | SEQ ID NO. 115 | Y | 5.8 | Y | Has better solubility |
| Other variants containing the R11Q change | | | | | | | |
| R11Q, A13D, D14A | R11Q;D14Up | GGEQNPIYWAQYDAWLFTTPLLLLDLALLVDADEGTCG | SEQ ID NO. 116 | Y | 5.51 | Y | |
| R11Q;Y12D, A13Y, D14A | R11Q;D14UpUp | GGEQNPIYWAQDYAWLFTTPLLLLDLALLVDADEGTCG | SEQ ID NO. 117 | Y | 5.9 | Y | |

FIG. 77S

| Denomination | Name | Sequence | Insertion Reversibility | Insertion pKa | pH 8 Solubility | Notes |
|---|---|---|---|---|---|---|
| D31N;D33N;E34Q | NNQ | GGEQNPIYWARYADWLFTTPLLLLDLALLVDANQGT SEQ ID NO. 118 | N | - | Y | Aggregates slightly |
| Other variants containing D31N, D33N, or E34Q | | | | | | |
| D25H; D14H; L26G; D31N; [G1/2D; Q4D; G35C] | D1 | DDDEDNPIYWARYABWLFTPLLLLHGALLVBADECT SEQ ID NO. 119 | N/A | 5.2 | Y | Contains D insertion before A1, and deletion of C37, G38 |
| D25H; D14H; L26G; D31N; D33N; [G1/2D; Q4D; G35C] | D0 | DDDEDNPIYWARYABWLFTPLLLLHGALLVNANECT SEQ ID NO. 120 | N/A | - | Y | Low percentage of insertion. Contains D insertion before A1, and deletion of C37, G38 |

FIG. 77T

| Denomination | Name | Sequence | | Insertion Reversibility | Insertion pKa | pH 8 Solubility | Notes |
|---|---|---|---|---|---|---|---|
| O14/25K | K-pHLIP | ACEQNPIYWARYAEWLFTTPLLLLKLALLVDADEGTG | SEQ ID NO. 121 | N | - | Y/N | No pH-dependent insertion |

Other variants containing O14/25K

FIG. 77U

| Denomination | Name | Sequence | | Insertion Reversibility | Insertion pKa | pH 8 Solubility | Notes |
|---|---|---|---|---|---|---|---|
| R11Q,Y12D,A13Y, D14A | R11Q;D14UpUp | GGEQNPIYWAQDYAWLFTTPLLLLDLALLVDADEGTCG | SEQ ID NO. 122 | Y | 5.9 | Y | |
| Other variants containing the R11Q or D14A or Y12D or A13Y change/s | | | | | | | |
| R11Q, A13D, D14A | R11Q;D14Up | GGEQNPIYWAQYDAWLFTTPLLLLDLALLVDADEGTCG | SEQ ID NO. 123 | Y | 5.51 | Y | |
| R11Q | same | GGEQNPIYWAQYADWLFTTPLLLLDLALLVDADEGTCG | SEQ ID NO. 124 | Y | 5.8 | Y | |
| D14A | Same | AAEQNPIYWARYAAWLFTTPLLLLDLALLVDADEGTCG | SEQ ID NO. 125 | N | N | - | |

FIG. 77V

| Denomination | Name | Sequence | | Insertion Reversibility | Insertion pKa | pH 8 Solubility | Notes |
|---|---|---|---|---|---|---|---|
| T19D; L insertions after residues T19 and L26 | 3D | AAEQNPIYWARYADWLFTDLPLLLLDLLALLVDADEGT | SEQ ID NO. 126 | - | - | N | Aggregates. Helical at pH8 on membrane |
| Other variants containing T18D change or L insertions | | | | | | | |

FIG. 77W

| Denomination | Name | Sequence | | Insertion Reversibility | Insertion pKa | pH 8 Solubility | Notes |
|---|---|---|---|---|---|---|---|
| D25L; L26D | D25Down | GGEQNPIYWARYADWLFTTPLLLLLDALLVDADEGTCG | SEQ ID NO. 127 | - | - | N | Aggregates |
| Other variants containing the D25Down (D25L; L26D) change | | | | | | | |
| D25L; L24D | D25Up | GGEQNPIYWARYADWLFTTPLLLDLLALLVDADEGTCG | SEQ ID NO. 128 | - | - | N | |

FIG. 77X

| Denomination | Name | Sequence | | Insertion Reversibility | Insertion pKa | pH 8 Solubility | Notes |
|---|---|---|---|---|---|---|---|
| P20G [G37/38 deleted] | same | AAEQNPIYWARYADWLFTTGLLLLDLALLVDADEGT | SEQ ID NO. 129 | Y | ~6.7 | Y | Helical at pH8 on membrane |

Other variants containing P20G or [G37/38 deleted]

FIG. 77Y

| Denomination | Name | Sequence | | Insertion Reversibility | Insertion pKa | pH 8 Solubility | Notes |
|---|---|---|---|---|---|---|---|
| D14A | Same | AAEQNPIYWARYAAWLFTTPLLLLDLALLVDADEGTCG | SEQ ID NO. 130 | N | N | - | Aggregates |
| Other variants containing the D14A change | | | | | | | |
| R11Q, A13D, D14A | R11Q;D14up | GGEQNPIYWAQYDAWLFTFLLLLDLALLVDADEGTCG | SEQ ID NO. 131 | Y | 5.51 | Y | |
| R11Q,Y12D, A13Y, D14A | R11Q;D14upup | GGEQNPIYWAQDYAWLFTTPLLLLDLALLVDADEGTCG | SEQ ID NO. 132 | Y | 5.9 | Y | |
| D14A; A13D | D14up | GGEQNPIYWARYDAWLFTTPLLLLDLALLVDADEGTCG | SEQ ID NO. 133 | Y | 5.6 | Y | |

FIG. 77Z

| Denomination | Name | Sequence | | Insertion Reversibility | Insertion pKa | pH 8 Solubility | Notes |
|---|---|---|---|---|---|---|---|
| D25A | same | AAEQNPIYWARYADWLFTTPLLLLALALLVDADEGTCG | SEQ ID NO. 134 | - | - | N | Aggregates |

Other variants containing the D25A change

FIG. 77AA

| Denomination | Name | Sequence | | Insertion Reversibility | Insertion pKa | pH 8 Solubility | Notes |
|---|---|---|---|---|---|---|---|
| K-(rhodamine);G37C-(phalloidin) | pHLIP-KC | AAEQNPIYWARYADWLFTTPLLLLDLALLVDADEGTKCG ......EGTK(rhodamine)K(phalloidin)G | SEQ ID NO. 135 | N/A | 6.16 | Y | Cargo molecules conjugated to C37 and K (inserted after T36) side |
| Other variants containing the same changes | | | | | | | |
| D25E;K-(rhodamine);G37C-(phalloidin) | D25E pHLIP-KC | AAEQNPIYWARYAEWLFTTPLLLLELALLVDADEGTKCG | SEQ ID NO. 136 | N/A | N/A | N/A | Cargo molecules conjugated to C37 and K (inserted after T36) side |
| G37C-(Phalloidin) | pHLIP-C | AAEQNPIYWARYADWLFTTPLLLLDLALLVDADEGTCG | SEQ ID NO. 137 | N/A | 6.14 | Y | Cargo conjugated to C37 side chain |

FIG. 77AB

| Denomination | Name | Sequence | | Insertion Reversibility | Insertion pKa | pH 8 Solubility | Notes |
|---|---|---|---|---|---|---|---|
| G37C-Phalloidin | pHLIP-C | AAEQNPIYWARYADWLFTTPLLLLDLALLVDADEGTC(phalloidin)G | SEQ ID NO. 138 | N/A | 6.14 | Y | Cargo conjugated to C37 side chain |

Other variants containing the same change

| G37C | WT-Cys3 | GGEQNPIYWARYADWLFTTPLLLLDLALLVDADEGTCG | SEQ ID NO. 139 | Y | 6 | Y | Translocation |

FIG. 77AC

| Denomination | Name | Sequence | | Insertion Reversibility | Insertion pKa | pH 8 Solubility | Notes |
|---|---|---|---|---|---|---|---|
| G1A; G2C [G35/37/38 deleted] | WT-2 | ACEQNPIYWARYADWLFTTPLLLLDLAL

FIG. 77AE

| Denomination | Name | Sequence | | Insertion Reversibility | Insertion pKa | pH 8 Solubility | Notes |
|---|---|---|---|---|---|---|---|
| D31N;D33N;E34Q | NNQ | GGEQNPIYWARYADWLFTTPLLLLDLALLVXXAXXGT | SEQ ID NO. 143 | N | - | Y | |
| Other variants containing D31N, D33N, or E34Q | | | | | | | |
| D25H; D14H; L26G; D31N; [G1/2D]; Q4D; G35C] | D1 | DDDDEDNPIYWARYABWLFTTPLLLLXXGALLVXXAGECT | SEQ ID NO. 144 | N/A | 5.2 | Y | Contains D insertion before A1, and deletion of C37, G38 |
| D25H; D14H; L26G; D31N; D33N; [G1/2D; Q4D; G35C] | D0 | DDDDEDNPIYWARYABWLFTTPLLLLXXGALLVXXAMECT | SEQ ID NO. 145 | N/A | - | Y | Low percentage of insertion. Contains D insertion before A1, and deletion of |

| Denomination | Name | Sequence | | Insertion Reversibility | Insertion pKa | pH 8 Solubility | Notes |
|---|---|---|---|---|---|---|---|
| WT-Cys | same | GGEQNPIYWARYADWLFTTPLLLLDLALLVDADEGTCG | SEQ ID NO. 146 | Y | 6 | Y | |
| Other variants containing C37 residue | | | | | | | |
| G37C-Phalloidin | pHLIP-C | AAEQNPIYWARYADWLFTTPLLLLDLALLVDADEGTC-(phalloidin)G | SEQ ID NO. 147 | N/A | 6.14 | Y | Cargo conjugated to C37 side chain |
| D25E-K-(rhodamine);G37C-(phalloidin) | D25E pHLIP-KC | AAEQNPIYWARYADWLFTTPLLLLELALLVDADEGTKCG | SEQ ID NO. 148 | N/A | N/A | N/A | Cargo molecules conjugated to C37 and K (inserted after T35) |
| K-(rhodamine);G37C-(phalloidin) | pHLIP-KC | AAEQNPIYWARYADWLFTTPLLLLDLALLVDADEGTKCG | SEQ ID NO. 149 | N/A | 6.16 | Y | Cargo molecules conjugated to C37 and K (inserted after T35) side chains |

FIG. 77AF

| Denomination | Name | Sequence | | Insertion Reversibility | Insertion pKa | pH 8 Solubility | Notes |
|---|---|---|---|---|---|---|---|
| D25H; D14H; [G1/2D]; L26G; Q4D; G35C] | 2H2 or D2 | DGGEDNPIYWARYADWLFTTPLLLLDGALLVDADHCT | SEQ ID NO. 150 | Y | 5.1 | Y | Contains D insertion before A1, and deletion of C37, G38 |
| Other variants containing D25H; D14H; L26G; [A1/2D; Q4D; G35C] | | | | | | | |
| D14H; L26G; [G1/2D;Q4D;G35C] | D2b | D:GEDNPITYWARYARWLFTTPLLLLDGALLVDADHCT | SEQ ID NO. 151 | N/A | 5.15 | Y | Contains D insertion before A1, and deletion of C37, G38 |
| D25H; D14H; L26G; D31N; [G1/2D; Q4D; G35C] | D1 | D:GEDNPITYWARYARWLFTTPLLLLDGALLVNADHCT | SEQ ID NO. 152 | N/A | 5.2 | Y | Contains D insertion before A1, and deletion of C37, G38 |
| D25H; D14H; L26G; D31N; D33N; [G1/2D; Q4D; G35C] | D0 | D:GEDNPITYWARYARWLFTTPLLLLDGALLVNANHCT | SEQ ID NO. 153 | N/A | - | Y | Low percentage insertion. Contains D insertion before A1, and deletion of C37, G38 |
| D25H; L26G; [G1/2D;Q4D;G35C] | 2H3 or D3a | DGGEDNPIYWARYADWLFTTPLLLLDGALLVDADHCT | SEQ ID NO. 154 | Y | 5.25 | Y | Contains D insertion before A1, and deletion of C37, G38 |

FIG. 77AG

| Denomination | Name | Sequence | Insertion Reversibility | Insertion pKa | pH 8 Solubility | Notes |
|---|---|---|---|---|---|---|
| D25H; L26G; [A1/2D;Q4D;G35C] | 2H3 or D3a | DDGEDNPIWARYADWLFTTPLLLLHGALLVDADECT SEQ ID NO. 155 | Y | 5.25 | Y | Contains D insertion before A1, and deletion of C37, G38 |
| Other variants containing the D25H; L26G (A1/2D; Q4D; G35C) changes |||||||
| D14H; L26G; [A1/2D;Q4D;G35C] | D3b | DDGEDNPIYWARYAHWLFTTPLLLLDGALLVDADECT SEQ ID NO. 156 | N/A | 5.15 | Y | Contains D insertion before A1, and deletion of C37, G38 |
| D25H; D14H; L26G; [A1/2D; Q4D; G35C] | 2H2 or D2 | DDGEDNPIYWARYAHWLFTTPLLLLHGALLVDADECT SEQ ID NO. 157 | Y | 5.1 | Y | Contains D insertion before A1, and deletion of C37, G38 |
| D25H; D14H; L26G; D31N; [A1/2D; Q4D; G35C] | D1 | DDGEDNPIYWARYAHWLFTTPLLLLHGALLVNADECT SEQ ID NO. 158 | N/A | 5.2 | Y | Contains D insertion before A1, and deletion of C37, G38 |
| D25H; D14H; L26G; D31N; D33N; [A1/2D; Q4D; G35C] | D0 | DDGEDNPIYWARYAHWLFTTPLLLLHGALLVNAMECT SEQ ID NO. 159 | N/A | - | Y | Low percentage of insertion. Contains D insertion before A1, and deletion of C37, G38 |

FIG. 77AH

| Denomination | Name | Sequence | | Insertion Reversibility | Insertion pKa | pH 8 Solubility | Notes |
|---|---|---|---|---|---|---|---|
| D25H; D14H; L26G; D31N; D33N; [G1/2D; Q4D; G35C] | D0 | DDBEDNPIYWARYAXWLFTTPLLLLXGALLVXAXECT | SEQ ID NO. 160 | N/A | - | Y | Low percentage of insertion. Contains D insertion before A1, and deletion of C37. |
| Other variants containing D25H; D14H; or L26G; D31N; D33N; [A1/2D; Q4D; G35C] | | | | | | | |
| D25H; D14H; L26G; D31N; [G1/2D; Q4D; G35C] | D1 | DDBEDNPIYWARYAXMLFTTPLLLLXGALLVXADECT | SEQ ID NO. 161 | N/A | 5.2 | Y | Contains D insertion before A1, and deletion of C37, G38 |
| D25H; L26G; [G1/2D; Q4D; G35C] | 2H3 or D3 | DDBEDNPIYWARYADWLFTTPLLLLXGALLVDADECT | SEQ ID NO. 162 | Y | 5.25 | Y | Contains D insertion before A1, and deletion of C37, G38 |
| D25H; D14H; L26G; [G1/2D; Q4D; G35C] | 2H2 or D2 | DDBEDNPIYWARYAXWLFTTPLLLLXGALLVDADECT | SEQ ID NO. 163 | Y | 5.1 | Y | Contains D insertion before A1, and deletion of C37, G38 |
| D14H; L26G; [G1/2D; Q4D; G35C] | D3b | DDBEDNPIYWARYAXWLFTTPLLLLDGALLVDADECT | SEQ ID NO. 164 | N/A | 5.15 | Y | Contains D insertion before A1, and deletion of C37, G38 |
| D31N;D33N;E34Q | NNQ | GGEQNPIYWARYADWLFTTPLLLLDLALLVXANQGT | SEQ ID NO. 165 | N | - | Y | |

FIG. 77AI

| Denomination | Name | Sequence | | Insertion Reversibility | Insertion pKa | Solubility pH 8 | Notes |
|---|---|---|---|---|---|---|---|
| D25H; D14H; L26G; D31N; [G1/2D; Q4D; G35C] | D1 | DDDEDNPIYWARYAWWLFTTPLLLLHGALLVNADECT | SEQ ID NO. 166 | N/A | 5.2 | Y | Contains D insertion before A1, and deletion of C37, G38 |
| Other variants containing D25H; D14H; L26G; D31N; or [G1/2D; Q4D; G35C] | | | | | | | |
| D25H; L26G; [G1/2D;Q4D];G35C] | 2H3 or D3a | DDDEDNPIYWARYADWWLFTTPLLLLHGALLVDADECT | SEQ ID NO. 167 | Y | 5.25 | Y | Contains D insertion before A1, and deletion of C37, G38 |
| D25H; D14H; L26G; [G1/2D;Q4D]; G35C] | 2H2 or D2 | DDDEENPIYWARYAHWLFTTPLLLLHGALLVDADECT | SEQ ID NO. 168 | Y | 5.1 | Y | Contains D insertion before A1, and deletion of C37, G36 |
| D14H; L26G; [G1/2D;Q4D];G35C] | D3b | DDDEDNPIYWARYAHWLFTTPLLLLDGALLVDADECT | SEQ ID NO. 169 | N/A | 5.15 | Y | Contains D insertion before A1, and deletion of C37, G38 |
| D25H; D14H; L26G; D31N; D33N; [G1/2D; Q4D; G35C] | D0 | DDDEENPIYWARYAHWLFTTPLLLLHGALLVNANECT | SEQ ID NO. 170 | N/A | - | Y | Low percentage of insertion. Contains D insertion before A1, and deletion of C37. |

FIG. 77AJ

| Denomination | Name | Sequence | | Insertion Reversibilit | Insertio n pKa | pH 8 Solubility | Notes |
|---|---|---|---|---|---|---|---|
| D14H; L26G; [A1/2D;Q4D;G35C] | D3b | DDDEDNPIYWARYADWLFTTPLLLLHSALLVDADECT | SEQ ID NO. 171 | N/A | 5.15 | Y | Contains D insertion before A1, and deletion of C37, G38 |
| Other variants containing D14H, L26G, or [A1/2D;Q4D;G35C] | | | | | | | |
| D25H; L26G; [A1/2D;Q4D;G35C] | 2H3 or D3a | DDDEDNPIYWARYADWLFTTPLLLLHSALLVDADECT | SEQ ID NO. 172 | Y | 5.25 | Y | Contains D insertion before A1, deletion of C37, G38 |
| D25H; D14H; L26G; [A1/2D; Q4D; G35C] | 2H2 or D2 | DDDEDRPIYWARYAHWLFTTPLLLLHSALLVDADECT | SEQ ID NO. 173 | Y | 5.1 | Y | Contains D insertion before A1, and deletion of C37, G38 |
| D25H; D14H; L26G; D31N; [A1/2D; Q4D; G35C] | D1 | DDDEDNPIYWARYAHWLFTTPLLLLHSALLVADECT | SEQ ID NO. 174 | N/A | 5.2 | Y | Contains D insertion before A1, and deletion of C37, G38 |
| D33N; D14H; L26G; D31N; [A1/2D; Q4D; G35C] | D0 | DDDEDNPIYWARYAHWLFTTPLLLLHSALLVNAHECT | SEQ ID NO. 175 | N/A | - | Y | Low percentage of insertion. Contains D insertion before A1, and deletion of C37, G38 |

FIG. 77AK

| Denomination | Name | Sequence | | Insertion Reversibility | Insertion pKa | pH 8 Solubility | Notes |
|---|---|---|---|---|---|---|---|
| P20G | same | AAEQNFIYWARYADWLFTTGLLLLDLALLVDADEGT | SEQ ID NO. 176 | Y | ~6.7 | Y | |
| Other variants containing P20G | | | | | | | |

FIG. 77AL

| Denomination | Name | Sequence | | Insertion Reversibility | Insertion pKa | pH 8 Solubility | Notes |
|---|---|---|---|---|---|---|---|
| D14W; W15D | D14Down | GGEQNPIYWARYAWDLFTTPLLLLDLALLVDADEGTCG | SEQ ID NO. 177 | - | - | N | |
| Other variants containing the D14Down (D14W; W15D) change | | | | | | | |

FIG. 77AM

| Denomination | Name | Sequence | | Insertion Reversibility | Insertion pKa | pH 8 Solubility | Notes |
|---|---|---|---|---|---|---|---|
| D14A; A13D | D14Up | GGEQNPIYWARYDAWLFTTPLLLLDLALLVDADEGTCG | SEQ ID NO. 178 | Y | 5.6 | Y | |
| Other variants containing the D14Up (D14A; A13D) change | | | | | | | |
| R11Q, A13D, D14A | R11Q;D14Up | GGEQNPIYWAQYDAWLFTTPLLLLDLALLVDADEGTCG | SEQ ID NO. 179 | Y | 5.51 | Y | |
| R11Q,Y12D, A13Y, D14A | R11Q;D14UpUp | GGEQNPIYWAQYAWLFTTPLLLLDLALLVDADEGTCG | SEQ ID NO. 180 | Y | 5.9 | Y | |
| D14A | same | AAEQNPIYWARYAAWLFTTPLLLLDLALLVDADEGTCG | SEQ ID NO. 181 | N | N | - | |

FIG. 77AN

| Denomination | Name | Sequence | | Insertion Reversibility | Insertion pKa | pH 8 Solubility | Notes |
|---|---|---|---|---|---|---|---|
| D25L; L26D | D25Down | GGEQNPIYWARYADWLFTTPLLLLLDALLLDALLVDADEGTCG | SEQ ID NO. 182 | - | - | N | |
| Other variants containing the D25Down (D25L; L26D) change | | | | | | | |
| D25L; L24D | D25Up | GGEQNPIYWARYADWLFTTPLLLLDLLALLVDADEGTCG | SEQ ID NO. 183 | - | - | N | |

FIG. 77AO

| Denomination | Name | Sequence | Insertion Reversibility | Insertion pKa | pH 8 Solubility | Notes |
|---|---|---|---|---|---|---|
| D25L, L24D | D25Up | GGEQNPIYWARYADWLFTTPLLLLLLLALLVDADEGTCG | - | - | N | |
| Other variants containing the D25up (D25L, L24D) change | | | | | | |
| D25L, L26D | D25Down | GGEQNPIYWARYADWLFTTPLLLLLVDALLLDADEGTCG | - | - | N | |

FIG. 77AP

| Denomination | Name | Sequence | | Insertion Reversibility | Insertion pKa | pH 8 Solubility | Notes |
|---|---|---|---|---|---|---|---|
| R11Q | same | GGEQNPIYWAQYADWLFTTPLLLDLALLVDADEGTCG | SEQ ID NO. 186 | Y | 5.8 | Y | |
| Other variants containing the R11Q change | | | | | | | |
| R11Q, A13D, D14A | R11Q;D14Up | GGEQNPIYWAQYDAWLFTTPLLLDLALLVDADEGTCG | SEQ ID NO. 187 | Y | 5.51 | Y | |
| R11Q,Y12D, A13Y, D14A | R11Q;D14upUp | GGEQNPIYWADSYAWLFTTPLLLDLALLVDADEGTCG | SEQ ID NO. 188 | Y | 5.9 | Y | |

FIG. 77AQ

| Denomination | Name | Sequence | | Insertion Reversibility | Insertion pKa | pH 8 Solubility | Notes |
|---|---|---|---|---|---|---|---|
| R11Q, A13D, D14A | R11Q;D14A | GGEQNPIYWAQYDAWLFTTPLLLLDLALLVDADEGTCG | SEQ ID NO. 189 | Y | 5.51 | Y | |
| Other variants containing the R11Q (R11Q;A13D;D14A) change | | | | | | | |
| R11Q,Y12D, A13Y, D14A | R11Q;D14Upt | GGEQNPIYWAQDXAWLFTTPLLLLDLALLVDADEGTCG | SEQ ID NO. 190 | Y | 5.9 | Y | |
| R11Q | same | GGEQNPIYWAQYADWLFTTPLLLLDLALLVDADEGTCG | SEQ ID NO. 191 | Y | 5.8 | Y | |
| D14A | Same | AAEQNPIYWARYAAWLFTTPLLLLDLALLVDADEGTCG | SEQ ID NO. 192 | N | N | | |

FIG. 77AR

| Denomination | Name | Sequence | | Insertion Reversibility | Insertion pKa | pH 8 Solubility | Notes |
|---|---|---|---|---|---|---|---|
| R11Q,Y12D,A13Y, D14A | R11Q;D14UpUp | GGEQNPIYWADYAWLFTTPLLLDLALLVDADEGTCG | SEQ ID NO. 193 | Y | 5.9 | Y | |
| Other variants containing the R11Q or D14A or Y12D or A13Y changes | | | | | | | |
| R11Q, A13D, D14A | R11Q;D14Up | GGEQNPIYWAQYDAWLFTTPLLLDLALLVDADEGTCG | SEQ ID NO. 194 | Y | 5.51 | Y | |
| R11Q | same | GGEQNPIYWAQYADWLFTTPLLLDLALLVDADEGTCG | SEQ ID NO. 195 | Y | 5.8 | Y | |
| D14A | Same | AAEQNPIYWARYAAWLFTTPLLLDLALLVDADEGTCG | SEQ ID NO. 196 | N | N | - | |

FIG. 77AS

| Denomination | Name | Sequence | | Insertion Reversibility | Insertion pKa | pH 8 Solubility | Notes |
|---|---|---|---|---|---|---|---|
| D25E;K-(rhodamine);G37C-(phalloidin) | D25E pHLIP-KC | AAEQNPIYWARYADWLFTTPLLLLSLALLVDADEGTKCG | SEQ ID NO. 197 | N/A | N/A | N/A | Cargo molecules conjugated to C37 and K (inserted after T36) side chains |
| | | ........EGTK(rhodamine)C(phalloidin)G | SEQ ID NO. 198 | | | | |
| *Other variants containing the same change* | | | | | | | |
| K-(rhodamine);G37C-(phalloidin) | pHLIP-KC | AAEQNPIYWARYADWLFTTPLLLLDLALLVDADEGTKCG | SEQ ID NO. 199 | N/A | 6.16 | Y | Cargo molecules conjugated to C37 and K (inserted after T36) side chains |

FIG. 77AT

| Denomination | Name | Sequence | | Insertion Reversibility | Insertion pKa | pH 8 Solubility | Notes |
|---|---|---|---|---|---|---|---|
| A2C | N-term C-pHLIP | ACEQNPIYWARYADWLFTTPLLLLDLALLVDADEGTG | SEQ ID NO. 200 | N/A | N/A | N/A | For N-term NBD conjugation |
| Other variants containing the A2C change | | | | | | | |

FIG. 77AU

| Denomination | Name | Sequence | | Insertion Reversibility | Insertion pKa | pH 8 Solubility | Notes |
|---|---|---|---|---|---|---|---|
| G37C-Phalloidin | pHLIP-C | AAEQNPIYWARYADWLFTTPLLLLDLALLVDADEGTC(phalloidin)G | SEQ ID NO. 201 | N/A | 6.14 | Y | Cargo conjugated to C37 side chain |
| Other variants containing the same change | | | | | | | |

FIG. 77AV

| Denomination | Name | Sequence | Insertion Reversibility | Insertion pKa | pH 8 Solubility | Notes |
|---|---|---|---|---|---|---|
| K-(rhodamine);G37C-(phalloidin) | pHLIP-KC | AAEQNPIYWARYADWLFTTPLLLLDLALLVDADEGTK&CG ............EGTK(rhodamine)&C(phalloidin)G | N/A | 6.16 | Y | Cargo molecules conjugated to C37 and K (inserted after T36) side |
| Other variants containing the same change | | | | | | |
| D25E;K-(rhodamine);G37C-(phalloidin) | D25E pHLIP-KC | AAEQNPIYWARYADWLFTTPLLLL&LALLVDADEGTK&CG | N/A | N/A | N/A | Cargo molecules conjugated to C37 and K (inserted after T36) side |

FIG. 77AW

| Denomination | Name | Sequence | | Insertion Reversibility | Insertion pKa | pH 8 Solubility | Notes |
|---|---|---|---|---|---|---|---|
| T19D, L insertions after residues T19 and L26 | 3D | AAEQNPIYWARYADWLFTTPLLLLDLLALLVDADEGT | SEQ ID NO. 204 | - | - | N | |
| Other variants containing T19D change or L insertions | | | | | | | |

FIG. 77AX

| Denomination | Name | Sequence | | Insertion Reversibility | Insertion pKa | pH 8 Solubility | Notes |
|---|---|---|---|---|---|---|---|
| D14A | Same | AAEQNPIYWARYADWLFTTIPLLLLDLALLVDADEGTCG | SEQ ID NO. 205 | N | N | - | |
| Other variants containing the D14A change | | | | | | | |
| R11Q, A13D, D14A | R11Q;D14Up | GGEQNPIYWAQYDAWLFTTPLLLLDLALLVDADEGTCG | SEQ ID NO. 206 | Y | 5.51 | Y | |
| R11Q, Y12D, A13Y, D14A | R11Q;D14UpUp | GGEQNPIYWAQDYAWLFTTPLLLLDLALLVDADEGTCG | SEQ ID NO. 207 | Y | 5.9 | Y | |
| D14A; A13D | D14Up | GGEQNPIYWARYDAWLFTTPLLLLDLALLVDADEGTCG | SEQ ID NO. 208 | Y | 5.6 | Y | |

FIG. 77AY

| Denomination | Name | Sequence | Insertion Reversibility | Insertion pKa | pH 8 Solubility | Notes |
|---|---|---|---|---|---|---|
| D14E | same | AAEQNPIYWARYADWLFTTPLLLLDLALLVDADEGTCG | SEQ ID NO. 209 Y | 6.46 | Y | |
| Other variants containing the D14E change: | | | | | | |
| D14/25E | same | AAEQNPIYWARYADWLFTTPLLLLELALLVDADEGTCG | SEQ ID NO. 210 - | - | N | |

FIG. 77AZ

| Denomination | Name | Sequence | | Insertion Reversibility | Insertion pKa | pH 8 Solubility | Notes |
|---|---|---|---|---|---|---|---|
| D25A | same | AAEQNPIYWARYADWLFTTPLLLLALALLVDADEGTCG | SEQ ID NO. 211 | - | - | N | |

Other variants containing the D25A change

FIG. 77AAA

| Denomination | Name | Sequence | | Insertion Reversibility | Insertion pKa | pH 8 Solubility | Notes |
|---|---|---|---|---|---|---|---|
| D25E | same | AAEQNPIYWARYADWLFTTPLLLLELALLVDADEGTCG | SEQ ID NO. 212 | N/A | 6.49 | Y | |
| Other variants containing D25E | | | | | | | |
| D14/25E | same | AAEQNPIYWARYAEWLFTTPLLLLELALLVDADEGTCG | SEQ ID NO. 213 | - | - | N | |
| D25E; K-(rhodamine); G37C-(phalloidin) | D25E; pHLIP-KC | AAEQNPIYWARYADWLFTTPLLLLELALLVDADEGTKCG | SEQ ID NO. 214 | N/A | N/A | N/A | Cargo molecules conjugated to C37 and K (inserted after T36) side chains |

FIG. 77AAB

| Denomination | Name | Sequence | | Insertion Reversibility | Insertion pKa | pH 8 Solubility | Notes |
|---|---|---|---|---|---|---|---|
| D14/25K | K-pHLIP | ACEQNPIYWARYAKWLFTTPLLLLKLALLVDADEGTG | SEQ ID NO. 215 | N | - | Y/N | |
| Other variants containing D14/25K | | | | | | | |

FIG. 77AAC

| Denomination | Name | Sequence | | Insertion Reversibility | Insertion pKa | pH 8 Solubility | Notes |
|---|---|---|---|---|---|---|---|
| D14/25N | N-pHLIP | ACEQNPIYWARYANWLFTTPLLLLNLALLVDADEGTG | SEQ ID NO. 216 | N | - | Y | |
| Other variants containing the D14/25N change | | | | | | | |

FIG. 77AAD

| Denomination | Name | Sequence | Insertion Reversibility | Insertion pKa | pH 8 Solubility | Notes |
|---|---|---|---|---|---|---|
| P20A | same | AAEQNPIYWARYADWLFTTALLLLDLALLVDADEGT SEQ ID NO. 217 | - | - | N | |
| Other variants containing P20A | | | | | | |

FIG. 77AAE

ENVIRONMENTALLY SENSITIVE COMPOSITIONS AND METHODS OF USE THEREOF

RELATED APPLICATIONS

This application is a continuation of the U.S. application Ser. No. 13/182,441, filed Jul. 13, 2011, now U.S. Pat. No. 9,289,508, issued Mar. 22, 2016, which claims the benefit of priority under 35 U.S.C. §119(e) to U.S. Provisional Application No. 61/363,891, filed Jul. 13, 2010, the contents of each of which are incorporated herein by reference in their entireties.

STATEMENT AS TO FEDERALLY SPONSORED RESEARCH

This invention was made with government support under Grant Number W81XWH-07-1-0498 awarded by the Department of Defense (Army/MRMC), and Grant Numbers CA125280, CA133890, and GM073857 by the National Institutes of Health. The Government has certain rights in the invention.

INCORPORATION-BY-REFERENCE OF SEQUENCE LISTING

The contents of the text file named "40984_502C01US_SEQUENCE_LISTING.txt", which was created on May 31, 2016 and is 139 KB in size, is hereby incorporated by reference in its entirety.

FIELD OF THE INVENTION

The invention relates to compositions and methods for delivery of molecules to cells and cell membrane insertion.

BACKGROUND OF THE INVENTION

Despite many advances in the field of cancer diagnosis and treatment, a reliable method of identifying and treating cancer cells while sparing non-cancerous cells has been elusive. One of the limitations is the heterogeneity of human cancers. It has therefore been problematic to rely on any single tumor biomarker even for one type of cancer. Detection of tumor acidity may be an alternative strategy for targeting tumor cells. A pH-sensitive polypeptide with a predominantly hydrophobic sequence long enough to span a membrane lipid bilayer as a transmembrane helix and two flanking sequences (FS) has been described (WO 2006/078816 A2). Selective and efficient targeting and delivery of therapeutic agents to tumor cells remains a challenge.

SUMMARY OF THE INVENTION

The compositions and methods described herein solve this problem with improved environmentally sensitive membrane binding polypeptides with improved insertion kinetics balanced with solubility. The invention is based on the discovery that certain changes to a pH-sensitive membrane peptide (pHLIP), e.g., AAEQNPIYWWARYAD-WLFTTPLLLLDLALLVDADEGTCG (SEQ ID NO: 1), dramatically affect the performance of the polypeptide in clinical situations. For example, alterations in the peptide lead to faster or slower insertion into lipid bilayer structures, e.g., cell membranes. Moreover, the definition of critical amino acids comprising a nominal membrane insertion sequence (eight amino acids) has lead to improved performance and design of customized constructs for both diagnostic and therapeutic applications. Variations in amino acid sequence of the membrane sequence lead to classification of pHLIP peptides into (I) fast-inserting and (II) slow-inserting classes.

Accordingly, an environmentally sensitive composition comprises a pH triggered peptide with a membrane sequence that comprises at least 8 amino acids. Preferably, the length of the peptide does not exceed 50 amino acids (excluding the cargo moiety). Thus, the environmentally sensitive composition is characterized by pH-dependent membrane-binding or membrane-inserting activity. A membrane sequence is an amino acid sequence of a peptide that associates with or inserts into a lipid bilayer. For example, the membrane sequence of the peptide spans a cell membrane structure. The membrane sequence mediates translocation of a composition (e.g., cargo compounds) that is attached to, e.g., conjugated to, the membrane sequence. The peptide component of the composition (e.g., membrane sequence) is monomeric and non-pore forming, i.e., a peptide comprising the membrane sequence does not assemble into a multimeric pore or channel structure in a lipid bilayer or cell membrane. For example, insertion of the membrane sequence of the composition into a lipid membrane does not cause calcium release out of lipid vesicles and does not cause hemoglobin leakage out of red blood cells.

The membrane sequence comprises greater than 8 and less than 50 residues. Preferably, the range is 13-25 residues. At least 6 of the 8 amino acids of the insertion sequence are non-polar; the 6 non-polar amino acids of the membrane sequence are contiguous. At least one of the 8 amino acids of the insertion sequence is protonatable. The protonatable amino acid is located within 10 amino acids (e.g., within 2, 3, 4, 5, 6, 7, 8, or 9 residues) of the non-polar amino acids (not immediately contiguous to a non-polar amino acid). The peptide comprises naturally-occurring amino acids, non-naturally occurring amino acids, amino acids that are DNA-encoded as well as those that are not encoded by DNA or RNA. The peptide includes L-amino acids as well as D-amino acids.

The peptide has a higher affinity for a membrane lipid bilayer at pH compared to that at pH8. For example, the affinity is at least 5 times higher at pH5.0 than at pH 8.0. In some embodiments, the affinity is at least 10 times higher at pH5.0 than at pH 8.0. Preferably, the composition does not comprise the amino acid sequence of SEQ ID NO: 1. A non-polar amino acid is defined as one having a solvation energy ≥0.5 kcal/mol. The values of solvation energy ($\Delta G_x^{corr}$) for 20 natural amino acids are known, e.g., as determined by Wimley W C, Creamer T P & White S H (1996). Biochemistry 35, 5109-5124. Values for solvation energy are provided below in Table 3. Coded amino acids and exemplary non-coded amino acids are provided below in Table 4.

The composition further comprises a single flanking domain at an N-terminus or at a C-terminus of the membrane insertion sequence. In another embodiment, the composition comprises two flanking domains on either side of the insertion sequence: a first flanking domain at C-terminus of the insertion sequence and a second flanking domain at the N-terminus of the insertion sequence. For example, the composition comprises a polypeptide comprising the amino acid sequence selected from the group consisting of SEQ ID NO:21-51. Numerous examples of environmentally sensitive membrane-binding/membrane-inserting peptides are shown in Tables 1-2. pHLIP peptide may be classified by attributes of the flanking domains: (I) Cys present solely in the amino-terminal flanking region; (II) Cys present solely in the carboxy-terminal flanking region; (III) Cys present in both the amino-terminal flanking region and in the carboxy-terminal flanking region. The cysteine residues serves as points of conjugation of cargo, e.g., using S—S(thiol) linkage. Other means of linking cargo to the pHLIP peptide include an ester linkage. Ester linkages are particularly useful in humans, the cells of which contain esterases in the cytoplasm to liberate the cargo inside the cells. This system is less useful in the mouse or other rodents, which species are characterized by a high level of esterases in the blood (thereby leading to premature release of cargo molecules).

The peptide constructs of the composition are useful for medical applications, e.g., therapeutic, diagnostic, prophylactic, imaging, gene regulation, or as research reagents/tools, e.g., to evaluate cell function regulation, apoptosis, or other cell activities. For such applications, the composition further comprises a moiety attached to one (or both) of the flanking domains. Exemplary moieties include dyes or other detectable labels and cytotoxic agents. For example, pHLIP peptides translocate cell impermeable cargo molecules, such as nanoparticles, organic dyes, peptides, peptide nucleic acids and toxins, across the plasma membrane into the cytoplasm of tumor cells. pHLIP itself is non-toxic. Additional examples of cargo molecules are magnetic resonance (MR), positron emission tomography (PET), single photon emission computed tomography (SPECT), fluorescence imaging agents, natural toxins, DNA intercalators, peptide nucleic acids (PNA), morpholino (e.g., morpholino oligomers), peptides, and naturally-occurring or synthetic drug molecules. Other examples therapeutic or diagnostic moieties or cargo compounds include radiation-enhancing or radiation-sensitizing compounds such as nanogold particles to enhance imaging or cell destruction, e.g., tumor cell killing, by radiation or boron-containing compounds such as Disodium mercapto-closo-dodecaborate (BSH) for boron neutron capture therapy (BNCT) that kills labeled target cells while sparing unlabeled non-target (non-diseased) cells. For imaging or other applications for which detection is desired, one or more atoms are optionally replaced by radioactive isotopes. For example, one or more of the amino acid side chains are chemically modified to render them radioactive or detectable by probing radiation.

The moiety is attached to the flanking region via linkage such as a thiol linkage or ester linkage. Other types of linkages, chemical bonds, or binding associations are also used. Exemplary linkages or associations are mediated by disulfide, and/or a peptide with a protein binding motif, and/or a protein kinase consensus sequence, and/or a protein phosphatase consensus sequence, and/or a protease-reactive sequence, and/or a peptidase-reactive sequence, and/or a transferase-reactive sequence, and/or a hydrolase-reactive sequence, and/or an isomerase-reactive sequence, and/or a ligase-reactive sequence, and/or an extracellular metalloprotease-reactive sequence, and/or a lysosomal protease-reactive sequence, and/or a beta-lactamase-reactive sequence, and/or an oxidoreductase-reactive sequence, and/or an esterase-reactive sequence, and/or a glycosidase-reactive sequence, and/or a nuclease-reactive sequence.

One use of the environmentally-sensitive compositions is to shuttle molecules across a cell membrane. For example, the composition is used as an agent to deliver a functional moiety across cell membranes to cells in a diseased tissue with a naturally acidic extracellular environment or in a tissue with an artificially induced acidic extracellular environment relative to normal physiological pH. Many diseased tissues are characterized by an acidic microenvironment. However, acidity in tumors or non-tumor target tissues is optionally induced by co-injection of glucose or a diluted solution of acid at the tissue site at which therapy using the compositions is desired. For example, an acidifying composition (e.g., glucose or dilute acid) is administered, e.g., injected subcutaneously, before delivery of the pH sensitive compositions (30 s, 1 min., 5 min., 10 min., 30 min., 1 hr., 2 hrs, 6 hrs, 12 hrs, 24 hrs, 48 hrs, or more prior to administration of the environmentally sensitive composition to the target tissue site). Alternatively, the tissue acidifying agent and the pHLIP composition are co-administered. For example, the diseased tissue is selected from the group consisting of cancer, inflammation/inflamed tissue, ischemia/ischemic tissue, tissue affected by stroke, arthritis, infection with a microorganism (e.g., a bacteria, virus, or fungus), or atherosclerotic plaques. The compositions are also useful to deliver a functional moiety to cell surfaces in a diseased tissue with a naturally acidic extracellular environment or in a tissue with an artificially induced acidic extracellular environment relative to normal physiological pH. Administration of a neutralizing agent to an acidic site, e.g., a bicarbonate solution, is used to reduce pHLIP binding/insertion and pHLIP labeling or targeting of cells at that site.

A subclass of environmentally-sensitive peptide compositions is characterized by relatively fast membrane insertion. For example, the compositions are comprises a rate of membrane insertion is at least 10 times faster compared to that of SEQ ID NO: 1. In some case, the compositions, e.g., variants of SEQ ID NO: 1, insert into the membrane at least 25 times, 50 times, or 100 times faster compared to that of SEQ ID NO: 1.

As is described above, the compositions are used in a clinical setting for diagnostic and therapeutic applications in humans as well as animals (e.g., companion animals such as dogs and cats as well as livestock such as horses, cattle, goats, sheep, llamas). A diagnostic conjugate comprises the environmentally-sensitive composition and a pharmaceutically-acceptable detectable marker linked thereto. Exemplary detectable markers include a fluorescent dye, and MR, PET, SPECT, and other imaging agents. Such conjugates are used in a variety of clinical diagnostic methods, including real-time image-guided therapeutic interventions. For example, a method of guiding surgical tumor excision is carried out by administering to an anatomical site comprising a tumor the conjugate to an anatomical site described above, removing a primary tumor from the site, and detecting residual tumor cells by virtue of binding of the conjugate to residual tumor cells.

The compositions are administered to the body for diagnostic and therapeutic use using methods known in the art. For example, the methods are carried out by infusing into a vascular lumen, e.g., intravenously, via a jugular vein, peripheral vein or the perivascular space. In some embodiments, the composition is infused into the lungs of said mammal, e.g., as an aerosol or lavage. In other embodiments, the composition of the invention is administered by injection, e.g., into an anatomical region of interest such as a tumor site or site of another pathological condition or suspected pathological condition. In various embodiments, the injection can be into the peritoneal cavity of the mammal, subdermally, or subcutaneously. The compositions can also be administered transdermally. Solutions containing the imaging conjugates or therapeutic conjugates are administered intravenously, by lavage of the area (e.g., peritoneal tissue or lung tissue), topically, transgermally, by inhalation, or by injection (e.g., directly into a tumor or tumor border area). For example, 1-50 mg in 100 mL is used for lavage and 0.1-100 mg/kg is used for other routes of administration.

In addition to image-guided therapies, the compositions are useful to diagnose or measure the severity of a pathological condition. For example, a method of determining the aggressiveness of a primary tumor is carried out by contacting the tumor with the environmentally-sensitive composition, and an increased level of binding of the composition compared to a control level of binding indicates an increased risk of metastasis from primary tumor. Thus, the compositions aid the physician in determining a prognosis for disease progression and appropriately tailoring therapy based on the severity or aggressiveness of the disease.

Therapeutic uses involve delivery of a composition to diseased (or artificially acidified tissue) for clinical benefit. Thus, a therapeutic conjugate comprises an environmentally-sensitive composition that includes a therapeutic cargo. In some cases, the conjugate comprises a first cargo comprising a cytotoxic agent and a second cargo comprising a hydrophobicity-balancing moiety. The aggregate (environmentally-sensitive peptide construct and cargo is characterized by Log P of cargoes together in range of 0 to −3. Thus if a cargo is very polar with Log P<−3, it is combined with a hydrophobic cargo of Log P>0, thereby leading to a balanced polarity. One example of such a balancing strategy is pHLIP-KC, where phalloidin (Log P=−1.5) is attached to the C-terminus together with Rhodamine (hydrophobic). The resulting total Log P is then the same or similar to log P of phalloidin-rhodamine, which is −0.05. This balancing strategy is particularly useful for delivery of polar drugs to target cells. Other exemplary cytotoxic agents include phallo and amanitin toxins as well as DNA intercalators.

A method of preferentially inhibiting proliferation of tumor cells is carried out by administering to a subject suffering from or at risk of developing a tumor the therapeutic conjugate compositions described above to the subject. Tumor cells are preferentially inhibited compared to normal non-tumor cells. The pHLIP delivery system, e.g., exemplified by the therapeutic conjugates, are therefore used in a method of manufacturing a pharmaceutical composition or medicament for treatment of tissues characterized by disease or an acid microenvironment.

The compositions and elements of the compositions (e.g., peptides, moieties, and other components of the compositions) described herein are purified. For example, purified naturally-occurring, synthetically produced, or recombinant compounds, e.g., polypeptides, nucleic acids, small molecules, or other agents, are separated from compounds with which they exist in nature. Purified compounds are at least 60% by weight (dry weight) the compound of interest. Preferably, the preparation is at least 75%, more preferably at least 90%, and most preferably at least 99% or 100%, by weight the compound of interest. Purity is measured by any appropriate standard method, for example, by column chromatography, polyacrylamide gel electrophoresis, or HPLC analysis.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification, including definitions, will control. In addition, the materials, methods, and examples are illustrative only and not intended to be limiting. All patents and publications, including sequences identified by GENBANK accession numbers, cited in this specification are incorporated herein by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a diagram of the sequence of a pHLIP peptide (SEQ ID NO:2) showing various domains of the polypeptide.

FIGS. 3A-B are schematic representations showing the dual delivery capabilities of pHLIP. A) tethering of cargo molecules to the surface of cells with low extracellular pH and B) translocation of cell-impermeable polar cargo molecules across the membrane lipid bilayer. State I corresponds to the peptide in solution at normal and basic pHs. By addition of vesicles, the unstructured peptide is adsorbed on the membrane surface, raising the local concentration (State II). A drop of pH leads to the protonation of Asp residues, increasing peptide hydrophobicity, and resulting in the insertion and formation of a transmembrane alpha-helix (State III). Lipids interacting with the peptide directly are marked with blue head groups, lipids influenced by the interaction but not interacting with the peptide directly have cyan head groups, and lipids that are not involved in the interaction with pHLIP have yellow head groups. (chemistry-today.teknoscience.com).

FIGS. 10A-E are a series of photomicrographs showing cell morphology following contact with pHLIP constructs. Following incubation with pHLIP-K(rho)C(aph) (4 µM, 3 h) at pH 7, HeLa cells rounded and dissociated quickly after trypsinization: compare phase contrast image C taken before trypsinization with image D of the same view taken 5 min after addition of trypsin/EDTA. In contrast, HeLa cells treated with pHLIP-K(rho)C(aph) at pH 6.1 (also 4 µM, 3 h) resisted to contract—a sign of cytoskeleton rigidification, evident from images taken before (A) and 5 min after (B) the addition of trypsin/EDTA solution. (E) M4A4 cells also did not round-up when trypsinized after treatment with pHLIP-K(rho)C(aph) at pH 6.1-6.2. All trypsinizations were carried out at room temperature in PBS (at pH 7.4). The images were taken at the epi-fluorescence inverted microscope (Olympus IX71) at 20× magnification.

FIGS. 18A-L are a series of photomicrographs (×10) of gold nanoparticles in tumor, kidney and liver sections after silver staining.

FIGS. 38A-F are a series of line graphs showing circular dichroism in buffer and POPC vesicles. Far-UV CD spectra were recorded for all variants under different conditions: buffer pH 7.5 (black lines), POPC pH 7.4 (blue lines), and POPC pH 4 (red lines). The reversibility of the insertion process was studied by raising the pH of samples at pH 4 (dashed blue line) to 7.4. Reversibility for D0 was not studied, as the ellipticity changes between the states at pH 7.5 and 4 were negligible. In all samples, final peptide and lipid concentrations were 5 µM and 1.5 mM, respectively.

FIGS. 39A-C are a series of line graphs showing oriented circular dichroism. OCD spectra of D2, D1 and D0 measured on POPC supported bilayers at neutral (blue lines) and acid (red lines) pHs. The OCD spectrum of D2 at pH 1.9 was also recorded (purple line). The experimental spectra are corrected for the lipid background.

FIGS. 41A-F are a series of line graphs showing fluorescence spectral maximum changes upon pH titration. The pH-controlled transitions of the peptides in POPC were followed by monitoring the variations in the spectral maxima. The experimental data for the different peptides were fitted to Equation 1 (black lines). Representative experiments are shown.

FIGS. 45A-D are a series of line graphs and dot plots showing the fluorescence of wt and D2 at low pHs. The usual range of pHs was extended to lower values to study the protonation state of His residues. D2 was employed as an example of peptide containing two His residues. Upper panels: Emission spectra in POPC liposomes at pH 2.2, 3.3 and 6.3. Lower panels: the fluorescence intensity and center of mass were calculated for the complete pH range studied for D2 and wt pHLIP.

FIGS. 47A-C are a diagram and a series of line graphs showing that protein unfolding leads to H-type dimer release.

FIGS. 60A-F are a series of bar charts showing tumor/organ ratios calculated at 4 & 24 hs post-injection.

FIG. 67 is a diagram showing pHLIP sequences.

FIGS. 72A and B show pHLIP variants.

FIG. 73 is a table relating to pHLIPs.

FIG. 74 is a table relating to pHLIPs.

FIG. 75 shows pHLIP sequences that were selected for the investigation with cargo.

FIG. 76 is a table showing pHLIP peptides.

DETAILED DESCRIPTION OF THE INVENTION

Figure 2:
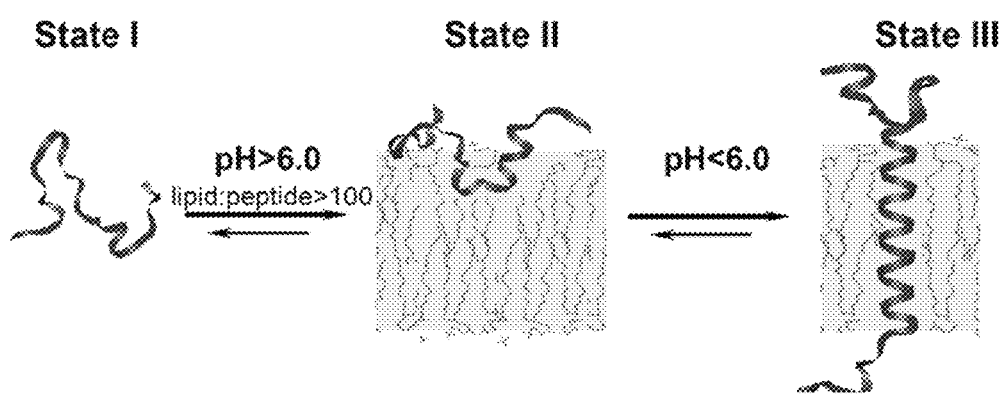
FIG. 2 is a diagram showing the topology of the protein in three different states. The three major states of pHLIP at a concentration of <30 μg/mL are illustrated: unstructured and soluble in water at pH >7 (state I), unstructured and bound to the surface of a lipid bilayer at the same pH and at a lipid:peptide molar ratio >100 (state II), and inserted across the bilayer as an α-helix at low pH (state III).

The invention features diagnostic or therapeutic agents comprising improved pHLIP constructs that selectively deliver compositions to a diseased tissue compared to non-diseased tissue, thereby significantly improving diagnosis and treatment. A class of delivery vehicles based on pH-sensitive, water soluble membrane peptides, pHLIPs, that target cells located in an acidic microenvironment found in many diseased tissues, including tumors, was developed. Specific targeting by pHLIPs is achieved as a result of helix formation and membrane insertion. In contrast to the earlier technologies based on cell-penetrating peptides (CPPs), pHLIPs act as monomeric membrane-inserting peptides that translocate one terminus across a membrane into the cytoplasm, while the other terminus remains in the extracellular space, locating the peptide in the membrane lipid bilayer. pHLIP peptides insert into a lipid bilayer membrane at low pH but not at high pH (<7.0). Once inserted into the membrane, they can exit the membrane under conditions of high pH (e.g., a change in pH), exiting from the same side from which they entered. pHLIP peptides do not traverse the membrane and emerge in their entirety on the inside of the cell. Therefore, pHLIP has a dual delivery capability: it can tether cargo molecules or nanoparticles to the surfaces of cells in diseased tissues and/or it can move a cell-impermeable cargo molecule across the membrane into the cytoplasm. The source of energy for moving polar molecules attached to pHLIP through the hydrophobic layer of a membrane bilayer is the membrane-associated folding of the polypeptide. A drop in pH leads to the protonation of negatively charged residues (Asp or Glu), which enhances peptide hydrophobicity, increasing the affinity of the peptide for the lipid bilayer and triggering peptide folding and subsequent membrane insertion. The process is accompanied by the release of energy that is utilized to move cell-impermeable cargo across a membrane. pHLIP acts as a monomer in the following diagnostic and therapeutic applications: targeted therapy—selective delivery of therapeutic and imaging agents to diseased tissue, thereby increasing the effective concentration of these agents and reducing their accumulation in healthy tissue; improved route of drug administration: agents with improved pharmacokinetic properties of a drug; locally activated therapy—activation of a targeted therapeutic agent by local microenvironment of diseased tissue; fine specificity—cell-impermeable molecules translocated into cells only in diseased tissue while not affecting healthy cells; and multifunctionality—simultaneous targeted delivery of a therapeutic agent and an imaging probe to monitor drug distribution.

The compositions described herein are characterized by much higher efficacy and/or significantly reduced side effects compared to other cell-penetrating constructs/carriers. Such improvements are especially important for cancer treatment, since the majority of anti-cancer drugs are poisons that damage normal cells. Other diseased tissues are treated using the same compositions.

The challenge of selective delivery to tumors or other tissues characterized by a pH lower that physiological pH has been answered by the pHLIP peptides and constructs described herein. Disease-specific delivery coupled with local activation allows i) accumulating and, therefore, increasing the effective concentration of therapeutic or diagnostic agents in a diseased area and ii) reducing the side effects associated with treatment by reducing the targeting of normal cells. Local activation further improves the protection of normal tissue.

Tissue Acidosis

Hypoxia and acidosis are physiological markers of many diseased processes such as a cancer (Stubbs et al., 2000, Mol. Med. Today, 6, 15; Helmlinger et al., 2002, Clin. Cancer Res. 8, 1284; Izumi et al. 2003, Cancer Treat. Reviews. 29, 541); an infarction (Graham et al., 2004, J Exp Biol., 207, 3189; Yao and Haddad, 2004, Cell Calcium., 36, 247; Yamamoto and Ehara, 2005, Am J Physiol Heart Circ Physiol., in press); a stroke (Rehncrona 1985, Ann. Emerg. Med. 14, 770; Siesjo et al., 1996, Adv. Neurol. 71, 209; Ying et al., 1999, J. Neurochem. 73, 1549); an atherosclerotic lesion (Leake 1997, Atherosclerosis, 129, 149); a trauma (Mikhail, 1999, AACN Clin Issues, 10, 85; Clausen et al., 2005, J Neurosurg, 103, 597); an inflammation (Kalantar-Zadeh et al., 2004, Semin Dial, 17, 455); an infection (Holloway et al., 1995; Exp Parasitol., 80, 624; Headley, 2003, Am Fam Physician., 68, 323). The compositions are useful for pH-selective delivery of molecules to diseased tissue, e.g., tumors.

The most important limitation of specific cancer cell receptor targeting is the heterogeneity of human cancers. Recent studies of gene expression in cancer cells indicate that a number of genes are up- and down-regulated, and that cells in a tumor are heterogeneous. It is therefore problematic to rely on any single tumor biomarker even for one type of cancer. Using tumor acidity may be an alternative, since it is well established that salient features of the microenvironment of solid tumors include hypoxia and extracellular acidity. These factors contribute to the selection of the cancerous phenotype, and also to the progression from benign to malignant tumors. Acidosis is associated with tumor development both at very early and at advanced stages. Rapidly proliferating cancer cells become partially anaerobic, leading to the elevation of glycolysis in response to hypoxia (Pasteur effect). Hypoxia and acidity are partly a result of the chaotic and heterogeneous microvasculature structure of solid tumors, where the oxygen concentration decreases with distance from a capillary. Hypoxia and low blood supply are involved in cancer progression, but they are not the only mechanism responsible for the development of an acidic environment within solid tumors. A hallmark of malignant cancers is an elevated glucose uptake even under normal oxygen conditions, known as "aerobic glycolysis" or the Warburg effect. Cells exhibiting a Warburg effect catabolize glucose at a high rate.

The consequence of glycolytic metabolism in any tissue is the formation of $H^+$, which must be removed from the cell if the internal milieu is to maintain its normal pH, because many cellular processes have a narrow pH optimum. Four major types of intracellular pH (pHi) regulatory mechanisms have been identified in tumor cells: $Na^+/H^+$ exchangers, bicarbonate transporters, proton-lactate symporters and proton pumps. These transmembrane proteins are ion pumps or ion exchangers that pump protons across the plasma membrane from the cytoplasm to the opposite site of the membrane, the extracellular space or the lumen of various organelles. A consequence of the activity of ion pumps is an enhanced pH gradient across the plasma membrane of cancer cells in comparison with normal cells, and a lower pH in the extracellular milieu.

Usually, exposure to an acidic environment results in cell death, however cancer cells adapt through resistance to apoptosis and up-regulation of membrane ion channels in order to maintain intracellular pH in the range of normality. Indeed, the unfavorable environment may favor tumor cell survival in acidic conditions via selection of cells that are resistant to acid-induced cell toxicity and hypoxia-induced, p53-dependent apoptosis, and promote invasiveness by killing normal tissue cells. Malignant tumor cells not only survive better in acidic environments, but they also demonstrate phagocytotic and cannibalistic behavior. Extracellular acidification promotes cancer invasion and metastasis by increased secretion and activation of proteases, matrix metalloproteinases, bone morphogenetic protein-1-type metalloproteinases, tissue serine proteases, and adamalysin-related membrane proteases. Enhanced mutation rates, chromosomal instability, and spontaneous transformation are associated with acidity. Hypoxia and acidity also cause resistance to radiotherapies and chemotherapies, and promote the expression of the human multi-drug-resistance protein.

Tumor acidity is an alternative targeting strategy to specific molecular biomarkers for tumor targeting and detection and is also useful for monitoring therapy outcomes. For example, the level of extracellular pH is related to the overall survival of canines with spontaneous sarcomas. Thus, the pH was predictive of a clinical outcome. The advantages of targeting acidity include its generality and the absence of tumor heterogeneity issues.

Hydrophobicity and Drug Development

If the target of a therapeutic is cytoplasmic, the selective delivery of therapeutics to a tumor is not enough to improve treatment; the strategy must also enable the agent to cross the hydrophobic barrier of a cell membrane and release its payload inside cells. The two major mechanisms for the translocation of molecules and nanoparticles across the membrane are passive diffusion and endocytosis. Neither is specific for cancer cells, so each would promote translocation of therapeutics across the membranes of cells in both diseased and healthy tissues. In conventional drug design and discovery the Lipinski rules of five are widely used to guide molecular designs. The rules postulate that a successful drug should be hydrophobic and small in order to traverse membranes and reach cytoplasmic targets (e.g. the logarithm of the octanol-water partition coefficient Log Po/w is −0.4 to +5.6 and the MW is 160 to 480 g·mol-1). Drugs designed in this way will indiscriminately enter all cells they encounter, and are also likely to be substrates for efflux pumps that reduce their efficacy. It is important to note that the majority of inhibitors found for biological targets located inside a cell are molecules that cannot cross a membrane. Another large class of cell-impermeable functional molecules comprises gene regulation agents such as DNA, siRNA, and PNA (peptide nucleic acid. Gene-targeted therapies also involve passage through the cell membrane, which appears to be a general problem associated with that approach.

Cell-penetrating peptides have been used for the delivery of liposomes, nanoparticles, adenoviruses, and a variety of biological molecules into cells. Among these peptides are TAT, antennapedia, arginine-rich and others. In contrast to the pHLIP peptides described herein, these peptides enter the cell via endocytic pathway. When taken up by endocytosis, molecules or nanoparticles are trapped in the lysosome compartment and need to be released into the cytoplasm.

Selective Delivery and Advantages of Environmentally-Sensitive Conjugates

Diagnostic and treatment would be improved dramatically by improving the selective delivery of imaging and therapeutic agents to diseased tissue. Traditionally, receptors and enzymes overexpressed in cancer cells are considered as cancer biomarkers. They are indicators of the change in physiologic state during a disease process (Srinivas et al., 2001, 2002; Hanke et al., 2004; Janssens et al., 2004; Kennedy and Hirsch, 2004). There has been a great deal of research into the development of peptides and antibody fragments directed toward cell surface receptors (Goldsmith, 1997; Freimark et al., 2007). Initially, monoclonal antibodies were the most promising candidates for specific targeting strategies. However, because of problems associated with their specificity and high molecular weight, clinically successful developments were difficult. Only over the last few years has advanced antibody engineering technology enabled therapeutic concepts based on antibodies and conjugates thereof to successfully enter clinical practice (Carter, 2001; Payne, 2003). Antibodies and their fragments have been used to map the expression or overexpression of tumor-related proteins, such as prostate-specific membrane antigen (Polascik et al., 1999), human epidermal growth factor receptor-2 (HER2) (Moasser, 2007); carcinoembryonic antigen (Hughes et al, 1997; Lu et al., 2007), TAG-72 (Muxi et al. 1999), Ep-CAM (Breitz et al., 1997; de Bono et al., 2004) and others. However, a number of complications still vex development of antibody applications, such as purity, immunogenicity, slow diffusion in tissues, plasma clearance, and production difficulties (Blattler and Chari, 2001). An attractive direction is the development of low molecular weight peptides for rapid tumor targeting. In contrast to antibodies, peptides can be easily synthesized, modified and stabilized to obtain optimized pharmacokinetic parameters (Lister-James et al., 1997; Signore, 2001). Usually they are not immunogenic and have high receptor affinity. The most developed and widely accepted are somatostatin analogs introduced to visualize various somatostatin receptor-positive tumors (Buchsbaum, 2004; Krenning et al., 2004). Furthermore, a number of other peptides targeting various receptors expressed in cancer cells have recently been tested for tumor detection (Signore, 2001; Ma et al., 2007).

An important limitation of approaches based on targeting specific cancer cell receptors is the variability of cells in human cancers (Jeffrey et al., 2005). Recent studies of gene expression in cancer cells indicate that a number of genes are up- and down-regulated, so that cell surfaces in a tumor are heterogeneous. It is therefore problematic to rely on any single tumor biomarker even for one type of cancer (Bild et al., 2006). On the other hand, tumor acidity, which is a feature of most solid tumors, is a reliable cancer biomarker that is exploited by the compositions and methods described herein.

Several nano sized systems with pH-sensitive properties have been developed, among them are polymers, dendrimers, micelles, liposomes, and hydrogel nanoparticles (Blume and Cevc, 1990; Kobayashi et al, 2001; Lian and Ho, 2001; Portney and Ozkan, 2006; and see review by Ganta et al., 2008). The main feature of these nanocarriers is their ability to release encapsulated therapeutic and/or imaging agents in response to changes in pH Bulmus et al., 2003; Murthy et al., 2003; Na et al., 2003; Tomlinson et al., 2003; Kamada et al., 2004; Ulbrich et al., 2004; Simoes et al., 2004; Stayton et al., 2005; Henry et al., 2006; Devalapally et al., 2007). However, most such pH-sensitive carriers are used to enable drug release in the environment of endosomes and/or lysosomes after cellular uptake of the conjugates by endocytosis. A significant advantage of the compositions and methods described is that they do not rely on or involve endocytosis. An additional advantage is that little or no immunogenicity is associated with the compositions.

pHLIP Peptide is Monomeric pHLIP peptides, e.g., (SEQ ID NO:2, shown in FIG. 1) are a water-soluble polypeptides based on the bacteriorhodopsin C helix, which was found to insert across a membrane to form a stable transmembrane alpha helix. Peptide folding and membrane insertion are driven by a drop of pH from neutral or high (>7.4) to slightly acidic (7.0-6.5 and less) pHs. The apparent pK of insertion was found to be 6.0. pHLIP is a monomer in each of its three major states: unstructured and soluble in water (state I) at neutral pH, unstructured and bound to the surface of a membrane at neutral pH (state II), and inserted across the membrane as an α-helix at low pH (state III) (FIG. 2). In contrast, all pore forming peptides, first form aggregates on the membrane surface and then "fall" into membrane and form pores. Thus, an additional advantage of the environmentally-sensitive compositions is their monomeric nature, e.g., they do not require assembly into a multimeric superstructure like pore formers.

State II pHLIP peptides are particularly well suited for imaging uses, and State III pHLIP peptides are ideally suited for delivery of cargo molecules, e.g., toxins, across the cell membrane and into the cytoplasm of cells. State III pHLIP peptides are typically short peptides. Within the state III class of pHLIP peptides, binding to the cell membrane becomes stronger as the pH goes down. However, the pHLIP peptides do not move entirely across the cell membrane to emerge on the other (inside) of the cell (i.e., the cytoplasm). Rather the membrane sequence of the peptide remains lodged in the cell membrane, unless and until the local pH is raised, e.g., above 7. Under high pH conditions, the pHLIP peptide may exit the membrane, but only in the direction from which it came.

Toxicity

Toxicity is one of the most critical issues in the selection of any delivery agent. For example, the use of pore-forming membrane peptides as delivery agents is complicated by the toxicity associated with the formation of pores in cellular membranes in vivo. By contrast, the interaction of pHLIP with liposomes and cellular membranes at both neutral and low pHs does not lead to membrane leakage, and no cellular toxicity was seen over a range of peptide concentrations. Also, mice receiving a high dose (about 5 mg/kg) of peptide did not show any adverse effects within two months after intravenous peptide administration.

Selectivity of Targeting

The pH-dependent interaction of pHLIP with membranes allows selectivity in the targeting of acidic diseased tissue. As noted above, acidity and hypoxia are considered as universal cancer biomarkers, and pHLIP is used as an acidity-targeting probe. Besides cancer, many other pathological states, such as inflammation, ischemia, stroke, arthritis and others are characterized by acidity in the extracellular space, which may broaden the potential applications of pHLIP. In vivo fluorescence imaging in mice and rats demonstrated that pHLIP can target acidic tissues, such as kidneys, tumors of various sizes and origins, and the site of experimentally induced inflammatory arthritis. In addition to fluorescence imaging, PET (positron emission tomography) imaging of the acidic environment in human prostate tumors was performed using $^{64}$Cu-DOTA conjugated to pHLIP. PET studies demonstrated that the construct avidly accumulated in LNCaP and PC-3 tumors and that tumor uptake correlates with the differences in the bulk extracellular pH ($pH_e$) measured by MR spectroscopy. Feeding animals with bicarbonated water, which increases tissue pH, results in a reduction of tumor targeting by pHLIP.

Molecular Mechanism of pH-Dependent Membrane Insertion of pHLIP

The putative transmembrane (TM) part of pHLIP peptide contains two Asp residues (FIG. 1). At neutral pH these charged residues enhance peptide solubility and serve as anchors keeping the peptide at the surface of membrane, thereby preventing pHLIP partitioning into the hydrophobic membrane bilayer. A reduction of pH induces protonation of Asp residues, and as a result, the overall hydrophobicity of the peptide increases, enhancing the affinity of the peptide for the lipid bilayer core and triggering peptide folding and insertion. The replacement of the key Asp residues in by Lys, Ala or Asn leads to the loss of peptide of pH-dependent membrane insertion, as measured in liposomes, red blood cells and confirmed by in vivo fluorescence imaging. The K-pHLIP peptide, where the two Asp residues in the putative transmembrane region are replaced with Lys residues, does not demonstrate tumor targeting. The Ala substitutions give a peptide that aggregates in solution, while the Lys and Asn substitutions give peptides that are too polar to insert either at neutral or low pH. The replacement of one of the Asp residues in the TM part of the peptide by a Glu residue results in a shift of pH of membrane insertion from 6.0 to 6.5. Replacement of both Asp residues by Glu results in enhancement of peptide aggregation and formation of elements of secondary structure on the bilayer surface at neutral pH (see Tables 1 and 2). However, aggregation in solution is often concentration specific and reversible, i.e., a pHLIP peptide may exhibit aggregation in solution in vitro but the aggregation is reversible after administration to the subject due to dilution.

Data obtained on model systems (liposomes), cultured cells and mice confirmed that the mechanism of membrane entry of pHLIP is not mediated by endocytosis, interactions with cell receptors or pore formation; rather, the mechanism is the formation of a helix across the lipid bilayer, triggered by the increase of peptide hydrophobicity due to the protonation of negatively charged residues induced by low pH.

Solubility and Stability of pHLIP in Blood

Poor solubility due to aggregation is a typical property of membrane peptides, which has complicated studies and applications. pHLIP, as any membrane peptide, also has a tendency to aggregate, especially at high concentrations and/or low pH. However, in aqueous solution at neutral pH pHLIP exists as a monomer at concentrations less than 30 µg/mL (~7.0 µM), as studied by fluorescence and CD spectroscopy measurements, size exclusion chromatography coupled with "on-line" laser light scattering, ultraviolet and refractive index detection (SEC-LS/UV/RI) and analytical ultracentrifugation experiments. When the solubility of the peptide is compromised as a result of mutations, the affinity of the peptide for a membrane and its overall conformational properties change. Thus, studies were undertaken to design pHLIP peptides that are optimized for clinical diagnostic and therapeutic use.

The oligomeric state of the peptide on the surface of a membrane (state II) and inserted into the lipid bilayer (state III) were evaluated by FRET performed with two different donor-acceptor probes attached to the N-terminus of the peptide. The data demonstrate that, at low concentrations, the peptide is monomeric in both states II and III.

Peptide interactions with proteins, especially plasma proteins, and membranes determine the pharmacokinetics of the peptide at neutral pH. pHLIP demonstrates prolonged circulation in the blood (several hours), which is consistent with its ability to bind weakly to membrane surfaces at neutral and high pH, preventing the rapid clearance by the kidney expected for a small, soluble peptide. pHLIP binding to membranes is driven by hydrophobic interactions. If the peptide sequence were made more hydrophobic, tighter binding to red blood cells and epithelial cells and more aggregation in solution, and slower clearance and reduced bioavailability would occur. Making the peptide less hydrophobic accelerates clearance and prevents the peptide from finding its targets. Therefore, fine tuning of the solubility is an important property to optimize pHLIP performance in vivo.

Another important property is the stability of peptides in the blood, since proteases in the serum can degrade peptides consisting of L-amino acids within minutes. While polypeptides made from D-amino acids are much more stable, they are often unsuitable for specific receptor binding applications as a consequence of their altered chirality. Since the mechanism of pHLIP involves relatively nonspecific interactions with a fluid lipid bilayer, pHLIP peptides composed of L- or D-amino acids demonstrate the same biophysical and tumor targeting properties. This observation adds to the evidence that the pHLIP targeting does not require any specific molecular binding event. The only conspicuous difference is that D-pHLIPs form left-handed helices across membranes rather than the right-handed helices formed by L-pHLIPs.

Topology of Membrane Insertion

The topology of pHLIP insertion was probed using an NBD-dithionite quenching assay, and then confirmed in experiments on cultured cells. NDB (4-chloro-7-nitrobenz-2-oxa-1,3-diazole) and IANBD (N,N'-dimethyl-N-(iodoacetyl)-N'-(7-nitrobenz-2-oxa-1,3-diazol-4-yl)ethylenediamine) were covalently attached to the N- and the C-terminus of pHLIP peptides, respectively. Fluorescently labeled peptides were inserted into the lipid bilayer at low pH, and changes of fluorescence signal of NDB were measured after quenching by dithionite, a membrane-impermeable agent that abolishes NBD fluorescence if it contacts the dye. The data clearly indicate that the N-terminus of pHLIP stays outside of the bilayer, while the C-terminus inserts across the lipid bilayer at low pH.

Cargo Translocation by pHLIP Insertion

The partition of pHLIP into the outer leaflet of lipid bilayer at neutral pH and the folding/insertion at low pH are accompanied by the release of energy. Fluorescence spectroscopy, isothermal titration calorimetry and acid titration calorimetry were used to study the interactions of pHLIP with a POPC lipid bilayer and to calculate the transition energies between states. The Gibbs Free Energy of binding to a POPC surface (state I-state II transition) at 37° C. is about −7 kcal/mol near neutral pH and the additional free energy of insertion and folding across a lipid bilayer at low pH (state II-state III transition) is nearly −2 kcal/mol. The energy difference between state II and state III mediates the movement of cargo across the hydrophobic bilayer of membrane. By knowing this energy, it is possible to estimate the polarity of cargo molecules that can be translocated across a membrane by pHLIP: 2 kcal/mol might be enough to translocate molecules with Log $P_{o/w}$~−1.4 [$\Delta G$=−RT ln $P_{o/w}$, where RT ~0.6 kcal/mol at room temperature]. Thus, membrane-impermeable cargo molecules with Log $P_{o/w}$ in range of −0.5 to −3 are translocated (with probability proportional to the Log $P_{o/w}$) across a membrane. If the cargo is released, as in delivery to a cell using a link that is broken in the cytoplasm, the progressive mass action will exploit even a weakly favorable energy balance to accumulate delivered cargo in a cell.

Kinetics of pHLIP Insertion into Membrane

While the equilibrium thermodynamics favor binding and insertion of pHLIP, slow kinetics could be limiting for in vivo use, since blood flow is very fast. Kinetic studies of pHLIP folding and insertion across a POPC lipid bilayer triggered by a pH drop from 8.0 to 4.0 indicate that insertion takes 100 sec, with a rapid (0.1 sec) interfacial helix formation followed by insertion to give a transmembrane helix. In the case of a pH drop to 6.0 the insertion is slower, about 300 sec. However, data obtained on various pHLIP variants show that the process of insertion can be accelerated by 10-20 times and up to 100 times if acidic residues are removed from the C-terminus of the peptide.

Dual Delivery Capability of pHLIP pHLIP, in contrast to other cell-penetrating peptides, stays in the cellular membrane after insertion, translocating one end into cytoplasm and leaving the other end in the extracellular space. Therefore, the peptide possesses dual delivery capabilities: it can tether cargo molecules to the cell surface and/or it can inject and release cell-impermeable cargo molecules into the cytoplasm (FIG. 3). In the first scenario, a cargo molecule is attached to the pHLIP N-terminus. External cargo of wide range of polarity and size is reliably transported. One of the applications is to deliver imaging probes to acidic tissue, where they will be stably tethered to the surfaces of cells. pHLIP sequences deliver and tether various nanoparticles to the surface of cancer cells. The second delivery capability of pHLIP is based on conjugation of cargo molecules to the C-terminus via a bond that is cleaved in the environment of the cytoplasm, such as a disulfide. Since the energy released during peptide folding and insertion across a membrane is limited, and since strongly polar molecules will reach equilibrium slowly, there may be a limit on cargo polarity and on size. Preferably polarity is in range of 0.5<Log P<−3. Cargo size is preferably less than 100 kDa. For example, cargo size is in the range of 0.1-50 kDa, 1-25 kDa, and 1-10 kDa. The data indicated that cargo with a molecular mass of 5 kDa is effectively translocated/delivered across a membrane by pHLIP, even taking into account the mass action effect discussed above.

Phlip-Mediated Translocation of Cell-Impermeable Functional Cargos pHLIP peptides translocate cargo molecules attached to their C-terminus. Translocation is selective for low pH, and various types of cargo molecules attached by disulfides are subsequently released in the cytoplasm, including various fluorescent dyes, synthetic cyclic peptides, toxins and peptide nucleic acids (Reshetnyak et al., 2006, PNAS 103:6460-465.). Cell-impermeable fluorescently-labeled toxin, phalloidin-rhodamine, conjugated to the C-terminus of pHLIP via an S—S— bond, is moved across the membrane in a pH-dependent manner. The pH-dependent translocation of the fluorescent phalloidin by the peptide was confirmed by fluorescence microscopy and fluorescence activated cell sorting. If phalloidin-rhodamine enters a cell, it binds tightly to actin filaments at nanomolar concentration ($K_D$=40 nM) and strongly inhibits their depolymerization. Actin filaments stained with fluorescent phalloidin have an unmistakable filamentous pattern, distinct from the appearance of other cellular structures, organelles or membrane staining. The phalloidin translocated into the cytoplasm of live cells inhibits the proliferation, contractility, migration and division of cells. A long term effect of phalloidin is the formation of multinucleated cells, since nuclei can divide in treated cells, but the cell itself cannot. This process leads to the formation of multiple nuclei in one cell and eventual cell death.

Another example is the translocation of a class of cell-impermeable functional cargo-molecule, peptide nucleic acids (PNA), by pHLIP. PNAs can base pair specifically to target nucleic acid sequences, but lack the highly charged backbone of biological nucleic acids, and are therefore candidates for pHLIP delivery. In vitro studies show that PNA can inhibit both transcription and translation of genes to which it has been targeted, which suggests use of PNA in antigene and antisense therapy (Nelson, P E, 2005, Q. Rev. Biophys. 38:345-350). However, a major obstacle has been the delivery of PNA (as well as RNA or ODN) across membranes into cells. pHLIP has been shown to translocate a fluorescence-labeled 12 base PNA into cells. Treatment of cells with PNA-rhodamine alone did not give fluorescent staining of cells at pH 6.5 or 7.4, but fluorescence was observed in cells when the PNA was linked to the C-terminus of pHLIP via a disulfide and added at pH 6.5. The labeled cells were alive by using the dead cell marker SYTOX-Green. Additional in vivo studies showed that pHLIP delivered an 18-base PNA (MW 4.7 kDa) to a mouse tumor, translocated PNA across membranes, and activated luciferase expression in a result of splicing correction.

pHLIP Represents a New Class of Delivery Agents

Numerous variants of the parent pHLIP sequence (SEQ ID NO: 1) have been made. The base reference sequence has three main blocks (FIG. 1). The middle part is a moderately polar sequence that contains protonatable residues, and is the environment-sensitive, membrane inserting part of the peptide. The transmembrane helix can be as short as 15 residues. The membrane-inserting sequences is at least 8 amino acids, e.g., it ranges in size from 13 to 25 amino acids. The other two blocks are the two flanking sequences—a first flanking sequence on the C-terminal side and a second flanking sequence on the N-terminal side. The role of the flanking sequences is to modulate the peptide solubility, but may also include functional motifs; e.g., protease cleavage or receptor binding sequences, or amino acids that can undergo phosphorylation in the cytoplasm. There are several restrictions applied to the flanking sequence that inserts across the membrane: i) it should not contain many charged residues (especially positive charges); ii) it should not be long; iii) the speed and cooperativity of peptide insertion into membrane depends on the number of Asp or Glu residues present in this sequence.

There is no specific restriction to the flanking sequence that stays outside of membrane other than its role in peptide solubility; however a danger is that dramatic changes of peptide pharmacokinetics might result from extreme variations. Thus, numerous sequences have been made and tested. The results of testing led to the definition of key elements of pHLIP sequences that make them suitable for diagnostic and therapeutic applications. The membrane-inserting sequence of pHLIP does not contain Cys or Lys residues. Any of these residues or both could be placed at the N- or C-terminus of the peptide for the purpose of cargo conjugation to pHLIP (NHS and maleimide click chemistry is developed very well and widely used for conjugation purposes).

pHLIP Sequences

Tables 1-2 provide a summary of pHLIP sequences that have been made and tested. Table 1 includes long pHLIP sequences. The sequences of Table 1, if they insert into a membrane, go with their C-terminus across a membrane and leave N-terminus in the extracellular space. Some of the peptides lost main properties of pH-dependent insertion into membrane.

TABLE 1

| Name | Sequence | |
|---|---|---|
| WT-1 | GGEQNPIYWARYADWLFTTPLLLLDLALLVDADEGT | SEQ.ID NO. 3 |
| WT-2 | AEQNPIYWARYADWLFTTPLLLLDLALLVDADEGT | SEQ.ID NO. 4 |
| WT-Cys1 | AAEQNPIYWARYADWLFTTPLLLLDLALLVDADEGTCG | SEQ.ID NO. 5 |
| WT-Cys2 | Ac-AEQNPIYWARYADWLFTTPLLLLDLALLVDADEGCT | SEQ ID NO: 274 |
| WT-Cys3 | GGEQNPIYWARYADWLFTTPLLLLDLALLVDADEGTCG | SEQ.ID NO. 6 |
| Cys-WT1 | Ac-ACEQNPIYWARYADWLFTTPLLLLDLALLVDADEGTG | SEQ.ID NO. 7 |
| Var0-NT | ACEQNPIYWARYADWLFTTPLLLLDLALLVDADEGT | SEQ.ID NO. 8 |
| Lys-WT1 | AKEQNPIYWARYADWLFTTPLLLLDLALLVDADEGT | SEQ.ID NO. 9 |
| Lys-WT2 | Ac-AKEQNPIYWARYADWLFTTPLLLLDLALLVDADEGTG | SEQ ID NO: 275 |
| WT-KC | AAEQNPIYWARYADWLFTTPLLLLDLALLVDADEGTKCG | SEQ.ID NO. 10 |
| K-WT-C | AKEQNPIYWARYADWLFTTPLLLLDLALLVDADECT | SEQ.ID NO. 11 |
| N-pHLIP | ACEQNPIYWARYANWLFTTPLLLLNLALLVDADEGTG | SEQ.ID NO. 12 |
| N-pHLIP-b | ACEQNPIYWARYANWLFTTPLLLLNLALLVDADEGT | SEQ ID NO: 276 |
| K-pHLIP | ACEQNPIYWARYAKWLFTTPLLLLKLALLVDADEGTG | SEQ.ID NO. 13 |
| NNQ | GGEQNPIYWARYADWLFTTPLLLLDLALLVNANQGT | SEQ.ID NO. 14 |
| D25A | AAEQNPIYWARYADWLFTTPLLLLALALLVDADEGT | SEQ.ID NO. 15 |
| D25A-KC | Ac-AAEQNPIYWARYADWLFTTPLLLLELALLVDADEGTKCG | SEQ ID NO: 277 |
| D14A | AAEQNPIYWARYAAWLFTTPLLLLDLALLVDADEGT | SEQ.ID NO. 16 |
| P20A | AAEQNPIYWARYADWLFTTALLLLDLALLVDADEGT | SEQ.ID NO. 17 |
| D25E | AAEQNPIYWARYADWLFTTPLLLLELALLVDADEGT | SEQ.ID NO. 18 |
| D14E | AAEQNPIYWARYAEWLFTTPLLLLDLALLVDADEGT | SEQ.ID NO. 19 |
| 3D | AAEQNPIIYWARYADWLFTDLPLLLLDLLALLVDADEGT | SEQ.ID NO. 20 |
| R11Q | GEQNPIYWAQYADWLFTTPLLLLDLALLVDADEGTCG | SEQ.ID NO. 21 |
| D25Up | GGEQNPIYWARYADWLFTTPLLLDLLALLVDADEGTCG | SEQ.ID NO. 22 |
| D25Down | GGEQNPIYWARYADWLFTTPLLLLLDALLVDADEGTCG | SEQ.ID NO. 23 |
| D14Up | GGEQNPIYWARYDAWLFTTPLLLLDLALLVDADEGTCG | SEQ.ID NO. 24 |
| D14Down | GGEQNPIYWARYAWDLFTTPLLLLDLALLVDADEGTCG | SEQ.ID NO. 25 |
| P20G | AAEQNPIYWARYADWLFTTGLLLLDLALLVDADEGT | SEQ.ID NO. 26 |
| H1-Cys | DDDEDNPIYWARYADWLFTTPLLLLHGALLVDADECT | SEQ.ID NO. 27 |
| H1 | DDDEDNPIYWARYADWLFTTPLLLLHGALLVDADET | SEQ ID NO: 278 |
| H2-Cys | DDDEDNPIYWARYAHWLFTTPLLLLHGALLVDADEGCT | SEQ.ID NO. 28 |
| Cys-H2 | CDDDEDNPIYWARYAHWLFTTPLLLLHGALLVDADET | SEQ ID NO: 279 |

TABLE 1-continued

| Name | Sequence | |
|---|---|---|
| H2 | DDDEDNPIYWARYAHWLFTTPLLLLHGALLVDADEGT | SEQ ID NO: 280 |
| H2N-Cys | DDDEDNPIYWARYAHWLFTTPLLLLHGALLVNADECT | SEQ.ID NO. 29 |
| H2N | DDDEDNPIYWARYAHWLFTTPLLLLHGALLVNADEGT | SEQ.ID NO: 281 |
| H2N2-Cys | DDDEDNPIYWARYAHWLFTTPLLLLHGALLVNANECT | SEQ.ID NO. 30 |
| H2N2 | DDDEDNPIYWARYAHWLFTTPLLLLHGALLVNANEGT | SEQ.ID NO: 282 |
| 1a-Trp | AEQNPIYWARYADFLFTTPLLLLDLALLVDADET | SEQ.ID NO. 31 |
| 1b-Trp | AEQNPIYFARYADWLFTTPLLLLDLALLVDADEGT | SEQ.ID NO. 32 |
| 1c-Trp | AEQNPIYFARYADFLFTTPLLLLDLALLWDADET | SEQ.ID NO. 33 |
| Fast-1 or Var1 | AKEDQNPYWARYADWLFTTPLLLLDLALLVDG | SEQ.ID NO. 34 |
| Var1-2D1D | ACEDQNPYWARYADWLFTTPLLLLDLALLVDG | SEQ.ID NO. 35 |
| Fast1-Cys or Var1-2D1D-Cys | AEDQNPYWARYADWLFTTPLLLLDLALLVDCG | SEQ.ID NO. 36 |
| Fast1-E-Cys or Var1 | EAEDQNPYWARYADWLFTTPLLLLELALLVECG | SEQ.ID NO. 37 |
| Fast1-E-Lys | AKEDQNDPYWARYADWLFTTPLLLLLDLALLVG | SEQ.ID NO: 283 |
| Fast2 or Var2 | AKEDQNPYWRAYADLFTPLTLLDLLALWDG | SEQ.ID NO. 38 |
| Fast2-E-Cys or Var2E | AEDQNPYWRAYADWLFTTPLLLLELALLVCG | SEQ.ID NO: 284 |
| Var2-2D1D | ACEDQNPYWRAYADLFTPLTLLDLLALWDG | SEQ.ID NO. 39 |
| Var3-3D | ACDDQNPWRAYLDLLFPTDTLLLDLLW | SEQ.ID NO. 40 |
| Var3-3D-cys | AKDDQNPWRAYLDLLFPTDTLLLDLLWC | SEQ ID NO: 285 |
| Var4-3E | ACEEQNPWRAYLELLFPTETLLLELLW | SEQ ID NO: 286 |
| Var5-3Da | ACDDQNPWARYLDWLFPTDTLLLDL | SEQ ID NO: 287 |
| Var6-3Db | CDNNNPWRAYLDLLFPTDTLLLDW | SEQ ID NO: 288 |
| Var8-3Eb | CEEQQPWAQYLELLFPTETLLLEW | SEQ ID NO: 289 |
| Var9-3Ec | CEEQQPWRAYLELLFPTETLLLEW | SEQ ID NO: 290 |
| Var15-2N | CDDDDDNPNYWARYANWLFTTPLLLLNGALLVEAEET | SEQ ID NO: 291 |
| Var16-2P | CDDDDDNPNYWARYAPWLFTTPLLLLPGALLVEAEE | SEQ ID NO: 292 |

TABLE 2

| Name | Sequence | |
|---|---|---|
| Var14-Rev | Ac-TEDADVLLALDLLLLPTTFLWDAYRAWYPNQECA-Am | SEQ.ID NO. 41 |
| Sh | AEQNPIYWARYADWLFTTPL | SEQ.ID NO. 42 |
| Sh-Cys | AEQNPIYWARYADWLFTTPCL | SEQ.ID NO. 43 |
| Cys-Sh | ACEQNPIYWARYADWLFTTPL | SEQ.ID NO. 44 |
| Sh-1Trp | AEQNPIYFARYADWLFTTPL | SEQ.ID NO. 45 |
| Sh-W2 | AEQNPIYFARYADLLFPTTLAW | SEQ ID NO: 293 |
| Sh-W1 | AEQNPIYWARYADLLFPTTLAF | SEQ ID NO: 294 |
| Sh-2W | AEQNPIYWARYADLLFPTTLAW | SEQ ID NO: 295 |
| Sh-1D | KEDQNPWARYADLLFPTTLAW | SEQ.ID NO. 46 |
| Sh-1Db | KEDQNPWARYADLLFPTTLW | SEQ ID NO: 296 |
| Var12-1D | ACEDQNPWARYADLLFPTTLAW | SEQ.ID NO. 47 |
| Var10-2D | ACEDQNPWARYADWLFPTTLLLLD | SEQ.ID NO. 48 |
| Var13-1E | ACEEQNPWARYAELLFPTTLAW | SEQ.ID NO. 49 |
| Var11-2E | ACEEQNPWARYAEWLFPTTLLLLE | SEQ.ID NO. 50 |
| Var7-3E | ACEEQNPWARYLEWLFPTETLLLEL | SEQ.ID NO. 51 |
| Var7-3Eb | ACEEQNPQAEYAEWLFPTTLLLLE | SEQ ID NO: 297 |

TABLE 2-continued

| Name | Sequence | |
|---|---|---|
| Var7-K | AAEEQNPWARYLEWLFPTETLLLEL | SEQ ID NO: 298 |
| Var7-A | AKEEQNPWARYLEWLFPTETLLLEL | SEQ ID NO: 299 |

Ac means Acetylated N-terminus (peptide does not comprise free terminal NH4 group)
Am means Amidated C-terminus (peptide does not comprise a free terminal COOH group)

In SEQ ID NO: 298 and 299, Cys was replaced by Ala and Lys, respectively, for different chemical schemes of chelate conjugation.

Table 2 includes sequences termed short and medium pHLIP sequences. They all insert in membrane in a pH-dependent manner, while they do not have C-terminal flanking sequence. Double underline indicates residues (Cys or Lys), which are used to conjugate pHLIPs with cargo molecules. Translocation means translocation of cargo across membrane of liposomes and/or cells. Imaging means whole-body in vivo imaging on mice.

Biophysical studies were carried out with the following short pHLIP peptides:

(Short-W2)
                       (SEQ ID NO: 218)
AEQNPIYFARYADLLFPTTLAW (Short-W1)
                       (SEQ ID NO: 219)
AEQNPIYWARYADLLFPTTLAF (Short-2W)
                       (SEQ ID NO: 220)
AEQNPIYWARYADLLFPTTLAW All peptides were directly dissolved in buffer (pH8) and used for experiments using 50 nm liposomes. The concentration of peptide was 5 μM, and the POPC concentration was 1 mM. POPC blank was subtracted for CD and FL. Circular dichroism (CD) and fluorescence spectra showed insertion into lipid bilayers and formation of 3/10 or mixture of alpha and 3/10 helices at low pH. These data indicate that the short pHLIP peptides interact with lipid bilayers and cell membranes in a pH-dependent manner.

Table 3 shows salvation free energies of naturally-occurring amino acids.

TABLE 3

Solvation Free Energies of the Side Chains (X) of the 20 Natural Amino Acids in AcWL-X-LL (SEQ ID NO: 300) and Ac-X-Amide

| residue" | charge | A GZ' a | $\Delta G^{ell}_{1x'}$ | x | $\Delta x_{/s}$ | AG',' | ,GXG |
|---|---|---|---|---|---|---|---|
| Ala | | +0.65 | +0.81 | +0.42 | +0.13 | +0.69 | +0.99 |
| Arg | | −0.66 | −0.47 | −1.37 | | +1.44 | +1.81 |
| Asn | | +0.30 | +0.32 | −0.79 | | +1.06 | +1.10 |
| Asp | 0 | +0.72 | +0.75 | | | +1.33 | +1.39 |
| Asp | −1 | −2.49 | −2.46 | −2.46 (−L05) | −3.50 | −1.88 | −1.83 |
| Cys | | +1.17 | +1.39 | +1.39 (+2.10) | | +1.72 | +2.14 |
| Gln | | +0.38 | +0.50 | −0.30 | | +1.66 | +1 90 |
| Glu | 0 | +1.04 | +1.17 | | | +2 19 | +2.44 |
| Glu | −1 | −2.480 | −2.35 | −2.35 (−0.87) | −3.12 | −1.33 | −1.08 |
| GLY* | | | 0 | 0¹' | 0 | 0" | oh |
| His | +1 | −1.18 | −0.96 | | | +0.24 | +0.68 |
| His | 0 | +1.04 | +1.27 | +0.18 | +0.16 | +2.46 | +2.90 |
| Ile | | +2.27 | +2.70 | +2.46 | | +3.72 | +4.56 |
| Leu | | +2.40 | +2.77 | +2.30 | | +420 | +4.92 |
| Lys | +1 | −1.65 | −1.39 | −1.35 | | +0.17 | +0.67 |
| Met | | +1.82 | +2.18 | +1.68 | | +3.45 | +4.14 |
| Phe | | +2.86 | +3.24 | +2.44 | +2.19 | +4.96 | +5.71 |
| Pro | | +1.01 | +1.35 | +0.67 | +0.29 | +1.59 | +2.25 |
| Ser | | +0.69 | +0.74 | −0.05 | | +0.78 | +0.89 |
| Thr | | +0.90 | +1.08 | +0.35 | | +1.58 | +1.93 |
| Trp | | +3.24 | +3.62 | +3.07 | +2.52 | +6.15 | +6.88 |
| Tyr | | +1.86 | +2.21 | +1.31 | | +4.08 | +4.75 |
| Val | | +1.61 | +1.99 | +1.66 | | +2.86 | +3.61 |

Residue solvation free energies of the 20 natural amino acids relative to glycine calculated from the data in Table 1. Free energies were corrected for the occlusion of neighboring residue areas (see text) and for the anomalous properties of glycine (see text). Residue solvation free energies calculated with mole-fraction units.
' Residue solvation free energy calculated with the Flory-Huggins correction (Sharp et al.. 1991; De Young & Dill, 1990) (see Appendix). Constituent molar volumes were taken from Makhatadze et. al. (1990).
$^d$Residue solvation free energies for the X residue in the context of a AcWL-X-LL (SEQ ID NO: 300) peptide calculated from the free energies in Table I using the virtual glycine (GLY*) as the reference (see text).
AG'$_x$°= AGWLXLL AG⁻wLG*LL (SEQ ID NO: 301) Au$_{r,sp}$Ailh$_{,,,}$, where Ah$_{,,,}$(X) = AT$_{sp}$(WLXLL) (SEQ ID NO: 300) − A$_{,,,,}$(WI.XLL) (SEQ ID NO: 302). These "corrected" values account for X-dependent changes in the nonpolar ASA of the host peptide. Values for Arg and Lys were calculated from experimental free energies measured at pH 1 where the ionic interaction between the side chain and carboxyl group does not occur. AGT is the best estimate of the solvation energy of residues occluded by neighboring residues of moderate size.
$^e$Residue solvation free energies for the X residue in the context of a AcGG-X-GG (SEQ ID NO: 303) peptide calculated from AG'$_x$,' and the data in Table 1. AG', :$^{xe'}$ = AGV' + 22.8AAx where AAx = ,4$_{x,p}$(WLXLL) (SEQ ID NO: 300) − A$_{x,p}$(GGXGG) (SEQ ID NO: 303). This additional correction accounts for occlusion of the guest residue by the host (see text). AG$_{x}^{GxG}$ is the best estimate of the solvation energy of the fully exposed residue. Modified Fauchere and PliAa (1983) solvation energies, relative to Gly, for the transfer of acetyl amino acid amides from n-octanol to unbuffered aqueous phase. In this modified scale, the original values of FP for Asp, Glu. and Cys have been replaced by the AC.;$_{l}^{xG}$ in the left-hand adjacent column (see text). The original values of FP for Asp. Glu, and Cys are shown in parentheses.
g Residue solvation free energies relative, relative to Gly, for the transfer of AcA-X-AtBu tripeptides from n-octanol to buffer. pH 7.2. Data are those of Kim and Szoka (1992).
"Reference state is the experimentally determined Gly value rather than GLY*.

TABLE 4

Coded and Non-Coded Amino Acids

| no. | abbrev | name |
|---|---|---|
| 1 | Ala | Alanine |
| 2 | Arg | Arginine |
| 3 | Asn | Asparagines |
| 4 | Asp | aspartic acid |
| 5 | Cys | Cysteine |
| 6 | Gln | Glutamine |
| 7 | Glu | glutamic acid |
| 8 | Gly | Glycine |
| 9 | His | Histidine |
| 10 | Ile | Isoleucine |
| 11 | Leu | Leucine |
| 12 | Lys | Lysine |
| 13 | Met | Methionine |
| 14 | Phe | Phenyl-alanine |
| 15 | Pro | Proline |
| 16 | Ser | Serine |
| 17 | Thr | Threonine |
| 18 | Trp | Tryptophan |
| 19 | Tyr | Tyrosine |
| 20 | Val | Valine |
| 21 | Acpa | Aminocaprylic acid |
| 22 | Aecys | (S)-2-aminoethyl-L-cysteine•HCl |
| 23 | Afa | aminophenylacetate |
| 24 | Aiba | -aminoiso-bytyric acid |
| 25 | Aile | Alloisoleucine |
| 26 | Alg | L-allylglycine |
| 27 | Aba | aminobutyric acid |
| 28 | Aphe | p-aminophenylalanine |
| 29 | Bat | -alanine |
| 30 | Brphe | p-bromophenylalanine |
| 31 | Cha | cyclohexylalanine |
| 32 | Cit | Citrulline |
| 33 | Clala | -chloroalanine |
| 34 | Cle | Cycloleucine |
| 35 | Clphe | p-chlorophenylalanine |
| 36 | Cya | cysteic acid |
| 37 | Dab | 2,4-diamino-butyric acid |
| 38 | Dap | 2,3-diaminopropionic acid |
| 39 | Dhp | 3,4-dehydro-proline |
| 40 | Dhphe | 3,4-, dihydroxy-phenyl-Alanine |
| 41 | Fphe | p-fluorophenylalanine |
| 42 | Gaa | D-glucose-aminic acid |
| 43 | Hag | Homo-arginine |
| 44 | Hlys | hydroxyl-lysine•HCl |
| 45 | Hnvl | DL-hydroxynorvaline |
| 46 | Hog | Homoglutamine |
| 47 | Hoph | homophenylalanlne |
| 48 | Has | Homoserine |
| 49 | Hpr | hydroxyl-proline |
| 50 | Iphe | p-Iodophenylalanine |
| 51 | Ise | Isoserine |
| 52 | Mle | -methyl-leucine |
| 53 | Msmet | DL-methionine-s-methylsulfoniumchloride |
| 54 | 1Nala | 3-(1-naphthyl)alanine |
| 55 | 2Nala | 3-(2-naphthyl)alanine |
| 56 | Nle | norleucine (or 2-aminohexanoic acid) |
| 57 | Nmala | N-methyl-alanine |
| 58 | Nva | norvaline (or 2-aminopentanoic acid) |
| 59 | Obser | 0-benzylserine |
| 60 | Obtyr | O-benzyl-tyrosine |
| 61 | Oetyr | O-ethyltyrosine |
| 62 | Omser | O-methylserine |
| 63 | Omthr | 0-methythreonine |
| 64 | Omtyr | 0-methyl-tyrosine |
| 65 | Orn | Ornithine |
| 66 | Pen | Penicillamine |
| 67 | Pga | pyroglutamic acid |
| 68 | Pip | pipecolic acid |
| 69 | Sar | Sarcosine |
| 70 | Tfa | 3,3,3-trifluoroalanine |
| 71 | Thphe | 6-hydroxydopa |
| 72 | Vig | L-vinylglycine |
| 73 | Aaspa | (−)-(2R)-2-amino-3-(2-aminoethylsulfonyl)propanoic acid dihydrochloride |
| 74 | Ahdna | (2S)-2-amino-9-hydroxy-4,7-dioxanonanolc acid |
| 75 | Ahoha | (2S)-2-amino-6-hydroxy-4-oxahexanoic acid |
| 76 | Ahsopa | (−)-(2R)-2-amino-3-(2-hydroxyethylsulfonyl)propanoic acid |

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a residue in a pHLIP sequence (corresponding to a location relative to SEQ ID NO:1) is replaced with another amino acid residue from the same side chain family.

Physical Properties of the Membrane Influence the Insertion of pHLIP pHLIP interaction with a cell membrane or lipid bilayer is affected by membrane lipid composition. The cell membrane composition of normal cells is different from that of malignant cancer cells (or cells in tissue related to other pathological states). Thus, pHLIP binds differently to the plasma membrane of cells in a healthy compared to a diseased area, or interacts differently with lipid bilayer of membrane of various cellular compartments.

The cell plasma membrane is a complex medium that contains a high variety of lipid types. Studies were undertaken to understand whether the properties of pHLIP are maintained for bilayers composed of different lipids, e.g., whether the physical properties of the bilayer can alter the insertion of pHLIP. The conformation and membrane insertion properties of pHLIP were tested for a series of phosphatydylcholine (PC) lipids (the most abundant lipid type in human cells) of different length (X:1-PC; where X is the acyl chain length, ranging from 14 to 22 carbons, and :1 marks the presence of a single unsaturation per acyl chain).

The results show that the secondary structure of pHLIP for state II is highly sensitive to the acyl chain length (the amount of secondary structure is higher for lipids of longer acyl chain), while the changes observed for state III are smaller. To study the contribution of alpha helix formation to this phenomenon, P20G pHLIP mutant was used. P20G pHLIP contains a higher level of secondary structure for both state II and III, but reacts in a similar fashion to changes in the lipid length.

The insertion pKa was also observed to be greatly influenced by the acyl chain length for both wt and P20G pHLIP. High pKa values were determined for short lipids, which decreased in a linear fashion till a minimum pKa value was obtained for 20:1-PC. These results show that the acyl chain length controls both the conformation of state II and the insertion pKa, and that a more helical peptide inserts into the membrane at more physiological pHs.

Cells (but not artificial vesicles) demonstrate a pH lock phenomenon in which a pHLIP peptide is biased to tight binding once it has associated with a cell membrane. This situation is due to the an environment of a pH of near 7 inside the cell (cytoplasm) and an acidic pH outside of a cell in a diseased tissue. Once a pHLIP peptide or peptide portion of a pHLIP conjugate is inserted into the cell membrane, it is "locked" or "stapled" there due to the pH differential. This phenomenon leads to a persistence effect; a C-terminal flanking group enhances the persistence of binding. The phenomenon does not occur with artificial vesicles, because the pH on the inside and the outside of such constructs is the same or nearly so. This pH lock effect is particularly important for membrane-inserting peptides, e.g., tumor targeting pHLIP peptides, as it mediates persistence or the ability of the pHLIP peptide to stay in the cancer cell.

The Effects of Cholesterol on pHLIP's Biophysical Properties.

As complement to the studies of pHLIP insertion into lipids of different acyl chain length, the effect of cholesterol was examined. Since cholesterol is an essential component of many biological membranes, it was relevant to examine pHLIP's biophysical interactions relation to cholesterol as a membrane component. Liposomes of both different acyl chain length and different cholesterol concentration were made. The results indicated that increasing cholesterol content lowers the pK of insertion for all lipid types examined and raises the tryptophan fluorescence lambda max for pHLIP's membrane surface-bound state, State II.

Unilaminar vesicles were made with POPC lipids or single monounsaturated phosphatidylcholine lipids of 14, 16, 18, or 20 acyl chain lengths. Different samples of these lipids were made with 0, 10, 20, or 30 percent cholesterol. After the addition of pHLIP, a panel of samples was made with each sample adjusted to a different pH between 4.0 and 8.0. The resulting tryptophan fluorescence curves generated from each sample in the panel were examined to determine pHLIP's insertion pK. pKa of insertion of pHLIP decreased with the addition of cholesterol.

After the addition of pHLIP to the same unilaminar vesicles as described above (made with POPC lipids or single monounsaturated phosphatidylcholine lipids of 14, 16, 18, or 20 acyl chain lengths with varying amounts (0, 10, 20, or 30 percent) of cholesterol, a panel of samples was created with each sample adjusted to a different pH in the range between 7.0 and 7.5. The tryptophan fluorescence curves taken from each sample were fit using PFAST to determine the lambda max. State II Lambda Max was found to increase with cholesterol for all lipid types.

Redirecting the Immune System Towards Cancer Using pHLIP

Cancer cells are preferentially labeled with small molecules that recruit antibodies already present in the human bloodstream and redirect immune responses, resulting in targeted cell cytotoxicity. To achieve this goal, a small molecule such as 2,4-dinitrophenyl (DNP) group in conjugation with pHLIP is used as an antigen. pHLIP is conjugated to the immune active molecule (DNP), and DNP-pHLIP interaction with cells results in a pH-dependent cytotoxicity.

Anti-DNP antibodies are not only already found in the human bloodstream in a high percentage of the human population but also capable of redirecting immune responses such as complement dependent cytotoxicity (CDC) and antibody-dependent cell-mediated cytotoxicity (ADCC). An exemplary class of small molecules containing DNP is called ARM-Ps (antibody-recruiting molecules targeting prostate cancer). These molecules are capable of enhancing antibody-mediated immune recognition of prostate cancer cells. (Murelli et al., 2009, J Am Chem Soc 131, 17090-17092).

Such DNP molecules conjugated to a N-terminal cysteine on pHLIP recruited anti-DNP antibodies to cultured HeLa cells in a pH-dependent manner. Between two and four times more recruitment was observed at pH 6.2 than at pH 7.4. When the cells are treated with DNP in conjugation with the D25E pHLIP peptide (a variant with a pK of insertion of about 6.5), between 20 and 50 times more recruitment was seen at pH 6.2 than at pH 7.4. In each case, pHLIP alone was not capable of significantly recruiting anti-DNP antibodies to the surface of cells. Similar results have been obtained with PC-3 prostate cancer cells.

D-Amino Acids

Of the standard α-amino acids, all but glycine can exist in either of two optical isomers, called L or D amino acids, which are mirror images of each other. While L-amino acids represent all of the amino acids found in proteins during translation in the ribosome, D-amino acids are found in some proteins produced by enzyme posttranslational modifications after translation and translocation to the endoplasmic reticulum. D amino acids are abundant components of the peptidoglycan cell walls of bacteria, and D-serine acts as a neurotransmitter in the brain. The L and D convention for amino acid configuration refers not to the optical activity of the amino acid itself, but rather to the optical activity of the isomer of glyceraldehyde from which that amino acid can be synthesized (D-glyceraldehyde is dextrorotary; L-glyceraldehyde is levorotary).

pHLIP peptides either fully or partially built of D-amino acids possess advantages over L-pHLIP peptides. For example, D-pHLIP peptides are biodegraded slower than their levorotary counterparts leading to enhanced activity and longer biological half lives (Sela and Zisman, 1997 FASEB J, 11: 449-456, incorporated herein by reference). Thus, the invention provides for the use of D-pHLIP peptides in the methods described herein. For example, pHLIP peptides comprise solely L-amino acids or solely D-amino acids, or a combination of both D-amino acids and L-amino acids.

Isotopes pHLIP peptides optionally contain radioactive elements or stable isotopes, or a combination of both. Stable isotopes are chemical isotopes that may or may not be radioactive, but if radioactive, have half lives too long to be measured. Different isotopes of the same element (whether stable or unstable) have nearly the same chemical characteristics and therefore behave almost identically in biology (a notable exception is the isotopes of hydrogen). The mass differences, due to a difference in the number of neutrons, will result in partial separation of the light isotopes from the heavy isotopes during chemical reactions and during physical processes such as diffusion and vaporization. This process is called isotope fractionation. Examples of stable isotopes include oxygen, carbon, nitrogen, hydrogen and sulfur. Heavier stable isotopes include iron, copper, zinc, and molybdenum.

Gamma cameras are used in e.g. scintigraphy, SPECT and PET to detect regions of biologic activity that may be associated with disease. Relatively short lived isotope, such as $^{123}I$ is administered to the patient.

Scintigraphy ("scint") is a form of diagnostic test wherein radioisotopes are taken internally, for example intravenously or orally. Then, gamma cameras capture and form two-dimensional images from the radiation emitted by the radiopharmaceuticals.

SPECT is a 3D tomographic technique that uses gamma camera data from many projections and can be reconstructed in different planes. A dual detector head gamma camera combined with a CT scanner, which provides localization of functional SPECT data, is termed a SPECT/CT camera, and has shown utility in advancing the field of molecular imaging. In SPECT imaging, the patient is injected with a radioisotope, most commonly Thallium $^{201}$Tl, Technetium $^{99m}$TC, Iodine $^{123}$I, and Gallium $^{67}$Ga Positron emission tomography (PET) uses coincidence detection to image functional processes. Short-lived positron emitting isotope, such as 18F, is incorporated with an organic substance such as glucose, creating F18-fluorodeoxyglucose, which can be used as a marker of metabolic utilization. Images of activity distribution throughout the body can show rapidly growing tissue, like tumor, metastasis, or infection. PET images can be viewed in comparison to computed tomography scans to determine an anatomic correlate. Other radioisotopes used in nuclear medicine thallium-201, tellurium-123, cadmium-113, cobalt-60, and strontium-82.

Example 1: Measuring Tumor Aggressiveness and Targeting Metastatic Lesions with Fluorescent pHLIP Malignant cancers exhibit an elevated uptake of glucose that leads to tumor acidosis from the Pasteur and Warburg effects. Glucose uptake and acidosis show a positive correlation with a tumor's aggressiveness and metastatic potential. Therefore, extracellular acidity may be a useful biomarker to evaluate the prognosis of tumor development, pHLIP sequences are a water-soluble membrane peptide that inserts and folds across a cellular membrane lipid bilayer in response to low pH. Membrane-associated folding of pHLIP occurs within seconds and is accompanied by a release of energy (about 2 kcal/mol) that can be used to target acidic tumors in vivo and move cell-impermeable cargo-molecules across cellular membranes. The extent of tumor labeling, measured by conjugating pHLIP with fluorescent and PET imaging agents, is directly related to the level of acidity in tumors of various types. Accumulation of pHLIP in tumors correlates with tumor aggressiveness, and that metastatic lesions developed in lungs are targeted by pHLIP in response to the elevated level of acidity in metastatic nodules.

The following materials and methods were used to generate the data described in Example 1.

The pHLIP peptide with a single Cys residue on the N-terminus (ACEQNPIYWARYADWLFTTPLLLLD-LALLVDADET (SEQ ID NO: 221)) was synthesized and purified using standard methods. Cy5.5-maleimide (GE Healthcare) and Alexa750-maleimide (Invitrogen) were used for the conjugation with pHLIP in DMF. The conjugated peptides were purified on HPLC. The concentration of the labeled peptides and labeling ratio was determined by absorption, $\epsilon_{280}$=13940 M$^{-1}$cm$^{-1}$ for pHLIP, $\epsilon_{674}$=250,000 M$^{-1}$cm$^{-1}$ for Cy5.5 and $\epsilon_{750}$=240,000 M$^{-1}$cm$^{-1}$ for Alexa750. The purity of the constructs was tested by analytical HPLC and SELDI-TOF masspec.

HeLa, M4A4 (metastatic) and NM2C5 (non-metastatic) cancer cells with stable GFP expression were purchased from ATCC. Primary tumors were established by subcutaneous injection of cancer cells (~2×10$^7$ cells/flank/0.2 ml) of adult athymic nude mice. Intratumoral pH was measured using a microelectrode. To establish metastases in lungs, M4A4 cancer cells were given as multiple tail vein injections, resulting in metastatic lung lesions; alternatively, a primary tumor was established by subcutaneous injection of M4A4 cancer cells and allowed to grow until it metastasized to the lungs.

Fluorescence imaging was performed on an FX Kodak in-vivo image station. A typical imaging procedure includes tail vein injection of 1 mg/kg fluorescent pHLIP and imaging of mice 4, 24, 48 and 72 hours post injection. Imaging is performed while animals are under gas anesthesia with supplemental heat provided to maintain animal core body temperature. The contrast index (CI) was calculated according to the equation:

$$CI = \frac{Fl_{tumor} - Fl_{auto}}{Fl_{norm} - Fl_{auto}}$$

where, $Fl_{tumor}$ and $Fl_{norm}$ are the fluorescence mean intensities of tumor and normal contra lateral region of the same area (muscle), respectively, and $Fl_{auto}$ is the auto fluorescence from the corresponding region measured before injection. For tumor analysis, the animal is euthanized, adjacent skin is removed from the tumor site and images of tumor site are taken. Lungs are removed and immediately viewed under an inverted epi-fluorescent microscope (IX71 Olympus).

Measurements of pH in tumors are performed using a needle pH micro-electrode and reference electrode (Microelectrodes, Inc.). The needle pH micro-electrode is inserted into a central part of a tumor, and the micro-reference electrode is placed into the subcutis nearby. The pH is then measured in tumors and normal contra lateral region.

Tumor margins were established using the EdgeFinder program according to the algorithm published in Segala et al., 2009, Int. J. Mol. Sci 10:3478-3487.

Targeting of Tumors Using Detectably-Labeled pHLIP

To follow pH were covalently attached to the N-terminus of pHLIP. The dyes stay outside of the membrane after transmembrane insertion. A higher contrast index (tumor/muscle ratio) was seen with Alexa750 (FIG. 5A), apparently due to a lower accumulation of this probe in normal tissue. Possible reasons for the difference between the probes include: i) absorption and emission of the Alexa750 is long-wavelength shifted in comparison with Cy5.5 and so has better penetration in tissue and ii) differences in chemical properties of dyes (Cy5.5 is more hydrophobic and targets skin more than Alexa750). However, despite the differences, both dyes conjugated to pHLIP show pH-dependent tumor targeting (FIGS. 4A-D and 5A-C).

Figure 4A:
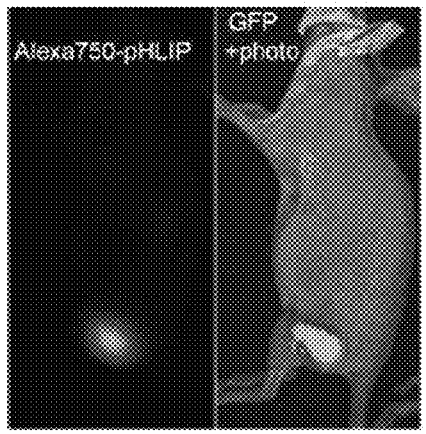
FIGS. 4A-D are a series of photographs showing targeting of tumors by fluorescent pHLIP as demonstrated by whole-body fluorescence imaging. A) NIR (Alexa750-pHLIP) fluorescence (yellow/red) and overlay of light (photo) and GFP (green) fluorescence images of mouse bearing tumor established by subcutaneous injection of GFP-expressing HeLa cancer cells in the right flank. Alexa750-pHLIP was given as a single iv injection and imaging was performed 72 hours post-injection. B) NIR fluorescence and overlay of light (photo) and GFP fluorescence images of a mouse tumor site are presented in (A) with skin removed from the tumor site (yellow color presents higher level of intensity than red color). The figure demonstrates that fluorescent pHLIP marks the tumor boundary with high precision. C) Fluorescent pHLIP can distinguish between metastatic (M4A4) and non-metastatic (NM2C5) tumors by better targeting of the more aggressive tumor phenotype. Light (photo), GFP and NIR (Alexa750-pHLIP) fluorescence images of mice bearing metastatic and non-metastatic tumors are presented. NIR fluorescence is given in rainbow presentation. D) Fluorescent pHLIP can target millimeter-size tumor spots identified by GFP fluorescence.
Figure 4B:
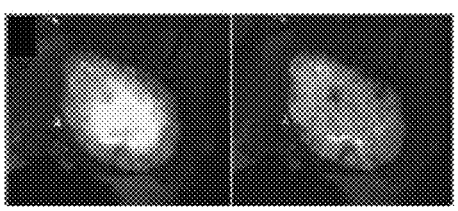
Figure 4C:
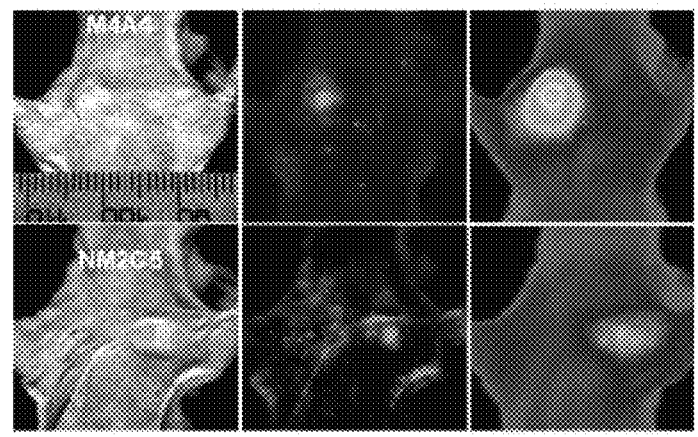
Figure 4D:
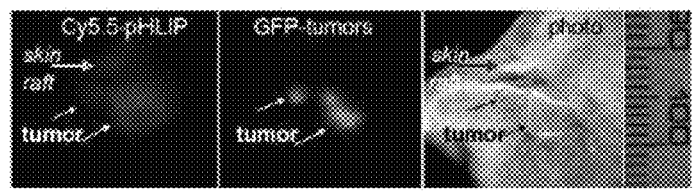
Figure 5A:
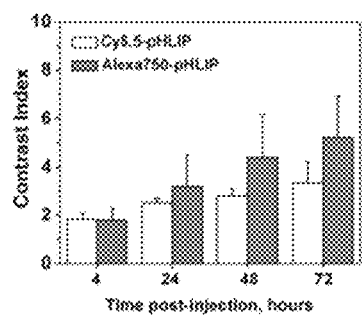
FIGS. 5A-C are a series of bar graphs showing contrast index over time. Contrast index (CI) calculated for various fluorescent constructs and for different tumor models (see methods section for CI calculations). A) Alexa750-pHLIP construct targets tumors slightly better than Cy5.5-pHLIP (see explanation in the text). B) Targeting of tumors (established by subcutaneous injection of HeLa cancer cells) by fluorescent pHLIP (Cy5.5-pHLIP) was enhanced by co-injection intraperitoneally of 200 µl of 25% solution of glucose. The non-inserting control peptide Cy5.5-K-pHLIP demonstrates significantly low tumor targeting, which does not change much with time. C) Targeting of a metastatic (M4A4) tumor with Alexa750-pHLIP was higher than of a non-metastatic (NM2C5) tumor. Mean fluorescence was calculated by using the Kodak image software. Data presented as Mean±SD, *=p<0.05 using two tailed t-test.
Figure 5B:
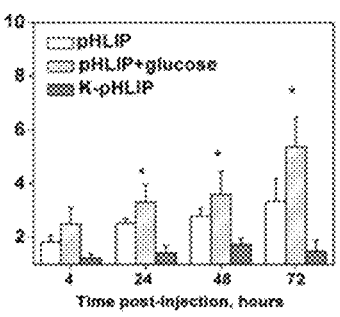
Figure 5C:
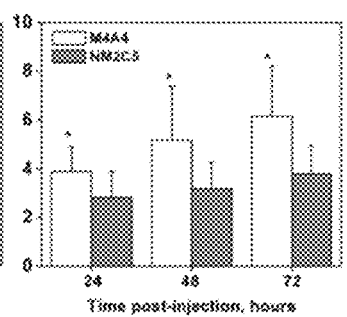

After tail vein injection, fluorescent pHLIP finds tumors in mice within the first 4 hours and remains for more than 72 hours, exhibiting a progressive rise in contrast index from 2 to 5 (FIGS. 5A-C). By using GFP expressing cancer cell lines, tumors, their borders and metastatic lesions are readily visualized if the overlying skin is removed, allowing co-localization of GFP fluorescence and NIR emission of fluorescent pHLIP to be determined in vivo (FIG. 4A). Targeting of an entire tumor mass with excellent staining of tumor margins is clearly seen (FIG. 4B). An important finding is that pHLIP targets millimeter-size tumor spots, which were identified by GFP fluorescence (FIG. 4D).

Feeding animals with bicarbonated water, which increases tissue pH, correlates with the reduction of tumor targeting by pHLIP. The results indicate a positive correlation between an increase of tumor targeting by pHLIP and intraperitoneal co-injection of 200 µl of a 25% solution of glucose, which is known to selectively acidify tumors due to the enhanced metabolism of cancer cells[16] (FIG. 5B).

As a control, K-pHLIP, a peptide where the two Asp residues in the putative transmembrane region are replaced with Lys residues, was used. Use of this pHLIP peptide (SEQ ID NO: 13) resulted in a loss of pH-dependent insertion across membranes (over a pH range from 8-3). The contrast index for the fluorescent-K-pHLIP is about 1.5 (FIG. 5B), which is similar to the contrast index of free dyes.

Fluorescently-labelled pHLIP distinguished between metastatic and non-metastatic tumor phenotypes. More aggressive metastatic tumor phenotypes have a lower extracellular pH, and that acidity promotes metastasis. Therefore, the extracellular pH of primary tumors is a useful prognostic tool for evaluating patients to determine severity of disease and based on those data prescribing an appropriate treatment regimen. Metastatic and non-metastatic tumors were established in mice by subcutaneous injection of two melanoma cell lines, M4A4 and NM2C5, respectively, derived from the human melanoma cancer cell line, MDA-MB-435. M4A4 is highly metastatic in nude mice, while NM2C5 is weakly metastatic. When the primary tumors reached 5-6 mm in diameter, Alexa750-pHLIP was given as single iv injection and imaging was performed within three days (FIGS. 4C and 5C). A statistically significant difference in tumor targeting was observed (FIG. 5C) and correlated with the pH measured in tumors by microelectrode. The more aggressive tumor phenotype created by injection of metastatic M4A4 cancer cells, with a measured pH value of 6.9±0.2 was stained by fluorescent pHLIP 1.5-1.6 times better than the non-aggressive tumor (NM2C5 cancer cells) with pH=7.1±0.2.

Figures 6A, 6B, 6C:
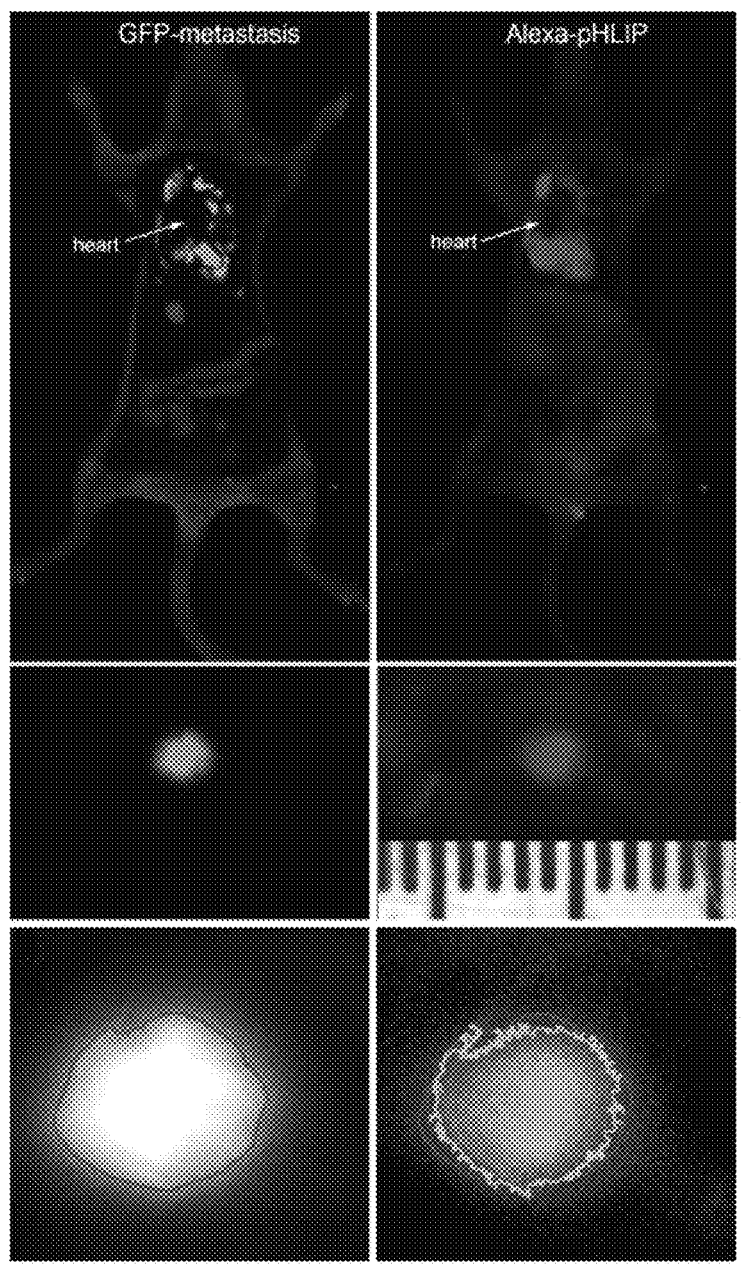
FIGS. 6A-C are a series of photographs showing fluorescent pHLIP targeting of metastatic lesions in lungs. A primary tumor was established by subcutaneous injection of M4A4 cancer cells, and the tumor was grown until it gave lung metastases. Then, the primary tumor was removed and Alexa750-pHLIP was given as a single iv injection. One day after injection, the animal was euthanized, the chest was opened, and whole-body imaging was carried out. A) Whole-body GFP and NIR (Alexa750-pHLIP) fluorescent images are shown. B) Targeting of millimeter-size metastatic lesion in ribs by fluorescent pHLIP is evident. The ruler is in millimeters. C) The magnified GFP and Alexa images of millimeter-size metastatic lesion in ribs shown on (B) with tumor margins calculated by using the EdgeFinder program. Contours of GFP and NIR fluorescence shown in red and light blue, respectively, coincide with sub-millimeter precession.

Metastasis is largely what makes cancer a lethal disease. Methods that allow identification and selective treatment of metastatic lesions are useful in reducing mortality, invasive neoplasms have enhanced glucose flux compared with normal tissues give an avenue to distinguish benign from malignant nodules using fluorodeoxyglucose-positron emission tomography. Elevated glucose uptake leads to the production of acid, which is pumped to the extracellular space, and results in its acidification. Therefore, acidification of malignant nodules is expected. To evaluate whether pHLIP discriminates between metastatic cells and normal or non-metastatic cells in vivo, Alexa750-pHLIP was used to mark metastases in lungs. M4A4 cancer cells expressing GFP were used in study to unmistakably visualize metastatic foci. Cancer cells were implanted by subcutaneous injection, and the tumor grew until it metastasized. Then the primary tumor was removed, and Alexa750-pHLIP was administrated as a single iv injection via tail vein. Comparison of whole-body fluorescence GFP and NIR images of mice with open chests revealed selective staining of lung metastases by fluorescent pHLIP (FIG. 6A). A two millimeter size metastatic rib lesion was marked by fluorescent pHLIP with high accuracy (FIG. 6B). The EdgeFinder program (Segala et al., 2009, Int. J. Mol. Sci 10:3478-3487) was applied to calculate tumor margins from GFP and Alexa fluorescent images (FIG. 6C). Contours of GFP and NIR fluorescence shown in red and light blue, respectively, coincide with sub-millimeter precession.

Figures 7A, 7B, 7C, 7D:
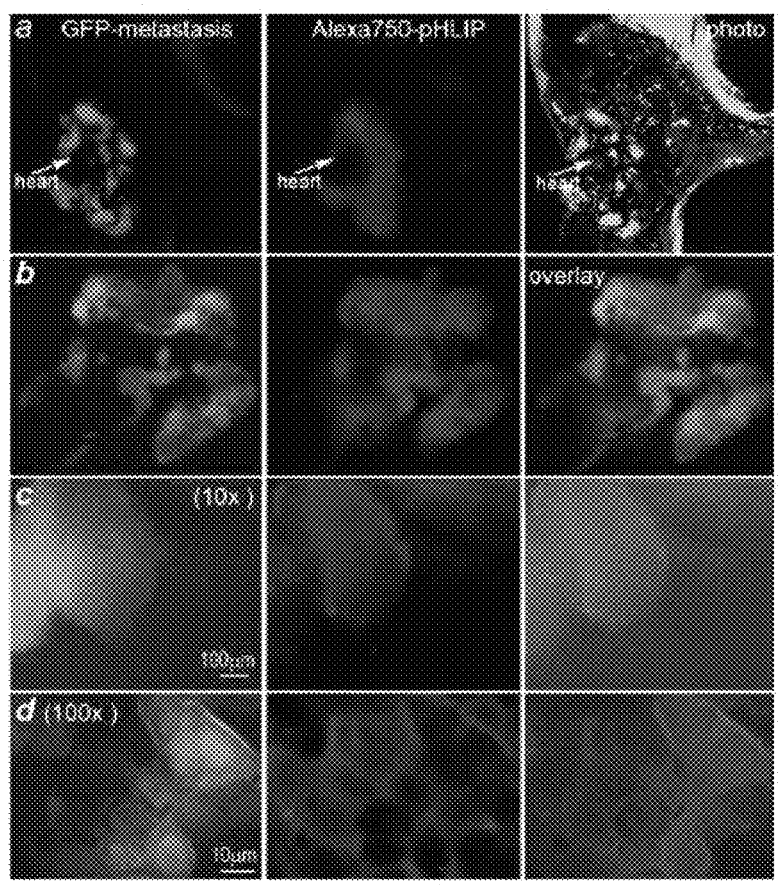
FIGS. 7A-D are a series of photographs showing that fluorescent pHLIP targets metastatic nodules in lungs and is distributed in the extracellular space and cellular membranes of the tumor cells. Metastases were established by i.v. injection of M4A4 cancer cells. Alexa750-pHLIP was given as a single iv injection. One day after injection, the chest was opened and imaging was carried out. A) Whole-body GFP, NIR (Alexa750-pHLIP) fluorescent and light (photo) images are shown. B) Co-localization of GFP and NIR fluorescence is shown on the excised lungs. C) A metastatic lesion analyzed under the fluorescence microscope at 10× magnification demonstrates co-localization of GFP and NIR emission. D) A detailed analysis of NIR (Alexa750-pHLIP) fluorescence distribution was carried at 100× magnification. It is clearly seen that NIR fluorescence is distributed in the extracellular space with staining of the cellular membrane, which confirms the mechanism of pHLIP action.

In another experiment, M4A4 cancer cells expressing GFP were administrated directly into the blood via tail vein injection. Cancer cells circulating in the blood accumulate in the lungs, creating small tumors, and Alexa750-pHLIP injected via tail vein targeted such tumor sites well (FIGS. 7A and 7B). Lungs were removed and immediately analyzed under the microscope to identify the relative localization of GFP and NIR fluorescent signals at the cellular level. Millimeter sized metastastatic lesions in lung tissue are marked by fluorescent pHLIP (FIG. 7C). Further analysis of the distribution of fluorescence was evaluated at higher magnification (100×), clearly showing extracellular and membrane localization of fluorescent pHLIP (FIG. 7D), as expected from biophysical studies indicating that pHLIP inserts across a lipid bilayer at low pH to form a stable transmembrane helix.

Altered glucose metabolism in cancer cells stimulates production and accumulation of acid in the extracellular space of tumors. Proliferation of cancer cells and metastases are promoted at low extracellular pH, while at the same time normal cells are susceptible to acid-induced apoptosis, facilitating tumor invasiveness. Altered glucose metabolism and acidification, characteristics of tumor growth and progression, are useful for the detection of primary tumors and metastatic sites, and for the prognosis of tumor development. pHLIP peptides reliably detect and discriminate tumor cells (and metastatic tumor cells) from non-tumor cells. The data clearly show that fluorescent pHLIP peptides target primary tumors with high accuracy, mark tumor borders and stain millimeter-sized tumor spots. The tumor targeting can be enhanced by co-injection of glucose and the extent of labeling directly correlates with tumor aggressiveness.

A related finding is the ability of pHLIP to identify small metastatic foci, indicating that metastatic lesions are also acidic. Combining fluorescent pHLIP with the EdgeFinder program, allows a surgeon to locate a tumor and identify its border, thereby guiding accurate removal of all cancer cells in real time during surgical intervention. pHLIP conjugated with PET, SPECT and MR imaging agents represents a powerful clinical tool for tumor diagnosis and therapeutic outcome monitoring.

An enhanced level of acidity correlates with the development and progression, not only of tumors, but also of other pathological states. Therefore the pHLIP technology is also applicable for imaging and therapeutic targeting of acidic tissues other then cancerous tissue.

Example 2: Cancer Cell Proliferation is Inhibited by Targeted Intracellular Delivery of Otherwise Membrane-Impermeable Cytotoxins Tumor cell proliferation was found to be inhibited by pHLIP-mediated delivery of an exemplary membrane impermeable toxin, phalloidin. The pHLIP construct acts as a nanosyringe that not only injects the cytotoxin into the cell targeted for killing but selectively does so by virtue of its ability to insert only under specific local environmental conditions.

Phlip peptides insert into a lipid bilayer under slightly acidic conditions (pH 6-6.5), forming a transmembrane helix. pHLIP-mediated translocation of a cell-impermeable, polar toxin phalloidin, inhibits the proliferation of cancer cells in a pH-dependent fashion. The delivery constructs, pHLIP-K(rho)C(aph) and pHLIP-C(aph), both carry the phalloidin toxin at the inserting C-terminus, via a disulfide linkage that is cleaved in cells. The constructs differ in that a lipophilic rhodamine moiety is also attached to the inserting end in pHLIP-K(rho)C(aph). After a 3-h incubation with 2-4 μM concentrations of pHLIP-K(rho)C(aph) at pH 6.1-6.2, proliferation of HeLa, JC, and M4A4 cancer cells are severely disrupted (>90% inhibition of cell growth observed). Cells treated with pHLIP-K(rho)C(aph) also showed signs of cytoskeletal immobilization and multinucleation, consistent with the knowledge that phalloidin binds to F-actin and stabilizes the filament against depolymerization. However, the antiproliferative effect was not observed with pHLIP-C(aph). The insertion behavior of both constructs were further studied in POPC liposomes using Trp fluorescence: pHLIP-K(rho)C(aph) and pHLIP-C(aph) insert with the same apparent pKa of ~6.15; however, kinetic experiments suggest that pHLIP-C(aph) inserts much slower than pHLIP-K(rho)C(aph), perhaps explaining its lack of biological effects with cells. Results obtained with pHLIP-K(rho)C(aph) indicated that pHLIP peptides are tailored to preserve characteristics, e.g., hydrophobicity, of anti-tumor agent/pHLIP conjugates that would selectively destroy cancer cells while not affecting normal cells. Such an approach may enhance the efficacy of cancer chemotherapy, as well as reducing side effects.

The following materials and methods were used to generate the data described in Example 2.

Antiproliferation Assays. Stock solutions of pHLIP-C(aph) 5, pHLIP-K(rho)C(aph) 6, phalloidin 1, pHLIP-K-C(aph) and pHLIP were prepared in DMSO at the 200 µM concentration. HeLa, JC or M4A4 cells were seeded in 96-well plates (Costar) at the density of ~1,000 cells per well, and then grown for 2 days before treatment. DMSO stock of pHLIP-K(rho)C(aph) (or a control agent) was diluted with pH-adjusted, sterile Leibovitz's L-15 Phenol Free Medium (L-15) to give treatment solutions in the 0.25-4 µM range. Appropriate amounts of DMSO were supplemented to ensure that all treatment samples contain ~2% by volume. After removal of cell media, the L-15 treatment solution was added to each well (volume for HeLa plate: 80 µL per well; JC and M4A4: 160 µL), and then the plate was incubated at 37° C. for 3 h. To minimize week-to-week cell variability, treatments at pH 6.1/6.2 and 7.4 were carried out on the same 96-well plate and all negative control data shown (in FIG. 9D/E/F) are from plates in which positive results were also obtained. After treatment, 200 µL of normal media was added to each well before returning the plate to the incubator. Cell density of the '0 µM, pH 7.4' controls usually reached 40,000 to 80,000 cells per well after 3-6 days of growth. The viable cell number was quantified using the MTS reagent (Promega CellTiter 96 AQueous One Solution Cell Proliferation Assay). OD 490 nm values were obtained using a plate reader (Spectramax M2 from Molecular Devices).

pHLIP Peptides were the pHLIP, pHLIP-C and pHLIP-KC peptides were prepared by using standard solid phase synthesis and purification methods. Their sequences are listed below, with the approximate TM region denoted in italic and C-terminus Cys and Lys residues in bold. In pHLIP-KC, the N-terminus NH$_2$ is capped with an acetyl group:

pHLIP:
(SEQ ID NO: 223)
NH$_2$-GGEQNPIYWARYADWLFTTPLLLLDLALLVDADEGT-CO$_2$H pHLIP-C:
(SEQ ID NO: 224)
NH$_2$-AAEQNPIYWARYADWLFTTPLLLLDLALLVDADEGTCG-CO$_2$H.

pHLIP-KC:
(SEQ ID NO: 225)
Acetyl-NH-AAEQNPIYWARYADWLFTTPLLLLDLALLVDADEGTKCG-CO$_2$H.

Syntheses of pHLIP Conjugates. Aminophalloidin 2 (HCl salt) is purchased from Alexis Biochemicals (Enzo Life Sciences), N-succinimidyl 3-(2-pyridyl-dithio)-propionate (SPDP) from Sigma, and 5-carboxytetramethyl-rhodamine, succinimidyl ester (5-TAMRA-SE) from Invitrogen or Anaspec.

Synthesis of pHLIP-C(aph) 5. To a solution of amino-phalloidin 2 (1 mg, 1.21 µmole, 1 eq.) in 500 µL of aqueous (aq.) potassium phosphate buffer (100 mM, pH 7.5) was added a solution of SPDP (0.452 mg, 1.45 µmole, 1.2 eq.) in 226 µL of N,N-dimethylformamide (DMF). The reaction (rxn) mixture was stirred at room temperature (r.t.) for 1.5 h. Rxn progress was monitored with reverse phase HPLC (Hewlett Packard Zorbax semi-prep 9.4×250 mm SB-C18 column; flow rate: 2 mL/min; phase A: water+0.01% TFA; phase B: acetonitrile+0.01% TFA; gradient: 70 min from 99:1 A/B to 1:99 A/B): The starting material (s.m.) 2 elutes at 65:35 A/B, whereas the SPDP linker at 43:57 A/B, and the desired product amino-phalloidin-PDP 3 at 52:48 A/B. This initial rxn is usually complete within 1 h. Afterwards, a solution of pHLIP-C (6.2 mg, 1.46 µmole, 1.21 eq., >95% monomer) in 400 µL of argon-saturated DMF was added. The resulting mixture was stirred at r.t. under argon for 2.5 h. The desired final product pHLIP-C(aph) 5 was isolated via HPLC (5 eluting at 35:65 A/B) in ~47% yield (0.57 µmole) over two steps, quantified using UV absorptions at two wavelengths ($\epsilon_{280}$=24,940 M$^{-1}$cm$^{-1}$, $\epsilon_{300}$=14,000 M$^{-1}$cm$^{-1}$, all UV-vis absorbance spectra were obtained in aq. solutions of 6M guanidinium chloride). MALDI-TOF MS+: M.W. calculated for pHLIP-C(aph) 5 (C$_{234}$H$_{344}$N$_{54}$O$_{69}$S$_3$): 5113.8; Found (MH+): 5114.6.

Synthesis of pHLIP-K(rho)-C(aph) 6. Linker-derivatized amino-phalloidin-PDP 3 (0.6 µmole, 1 eq.) was synthesized as described above. Subsequently, a solution of pHLIP-KC (3.5 mg, 0.79 µmole, 1.3 eq.) in 400 µL of 1:1 DMF/aq. potassium phosphate buffer (100 mM, pH 7.8) was added. The pH of this mixture was adjusted to 8.2, and the rxn was stirred at r.t. under argon for 13 h. After HPLC showed that the disulfide linking rxn was complete (s.m. pHLIP-KC eluting at 31:69 A/B, intermediate product pHLIP-K-C(aph) at 33:67 A/B; see above for HPLC methods), a solution of 5-TAMRA-SE (0.64 mg, 1.21 µmole, 2 eq.) in 100 µL of 1:1 DMF/aq. potassium phosphate buffer (100 mM, pH 7.8) was added. After stirring at r.t. for 7-12 h, HPLC usually showed that the 5-TAMRA conjugation had proceeded ~40-50% (final product pHLIP-K(rho)-C(aph) 6 eluting at 30:70 A/B). Longer rxn time and/or more equivalents (eq.) of 5-TAMRA-SE often led to a more intractable mixture. Thus, pHLIP-K-C(aph) and pHLIP-K(rho)-C(aph) 6 were separated via HPLC, and lyophilization provided each in 15-20% yield (0.12 mole) over two and three steps, respectively. The purified pHLIP-K-C(aph) was often treated with 5-TAMRA-SE again to give more of pHLIP-K(rho)-C(aph) 6, or used directly in cell experiments as a negative control agent. The products were quantified using UV-vis absorptions at multiple wavelengths (pHLIP-K-C(aph): $\epsilon_{280}$=24,940 M$^{-1}$cm$^{-1}$, $\epsilon_{300}$=14,000 M$^{-1}$cm$^{-1}$; pHLIP-K(rho)C(aph): $\epsilon_{560}$=85,000 M$^{-1}$cm$^{-1}$, $\epsilon_{300}$=27,603 M$^{-1}$cm$^{-1}$, $\epsilon_{280}$=40,300 M$^{-1}$cm$^{-1}$). MALDI-TOF MS+: M.W. calculated for pHLIP-K-C(aph) (C$_{242}$H$_{358}$N$_{56}$O$_{71}$S$_3$): 5284.0; Found (MH+): 5285.7. M.W. calculated for pHLIP-K(rho)-C(aph) 6 (C$_{267}$H$_{378}$N$_{58}$O$_{75}$S$_3$): 5696.4; Found (MH+): 5700.6.

Cell Cultures. Cancer cell lines (HeLa, JC, M4A4 and HT1080) were obtained from American Type Culture Collection (ATCC): HeLa (CCL-2) is a human cervix adenocarcinoma cell line; JC (CRL-2116) is a mouse mammary gland adenocarcinoma cell line; M4A4 (CRL-2914) is a human breast ductal carcinoma cell line; and HT1080 (CCL-121) is a human connective tissue fibrosarcoma cell line. HeLa and M4A4 cells were cultured in DMEM ([+]4.5 g/L D-glucose, [+] 40 mg/L sodium pyruvate, Gibco 10313), whereas JC cells in ATCC-formulated RPMI-1640 medium (with HEPES, sodium pyruvate, and L-glutamine, Cat No. 30-2001), and HT1080 cells in ATCC-formulated Eagle's Minimum Essential Medium (Cat No. 30-2003). All cell growth media were supplemented with 10% FBS (Gibco) and ciprofloxacin-HCl (1 g/mL) (from Cellgro, Voigt Global Distribution). Unless specified otherwise, cells were grown in an incubator (Revco Elite II, from Thermo Fisher Scientific) under a humidified atmosphere of air and 5% $CO_2$ at 37° C.

Anti-Proliferation Assays. Stock solutions of pHLIP-C (aph) 5, pHLIP-K(rho)C(aph) 6, phalloidin 1, amino-phalloidin 2, pHLIP-K-C(aph) and pHLIP were prepared in DMSO at the 200 μM concentration (1 or 2: $\in_{280}$=11,000 $M^{-1}cm^{-1}$, $\in_{300}$=10,100 $M^{-1}cm^{-1}$; pHLIP: $\in_{280}$=13,940 $M^{-1}cm^{-1}$) and stored at −20° C. HeLa, JC or M4A4 cells were seeded in 96-well plates (Costar) at the density of ~1,000 cells per well, and then grown for 2 days (or 2 doubling periods) before treatment. Leibovitz's L-15 Phenol Free Medium (L-15) was shaken with air (and/or incubated at 37° C.) to ensure that its final free thiol (SH) content is <15 μM (estimated using the Ellman test), pH-adjusted to 6.1-6.2 or 7.4, and then sterilized via filtration through a 0.2 μm filter. Subsequently, DMSO stock of pHLIP-K(rho)C (aph) (or a control agent) was diluted with the prepared L-15 to give treatment solutions in the 0.25-4 μM concentration range (see FIG. 9 for specific concentrations per cell line). Appropriate amounts of DMSO were supplemented to ensure that all treatment samples contain the same amount of DMSO (~2% by volume), including the '0 μM' blank prepared by mixing L-15 with DMSO. The treatment solutions were vortexed, and then small portions were removed to measure the reported pH values, obtained at 23° C. (the pH values are ~0.15-0.2 unit lower when measured at 37° C.). After removal of cell media, the L-15 treatment solution was added to each well (volume for HeLa plate: 80 μL per well; JC and M4A4: 160 μL), and then the plate was incubated at 37° C. for 3 h. Afterwards, treatment solutions were collected and their pH values re-measured at 23° C.: A small up-drift in pH was observed for the low pH samples (e.g. HeLa: pH 6.2→pH 6.5, M4A4: pH 6.1→pH 6.3), while a down-drift was seen for the neutral pH samples (e.g. HeLa: pH 7.4→pH 7.1, M4A4: pH 7.4→pH 6.9). To minimize week-to-week cell variability, treatments at pH 6.1/6.2 and 7.4 were carried out on the same 96-well plate (pH 6.1/6.2: columns 1-5; pH 7.4: columns 7-11) and all negative control data shown (in FIG. 9D/E/F) are from plates in which positive results were also obtained (pHLIP-K(rho)C(aph): rolls A-D; negative control: rolls E-H). After treatment, 200 μL of normal media was added to each well before returning the plate to the incubator. Cell density in the '0 μM, pH 7.4' control wells usually reached 40,000 to 80,000 cells per well after 3-6 days of growth (depending on the cell line, e.g. doubling time is 12-16 h for JC but 25-30 h for M4A4). The viable cell number was quantified using the MTS reagent (Promega CellTiter 96 AQueous One Solution Cell Proliferation Assay, with the One-Solution containing the tetrazolium compound 3-(4,5-dimethylthiazol-2-yl)-5-(3-carboxymethoxyphenyl)-2-(4-sulfophenyl)-2H-tetrazolium inner salt (MTS) and the electron coupling reagent phenazine ethosulfate (PES)): For each well, cell media was replaced with 100 μL of PBS plus 20 μL of MTS/PES One-Solution stock (also added to control wells with no cell). After 1-3 h of incubation, OD 490 nm values were obtained using a plate reader (Spectramax M2 from Molecular Devices). After correcting for background (using no cell controls), the OD 490 nm readings are usually less than 0.7, in the range where viable cell number has a linear relationship with OD 490 nm. All values shown (FIGS. 9A-F and FIG. 13) are normalized to the DMSO-only control (0 μM) at pH 7.4 as 100%.

Cell Morphology Assays and Microscopy. HeLa or M4A4 cells were seeded in the center of a 35-mm dish with a 14-mm poly-Lys-coated, glass-bottom window (Mat Tek Corp). After 2 days of culture (6,000-8,000 cells per dish) cells were incubated with 4 μM pHLIP-K(rho)C(aph) in L-15 for 3 h at pH 6.1 or 7.4 (volume: 160 μL, see main text Methods Anti-Proliferation Assays section for details of preparation of treatment solution).

Cell Dissociation Assay. After treatment with pHLIP-K (rho)-C(aph), (cells were grown in normal media for 1 day), cells were washed with PBS, and then 100 μL of Trypsin (0.25%)/EDTA cell dissociation solution (Gibco) was added to cells in 100 μL of PBS. Phase contrast images were taken before and 5 min after the addition of the Trypsin/EDTA solution, using inverted epi-fluorescence microscope (Olympus IX71) with a 20× objective and the software Q-Capture.

Multinucleation. After pHLIP-K(rho)-C(aph) treatment, cells were grown in normal media for two days, washed with PBS, incubated with the nucleus/DNA-staining fluorescent dye DAPI (5 μM in PBS) for 15 min, and then washed with PBS again. Phase contrast and DAPI fluorescence images (excitation wavelength: 488 nm) of multi-nucleated cells were acquired using a inverted epi-fluorescence microscope (Olympus IX71) equipped with a 100× oil objective, and the software Q-Capture.

Stability of pHLIP-K(rho)C(aph) in L-15. Incubations with pHLIP constructs were carried out in Leibovitz's L-15 Phenol Free medium, which contains ~1 mM cysteine/cystine in its formulation. Ellman tests were performed on L-15 (at pH 6.2 and 7.4) and found free thiol (SH) concentrations in the range of 5-13 μM, approximating the amount of free thiol in human plasma (10-15 μM). To address the concern that this free thiol content could prematurely cleave the disulfide bond in the constructs, releasing phalloidin before pHLIP can insert into cell plasma membrane. Therefore, a sample of incubation mixture (HT1080 cells with 4 μM pHLIP-K(rho)C(aph), pH 6.2, 3 h) was analyzed by HPLC. This experiment confirmed that no detectable decomposition of pHLIP-K(rho)C(aph) occurred during the cell incubation period. The HPLC test also revealed that pHLIP-K(rho)C(aph) was present in large excess of the amount required to saturate the surfaces of ~4,000 cells. This observation is consistent with the observation that similar anti-proliferative results were obtained using either 80 or 160 μL of per-well incubation volume. The effect does not seem to depend on the absolute amount of pHLIP-K(rho)C (aph) present, but rather on the concentration or perhaps kinetics of association to cell membranes.

Liposome Preparation. Liposomes of the 100 nm size were prepared via extrusion. A solution of 5 mg of 1-palmitoyl-2-oleoyl-sn-glycero-3-phosphocholine (POPC) (Avanti Polar Lipids) in 0.2 mL of chloroform was dried in a small round-bottom flask in vacuo (using a roto-evaporator) and/or under a stream of argon, and then held under house vacuum overnight. The dry film of lipid residue was re-hydrated with 0.5 mL of sodium phosphate buffer (pH 8.0, [Pi]: ~5 mM) for 30 min and vortexed vigorously to obtain the multi-lamellar vesicle suspension ('[POPC]': ~20 mM'). This mixture was freeze-thawed at least 7 cycles using a dry-ice/ethanol bath (−70° C.) (and a water bath at 25-35° C.). Final extrusions were performed using an Avanti Mini-Extruder:

At least 15 passages through a polycarbonate membrane with 100 nm sized pores (Whatman 800309: Schleicher & Schuell, Nuclepore Track-Etch Membrane, 0.1 μm) were carried out to give the desired large unilamellar vesicles.

Trp Fluorescence Measurements. Sample Preparation. A lyophilized sample or a concentrated aq. stock of pHLIP-C (aph) 5 or pHLIP-K(rho)C(aph) 6 was dissolved in or diluted with an aq. sodium phosphate buffer to reach the following final concentrations: [5 or 6]: 15-40 μM; [Pi]: ~1-5 mM (final pH: 7-8). This dilute aq. stock was stored at r.t. for 24 h (or at 0° C. for at least 3 days), allowing pHLIP species to reach the appropriate oligomer/monomer equilibrium (deaggregation), and then pHLIP construct concentration was estimated using UV-vis absorptions (see synthesis section for details). This aq. stock of pHLIP construct 5/6 was further diluted with water (Millipore), vortexed and then incubated with POPC liposomes for at least 2 h at pH 7-8 (to allow pHLIP constructs to partition to the lipid surface), with a final pHLIP-construct to lipid ratio of 1:400 and a pHLIP-construct concentration of 4 μM. To trigger pHLIP insertion, the pH of this mixture was adjusted to the desired value (between 4 and 8) using small volumes of concentrated sodium phosphate buffer (100 mM) of various pH (final concentrations: [Pi]~10-12 mM; [pHLIP-construct]~3.6 μM). For determination of pKa of insertion (data shown in FIGS. 12A-D, samples were equilibrated at the final pH for at least 30 min (at r.t.) before Trp fluorescence measurements were made.

Figure 12A:
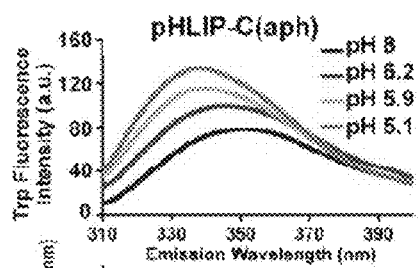
FIGS. 12A-F are line graphs showing the results of biophysical studies of pHLIP-K(rho)C(aph) and pHLIP-C (aph) in the presence of POPC liposomes. (A) Trp fluorescence spectra of pHLIP-C(aph) and (B) pHLIP-K(rho)C (aph) at different pHs are shown. Apparent pKa of insertion into POPC bilayer for pHLIP-C(aph) (C) and pHLIP-K(rho) C(aph) (D) were calculated from the pH-dependences of the position of maximum of fluorescence spectra fitted by the Henderson-Hasselbalch equation (see Supporting Information). Kinetics of pHLIP-C(aph) (E) and pHLIP-K(rho)C (aph) (F) insertion into lipid bilayer were monitored by changes of fluorescence intensity at 330 nm where the pH was dropped from 8 to 5.9. (data points for the first 35 sec are missing due to the time required to mix the sample and then initiate acquisition).

Trp Fluorescence Spectroscopy. Trp residues were excited at 295 nm, and fluorescence emission spectra were collected from 310-400 nm. Measurements were obtained using a SLM-Aminco 8000C spectrofluorimeter (ISS, Champaign, Ill.) equipped with a thermo-bath (model RTE-111, Neslab). All measurements were performed at 25° C. at the pHLIP-construct concentration of 3.6 μM. The widths of the excitation and emission slits were set to 4- and 8-nm, respectively. All spectra (e.g. as shown in FIGS. 12A/B) were corrected for background signals using spectra obtained with blank liposome solutions at pH 8, 7, 6, and 5 (the nearest pH blank was used for spectral subtraction) and smoothed based on the adjacent averaging of 5 points.

Figure 12B:
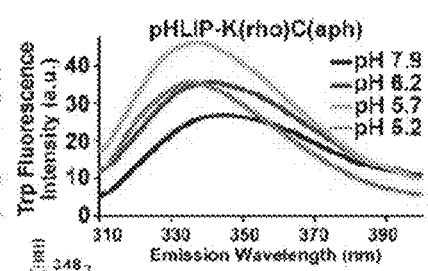
Figure 12C:
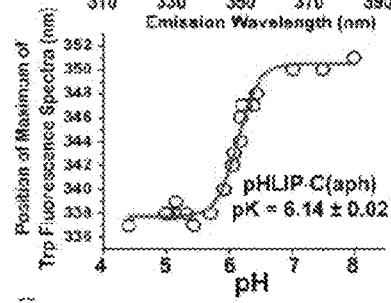

The apparent pKa values shown in FIGS. 12C/D were calculated by fitting (using Origin7 nonlinear fitting option) of the transition curve (obtained by potting of the changes of the position of maximum of fluorescence spectra versus pH) with the Henderson-Hesselbalch equation:

$$y = A_2 + \frac{A_1 - A_2}{1 + 10^{n(pKa-x)}}$$

where x is the pH, y is the wavelength of position of maximum of emission spectrum, pKa is the apparent pKa of insertion into a POPC bilayer and n is the Hill coefficient (which reflects cooperativity of the transition), $A_1$ and $A_2$ are the position of maximum of fluorescence spectra of constructs in the membrane-bound (at high pH) and inserted (at low pH) states, respectively. The data presented as mean±st.d.

To record kinetics of the pHLIP-C(aph) or pHLIP-K(rho)C(aph) constructs insertion into lipid bilayer, changes of emission signal at 330 nm was monitored immediately after lowering pH from 8.0 to ~5.9. The fluorescence was excited at 295 nm or 275 nm (to have higher emission signal) in case of pHLIP-C(aph) or pHLIP-K(rho)C(aph), respectively. Data for the initial period (the first 35-50 seconds) are missing due to the time required to mix the sample and place it in the fluorimeter.

Log P Measurements. A 5-, 20-, or 50-μM solution of phalloidin (or phalloidin-TRITC) in 500 μL of PBS was mixed with 500 μL of n-octanol. The mixture was vortexed for 5 min, allowed to settle at r.t. for 6 h, followed by a standing period of up to 2 days at 4° C. Afterwards, the octanol and PBS layers were separated and their UV absorbance measured (at 300 nm for phalloidin or at 545 nm for phalloidin-TRITC). Since the molar extinction coefficient in n-octanol or aq. PBS buffer is assumed to be the same, the ratio of the OD readings is used directly to calculate the Log P (n-octanol/water) values. The final Log P value of phalloidin or phalloidin-TRITC given in FIG. 1 is the average of Log P values obtained at 5 μM, 20 μM, and 50 μM concentrations. The phalloidin-TRITC shows several peaks on the HPLC in addition to main peak, different formulations have different contributions of polar and hydrophobic impurities and measured Log P values are in range of −0.15 to +0.2.

Figure 13:
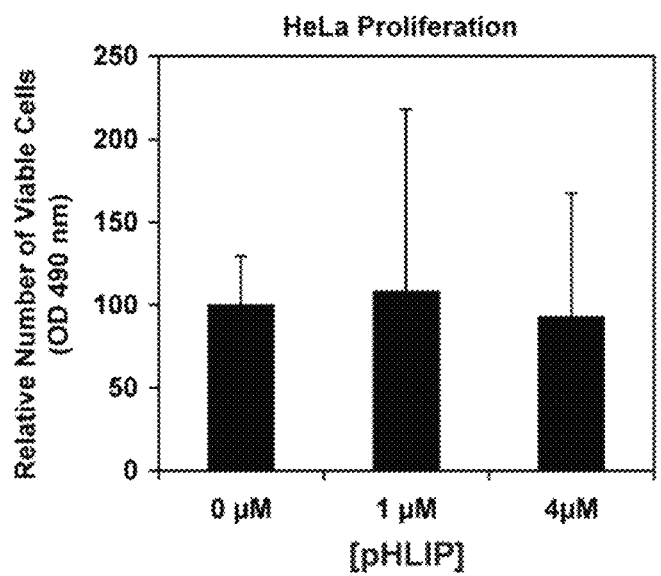
FIG. 13 is a bar graph showing that native pHLIP (without cargo) does not inhibit cancer cell proliferation. These results confirm that pHLIP insertion in itself is benign to cells. HeLa cells were treated with pHLIP at pH ~6.2 as described for pHLIP-K(rho)-C(aph) experiments (n=4).

Statistics (for data shown in FIGS. 9 and 13). All error range of the mean are estimated at 95% confidence level using the two-tailed confidence coefficient $t_{CL,v}$ for Student's t distribution with v degrees of freedom (v=n−1), according to the following equation:

$$\text{estimate of true value} \approx X_n \pm t_{CL,v} \frac{S_n}{\sqrt{n}}$$

where $\overline{X_n}$ is the mean, $S_n$ is the sample standard deviation and n is the sample size. In the experiments described herein, n varies from 4 to 12 ($t_{CL,v}$=3.18 when n=4 and $t_{CL,v}$=2.20 when n=12).

Figure 8:
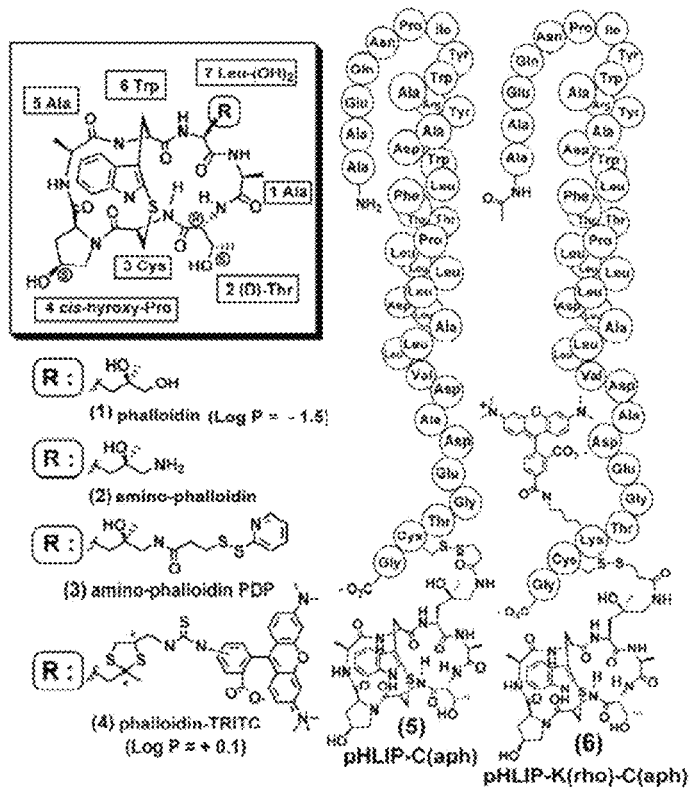
FIG. 8 is a diagram of structures (SEQ ID NOS 235 and 225, respectively, in order of appearance) of phalloidin and derivatives thereof. For phalloidin-TRITC 4, a star (*) denotes a carbon center of mixed or unspecific stereochemistry. Structures of pHLIP delivery constructs (constructs 5 and 6) are described in greater detail in Example 2.

Cancer Cell Proliferation is Inhibited by pHLIP Nanosyringe Mediated Delivery of Membrane Impermeable Toxin Phalloidin Phalloidin, a cytotoxin isolated from the Death Cap mushroom *Amanita phalloides*, binds tightly to actin filaments with a $K_d$<40 nM and stabilizes them against depolymerization. It is a cell-impermeable, polar, cyclic heptapeptide (FIG. 8). When a sufficient amount of phalloidin is micro-injected into the cytoplasm, cell growth and proliferation is inhibited. Phalloidin-TRITC (attached to the C-terminus of pHLIP) is translocated across the plasma membrane of HeLa, JC breast adeno-carcinoma and TRAMP prostate cancer cells (in a pH-dependent manner), inducing stabilization of actin cytoskeleton and formation of multinucleated cells. These results were obtained with a construct in which pHLIP-Cys is photo-crosslinked to phalloidin-TRITC via a thiol-reactive aryl azide linker (i.e. S-[2-(4-azidosalicyl-amido)ethylthiol]-2-thiopyridine). This synthetic approach was convenient for initial experiments, but it is unsuitable for further studies because it results in an undefined mixture of products, partly due to the photo-crosslinking chemistry, and partly due to the fact that phalloidin-TRITC 4 is a mixture of stereo- and regio-isomers (see FIG. 8 for its structural variations).

Design and Syntheses of Delivery Constructs pHLIP-C (Aph) and pHLIP-K(Rho)C(Aph)

To evaluate the therapeutic potential of phalloidin as a pHLIP-delivered cytotoxin, a chemically defined agent was made and characterized. Thus, a single isomer pHLIP-C (aph) (construct 5) in which phalloidin is directly attached to the C-terminus Cys via a short disulfide linker (FIG. 8) was made. The synthesis of construct 5 begins with the commercially available single isomer amino-phalloidin 2, which differs from phalloidin 1 only in that the terminal 6-hydroxyl group of side-chain 7 is replaced by an amino group (FIG. 8). Treatment of amino-phalloidin 2 with the bifunctional linker SPDP provided the pyridyl-disulfide-derivatized amino-phalloidin PDP intermediate 3 (FIG. 1), which is subsequently conjugated to pHLIP-Cys via disulfide exchange to give the final construct 5. This two-step procedure was carried out without purification of intermediate 3. To avoid side reactions and to simplify purification, near quantitative amounts of SPDP (1.2 eq.) and pHLIP-Cys (1.21 eq.) were added. HPLC purification provided the final construct 5 in >90% purity and ~50% yield over two steps, and its identity was confirmed via MALDI-TOF MS. Among all phalloidin side-chains, the position-7 Leu-(OH)$_2$ side-chain is least important for binding to F-actin. Therefore, the short linker attaching amino-phalloidin to pHLIP-Cys in construct 5 is expected to have only a minimal effect on F-actin binding after release into the cytoplasm.

Surprisingly, the pHLIP-C(aph) construct did not stop or suppress cell growth under conditions tested. Several cancer cell lines were studied: HeLa, JC, PC-3, MCF-7; see FIG. 9E for data with JC). Furthermore, pHLIP-C(aph) did not induce the expected cytotoxic effects such as multi-nucleation or cytoskeleton rigidification, which were observed with pHLIP-S-S-(phalloidin-TRITC).

Experiments were carried out to determine why pHLIP translocates phalloidin-TRITC into cells more effectively than phalloidin alone. The results indicated that the hydrophobic rhodamine dye (TRITC) renders phalloidin-TRITC less polar than phalloidin, thus reducing the energetic barrier for translocation (i.e., delivery construct insertion). Indeed, n-octanol/water distribution experiments indicate that phalloidin-TRITC is extracted into the n-octanol phase ~40× more readily than phalloidin, with a Log P value of +0.04 compared to that of −1.5 for phalloidin (FIG. 8). If the contribution of linker structures to cargo polarity is taken into consideration, the Log P difference between the two cargos could be even more pronounced, since the aryl azide photo-crosslinker used in pHLIP-S-S-(phalloidin-TRITC) is more non-polar than the SPDP-derived linker in pHLIP-C (aph).

These results obtained with pHLIP-C(aph) and data from pHLIP-S-S-(phalloidin-TRITC) indicated that the hydrophobicity of the cargo correlates with the efficiency of pHLIP-mediated translocation, and in turn, the ability to induce biological effects in cells. In order to further test this mechanism the pHLIP-K(rho)C(aph) construct 6 in which a rhodamine moiety (i.e. TAMRA) was placed on a Lys residue immediately preceding the Cys residue carrying the phalloidin cargo (FIG. 8). The delivery construct pHLIP-K (rho)C(aph) was designed such that the combined hydrophobicity of phalloidin and TAMRA cargos would be similar to the hydrophobicity of phalloidin-TRITC.

The pHLIP-K-C(aph) intermediate (without the TAMRA moiety) is synthesized in the same fashion as described above for pHLIP-C(aph) 5. By capping the pHLIP-KC peptide amino terminus with an acetyl group during solid-phase peptide synthesis, the rhodamine moiety was selectively conjugated to the Lys side-chain using the succinimidyl ester of 5-TAMRA. This sequence provides pHLIP-K(rho) C(aph) 6 in ~14% overall yield in three steps (starting from the pHLIP-KC peptide). HPLC purification was followed by MALDI-TOF MS of the purified material to ensure the integrity of the final construct 6.

Antiproliferative Effects of pHLIP-K(Rho)C(Aph)

Figure 9A:
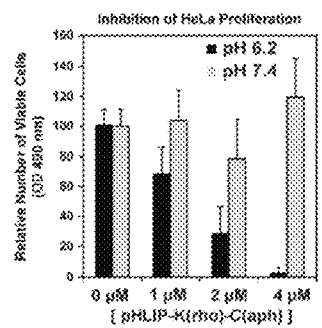
FIGS. 9A-F are a series of bar graphs showing inhibition of cell proliferation after contact with a pHLIP construct. (A) Phalloidin delivery construct pHLIP-K(rho)C(aph) inhibits HeLa cells proliferation in a pH-dependent fashion. HeLa cells in 96-well plates (~4,000 cells per well) were incubated with 1, 2, or 4 µM of pHLIP-K(rho)C(aph) for 3 h at pH 6.2 (black bars) or 7.4 (grey). After 4 days of growth, the number of proliferated cells was estimated using the MTS tetrazolium reagent (with OD 490 nm as read-out). All OD 490 nm readings are normalized to the DMSO control (0 µM, pH 7.4) as 100%, which is ~60,000 to 70,000 cells per well. Errors of the means were estimated at the 95% confidence level using the two-tailed Student's T distribution coefficient (n=12 except n=4 for 4 µM at pH 7.4, see Supporting Information for more details). (B) Inhibition of JC proliferation by pHLIP-K(rho)-C(aph) at pH 6.1 (n=4 except n=8 for 0 µM data). A two-tailed Student's T-test with unequal variance (heteroscedastic) was carried out for the comparison of 0 µM and 2 µM pH 6.1 data sets (*: p-value=0.00071). (C) Inhibition of M4A4 proliferation by pHLIP-K(rho)-C(aph) at pH 6.2 (n=4 except n=8 for 0 µM data). Two pairs of pH 6.2 data sets were compared: 0 µM vs. 2 µM (*: p-value=0.00063) and 0 µM vs. 4 µM (***: p-value=0.00015). (D) HeLa cells were treated with pHLIP-K-C(aph) (n=4), and the anti-proliferative effect was not observed. (E) pHLIP-C(aph) does not inhibit JC proliferation (n=4 except n=8 for 0 µM). (F) Phalloidin alone does not inhibit M4A4 proliferation (n=4 except n=8 for 0 µM).
Figure 9B:
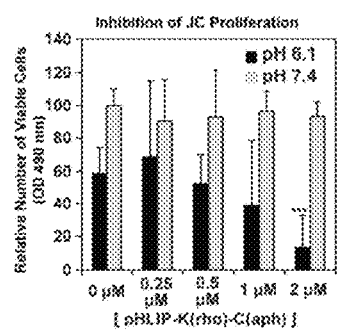
Figure 9C:
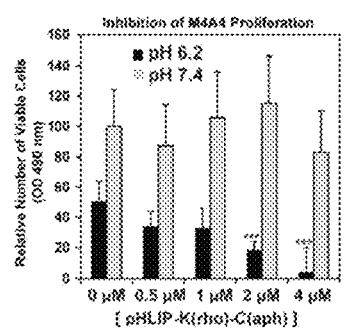

When HeLa cells are treated with pHLIP-K(rho)C(aph) for 3 h at 37° C. with an initial pH of 6.2, cell proliferation is severely disrupted (FIG. 9A). Treatment was carried out at pHLIP-K(rho)C(aph) concentrations ranging from 1-4 µM in 96-well plates with ~4,000 cells per well. After 4 days of growth at normal pH, wells treated with 4 µM of pHLIP-K(rho)C(aph) contained almost no viable cells (up to 97% inhibition was achieved). Meanwhile, cells treated only with DMSO (0 µM column in FIG. 9A) had proliferated to ~60,000 cells per well. The anti-proliferative effect is concentration dependent: When HeLa cells were treated at 1 and 2 µM concentrations, 31% and 71% inhibitions were observed, respectively. As expected, inhibition of proliferation is pH-dependent: Incubation with pHLIP-K(rho)C(aph) at pH 7.4 under the same conditions did not have any effect on cell growth (FIG. 9A), consistent with the notion that delivery of the cell-impermeable toxin phalloidin is mediated by pH-dependent pHLIP insertion across the membrane, (not involving the process of endocytosis). The low pH treatment in itself did not have any deleterious effect on the proliferation of HeLa cells, as shown by control experiments without pHLIP-K(rho)C(aph) (FIG. 9A Compare the 0 µM, pH 6.2, black bar with the 0 µM, pH 7.4, grey bar, there is almost no difference).

pHLIP-K(rho)C(aph)'s anti-proliferative effects were also tested using JC (mouse mammary gland adenocarcinoma) and M4A4 (human breast ductal carcinoma) cells (FIG. 9B/C). In order to inhibit JC cell growth, the pH of the incubation media had to be further lowered to pH 6.1. JC and M4A4 cells seem to be more sensitive to low pH than HeLa cells, because acidity at pH 6.1-6.2 caused non-specific cell death, reducing the number of viable cells by ~40-50% (FIG. 9B/C: 0 µM, black bar vs. grey bar). Nonetheless, growth inhibition specific to the presence of pHLIP-K(rho) C(aph) are prominent: treatment with 2 µM of pHLIP-K (rho)C(aph) inhibited 78% of JC growth (FIG. 9B pH 6.1 black bars: 0 µM vs. 2 µM), while 92% inhibition of M4A4 proliferation is observed at the 4 µM concentration (FIG. 9C, pH 6.2 black bars: 0 µM vs. 4 µM). Compared to the low pH DMSO controls (0 µM), reduction in the growth of JC and M4A4 cells are statistically highly significant (p-value <0.001) even at 2 µM of pHLIP-K(rho)C(aph). In short, the anti-proliferation effects observed with HeLa cells are completely reproducible with JC and M4A4 cells, including the concentration dependence pattern.

Figure 9D:
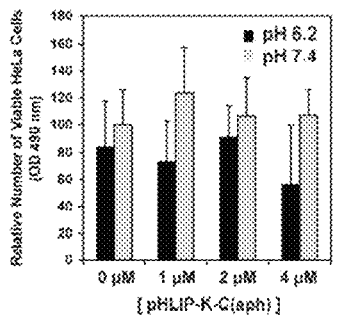
Figure 9E:
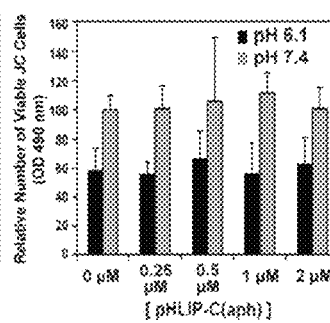
Figure 9F:
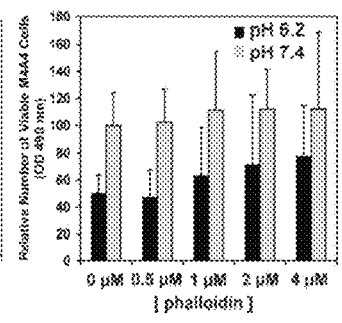
Figure 11A:
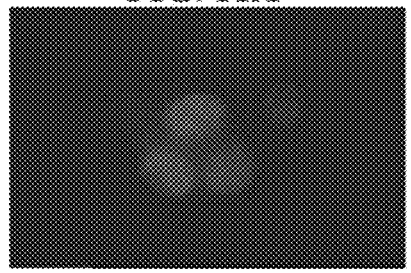
FIGS. 11A-F are photomicrographs showing nuclei of cells treated with pHLIP constructs. HeLa and M4A4 cells were treated with pHLIP-K(rho)C(aph) at 4 µM, pH 6.2 for 3 h. After 2-3 days of growth, a subpopulation of the treated cells became multinucleated. (A) DAPI fluorescence image (artificial blue color) of a M4A4 cell with four nuclei (DAPI selectively stains the nucleus); (B) Phase contrast image of the same multinucleated M4A4 cell; (C) Overlay of images A and B; (D) DAPI fluorescence image of a HeLa cell with four nuclei; (E) Phase contrast image of the same HeLa cell, showing an unusually large volume of cytoplasm; (F) Overlay of D and E. The images were taken at the epi-fluorescence inverted microscope (Olympus IX71) at 100× magnification.
Figure 11D:
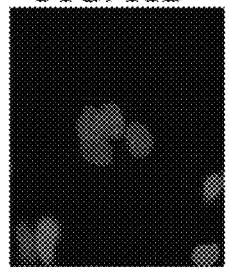
Figure 11B:
Figure 11E:
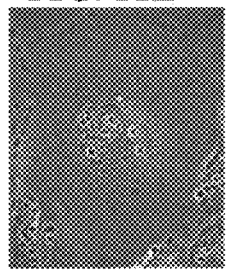
Figure 11C:
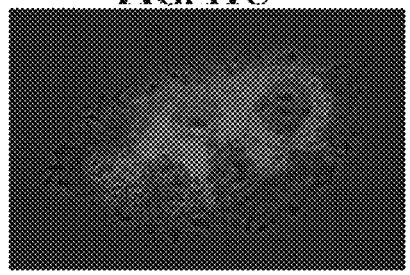
Figure 11F:
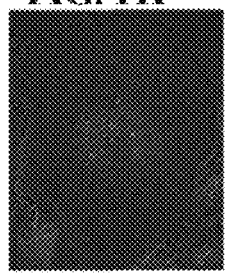

Under equivalent conditions phalloidin (or aminophalloidin) showed no inhibitory effect on M4A4/HeLa proliferation (FIG. 9F, data for phalloidin on M4A4 are shown), consistent with the knowledge that phalloidin is a cell-impermeable toxin. The rhodamine moiety on pHLIP-K (rho)C(aph) is absolutely necessary for inhibition, since: (a) under the same conditions pHLIP-C(aph) 5 does not stop the growth of JC or HeLa cells (FIG. 9E, data with JC cells shown); and (b) no inhibitory effect was observed when HeLa cells were treated with pHLIP-K-C(aph)—a construct missing the rhodamine moiety but otherwise identical to pHLIP-K(rho)C(aph) (FIG. 9D). However, in the case of pHLIP-K-C(aph), it is possible that the positively charged free Lys residue in the C-terminus further burdens pHLIP insertion, blocking cargo entry. Furthermore, when HeLa cells were treated with an unmodified, 'native' pHLIP peptide that does not contain Lys or Cys in its C-terminus (thus with no rhodamine or phalloidin cargo attached), no inhibition of proliferation was observed (FIG. 13). Hence, pHLIP insertion in itself does not hinder cell growth under these conditions, consistent with the data indicating that pHLIP is not toxic.

These data therefore indicate that the combined hydrophobicity of the cargo(s), manifested as the overall property of the pHLIP inserting C-terminus, determines the efficiency of cargo delivery into cells.

Morphological Changes of Cells Treated with pHLIP-K(Rho)C(Aph)

As observed in cells incubated with the heterogeneous pHLIP-S-S-(phalloidin-TRITC) construct, HeLa cells treated with pHLIP-K(rho)C(aph) showed signs of cytoskeletal immobilization. After incubation with 4 μM of pHLIP-K(rho)C(aph) at pH 6.1 for 3 h, HeLa cells exhibited a reduced ability to contract and 'round up' when trypsinized (FIGS. 10A-E), whereas cells treated at pH 7 rounded and detached as expected. A subpopulation of the low-pH treated cells also became multinucleated (FIGS. 11A-F). Both observations demonstrate that pHLIP-K(rho)C(aph) delivers the toxic cargo across the plasma membrane, and the released phalloidin molecules bind to actin filaments and stabilize them, interfering with F-actin dynamic turnover required for both cytokinesis and cell contraction.

Trp Fluorescence Studies of pHLIP-K(Rho)C(Aph) and pHLIP-C(Aph) in Liposomes

To further understand why pHLIP-K(rho)C(aph) showed promising anti-proliferative effects but not pHLIP-C(aph), the insertion behavior of both constructs were studied in 1-palmitoyl-2-oleoyl-sn-glycero-3-phosphocholine (POPC) liposomes using Trp fluorescence. The pHLIP sequence contains two Trp residues, both located in the transmembrane region. Upon helix formation and insertion, one Trp residue is likely positioned at the lipid headgroup region, while the other IS in the hydrophobic interior of the bilayer. In addition, phalloidin also has a Trp residue with maximum position of absorbance spectrum shifted to long wavelengths ~300 nm (compared to 280 nm for Trp residues).

Figure 12D:
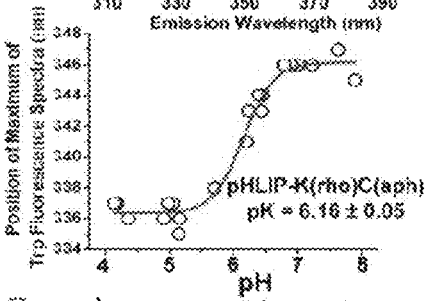

Trp residues were excited at 295 nm, and fluorescence emission spectra were collected from 310-400 nm. The emission maximum of pHLIP-C(aph) is centered on 350 nm at pH 8 (FIG. 12A). Lowering the pH leads to progressive emission maximum blue-shifts to ~338 nm, accompanied by increases in fluorescence intensity, and both features are most pronounced between pH 6.2 and pH 5.9. These spectral changes are very similar to what have been observed for pHLIP alone, consistent with the transition of Trp residues from lipid interface to deeply buried positions in the lipid bilayer, when pHLIP-C(aph) is inserted into membrane at pH 5. The change of fluorescence of phalloidin Trp would be insignificant, since phalloidin translocated across a membrane would be in an aqueous environment as it was before the translocation. A similar trend of spectral blue-shift is observed for pHLIP-K(rho)C(aph): when pH is decreased from 7.9 to 5.2, the wavelengths of emission maximum shifts from ~346 nm to ~336 nm (FIG. 12B). However, the fluorescence intensity seems to peak between pH 6 and pH 5.5, and further blue-shift of the emission maximum is accompanied by decrease in fluorescence intensity (e.g. compare pH 5.7 yellow trace to pH 5.2 green trace in FIG. 12B). Perhaps this is due to the more efficient quenching of phalloidin Trp fluorescence by the rhodamine moiety at lower pH, either intramolecularly, due to some inherent rhodamine pH-sensitivity, and/or intermolecularly, in response to pHLIP insertion. The values of apparent pKa of insertion are estimated from the Trp emission maximum blue-shifts: for pHLIP-C(aph), the pKa value is 6.14±0.02 (FIG. 12C), and for pHLIP-K(rho)C(aph) it is 6.16±0.05 (FIG. 12D). These data are consistent with a pKa of insertion ~6 for pHLIP and support the mechanism that both pHLIP-K(rho)C(aph) and pHLIP-C(aph) insert into POPC bilayers in a pH-dependent fashion similar to pHLIP without any cargo.

Figure 12E:
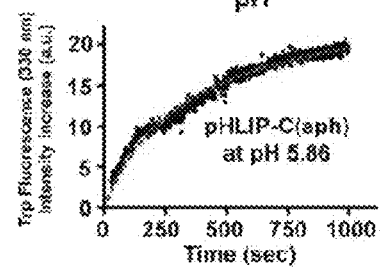
Figure 12F:
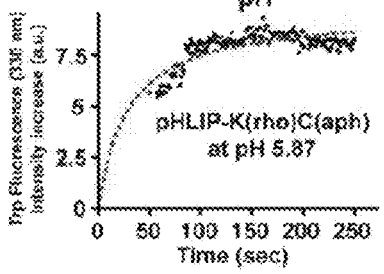

To test kinetics, studies were carried out to determine whether the polar phalloidin cargo may slow down the insertion process. To probe this possibility, Trp fluorescence at 330 nm was followed immediately after adjusting pH from 8 to ~5.9 without equilibration (usually >30 min). For pHLIP-C(aph), emission begins to plateau after roughly 15 min (FIG. 12E). In contrast, fluorescence increase for pHLIP-K(rho)C(aph) stopped after just 2 min (FIG. 12F). These results indicate that pHLIP-K(rho)C(aph) inserts into POPC bilayers at a rate that is almost a magnitude faster than pHLIP-C(aph).

Delivery of Cell-Impermeable Agents Across Lipid Bilayer Membranes pHLIP peptides deliver cell-impermeable agents across membranes and are therefore useful for delivery of therapeutic molecules in treating cancer. Depending upon the therapeutic cargo to be delivered, the hydrophobicity profile of the pHLIP peptide carrier is adjusted, e.g., by adding a second cargo or by making amino acid substitutions to compensate for a change in hydrophobicity resulting from the conjugated (first) therapeutic cargo.

Two delivery constructs, pHLIP-C(aph) and pHLIP-K(rho)C(aph), were synthesized; Both carry the phalloidin cargo at the C-terminus but differ in that the latter construct also carries a rhodamine moiety nearby at the insertion end. The pHLIP-K(rho)C(aph) construct severely disrupts the proliferation of cancer cells whereas pHLIP-C(aph) does not. A single 3 h treatment with 4 μM of pHLIP-K(rho)C(aph) at pH 6.1-6.2 led to >90% growth inhibition of HeLa and M4A4 cells. Thus, the additional rhodamine moiety enhances the combined hydrophobicity of the cargos, making the overall property of the inserting C-terminus more suitable for insertion. Biophysical experiments were also carried out using liposomes to further characterize both constructs. Under equilibrium conditions, both constructs insert into lipid bilayer with the same apparent pKa of ~6.15, similar to pHLIP without any cargo. This pKa of insertion for pHLIP-K(rho)C(aph) is completely consistent with the level of acidity required for biological effects in cell experiments (pH 6.1-6.2). The C-terminus appendages do not significantly alter the insertion equilibriums at different pHs. The result that pHLIP-C(aph) also seems to be able to insert, at least into POPC bilayer, is also in agreement with the finding that pHLIP insertion is not disrupted by C-terminus model cargos similar to phalloidin in polarity, size and shape. Surprisingly, preliminary kinetic experiments suggest that the rate of pHLIP-K(rho)C(aph) insertion into POPC bilayer is about a magnitude faster than in the case of pHLIP-C(aph).

Accordingly, slow rate of insertion of pHLIP-C(aph) limits the amount of phalloidin delivered during the 3 h incubation period with cells at pH 6.1-6.2. The time window for pHLIP insertion (and phalloidin translocation) was found to be shorter than 3 hours, exacerbating the kinetic disadvantage of the pHLIP-C(aph) construct. Observable biological effects (such as growth inhibition and morphological changes) are directly related to the amount of phalloidin translocated. The results of the biophysical studies with liposomes indicate that pHLIP-C(aph) is able to translocate phalloidin into cells; however, the amount of intracellular phalloidin accumulated is not enough to produce noticeable biological effect. In order to stabilize actin filaments against depolymerization, a critical intracellular concentration of phalloidin must be readed. Inhibition of cell growth (i.e, from delaying to stopping the proliferation of PtK2 kidney epithelium cells) required micro-injection of phalloidin solutions in the 0.2-1 mM concentration range, leading to intracellular phalloidin concentrations in the range of 50-500 µM.

Further studies were carried out to examine the biodistribution and therapeutic effect of pHLIP-Rhodamine-S-S-phalloidin. 20 ul of 100 uM pHLIP-Rhodamine-S-S-phalloidin were given as multiple (3 times) intratumoral injections (each second day). The tumor growth was monitored and animals were terminated 4 weeks after first administration of the construct. Tumors and organs were removed, weighted and imaged. Average tumor weight of animals treated with pHLIP-Rhodamine-S-S-phalloidin was 0.5±0.14 g, while average tumor weight of animals received just buffer was 1.9±0.5 g. The construct was also administered intravenously and intraperitoneally.

The results described herein show that pHLIP-K(rho)C (aph) delivers enough phalloidin molecules to kill cancer cells in vitro at pH 6.2 but has no effect on cells at neutral pH, indicating that hydrophobically-balanced pHLIP peptide-cargo constructs, e.g., anti-tumor constructs, selectively and efficiently destroy cancer cells while not affecting normal cells.

The data indicated that pHLIP-Rhodamine effectively delivers phalloidin to tumors in vivo via i.v., i.p. or intratumoral routes. pHLIP-Rhodamine-S-S-phalloidin promoted inhibition of tumor growth, and rhodamine imaging was observed only in tumor even 4 weeks after construct administration. No signal was observed in kidney or liver, which demonstrates ability of construct to stay in tumor site up to 4 weeks. Thus, compositions and methods using pHLIP-targeted intracellular drug delivery enhance the efficacy of treatment and significantly reduce side effects.

Example 3: pHLIP-Assisted Delivery of Amanitin to Cancer Cells

α-amanitin is a cytotoxin isolated from the Death Cap mushroom *Amanita phalloides*.

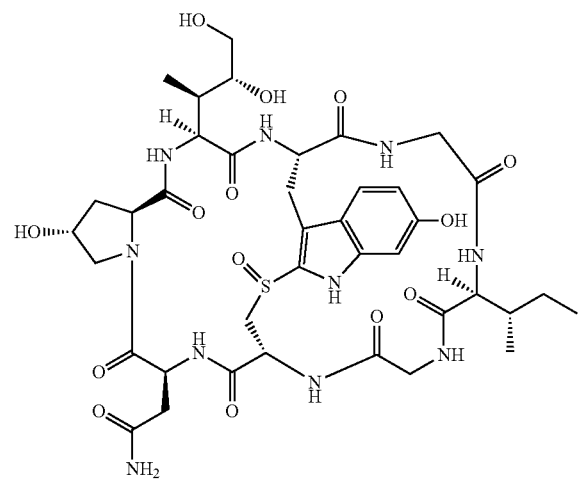 [SMILES: CC[C@H](C)[C@@H]1NC(=O)CNC(=O)[C@@H]2Cc3c([nH]c4cc(O)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

It is a cyclic peptide of eight amino acids, is cell impermeable, and acts as an inhibitor of RNA-polymerase II. Constructs are synthesized as follows:

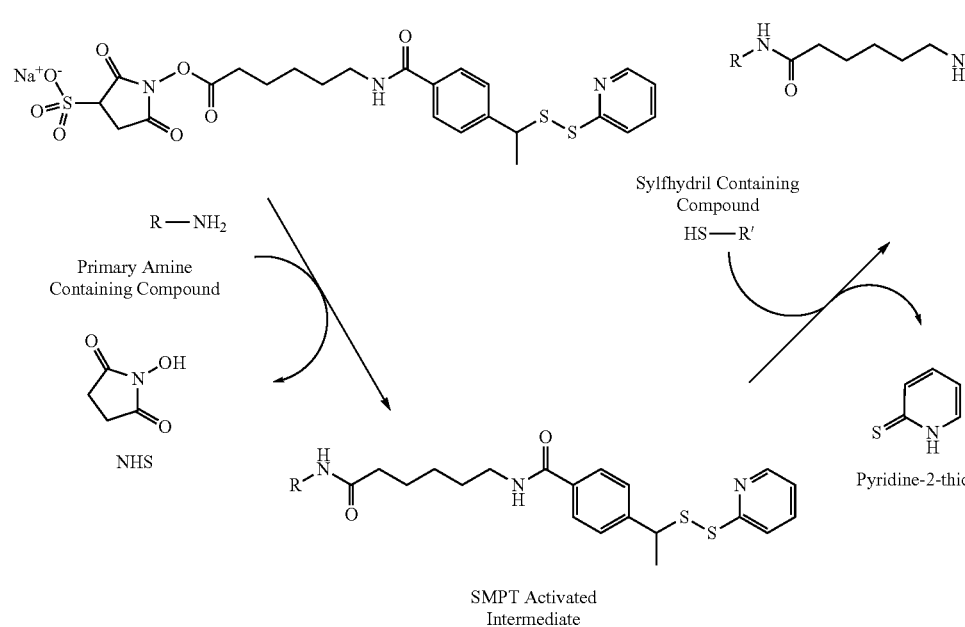

First stage: Conjugation of amanitin with Sulfo-LC-SMPT (activated NHS-ester reacts with the amine group to form amide linkage). Second stage: Conjugations of amanitin-LC-SMPT with pHLIP-C(activated 2-pyridyldithiol group reacts with sulfhydryl group to form a disulfide linkage).

In another approach, the linker SPDP was used.

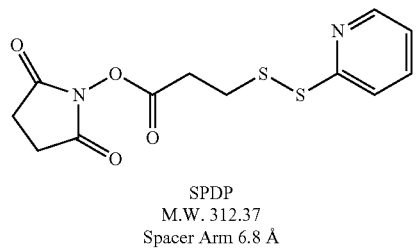 [SMILES: O=C(CCSSc1ccccn1)ON1C(=O)CCC1=O]

SPDP
M.W. 312.37
Spacer Arm 6.8 Å

SPDP is shorter chain cross-linker than SMPT, and as a result it is less hydrophobic. Thus SPDP-amanitin is more polar than SMPT-amanitin. HeLa cells were treated with pHLIP-SPDP-amanitin for 3 h in DMEM w/o FBS at pH 6.2 or 7.4. Constructs were removed, and Hela cells were incubated in standard medium for 24 h. MTS test was done. With SPDP as a linker, a strong difference in cytotoxicity was observed between pH7.4 and 6.5 especially at low concentrations, which is desirable for in vivo use.

Thus, Amanitin is another exemplary toxin that was conjugated to pHLIP and was delivered to cells in a pH-dependent manner and induced pH-dependent cytotoxicity. pHLIP effectively delivered amanitin to tumor cells, and the data indicate that pHLIP-amanitin conjugates (with or without a linker) are useful to treat malignant tumors.

In another amanitin study, pHLIP labeled with Alexa750 (covalently attached to the N-terminus) and amanitin (attached by SMPT (linker) via S—S bond to the C-terminus) was given to animals bearing tumor in right flank as a single iv or ip injection. Fluor 750-modified pHLIP-SMPT-amanitin is a double-labeled construct. K-pHLIP-C: AKEQN-PIYWARYADWLFTTPLLLLDLALLVDADECT (SEQ ID NO: 226).

Tumor was created by injection of HeLa-GFP cancer cells into right flank of athymic nude mice. Imaging was performed at 24 hrs post-injection. Alexa750-pHLIP-amanitin is an example of the construct in which pHLIP is conjugated with two cargo molecules on different termini. The construct is used for imaging and therapy at the same time.

Effect of Wt pHLIP-SMPT-Amanitin on Cancer Cells: pH-Dependent Cell Death

Figure 57:
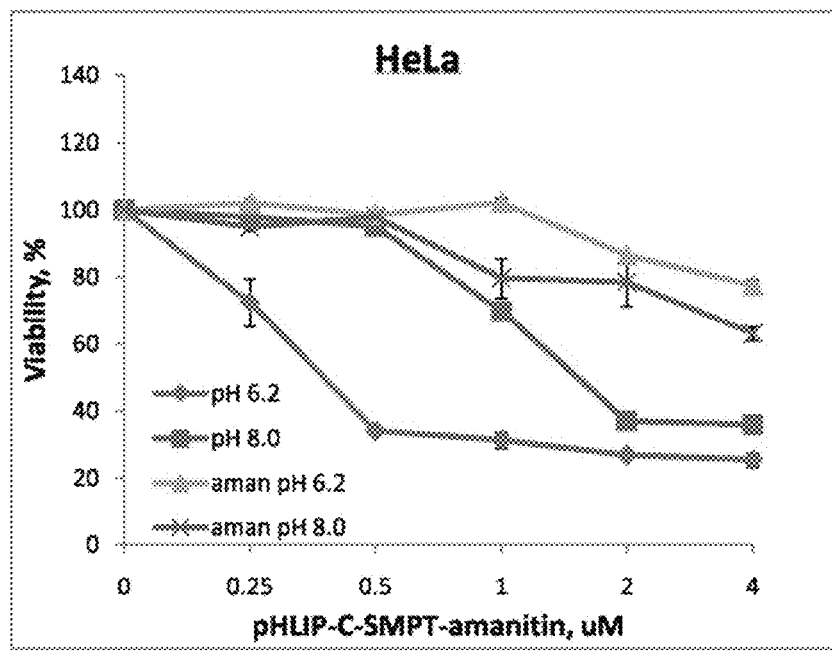
FIG. 57 is a line graph showing the Effect of wt pHLIP-SMPT-amanitin on cancer cells: pH-dependent cell death.

HeLa cells were treated with pHLIP-SMPT-amanitin or amanitin alone in PBS at pH 6.2 or pH 8.0 for 1.5 h. Constructs were removed and cells were incubated in 10% FBS/DMEM for 48 h (FIG. 57).

Figure 58:
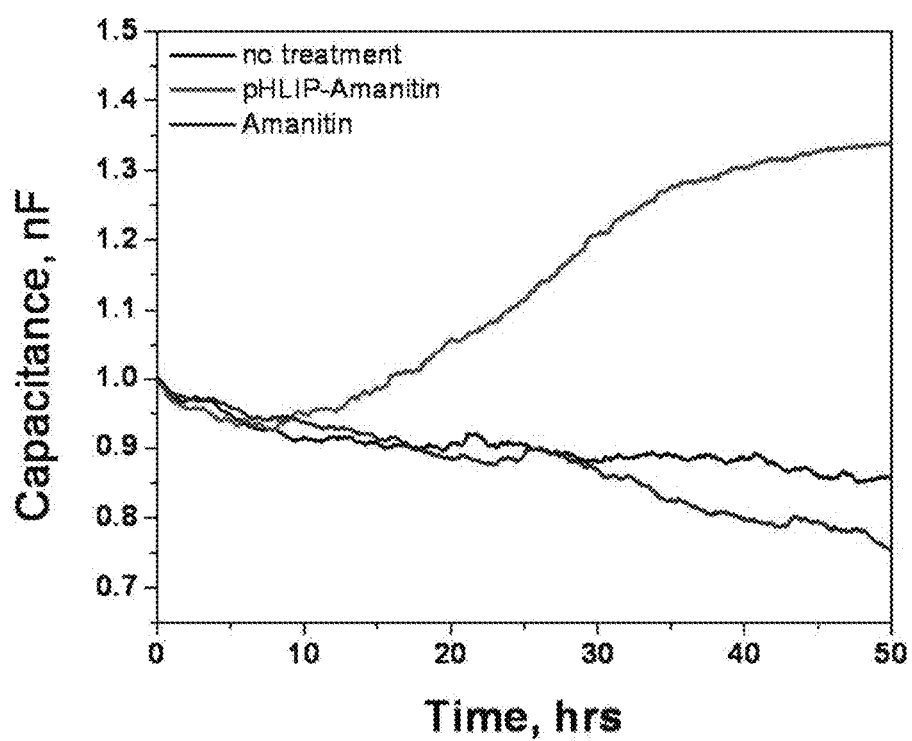
FIG. 58 is a line graph showing the electric Cell-substrate Impedance Sensing (ECIS) assay: Kinetics of induction of cell death by pHLIP-SMPT-amanitin.
Figure 59A:
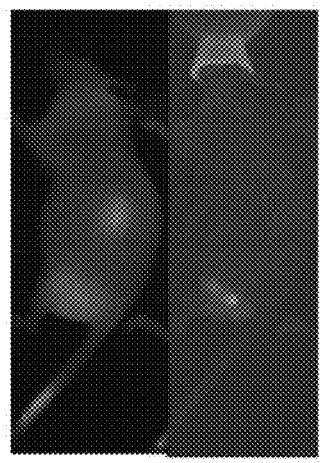
FIGS. 59A-B are a series of images showing pHLIP labeled with Alexa750 (covalently attached to the N-terminus) and amanitin (attached by SMPT via S—S bond to the C-terminus) administered to the tumors of mice.
Figure 59B:
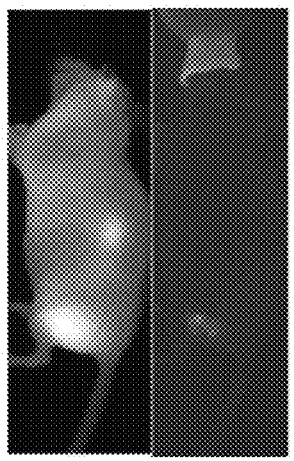
Figure 61:
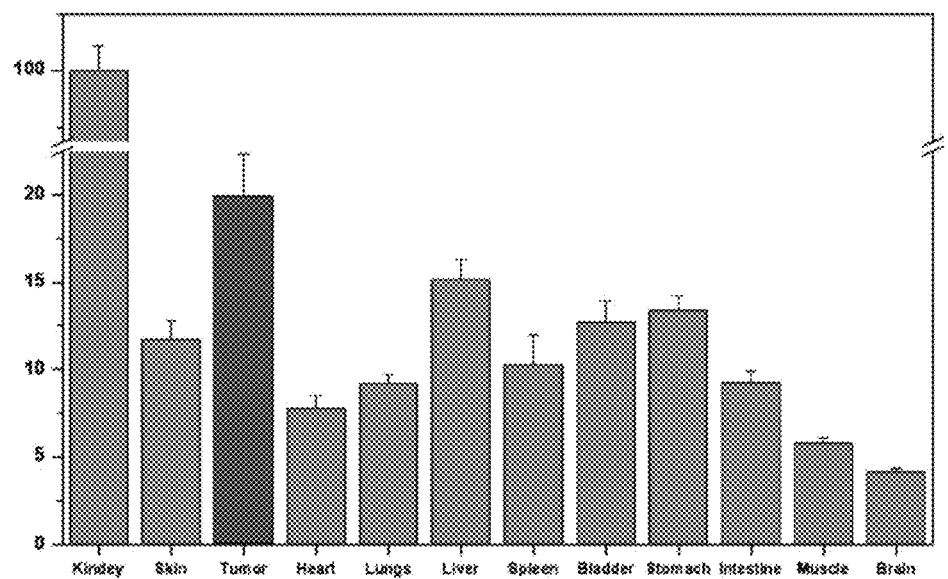
FIG. 61 is a bar chart showing normalized mean fluorescence of tumor and organs at 4 hours after injection of Var7 pHLIP.
Figure 62:
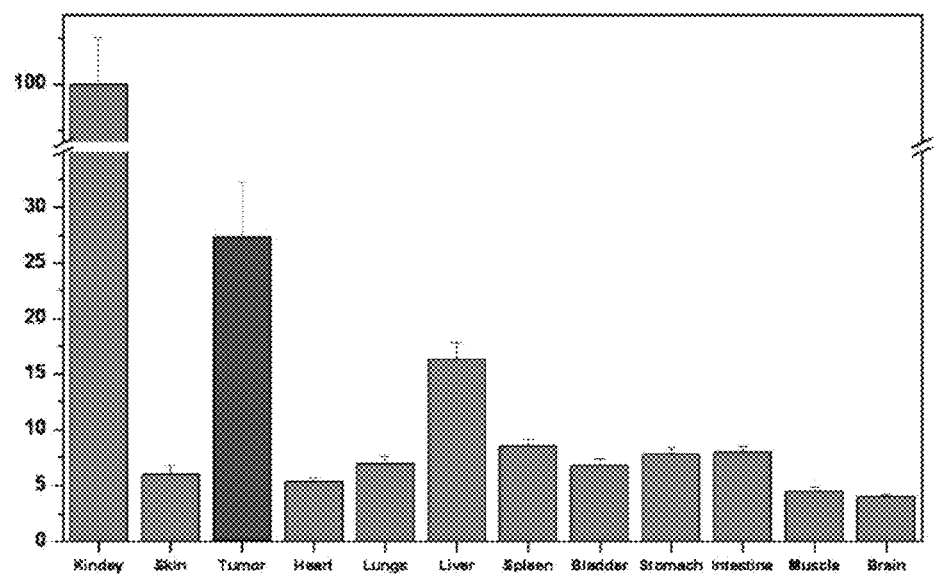
FIG. 62 is a bar chart showing normalized mean fluorescence of tumor and organs at 24 hours after injection of Var7 pHLIP.
Figure 63:
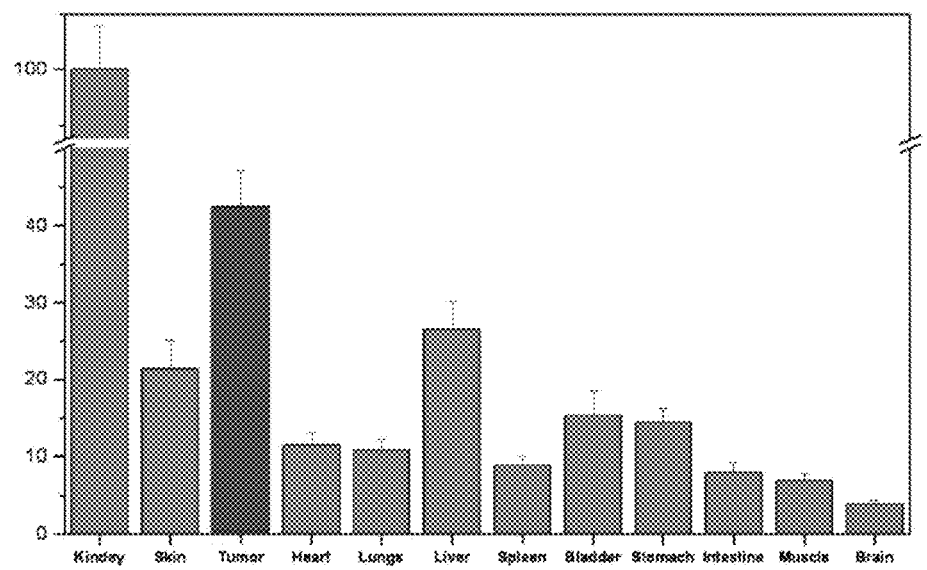
FIG. 63 is a bar chart showing Normalized mean fluorescence of tumor and organs at 4 hours after injection of Var3 pHLIP.
Figure 64:
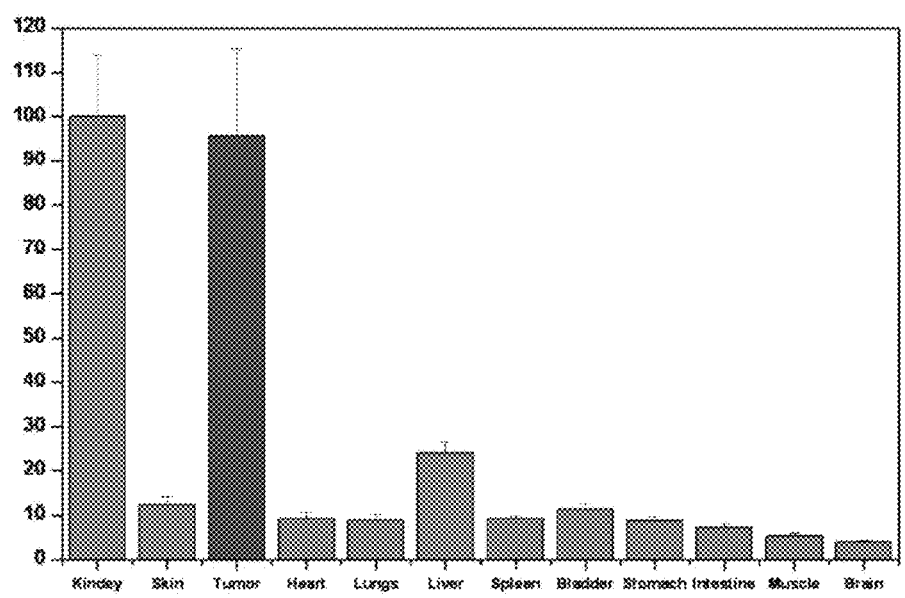
FIG. 64 is a bar chart showing normalized mean fluorescence of tumor and organs at 24 hours after injection of Var3 pHLIP.

Electric Cell-Substrate Impedance Sensing (ECIS) Assay: Kinetics of Induction of Cell Death by pHLIP-SMPT-Amanitin HeLa Cells were Treated with 1 uM of pHLIP-Amanitin or Amanitin at pH 6.2 for 1.5 h, then constructs were removed and cells were transferred to grow at pH 7.4. The increase of capacitance reflects cell death. The plot shows that cell continue to grow after treatment with amanitin, while cells were completely dead at about 40-45 hours after treatment (FIG. 58).

pHLIP labeled with Alexa750 (covalently attached to the N-terminus) and amanitin (attached by SMPT via S—S bond to the C-terminus) were give to animals bearing tumor in right flank as a single iv or ip injection. Tumor was created by injection of HeLa-GFP cancer cells into right flank of athymic nude mice. Imaging was performed at 24 hrs post-injection. NIR (red) and GFP (green) imaging 24 hrs post-injection (FIGS. 59A-B).

Example 4: pHLIP-Boron Cluster Conjugates for Boron Neutron Capture Therapy (BNCT)

pHLIP is conjugated to a boron-containing compound, which is later activated by neutrons to induce a toxic effect. The boron-containing compound was conjugated to the N-terminus and the C-terminus of pHLIP.

Boron Neutron Capture Therapy (BNCT). A major goal in tumor therapy is to develop an approach that targets cancer cells while sparing normal cells. BNCT provides a means to deliver targeted radiation at the cellular level, allowing selective cell ablation. BNCT is based on the irradiation of boron-10 ($^{10}$B) with thermal neutrons. Boron has no significant cytotoxic effect by itself, but when combined with low doses of neutrons, highly effective radiobiological particles are produced: An alpha particle ($^4$He) and lithium nucleus ($^7$Li) are released with a combined energy of 2.3 MeV, and the combined track length of these densely ionizing particles is approximately 14 µm, which is about the diameter of a single cell, so that efficient cell killing from the reaction products is confined to tumor cells containing boron.

Boron-carrying pHLIP constructs were synthesized and biodistribution studies were performed in tumor bearing mice. Studies were carried out to test whether pHLIP delivery can attain tumor boron concentrations of ~15 µg $^{10}$B/g (approximately $10^9$ $^{10}$B per cell), a prerequisite for therapeutic effect in BNCT. The boron cage molecule Disodium mercapto-closo-dodecaborate (BSH) was chosen as the boron cargo for pHLIP because (a) it has previously been used in human clinical trials, (b) it contains 12 boron atoms per cluster, and (c) a sulfhydryl group (SH) is available for standard conjugation chemistry.

To synthesize N-term and C-term pHLIP-boron constructs, chemistry was developed to attach BSH to either the N- (extracellular) or C- (intracellular) terminus of pHLIP. For the N-term BSH-pHLIP construct, BSH was conjugated to Lys at the N-terminus of pHLIP via the bifunctional crosslinker Sulfo-GMBS. For the C-term disulfide cleavable pHLIP-S-S-BSH construct, pHLIP-Cys was activated via treatment with the Ellman reagent DTNB, resulting in the pHLIP-S-S-TNB intermediate, which in turn provided the desired C-term pHLIP-S-S-BSH construct via disulfide exchange with BSH.

For biodistribution studies, aqueous solutions of N- or C-term pHLIP-BSH constructs were quantified by UV absorbance at 280 nm (pHLIP concentration). Corresponding boron concentrations were measured by prompt-gamma neutron activation analysis (PGNAA) to confirm the construct concentration. Four female C3D2F1 mice bearing murine breast adenocarcinomas (100 to 300 mg tumor) were each administered 100 µL of either the N- or C-term pHLIP-BSH solution in a single tail vein injection. The mice were killed 5 days after the injection and tissues were harvested for boron analysis by inductively coupled plasma atomic emission spectroscopy (ICP-AES). Tissues harvested from animals that received C-term pHLIP-BSH (30 µg of boron dose) all contained less than 0.3 µg g$^{-1}$. Mice administered the N-term BSH-pHLIP received a higher boron dose of 70 µg (or 3.5 µg boron per g of mice) and accumulation was evident in tumor as shown in the Table below.

| N-term BSH-pHLIP (~3.5 μg g$^{-1}$ $^{10}$B administered) | | |
|---|---|---|
| | Measured $^{10}$B concentration (μg g$^{-1}$) | |
| | Animal 1 | Animal 2 |
| Tumor | 0.79 | 0.61 |
| Kidney | 0.92 | <0.3 |
| Liver | 1.1 | <0.3 |
| Normal tissues* | <0.3 | <0.3 |

The table shows the results of boron biodistribution measurements on tumor bearing mice that received boronated N-term pHLIP. *—Other tissues analyzed include: muscle, skin, brain, lung spleen and heart.

Figure 65:
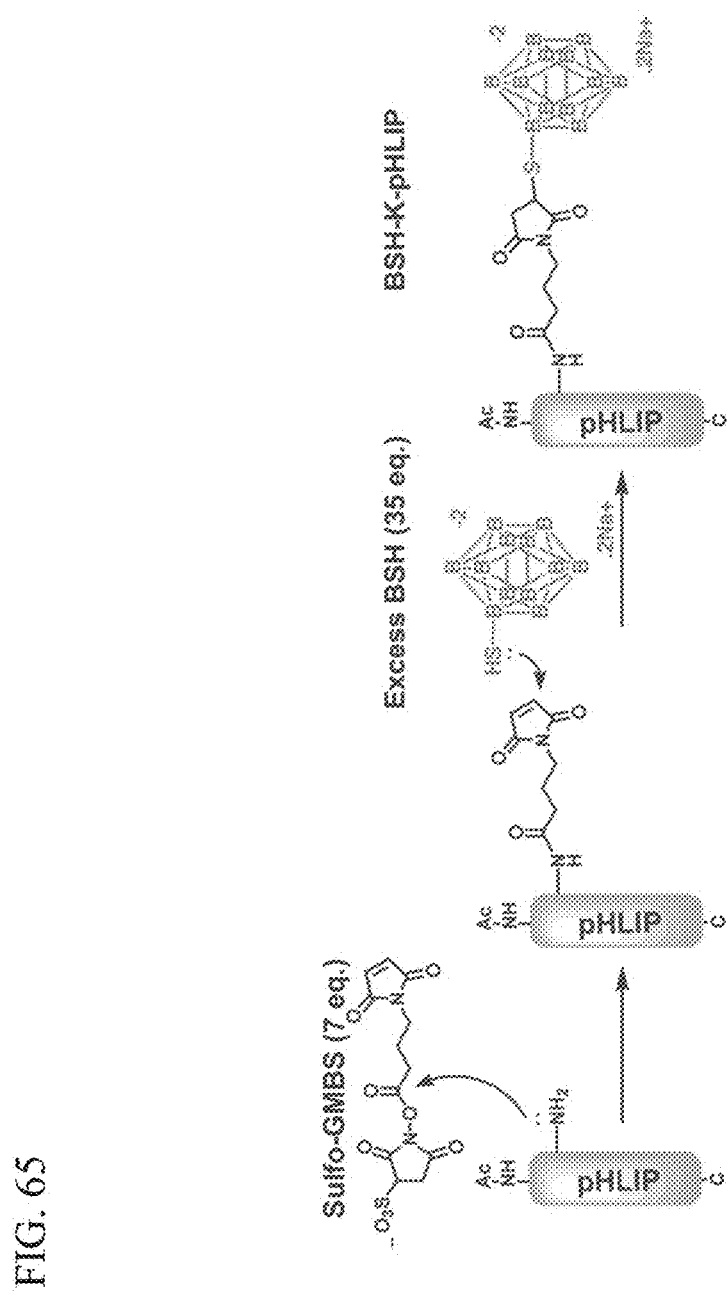
FIG. 65 is a diagram showing a synthesis method for making BSH-pHLIP.

A synthesis method for making BSH-pHLIP is shown in FIG. 65.

Synthesis of N-term BSH-pHLIP (2 step, one-pot). Step 1: To 10 mg of K-pHLIP (2.36 micromole, 1 equivalent) dissolved in 500 μL of aq. phosphate (Pi) buffer (100 mM, pH 7.9) was added 6.3 mg of the cross-linker Sulfo-GMBS (16.5 micromole, 7 equivalent, from Pierce). More aq. Pi buffer was added to the reaction mixture to give a total volume of 1.3 mL, final Pi concentration of 250 mM, and pH 8. The reaction mixture was allowed to sit at 0-4° C. over night. Small portions (1-2 μL) of the reaction mixture were removed at 2 hr and 14 hr, diluted with 10 μL of water, and analyzed on reverse phase HPLC (High Pressure Liquid Chromatography): disappearance of the starting material (s.m.) peak (K-pHLIP at ~48 min retention time) was observed along with the appearance of a new product peak (P) at ~52 min retention time ($t_r$), presumably corresponding to the crosslinker attached intermediate. Step 2: To the reaction mixture, 17 mg of BSH (80.5 micromole, 35 equivalent) was added. The resulting mixture was vortexed and allowed to stand at 0-4° C. for 4 hr. HPLC showed that the reaction was complete: the intermediate peak ($t_r$~52 min) disappeared and was replaced by a new peak with $t_r$~55 min, presumably that of the desired product BSH-K-pHLIP. The reaction mixture was purified on HPLC (6 injections). The fractions collected were neutralized with a few L of triethylamine and lyophilized to give 5.5 mg of desired product (~1.2 micromole, 52% yield over two steps). The product was quantified using 280 nm UV absorbance of the pHLIP peptide ($\in$ 280 nm~13,940 M$^{-1}$cm$^{-1}$).

HPLC conditions (for both analytical and purification purposes): Zorbax semi-prep 9.4×250 mm SB-C18 column; flow rate: 2 mL/min; phase A: water+0.01% TFA; phase B: acetonitrile+0.01% TFA; method: 10 min at 99:1 A/B, 50 min from 99:1 A/B to 10:90 A/B; 5 min at 10:90 A/B; 5 min from 10:90 A/B to 99:1 A/B; 10 min at 99:1 A/B). K-pHLIP retention time: ~48 min; intermediate retention time: ~52 min; desired product BSH-K-pHLIP retention time: ~55 min.

N-term BSH-K-pHLIP construct was further characterized with MALDI-TOF MS. Weak but correct molecular ion signals corresponding to the expected weight of the desired product BSH-K-pHLIP were found in both positive and negative ion modes of MALDI-TOF MS: positive ion mode [M+Na$^+$]$^-$ mass expected: 4634, found: 4647; negative ion mode [M-H$^+$]$^-$ mass expected 4610, found 4610. Further, in the positive ion mode, mass of the postulated intermediate was also identified (expected: 4402; found: 4405), since the C—S bond in BSH-K-pHLIP is weak and likely to be cleaved (in a homolytic fashion) during laser desorption.

Figure 66:
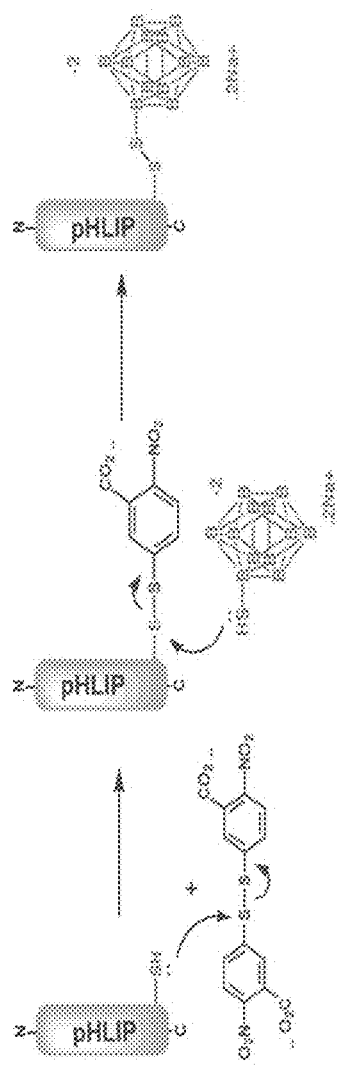
FIG. 66 is a diagram showing synthesis of C-term pHLIP-S-S-BSH.

Synthesis of C-term pHLIP-S-S-BSH is shown in FIG. 66.

BSH reactivity toward the Ellman's reagent. To investigate whether BSH has a free SH (as oppose to the oxidized BSH-S-S-BSH disulfide form), and whether it chemically behaves as a normal SH group in a SN2 disulfide exchange reaction, the Ellman test was performed with BSH. When 1 eq. of the Ellman reagent DTNB was titrated with 0.2 vs. 0.6 eq. of BSH, 330 nm absorbance of DTNB decreased, while 410 nm absorbance corresponding to the released thiol-nitro-benzoate product increased.

Synthesis of C-term pHLIP-S-S-BSH via disulfide exchange with activated intermediate pHLIP-S-S-TNB. pHLIP-Cys was activated via treatment with the Ellman reagent DTNB (step 1), resulting in the pHLIP-S-S-TNB intermediate, which provided the desired C-term pHLIP-S-S-BSH via disulfide exchange with BSH. Step 1. To 0.95 mg of DTNB (2.4 μmole, 2 eq.) dissolved in 368 μL of 0.1 M aq. Pi buffer (pH 7.3, saturated with Ar) was added 5.1 mg of pHLIP-Cys (1.2 μmole, 1 eq.) in 200 μL of 0.1 M aq. Pi buffer (pH 7.8, saturated with Ar). The addition was carried out in 10 small portions over one hour (i.e. 0.1 eq. of pHLIP-Cys was added every 5 min). After the reaction mixture was allowed to stand at room temperature for 2 h, it was purified on HPLC to give 2.7 mg of the desired product pHLIP-S-S-TNB (0.6 μmole, 50% yield). The fractions collected were analyzed by UV-vis absorbance. The identity of pHLIP-S-S-TNB was further assured by MALDI-TOF MS in unequivocal fashion (mass expected 4437, mass found 4437). HPLC method: 20 min at 99:1 A/B, 70 min from 99:1 A/B to 1:99 A/B; 3 min at 1:99 A/B; 10 min from 1:99 A/B to 99:1 A/B; 5 min at 99:1 A/B (otherwise same as previously described). s.m. DTNB retention time ($t_r$): ~63 min; pHLIP-S-S-TNB retention time: ~68 min. Step 2. To 1.1 mg of the activated pHLIP-S-S-TNB intermediate (0.25 μmole, 1 eq.) dissolved in 500 μL of 0.1 M aq. Pi buffer (final pH 6.5) was added 2.5 mg of BSH (11.9 μmole, 48 eq.). The resulting reaction mixture was vortexed and allowed to stand at room temperature for 5 h and then at 0-4° C. over night. The reaction progress was monitored and the desired product purified by HPLC. Approximately 1 mg of purified pHLIP-S-S-BSH was obtained (90% yield), i.e. the overall yield of pHLIP-S-S-BSH over two steps (from pHLIP-Cys) is 40%.

The UV-vis absorbance spectra of pHLIP-S-S-TNB (s.m. of step 2) and pHLIP-S-S-BSH (product of step 2) are also clearly different—the absorbance above 300 nm, which corresponds to the thiol-nitro-benzyl (TNB) ring, is absent in the product, consistent with the displacement of the TNB group by BSH.

Boron analysis. A bulk boron concentration in normal tissue and tumor is measured by PGNAA or ICP-AES. Prompt Gamma Neutron Activation Analysis (PGNAA): The method of PGNAA measures the 478 keV prompt photon emitted during $^{10}$B(n,a)$^7$Li reactions. It is a non-destructive technique that preserves the specimen being analyzed. A collimated beam of slow (thermal) neutrons is directed at a sample containing the unknown quantity of $^{10}$B. Gamma rays emitted during capture of thermal neutrons by both hydrogen and $^{10}$B are detected by a high purity germanium detector and associated pulse height spectroscopy system. By measuring the ratio of detected gamma rays from hydrogen and boron, and knowing the concentration of hydrogen in the sample, the unknown concentration of boron can be determined. The system allows rapid analysis for 2 μg or more of $^{10}$B.

Inductively coupled plasma atomic emission spectroscopy (ICP-AES) is used for the analysis of small (<0.1 mL) or low concentration (<0.5 µg g$^{-1}$) of samples. This destructive analysis system requires samples in liquid, particulate-free solution, but is capable of measuring bulk boron concentrations as low as 20 ng g$^{-1}$. The ability to perform analyses on 1.0 mL of digested tissue allows accurate measurement of boron concentrations in small tissue specimens weighing approximately 25-50 mg. Samples are digested at room temperature overnight in 0.15 mL of a 1:1 mixture of concentrated sulfuric and nitric acids; addition of 0.5 mL of a 10% solution of the detergent Triton X-100 and dilution to 1 mL with water results in a clear solution for analysis. The PGNAA and ICP-AES are cross-calibrated by analyzing the same boron standard solutions.

Tumor studies. A murine breast adenocarcinoma model was chosen, since it is known to create a low extracellular pH environment in vivo, and pHLIP selectively accumulates in this type of tumor at a high concentration. Female C3D2F1 mice ranging in age from 6 to 8 weeks and weighing approximately 20 g was used in these studies. Murine breast adenocarcinoma (CRL-2116) cell lines from the American Type Culture Collection (ATCC) was cultured in Dulbecco's modified Eagle's medium (DMEM) supplemented with 10% fetal bovine serum (FBS), 100 units/ml penicillin, 0.1 mg/ml streptomycin, and 2 mM glutamine in a humidified atmosphere of 5% CO$_2$ and 95% air at 37° C. Cancer cells were grown to 70% confluence, then harvested and resuspended in L-15 medium. Mouse tumors was established by subcutaneous injection of breast cancer cells (10$^5$-10$^7$ cells/flank/0.1 ml) in the right flank of adult female C3D2F1 mice. N-terminal and/or C-terminal pHLIP-boron constructs are useful in BNCT to kill tumor cells and reduce tumor burden in treated individuals.

Example 5: In Vivo Translocation of PNA by pHLIP

Gene therapy is an treatment that involves introducing genetic material into a person's cells to fight or prevent disease. Genetic material to be administered include DNA, pieces of DNA and RNA, or artificial DNA/RNA like PNA. PNA (peptide nucleic acid) is an artificial RNA or DNA analogue (Egholm et al., 1993 Nature, 365, 566-568). In a PNA, the highly charged sugar-phosphate backbone of RNA and DNA is replaced by an eclectically neutral peptide skeleton. PNAs bind DNA and RNA with high specificity and selectivity; however PNA is cell impermeable.

Cellular uptake of pHLIP-S-S-PNA constructs was evaluated. HeLa cells were transfected with a plasmid carrying the luciferase gene interrupted by a mutated (T to G) human β-globin intron. The mutation in the intron causes aberrant splicing of luciferase pre-mRNA, preventing luciferase translation. Treatment of the cells with oligoribonucleotide (or PNA) targeted to the aberrant splice sites induces correct splicing (leading to synthesis of the correctly folded luciferase) and restoring luciferase activity. The following constructs were tested in vitro and in vivo:

| Control | no injections |
|---|---|
| PNA | CCTCTTACCTCAGTTACA (SEQ ID NO: 227) |
| D-Arg8 | D-Arg8-CCTCTTACCTC AGTTACA (SEQ ID NO: 228) |
| D-Lys4 | D-Lys4-CCTCTTACCTC AGTTACA (SEQ ID NO: 229) |
| pHLIP | pHLIP-S-S-CCTCTTAC CTCAGTTACA (SEQ ID NO: 230) |
| pHLIP-mismatch | pHLIP-S-S-CCTCTGAC CTCATTTACA (SEQ ID NO: 231) |
| D-Arg8-Deca | D-Arg8-Deca-CCTCTT ACCTCAGTTACA (SEQ ID NO: 232) |
| D-Arg8-Deca-mismatch | D-Arg8-Deca-CCTCTG ACCTCATTTACA (SEQ ID NO: 233) |

(Deca is decanoic acid)

Significantly greater amounts of the pHLIP-PNA construct (pHLIP-S-S-CCTCTTACCTCAGTTACA (SEQ ID NO: 234)) were taken up by cells in vivo (i.p injection and intratumoral injection) compared to any of the other constructs. Animals treated with the pHLIP-PNA construct showed significantly higher luciferase activity localized to tumor sites compared to the other constructs. These date indicate that pHLIP reliably and effectively delivers PNA to tumor cells in an animal, mediates translocation of the PNA through the membrane, and lead to successful gene therapy (in this case, correction of a splicing defect).

The pHLIP sequences (each of which was conjugated to the PNA described above) shown in FIG. 67 were tested at pH6 and pH7.

Figure 56:
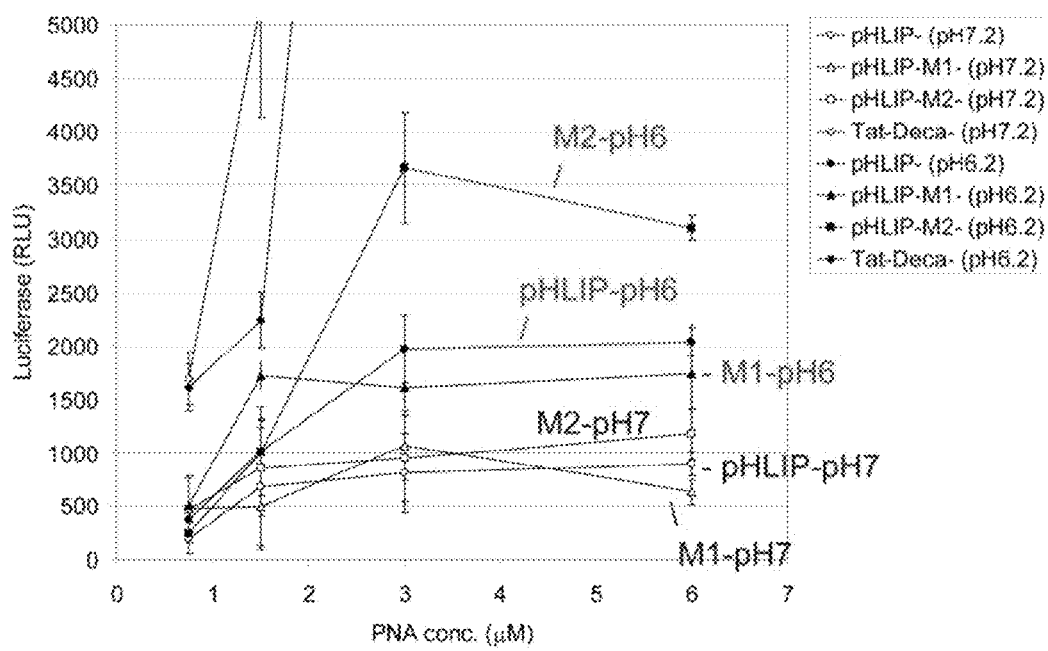
FIG. 56 is a line graph showing PNA translocation by pHLIP peptides.
Figure 68:
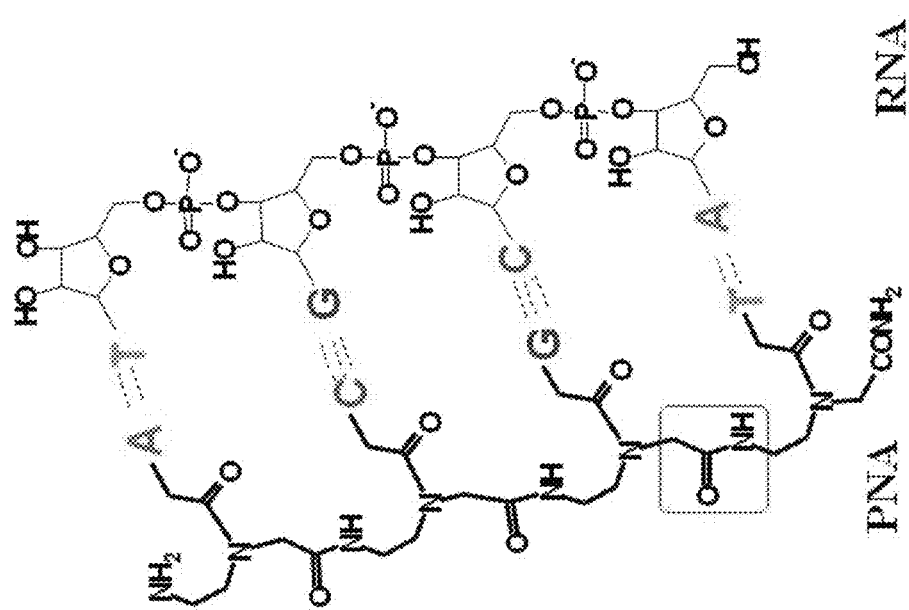
FIG. 68 is a diagram showing an exemplary PNA-RNA interaction.

The SEQ ID NOs for the schematic in FIG. 67 are as follows: pHLIP (SEQ ID NO: 235), M1 (SEQ ID NO: 236), M2 (SEQ ID NO: 237). FIG. 56 shows PNA translocation by each of the pHLIP peptides shown in FIG. 67. An exemplary PNA-RNA interaction is provided in the structure shown in FIG. 68.

Example 6: Tuning of Cargo Hydrophobicity

A drug molecule or other cargo should be hydrophobic and small in order to traverse membranes by itself and reach cytoplasmic targets unless special delivery system is used. The pHLIP delivery system described herein is a reliable and effective way to delivery polar molecules across a cell membrane or lipid bilayer. The spontaneous insertion and folding of a peptide into a lipid bilayer seeks the free energy minimum, an insertion event is accompanied by a release of energy, which is used to translocate cell-impermeable cargo molecules across a cellular membrane. An exemplary cargo, phalloidin (an inhibitor of cell proliferation), is moved across a cell membrane by pHLIP only when the hydrophobic facilitator (rhodamine) was attached to the peptide inserting end. Thus, studies were undertaken to tune the hydrophobicity of polar cargo, phallacidin, in a systematic manner. Described in this example is the design, synthesis and characterization of three phallacidin cargoes, where the hydrophobicity of cargo was tuned by attachment of diamines of various lengths of hydrophobic chains. The phallacidin cargo (phallC6) of similar polarity as phalloidin-rhodamine was conjugated to pHLIP, purified and characterized. pHLIP-phallC6 induces inhibition of proliferation of cancer cells selectively at low pH.

Targeted drug delivery allows drugs to preferentially affect diseased cells, enhancing therapeutic efficacy while reducing side effects. Targeting is particularly important for cancer therapy, since most anti-cancer drugs are toxic, not only killing cancer cells but also causing serious damage to healthy tissues. Despite significant progress toward drugs that specifically target protein biomarkers for certain kinds of cancer cells, there is still no "silver bullet" against cancer. One reason for the limited success so far is that cells in tumors are heterogeneous and selection for resistance to protein-targeted drugs and to the immune system can occur. A targeting mechanism that does not depend on a selectable marker, i.e., pHLIP-mediated delivery, provides a solution to many drawbacks of earlier approaches.

pHLIP facilitates the translocation of phalloidin, a cell-impermeable polar toxin, which leads to the inhibition of the proliferation of cancer cells in a pH-dependent fashion. However, the antiproliferative effect was observed only when a hydrophobic facilitator (rhodamine) was attached to the peptide inserting end. An alternative approach is to modify the properties of the cargo molecule to optimize delivery, and this example describes methods and compositions to tune properties of the pHLIP-cargo constructs to achieve the most efficient pH-dependent translocation of cargo molecules across the lipid bilayer. The properties of a molecule delivered into cells influences the chemical landscape available for the use of pHLIP. The hydrophobicity of an exemplary cargo, phallacidin, was tuned by attachment of diamines having various lengths of hydrophobic chains. One of the phallacidin cargoes (phallC6SH) has a similar polarity as phalloidin-rhodamine. A pHLIP-C6phall construct was synthesized and tested the antiproliferative effect on cultured cells.

The following materials and methods were used to generate data described in this example.

Peptide preparation. The pHLIP peptide (AEQNPIYWARYADWLFTTPLLLLDLALLVDADEGCT; SEQ ID NO: 238) was prepared by using standard solid-phase peptide synthesis. The lyophilized powder was soluble in 3 M urea or DMSO (dimethyl sulfoxide). When dissolved in urea the peptide was transferred to buffer using a G-10 size-exclusion spin column. The concentration of the peptide was determined spectrophotometricly by measuring absorbance at 280 nm ($\epsilon_{280}$=13,940 $M^{-1}cm^{-1}$).

Synthesis of Phallacidin-$(CH_2)_n$—SH:

Materials.

Phallacidin was purchased from GenoLite Biotek, N-hydroxysuccinimide (NHS), N,N'-dicyclohexylcarbodiimide (DCC), N-succinimidyl 3-(2-pyridyl-dithio)-propionate (SPDP) were from Thermo Scientific, Hexamethylenediamine 98%, 1,4-diaminobutane 99%, 1,10-diaminodecane 97% were from Sigma Aldrich.

Step 1:

Phallacidin (2.6 mg, 3.10 µmol) was dissolved in 100 µl dry DMF (dimethylformamide) and transferred into a 1.5 ml glass vial followed by addition of NHS (2.5 mg, 21.6 µmol, 7 eq) in 30 µl dry DMF and mixed well. DCC (1.15 mg, 5.57 µmol, 1.8 eq) was added to the reaction mixture. The reaction mixture was stirred at room temperature overnight, then the reaction mixture was centrifuged and separated from the urea crystals. The progress of the reaction was monitored by reverse phase HPLC (high-performance liquid chromatography) at t=0 and at t=12 hrs. (Agilent Technologies Zorbax SB-C18 4.6×250 mm column; flow rate 1 ml/min; phase A water+0.05% TFA (trifluoroacetic acid); phase B acetonitrile+0.05% TFA; gradient 30 min from 95:5 A/B to 50:50 A/B) The phallacidin starting material elutes at 24.9 min, while activated hydroxysuccinimidephallacidin elutes at 23.6 min. The reaction is complete by 12 hrs.

Step 2:

The supernatant from the step 1, which contained the activated hydroxysuccinimidephallacidin was added into diamines $H_2N$—$(CH_2)_n$—$NH_2$ (n=4, 6 or 10) dissolved in dry DMF (31 µmol, 10 eq of phallacidin) and the reaction mixture was stirred at room temperature for 10 hrs. The addition of the diamine resulted in the formation of a precipitate: dehydrated phallacidin diamine salt. The product, phallacidin-$(CH_2)_n NH_2$ (phallCn) was found both in the precipitate and in the supernatant. The precipitate was separated by centrifugation and dissolved in 120 µl MeOH/$H_2O$ (1:1). The product was purified using HPLC and lyophilized. The elution times of phallacidin-$(CH_2)_4 NH_2$ (phallC4), phallacidin-$(CH_2)_6 NH_2$ (phallC6) and phallacidin-$(CH_2)_{10} NH_2$ (phallC10) were 23.1, 24.6 and 29.5 min, respectively as expected from the increasing hydrophobicities. The lyophilized powder was then dissolved in 100 µl of MeOH/$H_2O$ (1:1), quantified by measuring OD (optical density) at 300 nm ($\epsilon_{300}$ of phallacidin: 10,100 $M^{-1}cm^{-1}$) and analyzed using ESI (electrospray ionization) mass spectrometry. Molecular weights (MW) of the phallotoxins phallC4, phallC6 and phallC10 were 917.23, 945.18 and 1001.22 Da, respectively (the expected MWs are 917.06, 945.12 and 1001.23 Da).

Step 3:

The products from step 2 (in 100 µl of MeOH/Water 1:1) were transferred into 200 µl of 100 mM phosphate buffer at pH 8. A solution of SPDP (starting from 5 eq of phallCn) in DMSO was added to the reaction mixture and stirred at room temperature. After about 2 hrs, most of the SPDP was hydrolyzed to PDP and no further progression of formation of the phallCn-PDP was observed. The pH of the reaction mixture was adjusted to pH 8 and more SPDP was added until almost all phallCn was reacted. The progress of the reaction was monitored using HPLC. Phallacidin-$(CH_2)_n$—SH (phallCnSH) was obtained by reducing the disulfide bond in the phallCn-PDP using TCEP (20 eq to SPDP added) in 100 mM phosphate buffer pH 8 for 30 min, purified using reverse phase C18 HPLC, lyophilized, and characterized using ESI mass spectrometry. The elution times and MWs of phallotoxins on HPLC runs with 30 min gradients from 99:1 A/B to 70:30 A/B (flow rate 1 ml/min) were: for phallacidin 30.3 min/846.15 Da, for phallC$_4$SH 32.4 min/1005.17 Da, for phallC$_6$SH 35.5 min/1033.03 Da and for phallC$_{10}$SH 44.4 min/1089.07 Da.

Synthesis of pHLIP-S-S-$(CH_2)_6$-phallacidin (pHLIP-C6phall). phallC6-PDP was synthesized as described above, purified using HPLC, and lyophilized. The lyophilized phallC6-PDP was dissolved in DMSO to about 5 mM of phallC6-PDP followed by the addition of pHLIP peptide (2 eq) dissolved in DMSO and incubated at room temperature. More pHLIP was added as needed until almost all phallC6-PDP was reacted. The progress of the reaction was monitored using HPLC (flow rate 1 ml/min; gradient 60 min from 99:1 A/B to 5:95 A/B). Elution times of phallC6-PDP, pHLIP-C6phall and pHLIP were 28.1, 47.2 and 48.5 min, respectively. The pHLIP-C6phall was analyzed using SELDI-TOF (surface-enhanced laser desorption/ionization time-of-flight) mass spectrometry and quantified by measuring OD at 280 and 300 nm. ($\epsilon_{280}/\epsilon_{300}$ of pHLIP and phallacidin is 13940 $M^{-1}cm^{-1}$/2999 $M^{-1}cm^{-1}$ and 10944

M$^{-1}$cm$^{-1}$/10100 M$^{-1}$cm$^{-1}$, respectively) MW of pHLIP and pHLIP-C6phall measured/expected were 4122.5/4111.7 Da and 5155.4/5143.0 Da.

Measurements of water-octanol partition coefficient. The polarities of the phallotoxin cargoes were determined by assessment of relative partitioning between aqueous and octanol liquid phases. Constructs dissolved in MeOH:Water 1:1 were added to 0.5 ml of 10 mM phosphate buffer pH 5.5 (saturated with argon) to concentrations of 20 and 30 µM, followed by the addition of argon saturated n-octanol (0.5 ml) and sealed under argon. The solutions were mixed by rotation for 24 hrs at room temperature and left for another 24-48 hrs to reach equilibrium. After phase separation, absorption at 300 nm was recorded. The molar extinction coefficients in n-octanol and phosphate buffer are assumed to be the same, and the ratio of the OD readings was used directly to calculate the partition coefficient, $P=OD_{n-octanol}/OD_{water}$, and Log P values. A fraction of aqueous solution was analyzed using HPLC to ensure that no dimers of the phallotoxin was formed.

Liposome preparations. Liposomes were prepared by extrusion: POPC (1-palmitoyl-2-oleoyl-sn-glycero-3-phosphocholine) (500 µl of 10 mg/ml in chloroform) was transferred to a 100 ml round bottom flask and a lipid layer was obtained by evaporating the chloroform in a rotary evaporator, followed by drying under high vacuum for 2 hrs. The lipid layer was resuspended in 10 mM phosphate buffer, pH8, and extruded 31 times through a 50 nm membrane to obtain large unilamellar vesicles.

Measurements of protein fluorescence and circular dichroism (CD) spectroscopic signals. Protein fluorescence and circular dichroism (CD) spectra were measured on a PC1 ISS spectrofluorometer (ISS, Inc.) and a MOS-450 spectrometer (Bioligic, Inc.), respectively, under temperature control. All measurements were performed at 25° C. Peptide fluorescence spectra were recorded from 310 nm to 400 nm using excitation wavelengths of 280 nm. Peptide CD spectra were recorded from 190 nm to 260 nm at 0.5 nm increments using a sample cuvette with an optical path length of 0.5 cm. The following samples were measured: i) pHLIP-C6phall (7 µM) in 10 mM phosphate buffer at pH8, ii) pHLIP-C6phall (7 µM) incubated with POPC liposomes (1.5 mM) in 10 mM phosphate buffer at pH8, and iii) sample (ii) with its pH lowered by the addition of an aliquot of HCl.

Binding Assay:

Materials and Preparation of Stock Solutions:

Rabbit muscle actin was purchased from Cytoskeleton Inc. To obtain polymerized filamentous actin (F-actin), the monomeric globular actin (G-actin) was dissolved in 100 µl of water and incubated for 1 hr at room temperature. After centrifuging at 13,000×g for about 15 min, the amount of G-actin in the supernatant was quantified by measuring the OD at 290 nm ($\epsilon_{290}$ of G-actin is 26600 M$^{-1}$cm$^{-1}$). G-actin was diluted to 3.5 mg/ml in 2 mM phosphate buffer pH 8 supplemented with 0.2 mM CaCl$_2$ and 0.2 mM ATP and incubated for 1 hr at 4° C. Polymerization was induced by addition of 50 mM KCl, 2 mM MgCl$_2$ and 1 mM ATP and incubation for 1 hr at room temperature. Texas Red-X phalloidin (PhallTxR) was purchased from Invitrogen Corp. PhallTxR was dissolved in DMF and quantified by measuring OD at 583 nm. ($\epsilon_{583}$ of PhallTx in MeOH is 95,000 M$^{-1}$cm$^{-1}$). Previously prepared and lyophilized phallotoxins (phallacidin, phallC4SH, phallC6SH and phallC10SH) were dissolved in DMSO and quantified by measuring OD at 300 nm. ($\epsilon_{300}$ of phallotoxins 10,100 M$^{-1}$cm$^{-1}$).

Binding Assay of phallTxR to Actin:

Samples of 0.6 µM of phallTxR with different F-actin concentrations (from 0 to 6.6 µM) were prepared in polymerizing buffer (2 mM phosphate buffer pH8 containing 50 mM KCl, 2 mM MgCl$_2$, 0.2 mM CaCl$_2$ and 1 mM ATP) and incubated for 2 hrs at room temperature. The fluorescence anisotropy and intensity of each sample were measured with excitation/emission setting at 570 nm/610 nm wavelength, respectively under temperature control.

Competition Binding Assay:

The assay is based on titration of 0.3 µM of phallTxR and 0.3 µM of phallotoxin by increasing concentrations of Factin. 10×TCEP was added to 60 µM stock solution of phallotoxins in polymerizing buffer and incubated for 10 min to reduce disulfide bond. Samples of 0.3 µM of phallTxR and 0.3 µM of each phallotoxin were prepared in polymerizing buffer followed by mixing with F-actin to obtain final concentrations of 0, 0.3, 0.6, 1.2 and 2.4 µM of Factin in each sample, and incubated overnight at 4° C. The fluorescence anisotropy of each sample was measured with excitation/emission setting to 570 nm/610 nm measured using PC1 spectrofluorometer under temperature control.

Cell Line.

Human cervical adenocarcinoma HeLa was purchased from the American Tissue and Culture Collection (ATCC). HeLa was propagated in DMEM (Dulbecco's Modified Eagle Medium) ([+] 4.5 g/L D-glucose, [+] 40 mg/L sodium pyruvate, Gibco) supplemented with 10% FBS (fetal bovine serum) (Gibco), ciprofloxacin-HCl (1 µg/mL) (from Cellgro, Voigt Global Distribution) in a humidified atmosphere of 5% CO$_2$ at 37° C. HeLa cells were adapted to pH 6.2 by propagation in pH 6.2 DMEM supplemented with 10% FBS, ciprofloxacin-HCl (1 µg/mL) in humidified atmosphere of 5% CO$_2$ at 37° C.

Proliferation Assay.

Stock solutions of pHLIP-C6phall, phallacidin (control agent) and phallC6SH (control agent) or phalloidin-oleate were prepared in DMSO at 400 µM. A human cervix adenocarcinoma cell line (HeLa) obtained from the ATCC (American Type Culture Collection) was grown at pH 6.2 and 7.4. HeLa cells were seeded in 96-well plates (Costar) at densities of 4000 and 2000 cells per well for treatment on the following day. A DMSO stock of pHLIP-phallC6 (or control agent) was diluted with sterile Leibovitz's L-15 phenol free medium (L-15) pH 5.9 or 7.4 to give treatment solutions in the 0-6 µM range. Appropriate amounts of DMSO were added to ensure that all treatment samples contain the same amount of DMSO by volume (1.5%). After removal of cell media, the L-15 treatment solutions pH 5.9-6.0 or 7.4 (95 µL) were added to cells grown at pH 6.2 and 7.4, respectively, and then the plate was incubated at 37° C. for 3 hrs. After treatment, 200 µL of DMEM at pH 6.2 or 7.4 were added to corresponding wells and 10 µl of FBS into each well to provide 10% of FBS in cell medium before returning the plate to the incubator. Cell density of the '0 µM, pH 6.2' and '0 µM, pH 7.4' controls usually reached 80%-90% saturation in well after 4-6 days of growth. The viable cell number was quantified using the MTS reagent (Promega CellTiter 96 AQueous One Solution Cell Proliferation Assay). OD values at 490 nm were obtained using a plate reader (iMark Microplate reader from Bio Rad). Since the rate of cells growth is slightly different at low and neutral pHs, all numbers were normalized to 100% using wells where no construct was added to the media.

Design and synthesis of phallacidin cargoes of different hydrophobicity. This example describes how to systematically vary the hydrophobicity of a polar cargo, phallatoxin, and to show delivery by a pH-dependent ant Phallacidin is a cyclic cell-impermeable toxin similar to phalloidin and that binds to F-actin with high affinity.

Figure 69:
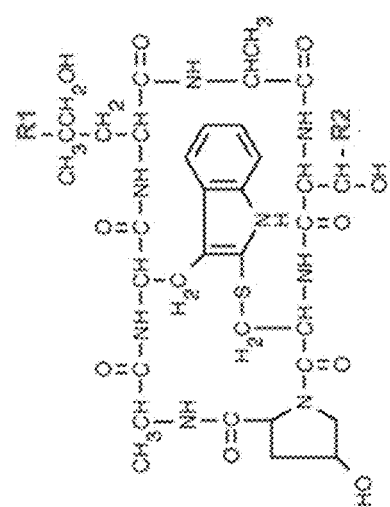
FIG. 69 shows a chemical structure of a cyclic peptides.

See FIG. 69.

Chemical structures of cyclic peptides: phalloidin, where R1=OH and R2=CH$_3$; phalloidin-rhodamine where R1=rhodamine; and phallacidin, where R1=H and R2=COOH.

Phallacidin has a free COOH group suitable for conjugation purposes, and the hydrophobicity of the phallacidin cargo was tuned/altered by reacting with diamines NH$_2$—(CH$_2$)$_n$—NH$_2$ with different lengths of hydrophobic chain (CH$_2$)$_n$, where n could be varied from 2 to 12 carbon atoms. Commercially available phalloidin-oleate, with 15 carbon atoms, has Log P value of +1.7, and inhibits Hela cell proliferation rate by 60%, 70% and 95% after treatment cells with 1, 2 and 4 μM of phalloidin-oleate, respectively, independently of pH. Three different lengths of hydrophobic chain diamines, where n is 4, 6 and 10 were chosen to work with. The phallacidin was conjugated to the various lengths diamines via NHS and DCC crosslinker. Three phallacidin cargoes with four (phallC4), six (phallC6) and ten (phallC10) carbon atoms were synthesized. The products were purified using reverse phase C18 HPLC, lyophilized and characterized by ESI mass spectrometry. The molecular weights obtained for phallacidin cargoes were 917.2 Da for phallC4, 945.2 Da for phallC6 and 1001.2 Da for phallC10 and were very close to expected values (917.1, 945.1 and 1001.2 Da).

Characterization of phallacidin cargoes of different hydrophobicity. To investigate the properties of cargo molecules, they were reacted with SPDP crosslinker, the S—S bond was reduced by TCEP and the reduced cargoes were purified and characterized (see Table below. Characterization of phallacidin and phallalacidin-C4, -C6 and -C10 cargoes: percentage of acetonitrile of cargo elutions from the column and the logarithms of the octanol-water partition coefficients (Log P).

|  | Acetonitrile, % | Log P |
| --- | --- | --- |
| phallacidin | 20.3 | −1.6 |
| phallC4SH | 22.4 | −0.74 |
| phallC6SH | 25.5 | −0.09 |
| phallC10SH | 34.4 | +1.28 |

The cargo hydrophobicities were evaluated by measuring the logarithm of the octanol-water partition coefficient P, calculated based on the amount of constructs distributed upon equilibration between octanol and water phases, measured by the ODs of phallacidin constructs at 300 nm. The Log P values of phallacidin and cargoes are presented in the Table. Phallacidin with a long chain FA of ten carbon atoms is preferably distributed into octanol, being hydrophobic, and shows a positive Log P of +1.28. Such molecules should cross cellular membranes by themselves, the hydrophobicity being in the range of conventional drugs. The polarity of phallC6SH with Log P=−0.09 was very close to the polarity of phalloidin-rhodamine, which has Log P=−0.05 measured previously. Phallacidin with four carbon atoms, as expected, was the most polar among modified phallacidin cargoes.

Modification of COOH group of phallacidin did not affect F-actin binding properties. Phallatoxin binds between actin monomers in filamentous actin and prevents depolymerization. A fluorescence anisotropy titration assay was used, where phalloidin conjugated to Texas Red (TxR) fluorescent dye was in competition with phallacidin and cargoes for F-actin binding. The assay is based on the increase of anisotropy of phallTxR when it binds to the F-actin. Samples of equal concentration (0.3 μM) of phallTxR and phallacidin cargoes were prepared with increasing concentrations of F-actin. The samples were incubated overnight, then the fluorescence anisotropy of each sample was measured at 610 nm wavelength with excitation at 570 nm. The anisotropy changes from 0.04 (for unbound phallTxR) up to 0.24 when all phallTxR is completely bound (the value of 0.24 was obtained in separate titration experiment of phalloidinTxR by F-actin in the absence of phallacidin or phallacidin cargoes). The results demonstrate that the anisotropy value in the presence of phallacidin cargoes changes in the same way as anisotropy in the presence of phallacidin, confirming that the attachment of hydrophobic tails to the phallacidin does not alter binding affinity to F-actin.

Synthesis and characterization of pHLIP-C6phall. Since phallC6SH has a similar hydrophobicity to rhodamine-phalloidin, this cargo was selected conjugated to pHLIP, spectroscopic characterization performed and anti-proliferative properties tested. PhallC6-PDP was conjugated with single Cys residue at the C-terminus of pHLIP to form a S—S bond. The product was purified using reverse phase C18 HPLC, lyophilized and characterized by SELDI-TOF mass spectrometry (MW of the pHLIP-C6phall was 5155.4 Da) and quantified by measuring OD at 280 and 300 nm.

Changes of intrinsic fluorescence and CD of pHLIP in the presence of liposomes resulting from pH changes is indicative of peptide insertion into the lipid bilayer. Spectroscopic characterization of pHLIP-C6phall construct was carried out and the characteristic increase of fluorescence signal and shift of the spectrum was observed in presence of POPC liposomes (expected from a drop of pH from 8 to 4, which indicates that tryptophan residues are buried in the membrane interior due to the peptide partition into bilayer). The construct is predominantly unstructured in aqueous solution and in the presence of POPC at pH8, while helical structure is formed at low pH. pH induced fluorescence and CD changes seen for pHLIP-C6phall in the presence of lipid bilayers were very similar to those observed for pHLIP alone. These results indicate that conjugation of phallC6SH cargo does not affect the pH-dependent ability of pHLIP to interact with the membrane lipid bilayer.

Antiproliferative effect of pHLIP-C6phall. The antiproliferative capability of the pHLIP-C6phall construct was evaluated. HeLa cells were adapted for low pH growth (pH 6.2). Cells grown at low and normal (7.4) pHs were treated with various concentrations of pHLIP-C6phall, phallC6SH and phallacidin in L-15 phenol free medium at pH 6.0 and 7.4 for 3 hrs. After treatment DMEM supplemented with 10% FBS at pH 6.2 or 7.4 was added to corresponding cells. When cell density in the control wells (treated with medium) reached 80%-90% saturation (after 4-6 days of growth) the number of viable cells was quantified using the MTS reagent. Since the rate of cells growth is slightly different at low and neutral pHs, all numbers were normalized to be 100% where no construct was added to the media. The data demonstrate that pHLIP-C6phall shows antiproliferative effect at low pH of treatment, while at neutral pH, no effect is observed. At 2 μM about 60% of cell death was observed at low pH. Phallacidin alone (i.e., not conjugated to a pHLIP peptide) (as well as phallC6SH) does not demonstrate an antiproliferative effect at either pH.

Tuning a Polar Molecule for Selective Cytoplasmic Delivery by pHLIP

In conventional drug design and discovery the Lipinski rules of five, or subsequently developed similar parameters, are widely used to guide drug designs. The rules postulate that a successful drug should be hydrophobic and small in order to traverse membranes and reach cytoplasmic targets (e.g. the logarithm of the octanol-water partition coefficient Log P is −0.4 to +5.6 and the MW is 160 to 480 g·mol$^{-1}$) (Lipinski et al., 2001, Adv. Drug Deliv. Rev. 46, 3-26). However, the majority of inhibitors found for biological targets located inside a cell are molecules that cannot cross a membrane. The use of pHLIP/drug conjugates solves this problem by mediating delivery of polar molecules across membranes, based on the insertion of a water-soluble, moderately hydrophobic membrane peptide, pHLIP. The spontaneous insertion and folding of the peptide into a lipid bilayer seeks the free energy minimum, and the insertion event is therefore accompanied by a release of energy, which is used to translocate cell-impermeable cargo molecules across a cellular membrane. The Gibbs Free Energy of binding of pHLIP to a POPC surface at 37° C. is about −7 kcal/mol near neutral pH and the additional free energy of insertion and folding across a lipid bilayer at low pH is nearly −2 kcal/mol. The energy difference between membrane-bound and membrane-inserted states favors the partition of cargo across the hydrophobic barrier of a membrane. To overcome limitations on cargo polarity (and most probably on size as well) that can be delivered across a membrane by pHLIP a method of altering or tuning the cargo was developed. pHLIP moves phalloidin across a membrane to inhibit cell proliferation, but only when a hydrophobic facilitator (e.g., rhodamine) is attached to the peptide inserting end. The hydrophobicity of a polar cargo, e.g., phallacidin, was altered or tuned in a systematic manner by conjugation of the cargo with diamines of different hydrophobic chain lengths. The hydrophobicity of the cargo is modulated by presence of 4 to 10 carbon atoms conjugated to the carboxyl group of phallacidin. The cargoes were synthesized and characterized. The logarithm of the octanol-water partition coefficient (Log P) of cargoes was varied from −1.6 for pure phallacidin to +1.28 for phallC10. A functional cargo molecule must bind to its cellular target. In the case of phallacidin, the target is an F-actin. Attachment of a chain of carbon atoms (up to 10 atoms) to the carboxyl group of phallacidin does not affect their ability to interact with F-actin. The phallC6SH cargo was conjugated via a cleavable S—S bond to the C-terminus of pHLIP (the end which goes across the membrane). The attachment of phallC6SH cargo to the inserting end of the peptide does not alter its pH-dependent membrane interaction. Phallacidin and phallC6SH are too polar to diffuse themselves across membrane in sufficient amount to induce any biological effect, while pHLIP facilitates translocation of phallC6SH across the cell membrane at slightly acidic pH, which in turns inhibits cell proliferation in a concentration-dependent manner.

In contrast to all other known peptide-based delivery technologies, selective delivery of molecules into the cytoplasm by pHLIP is achieved by the pH-dependent folding of a monomeric peptide across the plasma membrane. In response to the low extracellular pHs of cells in diseased tissues, pHLIP translocates polar therapeutic cargo molecules into cell cytoplasms, whereas at the normal extracellular pH of healthy tissue, only a minimal translocation of cargo across cell membranes occurs. Because the cargo is translocated across a cell membrane directly into the cytoplasm, endosomal trapping is avoided. Tuning the cargo hydrophobicity is a predictable and effective method to achieve the maximum difference between the therapeutic effect at low pH versus at neutral pH, thereby enhancing diseased-targeted delivery and reducing treatment side effects.

Example 7: Design and Synthesis of pHLIP-Nanoparticle Constructs

Nanotechnology is a field concerned with the interactions of cellular and molecular components and engineered materials, typically clusters of atoms, molecules, and molecular fragments at the most elemental level of biology. Such nanoscale objects are typically characterized by dimensions smaller than 100 nanometers.

A nanoparticle is a nanoscale spherical or capsule-shaped structure. Most, though not all, nanoparticles are hollow, which provides a central reservoir that can be filled with anticancer drugs, detection agents, or chemicals, known as reporters, that can signal if a drug is having a therapeutic effect. Most nanoparticles are constructed to be small enough to pass through blood capillaries and enter cells. Nanoshells are nanoparticles composed of a metallic shell surrounding a semiconductor. When nanoshells reach a target cancer cell, they can be irradiated with near-infrared light or excited with a magnetic field, either of which will cause the nanoshell to become hot, killing the cancer cell. The surface of a nanoparticle or nanoshell can be adorned with various targeting agents, such as antibodies, drugs, imaging agents, reporters, and in this case a means by which to deliver the particle preferentially to a target tissue—a pHLIP peptide.

A number of pHLIP-conjugated nanoparticles were made and studied. Water soluble single wall carbon nanotubes (SWNT) functionalized with PEG were purchased from Carbon Solutions, Inc. The water-soluble quantum dots, Qdot®800 modified with carboxyl group, were purchased from Invitrogen, Inc. 5 nm colloidal amino modified gold nanoparticles were from Sigma-Aldrich, Inc.

Carbon nanotube-pHLIP constructs were made as follows. The plain carbon nanotubes are insoluble in water, and they are coated with phospholipids. Alternatively, the nanoparticles are covalently attached to hydrophilic molecules having carboxyl or amino groups. Amino-modified single-walled carbon nanotubes (SWNTs) from Carbon Solutions, Inc. were used. pHLIP peptides were conjugated to amino-SWNT using cross-linker Sulfo-SMCC. SWNTs first were partially labeled with fluorescent dye (Cy5.5, GE Healthcare) and some amount of it was used as a control compound (without pHLIP) and other part was conjugated with pHLIP. The protocol is as follows:

1. Prepare 400 uL water solution of SWNT (1 mg/ml) using ultrasound for dissolving, precipitate big particles on centrifuge, and add Tris-HCl buffer pH 8.0 to final concentration 2 mM.
2. Add 1 uL NHS-Cy5.5 (stock solution 50 mM) to the SWNT and incubate for 2 hrs, dialyze against 1 liter of PBS buffer pH 7.4 for 12 hrs.
3. Dissolve 1 mg of pHLIP with Cys residue at N-terminus in 200 uL DMF.
4. Incubate the pHLIP solution with 2.5 mM Sulfo-SMCC at room temperature for 2 hours, remove the excess of Sulfo-SMCC by gel filtration on Sephadex G-10 column, measure the concentration of pHLIP.
5. Mixed the Sulfo-SMCC-pHLIP solution (200 uL) with the half of SWCN solution (200 uL). Incubate the mixed solution for 2 hours at room temperature. Store samples at −20° C.

Sulfosuccinimidyl-4-(N-maleimidomethyl) cyclohexane-1-carboxylate (Sulfo-SMCC) is a water-soluble, non-cleavable and membrane impermeable cross-linker. It contains an amine-reactive N-hydroxysuccinimide (NHS ester) and a sulfhydryl-reactive maleimide group (see diagram below). NHS esters react with primary amines of SWNT to form stable amide bonds. Spontaneously, maleimides react with sulfhydryl groups of pHLIP to form stable thioether bonds. The cross-linking reaction (cross-linking SWNT with pHLIP by Sulfo-SMCC) is shown below. Although not shown in the reaction below, each single carbon nanotube contain hundreds of amino groups.

rapidly cleared from blood and accumulated in the lymphatic nodes. The gold nanoparticles attached to the pHLIP reached tumors and accumulated there.

The injection of SWNT, SWNT-pHLIP and pHLIP itself did not induce any toxic effects in mice (9 nude mice were tested, 3 per each construct). The results demonstrated that specific delivery of nanoparticles to the tumors is successfully accomplished using pHLIP-nanoparticle conjugates. Targeting such particles to tumors (accumulation of nanoparticles in tumor) followed by irradiation of tumors by focusing laser light on tumor area leads to a clinically relevant therapeutic effect (i.e., increased tumor death).

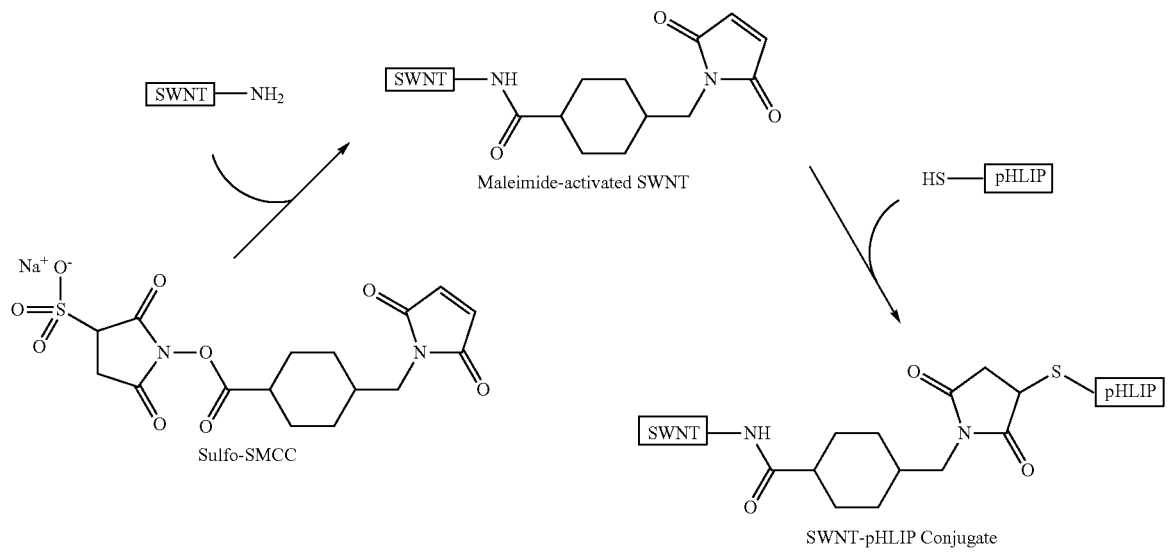

pHLIP-SWNT constructs were evaluated in cell culture using two human breast cancer cell lines: metastatic (M4A4) and non-metastatic (NM2C5). Both cell lines were derived from MDA-MB-435 breast cancer cell line. Both cell lines were transfected with GFP (green fluorescence protein), which allows to visualize cells in culture dishes and in mice. The cell lines were purchased from ATCC. Cytotoxicity of SWNT and pHLIP-SWNT was tested. SWNT and SWNT-pHLIP were found not to be toxic in absence of laser radiation. Irradiation of a cuvette with SWNT solution by 808 nm diode laser (800 mW power) induced rapid increase in temperature. The laser radiation induced rapid temperature rise in carbon nanotubes solution indicates that SWNT-pHLIP constructs are useful as thermosensitizers for infrared laser radiation.

pHLIP-mediated nanoparticle delivery to tumors was evaluated. SWNT-pHLIP showed high efficiency in tumor targeting. SWNT were labeled with Cy5.5 dye, which makes it possible to track the diffusion and accumulation of these constructs in mice by non-invasive whole body fluorescence imaging. The mice bearing GFP fluorescent tumors were intravenously injected (tail vein) with equal concentrations of SWNTs alone or conjugated to pHLIP and fluorescence images were taken after 4, 24, 48, 72 hours. The fluorescence images of mice injected with SWNT-Cy5.5 and contrast index (ratio of signal at tumor site to that at opposite site) plots were examined. The contrast index was significantly higher for SWCN-pHLIP than SWCN alone.

Other nanoparticles such as quantum dots and gold nanoparticles were also tested. Quantum dots (Invitrogen) were In vivo imaging using nanoparticles was evaluated. To demonstrate the tumor targeting ability of Nanogold-pHLIP, Cy5-Nanogold-pHLIP constructs were prepared by labeling 5 nm amino-nanogold particles with the fluorescence NIR probe, Cy5.5, and conjugating them to N-terminus of pHLIP peptides. The construct was injected (I.V.) into mice with established tumors (HeLa-GFP cells) at back right flank. Tumors sizes were 4-8 mm in diameter. Whole body fluorescence images were taken on Small Animal Kodak Imaging Station at 24 hrs after injection and revealed a significant improvement in targeting with the pHLIP construct, as is described in further detail below.

Example 8: pHLIP Peptide Targets Nanogold Particles to Tumors

Delivery of nanogold particles by pHLIP to tumors is useful for the enhancement of radiation therapy.

Targeted drug delivery would allow drugs to preferentially affect diseased cells, enhancing therapeutic efficacy while reducing side effects. It is particularly important for cancer therapy, since most anti-cancer drugs are toxic, killing not only cancer cells but also causing serious damage to healthy cells. Despite significant progress in the development of strategies that specifically target protein biomarkers for certain kinds of cancer cells, there is still no "silver bullet" against cancer, since the majority of human malignant tumors are heterogeneous and the cells they contain vary in the abundance of surface markers, potentially resulting in clonal selection of resistant tumors. As is described above, one universal difference between cancerous and normal tissues is that the former exhibits a significantly acidic extracellular environment. Acidosis is a hallmark of tumor development both at very early and advanced stages, as a consequence of anaerobic metabolism (the Pasteur effect), the activity of carbonic anhydrase IX, and the "aerobic glycolysis" (the Warburg effect). Thus, the targeting of most solid tumors is achieved by using pH-sensitive drugs and delivery systems.

At neutral pH, pHLIP is in equilibrium between soluble and membrane-bound unstructured forms, while in a low pH environment, the protonation of negatively charged residues (Asp or Glu) enhances peptide hydrophobicity, increasing the affinity of the peptide for the lipid bilayer and triggering peptide folding and subsequent membrane insertion. The Gibbs Free Energy of pHLIP binding to a liposome surface at 37° C. is about −7 kcal/mol near neutral pH and the additional free energy of folding and insertion across a lipid bilayer at low pH is nearly −2 kcal/mol. Thus the affinity of the peptide for a membrane at low pH is several times higher than at neutral pH, allowing pHLIP to distinguish and mark acidic diseased tissue. The N-terminus of pHLIP stays outside of the bilayer, while the C-terminus inserts across the lipid bilayer at low pH, and small molecules (mostly imaging agents) covalently conjugated with the N-terminus of pHLIP have been delivered to tumors and tethered to the surfaces of cancer cells.

In this example, pHLIP-mediated targeting of 1.4 nm gold nanoparticles to cancer cells in culture and tumors established in mice is demonstrated. Gold is an inert and non-toxic material with unique properties suitable for many applications such as cancer diagnosis and treatment. Targeting gold atoms with radiation energy appropriate for k-edge excitation generates Auger electrons or highly reactive species that may produce a clinically achievable dose enhancement of as much as 10 fold, capable of local inactivation of biological molecules. The targeted delivery of gold, e.g., gold nanoparticles, to diseased tissue is therefore of great utility in the diagnosis and treatment of pathological states.

A goal of nanomedicine is the preferential targeting of nanoparticles to diseased sites with decreased delivery to normal tissues and organs. The data described herein demonstrates the preferential accumulation of gold nanoparticles in tumors. pHLIP peptides successfully target various imaging agents to tumors. Tumor targeting was also shown by non-functionalized nanogold particles using nanogold-pHLIP conjugates, where nanogold was covalently attached to the N-terminus of pHLIP.

pH-dependent, pHLIP-mediated uptake of gold nanoparticles by cultured cells was shown. Direct injections of gold-pHLIP conjugates and gold nanoparticles into tumors resulted in accumulation of 45% and 8% of the injected gold doses, respectively, after 24 hours. Following intravenous injections, 6 times more gold-pHLIP (1.2%) was found in tumors than gold nanoparticles alone (0.2%). These results indicate that pHLIP can deliver about 5-6 times more gold to cancer cells in vitro and in vivo in comparison to the non-targeted delivery of gold nanoparticles. Gold nanoparticles and other types of nanoparticles enhance the effect of radiation therapy, therefore pHLIP targeting to tumors has a direct application in radiation oncology and for treatment of other types of diseased tissue.

The following materials and methods were used to generate the data described in this example.

Peptide conjugation with gold nanoparticles. The pHLIP peptide (ACEQNPIYWARYADWLFTTPLLLLDLALL-VDADET; SEQ ID NO: 239) was prepared using standard methods. Monomaleimido Nanogold® particles (1.4 nm, Nanoprobes; Yaphank, N.Y.), with a single maleimide group on the surface, were covalently conjugated with the single cysteine residue at the N-terminus of pHLIP. The progress of the coupling reaction was monitored by reverse phase HPLC. The concentration of peptide and nanogold was determined by absorbance at 280 nm ($\in$=13,940 $M^{-1}cm^{-1}$) and 420 nm ($\in$=155,000 $M^{-1}cm^{-1}$), respectively.

Circular dichroism measurements. Circular dichroism (CD) measurements were carried out on a MOS-450 spectrometer (BioLogic; Montrose, Colo.) at 25° C. Nonfunctionalized nanogold particles or nanogold-pHLIP conjugates were pre-incubated with 200 mol excess of POPC (1-Palmitoyl-2-Oleoyl-sn-Glycero-3-Phosphocholine from Avanti Polar Lipids, Alabaster, Ala.) liposomes in 20 mM phosphate buffer, pH8.0. Liposomes with 50 nm diameter were prepared by extrusion. To induce the folding/insertion of peptide into lipid bilayer of membrane, HCl was added to lower the pH value from 8 to 4. CD signals of gold nanoparticles were taken as baseline signals and were subtracted from the corresponding signals of nanogold-pHLIP conjugates.

Cell lines. HeLa cells (human cervix adenocarcinoma, ATCC; Manassas, Va.) without and with stable GFP expression, were cultured in Dulbecco's Modified Eagle's Medium (DMEM) supplemented with 10% fetal bovine serum, 10 µg/mL of ciprofloxacin in a humidified atmosphere of 5% $CO_2$ and 95% air at 37° C. Some cells were adapted by serial passages to grow in low pH medium (pH6.5). The pH 6.5 medium was prepared by mixing 13.5 g of dry DMEM with 0.2 g of sodium bicarbonate in 1 L of deionized water.

Experiments on cultured cells. HeLa-GFP cells grown in pH6.5 or 7.4 media were seeded in an 8-chamber slide (Lab-Tek™, Thermo Scientific; Rochester, N.Y.). At 80% confluency, cells were treated at pH 6.5 or 7.4 with 2 µM of nanogold or nanogold-pHLIP in 200 µL of serum-free DMEM at 37° C. under 5% $CO_2$. Cells not treated with nanogold were used as negative controls. After 1 h incubation, the treatment solution was removed and cells were washed twice with serum-free DMEM (pH 7.4), and once with sterile PBS (pH7.4). Subsequently, the cells were fixed with cold methanol at −20° C. for 15 min, and then washed twice with sterile PBS (pH7.4) and once with deionized water. After air drying, the chamber walls were removed and the cell slides were developed with freshly prepared HQ SILVER™ reagent (Nanoprobes; Yaphank, N.Y.). The reagent nucleates on the nanogold particles, resulting in the precipitation of metallic silver and the formation of micrometer sized particles with low background. The developing time was varied until optimal conditions were found (about 20 min). Subsequently, the cell slides were rinsed twice with deionized water, and viewed under a light microscope.

Estimation of cellular uptake of gold/silver based on the analysis of cell images. After silver staining, the brightfield images of cells were analyzed with the ImageJ program. For cells treated with nanogold, the mean intensities of the fields with cells ($I_i$) and without cells ($I_{0,i}$, background) were calculated. Concentration of gold/silver ($c_i$) can be presented as mean intensity according to the Beer-Lambert law:

$$c_i = \frac{A_i}{\varepsilon d} = \frac{1}{\varepsilon d}\ln\frac{I_{0,i}}{I_i} \tag{1}$$

$$\frac{c_i}{c_{nt}} = \ln(I_{0,i}/I_i)/\ln(I_{0,nt}/I_{nt}) \quad (2)$$

where $A_i$ is the absorbance; $\in$ is the extinction coefficient and d is the thickness of sample. For cells not treated with nanogold, $c_{nt}$, $I_{nt}$ and $I_{0,nt}$ correspond to the concentration of gold/silver, the mean intensities of the fields with and without cells, respectively. The extinction coefficient and thickness are assumed to be the same for all slides, so that the ratio of concentrations can be calculated according to equation (2) by knowing the mean intensities.

Tumor targeting in mice. Athymic female nude mice ranging in age from 4 to 6 weeks and weighing from 15 to 18 g were obtained from Harlan Laboratories (Indianapolis, Ind.). Mouse tumors were established by subcutaneous injection of HeLa cells ($10^6$ cells/0.1 ml/flank) in the right flank of each mouse. When tumors reached 5-8 mm in diameter, intratumoral or tail vein injections of nanogold samples were performed. For intratumoral injection, the total amount of 50 µL of 20 µM nanogold or nanogold-pHLIP in sterile PBS (pH7.4) was given at three different spots of each tumor. For tail vein injection, either a single intravenous (IV) injection of 100 µL of 100 µM nanogold-pHLIP (or nanogold), or two consecutive injections within 24 h of 150 µL of 20 µM nanogold-pHLIP (or nanogold) were given. Animals were euthanized at 4 or 24 hours after the last injection. Necropsy was performed immediately after euthanasia. Tumors and major organs were collected for further histological analysis and inductively coupled plasma mass spectroscopy (ICP-MS) study. Non-injected mice with similar-sized tumors were used as a negative control.

Histological analysis of tumors and organs. The excised tumors and organs were fixed in 4% formalin in PBS solution (pH 7.4) for 24 h at 4° C. Tissues were then rinsed with sterile PBS (pH7.4), blotted dry and placed in 30% sucrose in PBS solution for at least 24 h at 4° C. Samples were mounted in HistoPrep® frozen tissue embedding medium (Fisher Scientific; Pittsburgh, Pa.) and frozen in the quick freezer chamber of a cryostat (Vibratome Ultra-Pro5000, GMI; Ramsey, Minn.) at −80° C. Samples were frozen only one time to minimize tissue damage. When the temperature of mounted frozen samples was equilibrated with the working chamber temperature (−12° C.), the tissue was sectioned at a thickness of 10-20 µm. Sections were mounted on microscope slides coated with poly-lysine, dried in air, and washed with deionized water. Subsequently, silver enhancement of gold nanoparticles was carried out (developing time: 10 min). In some cases, further staining with 4', 6-diamidino-2-phenylindole (DAPI) was performed to stain cell nuclei. The stained section was covered with a drop of mounting medium (Permount®, Fisher Scientific; Pittsburgh, Pa.) and then a cover slide was placed over the medium. The slides were examined with an inverted fluorescence microscope (IX71 Olympus).

ICP-MS analysis. Mouse tissue samples were dissolved in aqua regia, freshly prepared by mixing concentrated nitric and hydrochloric acids in a volume ratio of 1:3. If necessary, sonication or heating was used to facilitate the digestion of tissue samples. Then the concentrated sample solutions were diluted up to 10 mL to have 2% nitric acid and analyzed via ICP-MS (Thermo scientific X7 series) against calibration standards IMS 103 (UltraScientific; N. Kingston, R.I.).

Studies were carried out to test pHLIP-mediated enhancement of nanogold delivery to tumors.

Biophysical Studies

Figure 14:
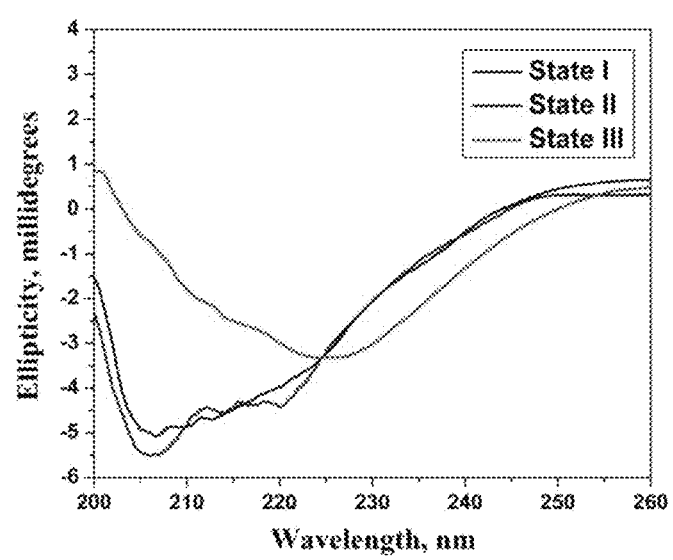
FIG. 14 is a line graph showing the circular dichroism spectra of nanogold-pHLIP in buffer pH 8.0 (state I), and in the presence of POPC liposomes at pH 8.0 (state II) and pH 4.0 (state III).

Changes of tryptophan fluorescence and CD spectral signals were used to monitor pHLIP binding to a membrane lipid bilayer at neutral pH and insertion at lower pH. Nanogold attached to pHLIP significantly quenches tryptophan fluorescence, making it unreliable for use in monitoring pHLIP insertion in a membrane (nevertheless, shift of position of maximum of tryptophan fluorescence was observed). Since gold nanoparticles are achiral in the UV range and do not interfere with the CD signals of peptide, the CD spectra of gold-pHLIP was measured to study peptide-bilayer interactions. The data indicate that pHLIP is predominantly unstructured at pH8 in the absence or presence of liposomes, whereas at low pH in the presence of POPC liposomes, we observe helix formation (FIG. 14). Thus, the data indicate that gold nanoparticles attached to the N-terminus of pHLIP do not interfere significantly with the process of peptide interaction with a membrane to form a helical structure at low pH.

Experiments on Cultured Cells

Figures 15A, 15B, 15C, 15D, 15E, 15F, 15G, 15H:
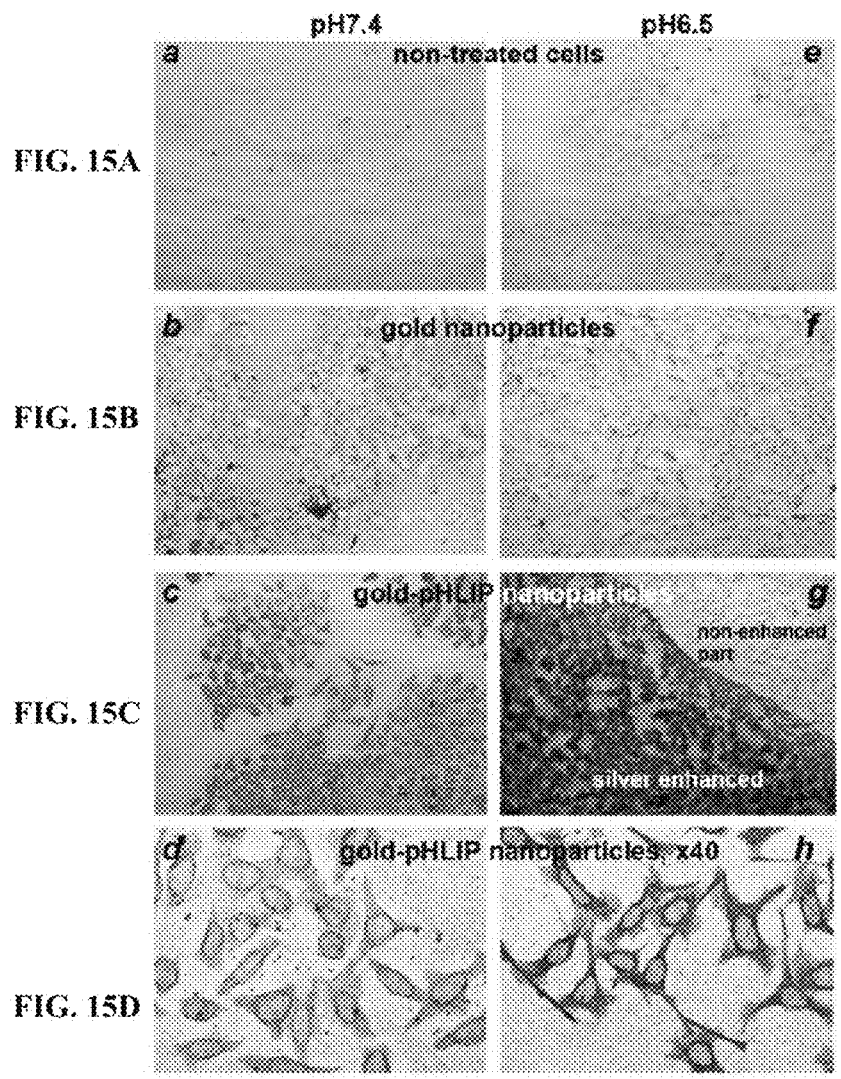
FIGS. 15A-H are a series of photomicrographs showing the cellular uptake of gold-pHLIP and gold nanoparticles. The images A-G and D-H were taken with ×10 and ×40 objectives, respectively.

The binding of gold-pHLIP or gold nanoparticles to cultured cells at neutral and low pH were compared. Nanoparticles (2 µM, 200 µL) were incubated with HeLa-GFP cells at pH7.4 or 6.5. After 1 hour, cells were washed, fixed and stained with silver enhancement solution, resulting in the deposition of silver on gold nanoparticles to form micrometer sized particles, which were visualized under a light microscope (FIGS. 15A-H). The images on FIGS. 15A-H were analyzed according to the equation 2 (see above) to establish the ratios of gold (and silver) concentration between the cells treated with gold-pHLIP or gold nanoparticles and the untreated cells at pH7.4 and 6.5. In the absence of silver deposition, the nanogold particles were not visible (FIG. 15G, "non-enhanced part"). No silver staining was observed in the cells without the treatment of gold-pHLIP or gold nanoparticles (FIG. 15A, FIG. 15E). The cells treated with gold-pHLIP nanoparticles at both pHs (FIG. 15C, FIG. 15G) show much stronger uptake of gold (3 times at pH7.4 and 6.4 times at pH6.5) than the cells treated with unmodified gold nanoparticles (FIG. 15B, FIG. 15F). The cellular uptake of gold-pHLIP nanoparticles at pH6.5 (FIG. 15G, FIG. 15H) is 1.6 times higher than that at pH7.4 (FIG. 15C, FIG. 15D). Thus the pH-dependent interaction of nanogold-pHLIP with cells was confirmed.

Animal Studies

HeLa cells were given as single subcutaneous injections into the right flanks of mice to establish tumors for study. When tumors reached 5-8 mm in diameter, intratumoral or IV injections of gold nanoparticles or gold-pHLIP were performed.

Figure 16A:
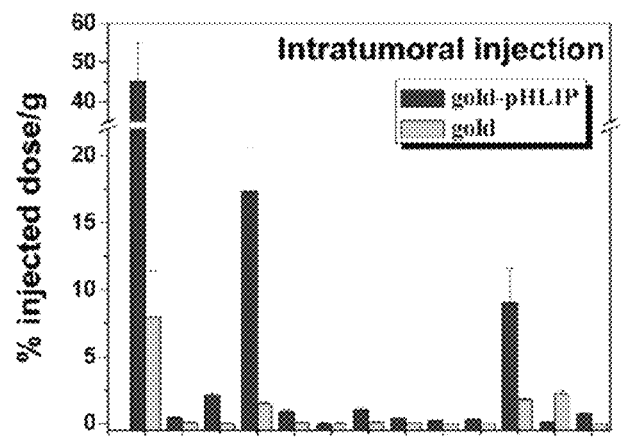
FIGS. 16A-B are a series of bar charts showing ICP-MS analysis of the amount of gold in the excised tissues. The detail values are given in the accompanying table.

Mice were euthanized, and then tumors and major organs were collected 24 hours after intratumoral administration of gold or gold-pHLIP nanoparticles (20 µM, 50 µL). The amount of gold in the tissues and organs was established by ICP-MS analysis (FIG. 16A and Table below). The results indicate that up to 45% of the injected gold-pHLIP (per gram of tumor) remained in the tumor after 24 h, in comparison with only 8% in the case of unmodified gold nanoparticles. Beside tumor, significant accumulation of gold was observed in the kidney, but still much less than in the tumor. Since small particles (1.4 nm) were used in our study, their clearance was predominantly urinary, leading to the kidney accumulation. Also, pHLIP has a tendency to target kidney due to the low pH in the tubules. It was unexpected to observe a rather high signal in muscle (9% of injected dose per gram of tissue). However, the tumor/muscle ratio reached 5.6 at 24 hours, and a higher tumor/muscle ratio might be achieved at later time points since the clearance of pHLIP in blood could be slow.

Figure 16B:
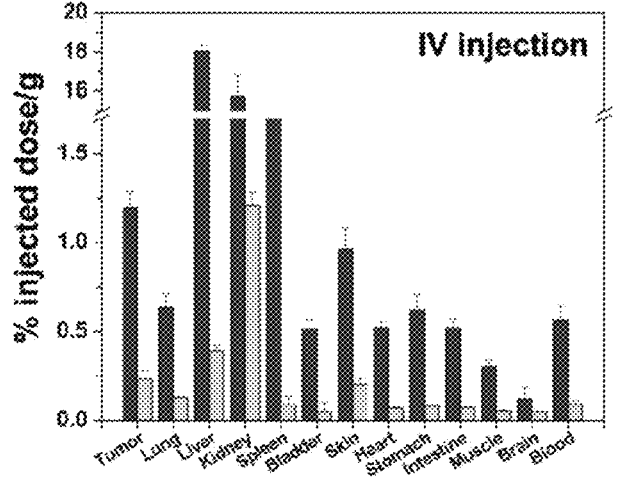

IV administration was given as two consecutive injections (20 μM, 150 μL each) within 24 hours. Necropsy was performed 24 hours after the last injection. The data show that 1.2% of the injected gold-pHLIP was delivered to the tumor, while 18%, 16% and 5.6% were taken up by liver, kidney and spleen, respectively (FIG. 16B and Table below).

| Organs | Au-pHLIP, intratumoral | Au-pHLIP, iv | Au, intratumoral | Au, iv |
|---|---|---|---|---|
| Tumor | 45.157 ± 9.781 | 1.195 ± 0.095 | 8.010 ± 3.462 | 0.233 ± 0.046 |
| Lung | 0.440 ± 0.046 | 0.639 ± 0.075 | 0.119 ± 0.025 | 0.128 ± 0.000 |
| Liver | 2.171 ± 0.153 | 18.057 ± 0.327 | 0.082 ± 0.082 | 0.392 ± 0.031 |
| Kidney | 17.360 ± 3.290 | 15.777 ± 1.026 | 1.561 ± 0.098 | 1.206 ± 0.078 |
| Spleen | 0.888 ± 0.128 | 5.899 ± 0.066 | 0.097 ± 0.039 | 0.089 ± 0.045 |
| Bladder | 0.001 ± 0.105 | 0.518 ± 0.044 | 0.010 ± 0.094 | 0.050 ± 0.050 |
| Skin | 1.013 ± 0.210 | 0.964 ± 0.116 | 0.129 ± 0.041 | 0.204 ± 0.029 |
| Heart | 0.391 ± 0.009 | 0.523 ± 0.031 | 0.075 ± 0.010 | 0.069 ± 0.004 |
| Stomach | 0.230 ± 0.002 | 0.623 ± 0.083 | 0.012-30.011 | 0.081 ± 0.000 |
| Intestine | 0.328 ± 0.025 | 0.521 ± 0.055 | 0.034 ± 0.021 | 0.073 ± 0.002 |
| Muscle | 9.016 ± 2.653 | 0.305 ± 0.0346 | 1.836 ± 0.071 | 0.053 ± 0.005 |
| Blood | 0.762 ± 0.044 | 0.562 ± 0.084 | 0.028 ± 0.028 | 0.091 ± 0.020 |

At least 2, 4, 6, 10 times or greater tumor targeting is achieved using nanogold-pHLIP compared the amount observed using by gold nanoparticles alone. Optimizing the surface of the nanoparticles to make them more polar may improve the biodistribution of nanoparticles, especially in the case of IV administration. Furthermore, it is likely that the pharmacokinetics of gold-pHLIP and gold nanoparticles are different. pHLIP has an affinity for membranes at neutral pH and, it binds reversibly to the surfaces of blood cells, sustaining longer blood circulation time. Nevertheless, tumor targeting by nanogold-pHLIP was 6 times higher than by gold nanoparticles alone.

Figures 17A, 17B, 17C, 17D, 17E:
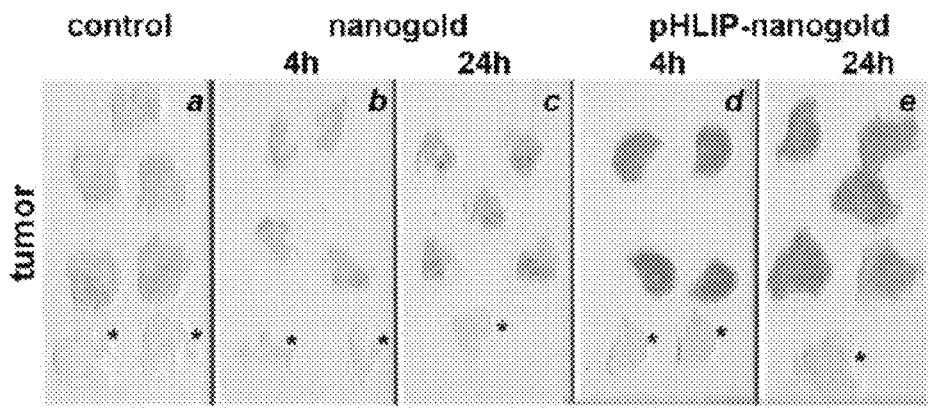
FIGS. 17A-O are a series of photomicrographs showing the accumulation of gold-pHLIP and gold nanoparticles in tumor, kidney and liver. The slices indicated by * were not treated with silver enhancement solution.
Figures 17F, 17G, 17H, 17I, 17J:
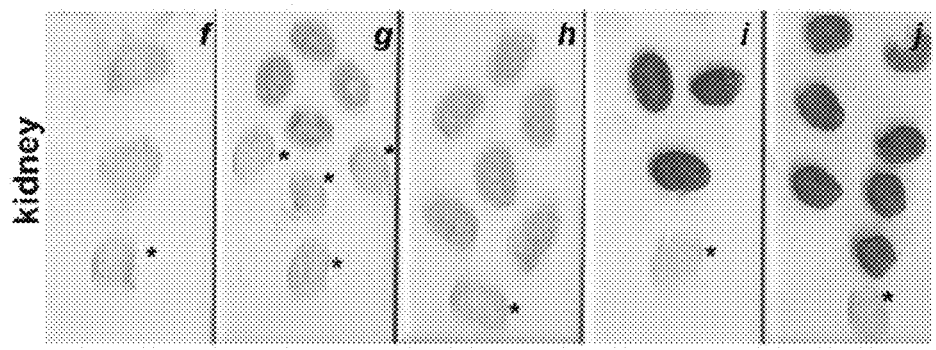
Figures 17K, 17L, 17M, 17N, 17O:
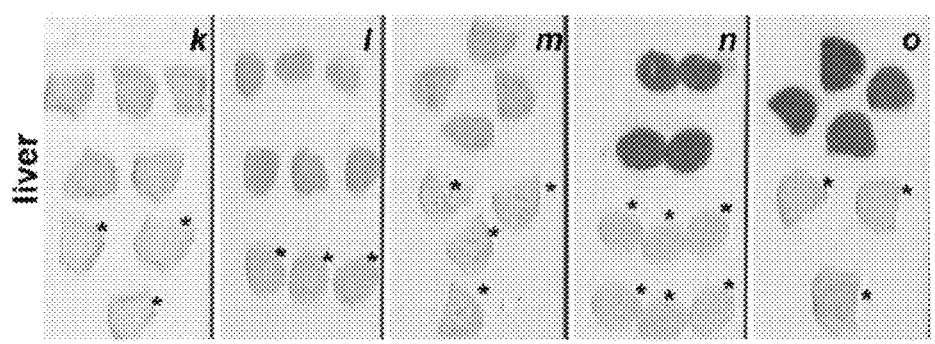

To establish the tissue distribution of gold nanoparticles, tumors, kidneys and livers were collected and sectioned at 4 h and 24 h after gold-pHLIP or gold nanoparticle administration. To visualize gold nanoparticles in tissue sections, silver enhancement was performed. The same conditions of silver enhancement were used for all slides shown in FIG. 17. The amount of gold/silver correlates with the darkness of tissue sections. It is clearly seen that gold uptake by the tumor (as well as kidney and liver) is higher at both time points for gold-pHLIP injection than for unmodified gold administration.

Figures 19A, 19B, 19C:
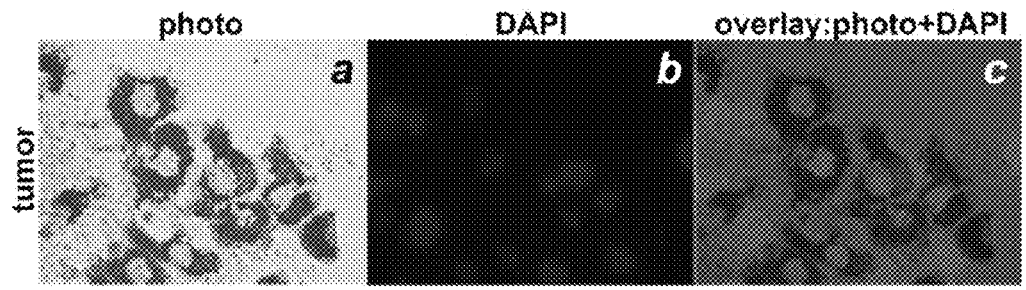
FIGS. 19A-I are a series of photomicrographs showing the distributions of gold-pHLIP enhanced by silver in tumor, kidney and liver. Slices were visualized under an inverted optical microscope with ×100 objective. The nuclei were stained with DAPI (blue color). Bright field (A, D, G) and fluorescent (B, E, H) images of the same sections and their overlays (C, F, I) of tumor, kidney and liver slices are presented.
Figures 19D, 19E, 19F:
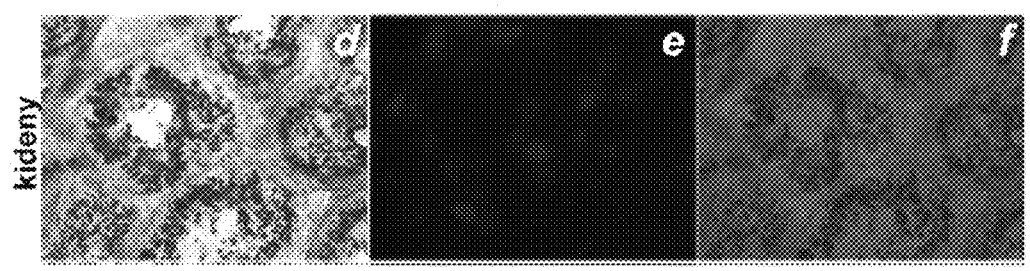
Figures 19G, 19H, 19I:
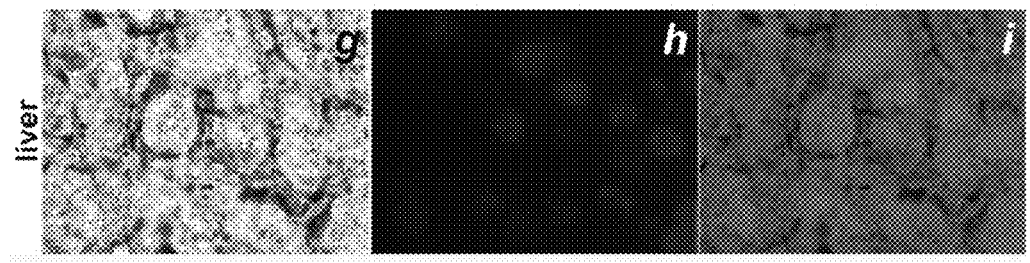
Figure 20A:
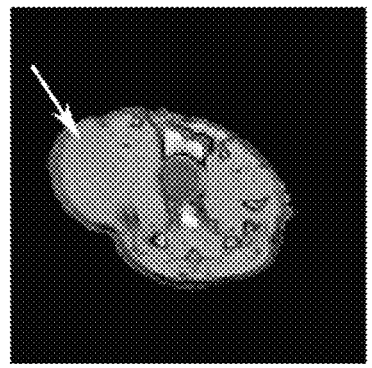
FIGS. 20A-D are a series of photographs showing T1 values for cross-section slices obtained in the result of the MRI on mouse before (pre pHLIP) and 24 hours after (24 h post pHLIP) Gd-DOTA-pHLIP administration are presented in gray and rainbow scales. Tumor is indicated by arrow. There was no change at 3 hours (data not shown), but there was a significant change at 24 hours. T1 in the bladder has gone way down, indicating extraction in progress. In the 24 h case, there is 25% decrease in average T1 for tumor tissue while no changes in other tissues.
Figure 20B:
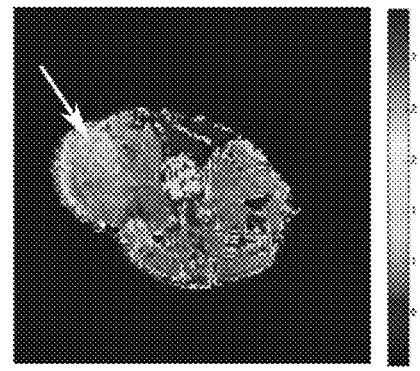
Figure 20C:
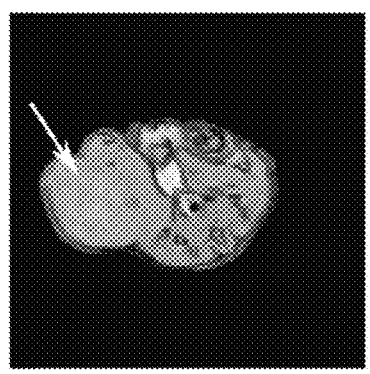
Figure 20D:
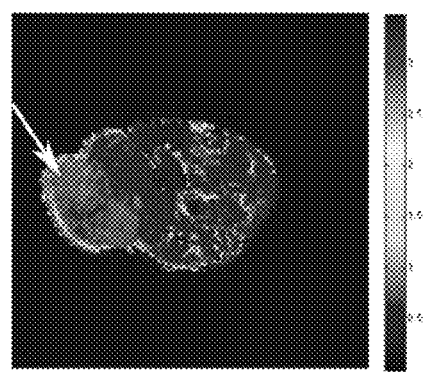

The sections were further analyzed under a microscope with ×10 (FIG. 18) and ×100 (FIG. 19) objectives. The gold distribution in the tumor and liver (FIG. 18D, FIG. 18L) is homogeneous in contrast to the distribution in kidney (FIG. 18H), where the gold is mostly accumulated in the cortex. The cellular localization was confirmed by staining of cell nuclei with DAPI (FIGS. 19A-I). The images of the tumor sections demonstrate that pHLIP stains the entire tumor mass, penetrating to the cells in the tumor interior and labeling the extracellular space and cellular membrane (FIGS. 19A-C).

The targeted delivery of nanoparticles to solid tumors is an important and challenging task in cancer nanomedicine. The methods described herein overcome many of the drawbacks of earlier methods. For example, although delivery of nanoparticles can be accomplished by conjugating them to antibodies or ligands that target proteins overexpressed on cancer cell surfaces, this approach has some fundamental limitations. Not all cancer cells have well-defined biomarkers, and most tumors are heterogeneous in their expression. Therefore, in many cases, it is not known which biomarkers are present in the tumors of a particular patient. Also, clonal selection from the heterogeneous cell population may induce cancer cells resistant to antibodies or ligand-based drugs as has unfortunately happened, for instance, with Herceptin, which was considered as a promising treatment of Her2 positive breast cancer. Moreover, antibodies conjugated with gold nanoparticles do not penetrate deeply into tumors, but mostly stain peripheral tumor regions, compared to membrane-insertion of pHLIP-conjugated nanoparticles.

The pHLIP-mediated nanoparticle targeting method has several advantages, because it is exploits an important environmental marker present in almost all solid tumors—acidity and because of the membrane spanning insertion mechanism of pHLIP. In practice, gold nanoparticle-pHLIP conjugates were found to accumulate in tumors at a level sufficient for radiation therapy. Gold nanoparticles, e.g., pHLIP-conjugated nanoparticles, are useful diagnostic and therapeutic agents in vivo as, e.g., X-ray contrast agents, radiation enhancers, as well as laser and radiofrequency thermotherapy enhancers. For example, a higher dose of radiation is received by cancerous tissue labeled with gold compared with the dose received by normal tissue during radiotherapy. Calculations indicate that the dose enhancement is significant, even 200% or greater. Gold nanoparticles are not toxic: the $LD_{50}$ of this material is approximately 3.2 g Au $kg^{-1}$.

However, the direct injection of micron-sized gold particles did not lead to a successful treatment since they stayed only at the injection site and were not able to diffuse even within a tumor, hindering tumor coverage. On the other hand, nano-sized gold particles were washed out quickly from tumors. By contrast, the direct injection in tumor of gold-pHLIP showed stable and almost uniform labeling of cancer cells throughout the entire tumor with gold nanoparticles. After 24 hours, 45% of the entire injected gold dose stayed in the tumor. Intravenous administration of gold nanoparticles resulted in much less uptake by the tumor than intratumoral injection; however, the uptake of gold-pHLIP was 6 times higher than the uptake of unmodified gold nanoparticles. For both direct and IV administrations, the gold-pHLIP was accumulated on cancer cells throughout the entire tumor mass. Blood clearance and uptake by kidney and liver can be minimized by increasing the size of the particle, e.g., to 2, 4, 5, 6, 8, 10, 12 or up to 14 nm in diameter and/or altering the conjugation agent or coating, e.g, polyethylene glycol (PEG) as a coating. The N-fold increase in diameter gives $N^3$ increase in number of gold atoms per particles, but it may decrease the ability of a particle to diffuse to the tumor center. Gold particles of 14 nm are mostly concentrated in the tumor periphery and may not provide a clinically beneficial enhancement of radiation in the main tumor body. Since 5 nm is a typical intracellular space in tumor tissue, the use of nanoparticles of 5 nm size or less may be most clinically useful.

The data described in this example indicate that pHLIP technology substantially improves the delivery of gold nanoparticles to primary tumors and metastatic lesions by providing specificity of targeting, enhancing local concentration in tumors, and allowing staining of entire tumor mass for an extended period of time (several days, e.g, at least 24 hours, 48 hours, 72 hours, or more).

Example 9: Magnetic Resonance Imaging Using pHLIP-Gd Constructs

MRI is the one of most widely used imaging methods in clinical settings. MRI is a medical imaging technique used in radiology to visualize detailed internal structures. MRI makes use of the property of nuclear magnetic resonance (NMR) to image nuclei of atoms inside the body.

An MRI machine uses a powerful magnetic field to align the magnetization of some atoms in the body, and radio frequency fields to systematically alter the alignment of this magnetization. This causes the nuclei to produce a rotating magnetic field detectable by the scanner. This information is recorded to construct an image of the scanned area of the body. Strong magnetic field gradients cause nuclei at different locations to rotate at different speeds. 3-D spatial information can be obtained by providing gradients in each direction.

MRI provides good contrast between the different soft tissues of the body, which make it especially useful in imaging the brain, muscles, the heart, and cancers compared with other medical imaging techniques.

The accuracy and quality of MRI imaging is significantly enhanced by targeting MRI contrast agents to the disease tissue. Complexes containing Gd (gadolinium) atoms are commonly used as enhancing agents. However, the challenge is to selectively or preferentially deliver Gd complexes to the disease tissue. Since pHLIP targets diseased tissue with low extracellular pH, pHLIP was used for delivery of Gd contrast agents to selective tumors.

MRI is based on measurements of relaxation times (T1 or T2) of hydrogen atoms in the body. A cyclic paramagnetic complex, Gadolinium-tetraazacyclododecanetetraacetic acid (Gd-DOTA) was used in the studies described herein. Other non-cyclic complexes such as gadolinium-diethylenetriaminepentaacetic acid (Gd-DTPA) or gadolinium-ethylenediaminetetraacetic acid (Gd-EDTA) or formulations (gadodiamide (Omniscan), gadobenic acid (Multihance), gadopentetic acid (Magnevist), gadoteridol (Prohance), gadofosveset (Ablavar), gadoversetamide (OptiMARK), gadoxetic acid (Eovist or Primovist), gadobutrol (Gadavist), gadocoletic acid, gadodenterate, gadomelitol, gadopenamide, or gadoteric acid (Dotarem)) can also be used. Other MRI contrast agents such as iron oxide (superparamagnetic Iron Oxide (SPIO) or Ultrasmall Superparamagnetic Iron Oxide (USPIO) e.g., Cliavist, Combidex, Endorem, Feridex, Resovist, or Sinerem) as well as paramagnetic manganese chelates such as Mn-DPDP are used.

pHLIP was conjugated with DOTA-Gd and injected peritoneally into nude mice with established tumors (5-10 mm in diameter). MRI images were taken before injection and 3 and 24 hrs after injection of pHLIP-Gd. Representative images (T1 maps) for one of the studied mice are shown on FIGS. 20A-D. The data for 4 mice are presented in the Table below. All scanning was performed on a Siemens 3T Tim Trio system. This scanner is equipped with a Siemens AC88 insert gradient system to facilitate high resolution imaging of small animal models while permitting visualization of contrast agent effect at clinically relevant field strength. All scans were performed using the insert gradient and a 45 mm inner diameter volume resonator designed for rodents. Animals were scanned under gas anesthesia. Heart rate, respiration, and arterial oxygen saturation were continuously monitored during the entire scan procedure using a Starr Life Sciences (Oakmont, Pa.) MouseOx physiologic monitoring system.

| Construct/animal | $T_1$ Baseline | $T_1$ 3 hrs | % $T_1$ Change | $T_1$ 24 hrs | % $T_1$ Change |
|---|---|---|---|---|---|
| Gd-DOTA-pHLIP, mouse #1 | 888.3 ms | 879.7 ms | −0.968% | 751.5 ms | −15.4% |
| Gd-DOTA pHLIP, mouse #2 | 977.1 ms | 1007 ms | 3.06% | 724.9 ms | −25.8% |
| Gd-DOTA control, mouse #3 | 874.3 ms | 920.4 ms | 5.27% | 967.6 ms | 10.7% |
| Gd-DOTA control, mouse #4 | 906.9 ms | 879.2 ms | −3.05% | 952.4 ms | 5.02 |

$T_1$ values were determined by identifying image slices containing tumor tissue using the 3D $T_1$-MPRAGE image dataset. Regions of interest were manually drawn on the $T_1$ maps to enclose the interior of the tumor to produce a mean $T_1$ value for each slice. A weighted average of the $T_1$ values for all of the slices was taken with weighting based on the number of pixels in each slice ROI to produce the mean $T_1$ for the tumor.

$T_1$ maps were generated by performing a three-parameter non-linear least squares fit to the partial saturation expression (including a DC offset term) on a pixel basis using the three gradient echo images with TR=300 ms, 500 ms, and 1000 ms.

The results demonstrated that use of pHLIP for delivery of Gd MRI contrast agents is accurate and reliable for tumor diagnosis by MRI method. FIGS. 20A-D are a series of MRI images. T1 values for cross-section slices obtained in the result of the MRI on mouse before (pre pHLIP) and 24 hours after (24 h post pHLIP) Gd-DOTA-pHLIP administration are presented in gray and rainbow scales. Tumor is indicated by arrow. There was no change at 3 hours, but there was a significant change at 24 hours. T1 in the bladder has gone way down, indicating indicating that Gd is extracted from the tissue and excreted with urine. In the 24 h case, there is 25% decrease in average T1 for tumor tissue while no changes in other tissues.

Example 10: Double-Labeled pHLIP

As described in detail below, pHLIP-K(TAMRA)C (TAMRA) is a self-quenched, switchable pHLIP imaging probe based on H-type dimer formation. Described herein is an example of a construct, wherein pHLIP is conjugated with two cargo molecules on one terminus. The construct is useful for fluorescence imaging, fluorescence guided surgery, circulating cancer cells, and tissue characterization by a fluorescent signal. In comparison with pHLIP labeled with single fluorescent probes, double labeled pHLIP allows to enhance contrast index, since fluorescence is enhanced, when one of the dye molecules is released in the cytoplasm as a result of cleavage of the S—S bond. Any kind of cargo is useful in the methods described herein, e.g., 2-therapeutic cargoes, 2-imaging cargoes, therapeutic and imaging cargo.

Figure 70:
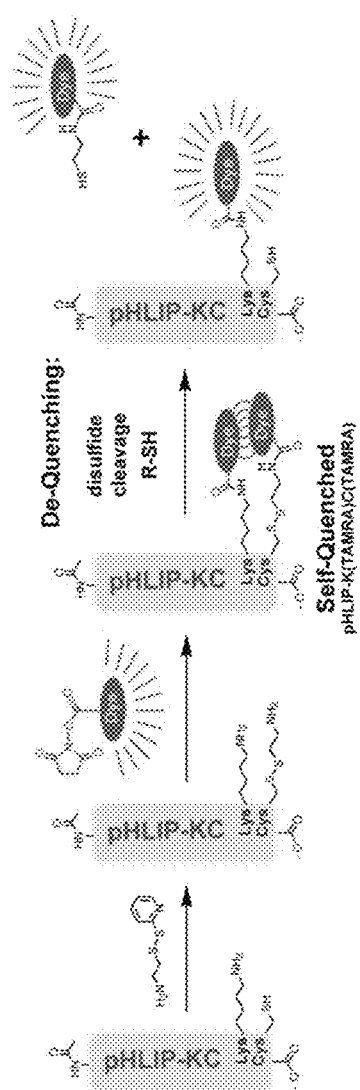
FIG. 70 is a diagram shoring a pHLIP self-quenched construct.

The pHLIP self-quenched construct is an activatable, 'smart' optical imaging probe that only becomes fluorescent at the targeted site, e.g., the acidic solid tumor. Two fluorescent dye molecules are conjugated to the inserting C-terminus of pHLIP. Due to the close physical proximity of the dye molecules, fluorescence is quenched until one of the dye molecules is released (see diagram in FIG. 70).

The self-quenched pHLIP construct has two advantages over previous pHLIP-dye imaging probes: (1) pHLIP insertion across cellular membranes is imaged directly if dye release (i.e., de-quenching) is mediated by intracellular components; (2) the self-quenched state reduces the background fluorescence signal of the probe during circulation, improving signal to noise ratio in vivo.

Design Principles of pHLIP-K(TAMRA)-C(TAMRA)

In this construct, a tetramethylrhodamine (TAMRA) dye is conjugated to a C-terminus Cys residue of pHLIP-KC via a disulfide linker. This disulfide bond is relatively stable (with a half-life of ~24 h) in blood during circulation, but preferentially cleaved inside of cells (which is a much stronger reducing environment than extracellular milieu). The disulfide cleavage, leading to TAMRA release (and de-quenching), is contingent upon pHLIP insertion delivering the C-terminus across the cellular membrane. In order to form the intramolecular, quenched dimer in the intact pHLIP construct, another TAMRA dye molecule is attached to a Lys residue immediately preceding the Cys residue in the C-terminus region.

TAMRA was chosen on the basis that this particular type of rhodamine dye has a strong tendency to form H-type dimers, which almost completely quench fluorescence. Homo-FRET interactions also contribute to self-quenching, but to a lesser extent (~15% in the case of TAMRA). In one aspect, upon de-quenching (H-dimer to monomer), the fluorescence signal increases by more than 10-fold. A short blue-shift in the absorbance peaks (λ max changing from ~550 nm to ~520 nm) is diagnostic of TAMRA H-dimer formation.

Figure 71:
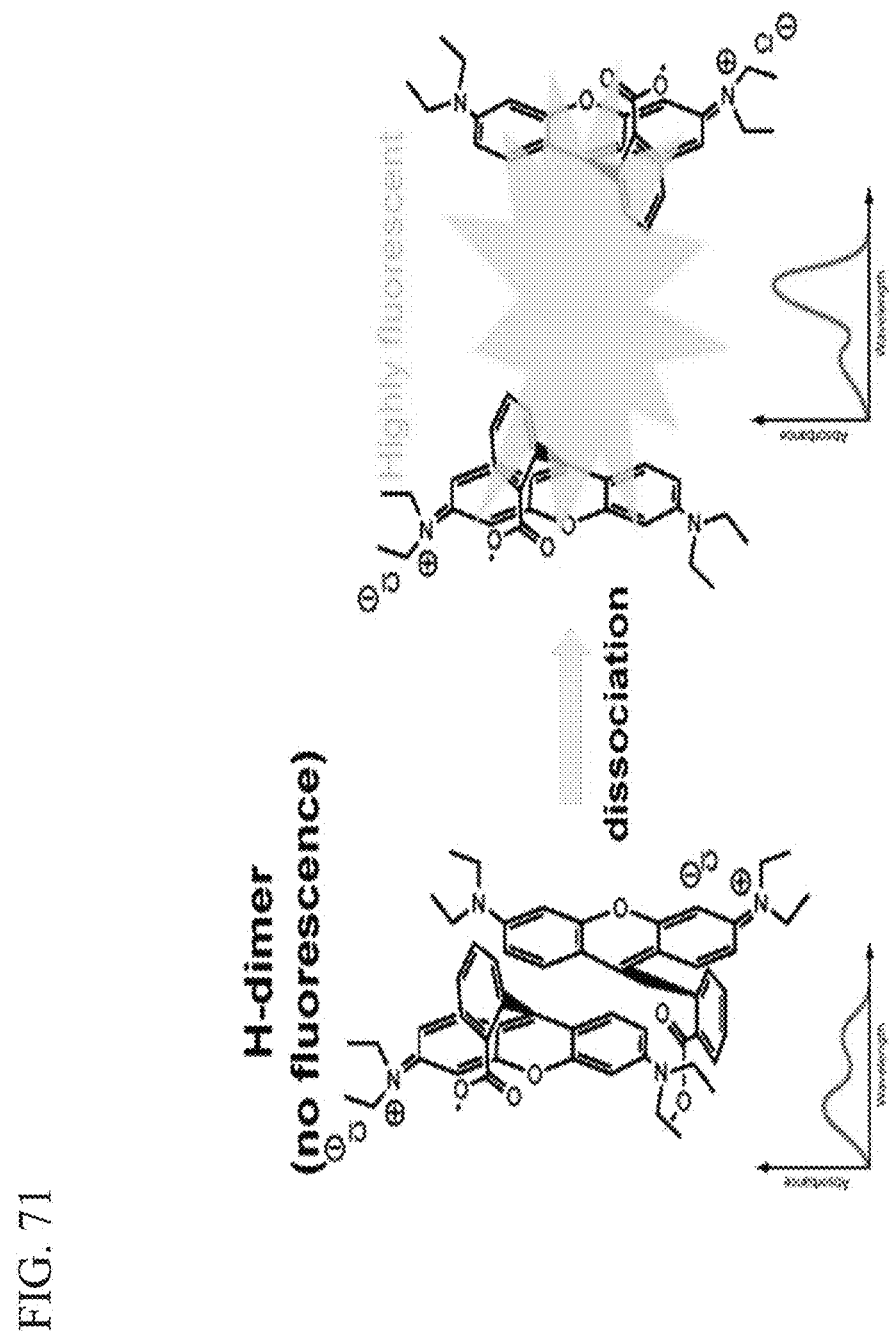
FIG. 71 is a diagram for H-Type dimer formation and blue shift in Ab.
Figure 77C:
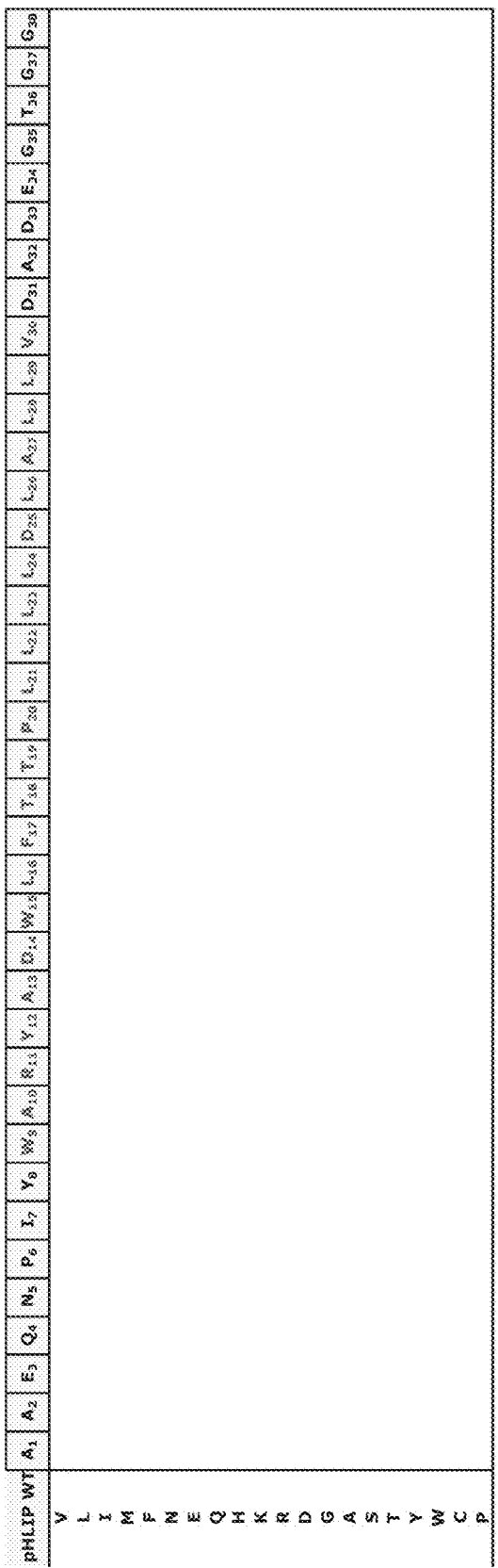
FIGS. 77A-AAE is a set of tables relating to pHLIPs.
Figure 77G:
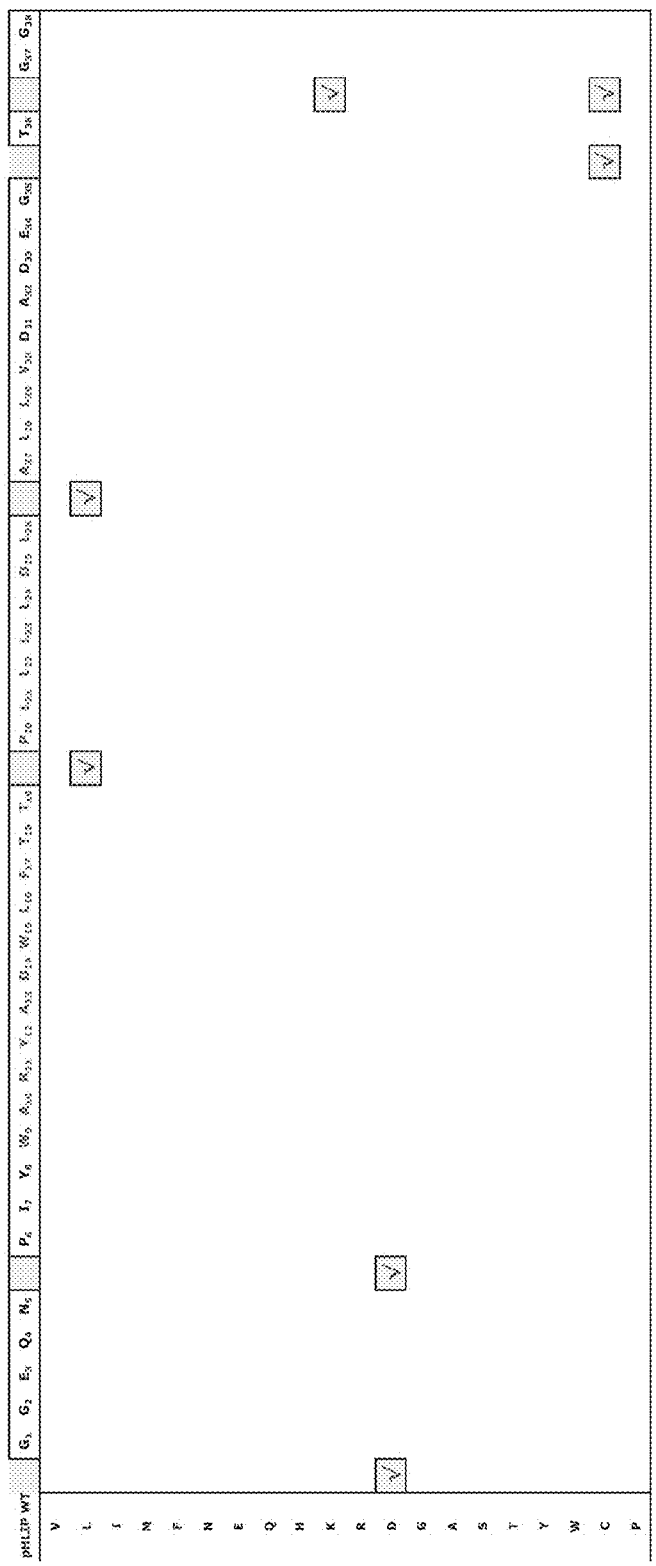

A diagram for H-Type dimer formation and blue shift in Ab is provided in FIG. 71.

The H-type dimer has a short Ab shift, while the J-type dimer has a long Ab shift.

The structures of common dye types are provided below.

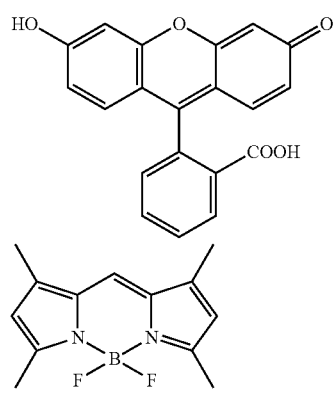

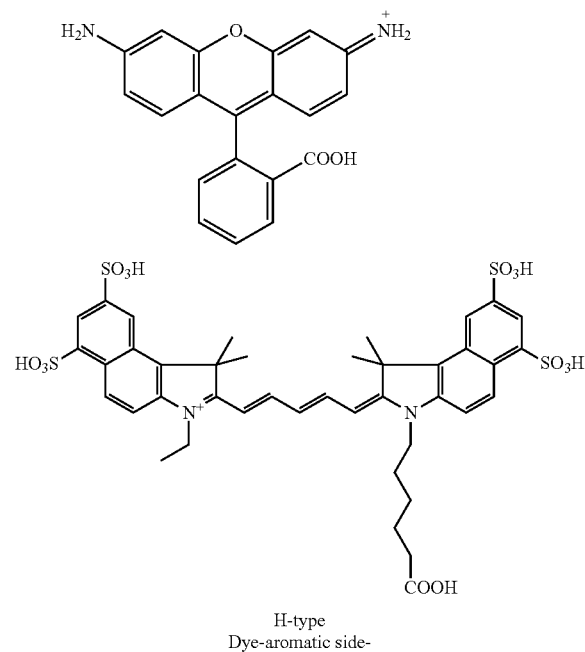

H-type
Dye-aromatic side-

Other exemplary dyes include the following.

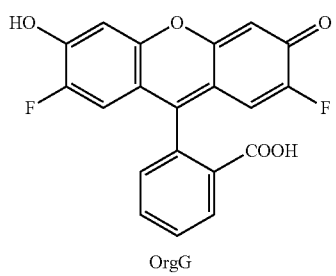

OrgG

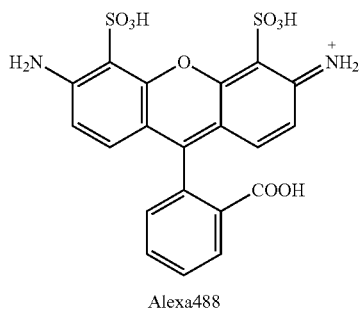

Alexa488

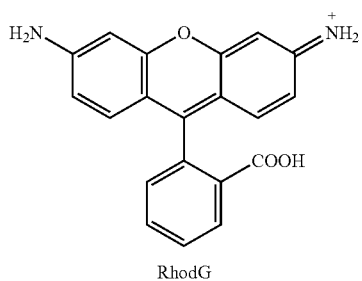

RhodG

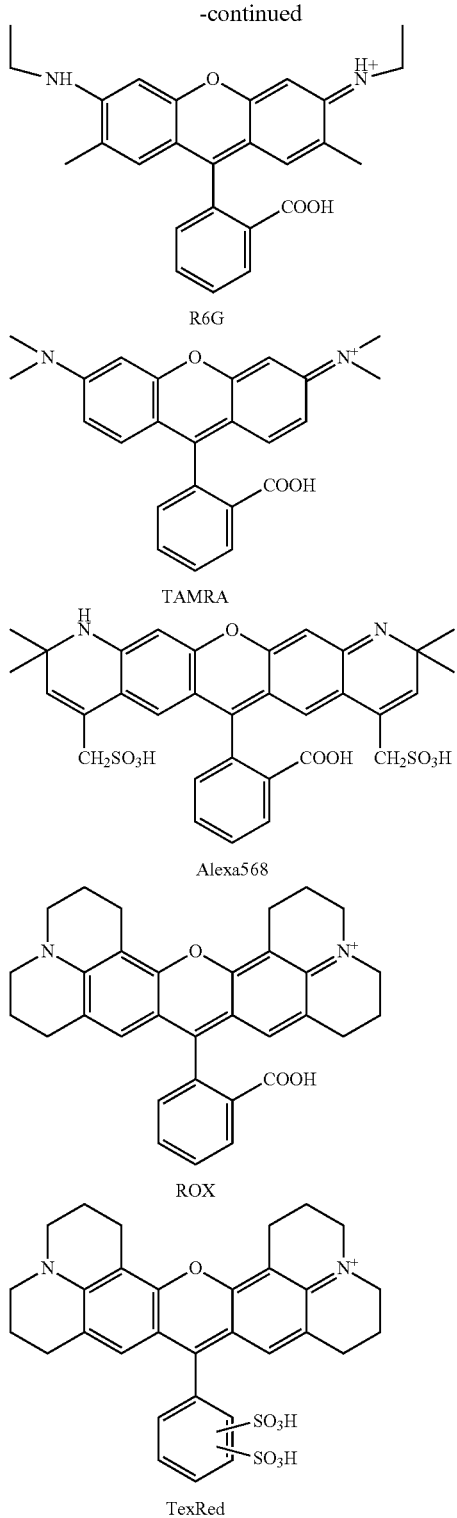

R6G

TAMRA

Alexa568

ROX

TexRed

As shown in FIGS. 47A-C, protein unfolding leads to H-type dimer release.

Synthesis and Characterization of pHLIP-K(TAMRA)-C (TAMRA)

The N-terminus free amino group of pHLIP-KC is capped with an acetyl group (during solid-phase peptide synthesis). Treatment of N-capped pHLIP-KC with S-(2-pyridylthio)-cysteamine (1.2 eq.) extended the C-terminus Cys side-chain into a disulfide cleavable linker with a terminal primary amino group (>90% yield). Subsequently, 4 eq. of 5-carboxy-tetramethylrhodamine, succinimidyl ester (5-TAMRA, SE) was added to attach the TAMRA dyes to Lys and extended Cys side-chains, giving the self-quenched construct pHLIP-K(TAMRA)-C(TAMRA) in 69% overall yield after HPLC purification. The identity of this construct was verified by MALDI-TOF MS (mass expected: 5311; found: 5312). Absorbance spectra of pHLIP-K(TAMRA)-C (TAMRA) showed characteristic blue-shifts, with the H-dimer peak at 520 nm replacing the monomer peak at 550 nm as the overall λ max (indicating significant amount of H-dimer formation).

The interaction of pHLIP-K(TAMRA)-C(TAMRA) with lipid bilayers were investigated following changes in circular dichroism (CD) measurements. CD spectra of pHLIP-K (TAMRA)-C(TAMRA) (5 µM) in solution (5 mM NaPi aq. buffer, pH 8) (state I) and in the presence of POPC vesicles (1:300 pHLIP/lipid ratio) at pH 8 (state II) or pH 5 (state III) showed characteristic changes indicative of pHLIP transitions from an unstructured state I in solution (at pH 8) to a minimally structured state II (presumably on the surface of the bilayer at pH 8), and then to a helical state III at pH 5 (inserted). Therefore, pHLIP-K(TAMRA)-C(TAMRA) retains the trademark pHLIP property of pH-dependent membrane insertion.

Figure 48:
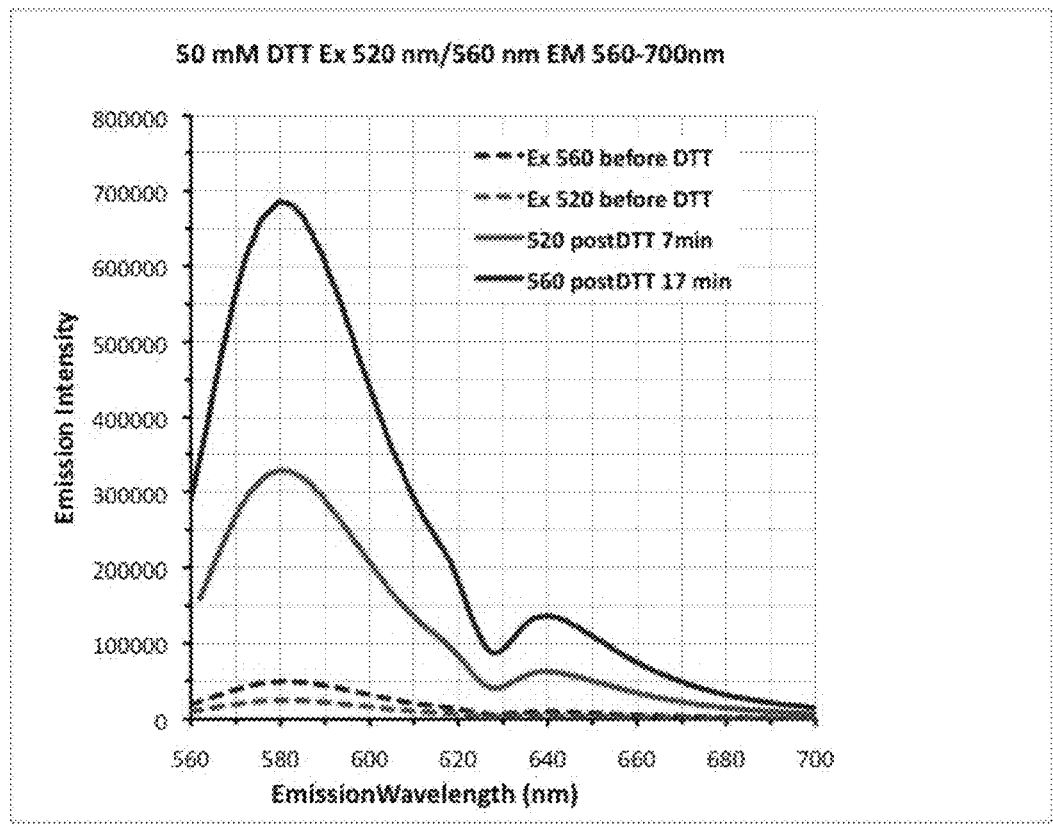
FIG. 48 is a line graph showing that DTT treatment releases self-quenching.

Dequenching of pHLIP-K(TAMRA)-C(TAMRA) in Solution and in the Presence of POPC Liposomes In one aspect, cleavage of disulfide by intracellular free thiol populations releases the TAMRA dye from the Cys side-chain (i.e., H-dimer to monomers transition), thus activating the probe into the fluorescent state (pHLIP-K (TAMRA)C and the released free TAMRA should both be fluorescent). This scenario was simulated by treating pHLIP-K(TAMRA)-C(TAMRA) (~0.5-1 µM) with dithiothreitol (DTT) (1-50 mM) in 5 mM sodium phosphate aq. buffer (pH 7.4). TAMRA fluorescence was measured before and after DTT addition. The samples were excited at either the monomer λ max of 560 nm or the H-dimer wavelength of 520 nm. In general, DTT treatment releases self-quenching. DTT dequenching resulted in as much as 13-14 fold increase in TAMRA fluorescence and FRET 14.5% (0.5-1 microM pHLIP-K(rho)C(rho); FIG. 48). FIG. 48 shows Ex at monomer (Ab max 550 nm) or H-type dimer (Ab max 520 nm). This fluorescence increase is independent of the specific excitation wavelength, although excitation at the monomer absorbance maximum (560 nm) gives more fluorescence both before and after DTT addition. All these observations are consistent with known literature on TAMRA monomer/H-dimer fluorescence. Further, absorbance spectra of DTT treated samples showed λ max redshift (from 520 nm to 560 nm) indicative of H-dimer to monomer transition.

While similar DTT treatments were carried out in the presence of POPC vesicles, fluorescence increase of 13-14 fold was observed at pH 8 (state II) but not at pH 5 (state III). In fact, after 10 min of 9 mM DTT treatment at pH 5 (i.e., the standard DTT condition that gives >10 fold fluorescence increase in state II at pH 8), fluorescence only increased by 1.3 fold; and even after 10 min of 58 mM DTT treatment at pH 5.3, the fluorescence increase was no more than 2.5 fold. The slow and compromised dequenching under state III conditions is a result of DTT's diminished chemical reactivity toward cleaving disulfide bond under acidic conditions (reaction much slower at pH 5 vs pH 8). This issue is clarified by the control experiment of DTT treatment of pHLIP-K(TAMRA)C(TAMRA) in solution at pH 5. However, in another aspect, the following scenario also plays a role: (1) In state III, the cleavable disulfide bond is located inside the liposome or inside the bilayer; (2) DTT only has quick access to the outside of the liposomes, thus unable to reach the disulfide; (3) although DTT is considered membrane permeable, its crossing of the POPC bilayer may be slow.

Example 11: Use of GFP-pHLIP Chimera and Random PCR to Identify New pHLIP Variants Green fluorescent protein fused to pHLIP (GFP-pHLIP) is an example of expression of a whole protein together with pHLIP. GFP is an exemplary marker that can be fused to the pHLIP proteins described herein. However, any other protein could be fused to pHLIP, such as a fragment of an antibody (for example an Fc fragment), or any other biologically active protein. Attachment of GFP to the N-terminus of pHLIP reduces uptake by the kidney and liver, thereby regulating uptake by the kidney and liver. IV injection of GFP-pHLIP shows that pHLIP can deliver protein (GFP) to tumors.

Described herein is the identification and generation of a library of peptide sequences that have pHLIP-like membrane insertion properties. The GFP-fusion tag enables high levels of expression in $E.\ coli$, facilitates purification, and mediates detection by monitoring GFP fluorescence in conjunction with dot blotting using anti-GFP antibody.

The GFP-pHLIP protein construct is generated by fusing pHLIP at the C-terminus of GFP. The expression of this fusion protein construct is under the control of the t7 promoter. Variations in the pHLIP sequence are introduced by random PCR in the pHLIP coding sequence, and the mutations are confirmed by sequencing of the resulting plasmids.

The GFP-pHLIP fusion protein is expressed in $E.\ coli$ by induction with IPTG. Purification of the fusion construct is performed using an Ni-NTA column, facilitated by the $his_6$-tag (SEQ ID NO: 304) at the N-terminus of GFP.

Figure 49:
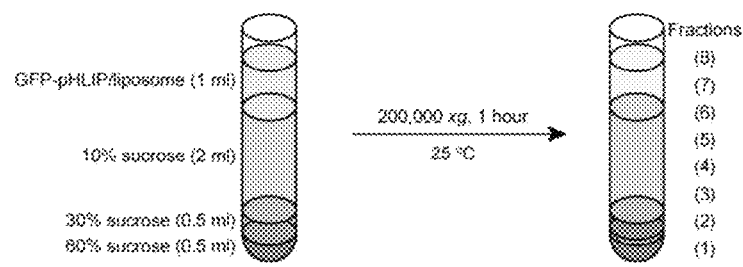
FIG. 49 is a schematic showing that sedimentation ultracentrifugation is employed to examine the membrane insertion property of GFP-pHLIP fusion protein. The fusion protein is mixed with lipid vesicles, and the pH of the solution is subsequently adjusted. The resulting mixture is then laid on top of sucrose gradient and fractionated by ultracentrifugation at 200,000×g for 1 hour at 25° C. Fractions are collected from the bottom of the tube and analyzed for the presence of the fusion protein using fluorescence spectroscopy and dot blotting.

The pHLIP membrane insertion property is analyzed by mixing the GFP-pHLIP fusion protein with lipid vesicles and adjusting the pH of the solution. Membrane-inserted and free protein were then fractionated by sedimentation ultracentrifugation, and the presence of the protein in the fractions were detected by monitoring GFP fluorescence and dot blotting (FIG. 49).

Analysis with the GFP-pHLIP fusion construct. Similar to what has been documented in the study with pHLIP peptide, the pHLIP sequence can mediate membrane insertion of the GFP-pHLIP protein when the pH of the solution is adjusted from 8.0 to 5.0, indicated by co-localization of GFP-pHLIP with lipid vesicles to the higher density fractions (top panels). By contrast, in the absence of pHLIP, the GFP protein remains in the low density fractions after sedimentation ultracentrifugation, both at ph 8.0 and 5.0 (bottom panels). Thus, the data supports the notion that the pHLIP sequence is sufficient to drive membrane insertion of the GFP-pHLIP fusion construct. Thus, this approach is also suitable to examine the membrane insertion properties of other pHLIP sequences.

Figure 50:
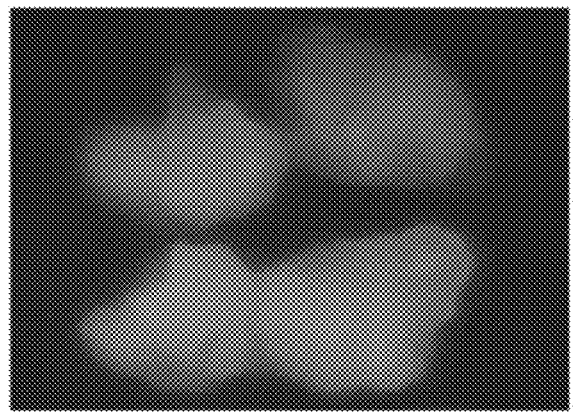
FIG. 50 is a photomicrograph showing GFP fluorescent images of two tumors cut in half after 24 hours after iv (tail vein) injection of 200 uL of 33 uM of GFP-pHLIP. Tumors were implanted by subcutaneous injections of human cervical cancer cells (HeLa) into right flank of athymic nude mice.
Figure 51:
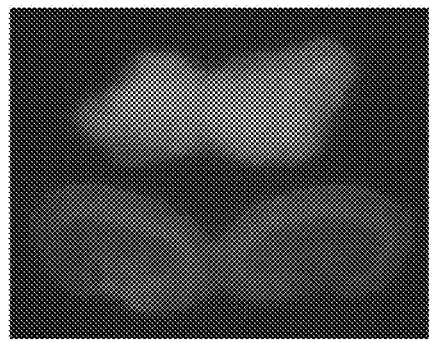
FIG. 51 is a photomicrograph showing GFP fluorescent images of tumor and kidney cut in half after 24 hours after iv (tail vein) injection of 200 uL of 33 uM of GFP-pHLIP. Tumor uptake of GFP-pHLIP is higher than kidney uptake. The average fluorescence signal in liver, kidney and tumor is 147.0±5.7, 201.5±12.0, 388.5±10.8, respectively, which shows that tumor uptake is higher than kidney and liver uptake.

Tumors were implanted by subcutaneous injections of human cervical cancer cells (HeLa) into right flank of athymic nude mice. FIG. 50 shows GFP fluorescent images of two tumors cut in half after 24 hours after iv (tail vein) injection of 200 uL of 33 uM of GFP-pHLIP. FIG. 51 shows GFP fluorescent images of tumor and kidney cut in half after 24 hours after iv (tail vein) injection of 200 uL of 33 uM of GFP-pHLIP. Tumor uptake of GFP-pHLIP is higher than kidney uptake. The average fluorescence signal in liver, kidney and tumor is 147.0±5.7, 201.5±12.0, 388.5±10.8, respectively, which shows that tumor uptake is higher than kidney and liver uptake.

Example 12: Membrane-Associated Folding. Spontaneous Insertion/Exit of a Polypeptide into a Lipid Bilayer and Formation of Helical Structure This study is a continuation of a recent investigation of the membrane-associated folding/unfolding of pHLIP® (pH (Low) Insertion Peptide), where it was demonstrated that the helix forms first on the surface of a bilayer followed by slow insertion of the peptide to adopt transmembrane configuration. Described herein are results of the steady-state and kinetics investigation of several pHLIP variants with a different number of charged residues at the membrane-inserting end, and three single-Trp variants where Trp residues were placed at the beginning, middle and end of the transmembrane helix. As described below, pHLIP variants preserve pH-dependent properties of interaction with membrane. As described in detail below, the number of protonatable residues at the inserting end does not affect the formation of helical structure, but correlates with the time of peptide insertion into a membrane and number of the intermediate states on the folding pathway, and the rates of peptides unfolding and exit. Thus, the existence of intermediate states on the folding and unfolding pathways are non-mandatory, and in a simple case of a polypeptide with non-charged and non-polar inserting end, the folding and unfolding transitions will be all-or-none transitions. The model of membrane-associated insertion/folding and exit/unfolding is described below.

Insertion/Folding and Exit/Unfolding of Membrane Peptides

Prior to the invention described herein, the molecular mechanism of spontaneous polypeptide folding and insertion into a membrane as well as its exit and unfolding was poorly understood. The majority of membrane proteins that mostly consist of hydrophobic amino acids insert into a lipid bilayer with the assistance of translocon machinery (Van den Berg B et al., 2004 Nature, 427:36-44; Osborne A R et al., 2005 Annu Rev Cell Dev Biol, 21:529-550). However, nonconstitutive membrane proteins from the moderately hydrophobic and polar amino acids can bypass the assistance of translocon machinery, and they can spontaneously insert and fold themselves into a lipid bilayer (Brambillasca S et al., 2005 Embo J, 24:2533-2542; Brambillasca S et al., 2006. J Cell Biol, 175:767-777; Sperotto M et al., 2006 Chem Phys Lipids, 141:2-29). The stability and folding of both nonconstitutive and constitutive membrane proteins are strongly constrained by the formation of secondary structures in the lipid bilayer environment driven by the hydrophobic effect and hydrogen bonding. Therefore, the molecular mechanism of polypeptide insertion into a lipid bilayer and formation of secondary structure is a key in the understanding of the first step of the membrane-associate folding. The process of a peptide insertion into bilayer could be triggered by a pH jump, which leads to the protonation/deprotonation of charged groups, and an increase of a peptide hydrophobicity and affinity to membrane. As a result, a polypeptide insertion into a membrane that is accompanied by the formation of a helical structure would occur.

Described herein are the properties of a pH (Low) Insertion Peptide (pHLIP®). The insertion into a membrane and folding of the pHLIP is modulated by pH. At neutral and high pHs, pHLIP is monomeric, and in equilibrium between unstructured forms in aqueous solution and bound to the surface of a lipid bilayer. A drop of pH shifts equilibrium toward inserted TM helical form, while an increase of pH promotes the peptide unfolding and exit from a membrane core. The process of insertion is accompanied by an energy release of about 1.8-2.0 kcal/mol in addition to the binding energy of 6-7 kcal/mol locating the peptide at the membrane surface (Reshetnyak Y et al., 2007 Biophysical journal, 93:2363-2372; Reshetnyak Y et al., 2008 Proceedings of the National Academy of Sciences of the United States of America, 105:15340-15345).

pHLIP insertion is associated with protonation of Asp residues, which leads to an increase of the pHLIP hydrophobicity that triggers folding and insertion of the peptide across a lipid bilayer (Andreev O et al., 2007 Proceedings of the National Academy of Sciences of the United States of America, 104:7893-7898; Musial-Siwek M et al., 2010. Biochimica et biophysica acta, 1798:1041-1046). Insertion of the pHLIP into a membrane is unidirectional: the C-terminus goes across a lipid bilayer, and the N-terminus stays outside (Reshetnyak Y et al., 2007 Biophysical journal, 93:2363-2372; Reshetnyak Y K et al., 2006 Proceedings of the National Academy of Sciences of the United States of America, 103:6460-6465). Fluorescence and circular dichroism (CD) spectroscopy was employed in steady-state mode to monitor pHLIP association with a membrane at high and neutral pHs, and its insertion into the lipid bilayer induced by a drop of pH to form helical structure, orientation of which was established by an oriented circular dichroism (OCD) (Reshetnyak Y et al., 2007 Biophysical journal, 93:2363-2372; Musial-Siwek M A et al., 2010 Biochimica et biophysica acta, 1798:1041-1046; Hunt J F et al., 1997 Biochemistry, 36:15177-15192; Andreev O A et al., 2010 Proceedings of the National Academy of Sciences of the United States of America, 107:4081-4086).

Since fluorescence and CD signals reflect different states of the peptide interaction with the lipid bilayer, and since the pH changes can be accomplished by the rapid mixing, it opens an opportunity to study kinetics of the insertion/folding and exit/unfolding processes. The pHLIP inserts into a POPC phospholipid bilayer in several steps, with rapid (~100 ms) interfacial helix formation followed by slow insertion pathway, which contains several intermediates. The exit of the peptide from a bilayer core proceeds ~800 times faster and through the different intermediates (Andreev O A et al., 2010 Proceedings of the National Academy of Sciences of the United States of America, 107:4081-4086). Prior to the invention described herein, it was unclear why it takes 1000 times longer for the helix to insert into a bilayer after it formed on the membrane surface. Prior to the invention described herein, the intermediates on the insertion/exit pathways were also unclear. To gain more insights into the process of spontaneous polypeptide insertion/folding and exit/unfolding and to elucidate the nature of the intermediates along the folding and unfolding pathways, described herein is the design and investigation of several pHLIP-variants.

Synthesis of Peptides

All variants were prepared by solid-phase peptide synthesis using Fmoc (9-fluorenylmethyloxycarbonyl) chemistry and purified by the reverse phase chromatography at W.M. Keck Foundation Biotechnology Resource Laboratory at Yale University. The lyophilized powder of the peptides was dissolved in a solution containing 3M urea. The peptides were transferred to buffer using a G-10 size-exclusion spin column. The concentration of the peptides were determined using standard methods.

Liposomes Preparation

Large unilamellar vesicles were prepared by extrusion. 2.5 ml of 25 mg POPC (1-palmitoyl-2-oleoyl-sn-glycero-3-phosphocholine, Avanti Polar Lipids, Inc.) or 90 mol % of POPC and 10 mol % of fluorescein DHPE (N-(fluorescein-5-thiocarbamoyl)-1,2-dihexadecanoyl-sn-glycero-3-phosphoethanolamine, triethylammonium salt, Invitrogen) lipids in chloroform was desolvated on a rotary evaporator and dried under the high vacuum for several hours. The phospholipid film was rehydrated in 10 mM phosphate buffer, pH 8.0, vortexed for 2 hours, and repeatedly extruded using 100 or 50 nm membrane pore size. The concentration of the fluorescein lipids was determined by absorbance of fluorescent dye $\epsilon_{492}=70,000$ $M^{-1}cm^{-1}$ in phosphate buffer at pH9.

Steady-State Fluorescence and Circular Dichroism Measurements

Tryptophan fluorescence and circular dichroism (CD) measurements were carried out on a PC1 ISS spectrofluorometer (ISS, Inc.) and a MOS-450 spectrometer (Bioligic, Inc.), respectively, under temperature control. All measurements were performed at 25° C. Peptide fluorescence spectra were recorded from 310 nm to 410 nm with the spectral widths of excitation and emission slits set at 4 nm and 2 nm, respectively, using excitation wavelengths of 295 nm. The polarizers in the excitation and emission paths were set at the "magic" angle (54.7° from the vertical orientation) and vertically (0°), respectively, to reduce Wood's anomalies from the reflecting holographic grating. Peptide CD spectra were recorded from 190 nm to 270 nm with 0.5 nm increment using a sample cuvette with an optical path length of 0.5 cm. The concentration of the peptides and POPC was 7 µM and 1.5 mM, respectively pH-Dependence pH-dependent partition of the peptides into a lipid bilayer of membrane were investigated by the shift of the position of maximum of fluorescence spectra of the pHLIP variants in presence POPC liposomes induced by a drop of pH from 8 to 3 by addition of HCl. 3 µM of the peptide was incubated overnight with 2 mM of 100-nm POPC liposomes, and pH decrease was achieved by the addition of aliquots of 4, 2, 1 and 0.1 M HCl. pH was measured by micro-electrode probe (Thermo Electron Corporation, Orion Ross Micro pH electrode). Fluorescence spectra were recorded at each pH value. The spectra were analyzed by the decomposition algorithms using on-line PFAST toolkit (Protein Fluorescence And Structural Toolkit: http://pfast.phys.uri.edu/) to establish the position of maximum of emission. Finally, the position of maximum of fluorescence spectra ($\lambda_{max}$) were plotted versus pH and the Henderson-Hasselbalch equation was used to fit the data (using Origin 8.5 software):

$$\lambda_{max} = \lambda_{max}^2 + \frac{(\lambda_{max}^1 - \lambda_{max}^2)}{1 + 10^{n \cdot (pH - pKa)}}$$

where $\lambda_{max}^1$ and $\lambda_{max}^2$ are the beginning and end of the transition, n is the cooperativity parameter, and pKa—is the mid of transition.

Oriented Circular Dichroism Measurements

Oriented circular dichroism was measured from the supported bilayer deposited on quartz slides with special polish for far UV measurements and with spacers of 0.2 mm thickness on one side of each slide (Starna). Quartz slides were cleaned by sonication for 10 min in cuvette cleaner solution (Decon Contrad 70% and 5% water), 2-propanol, acetone, 2-propanol and rinsed with deionized water. Then, the slides were immersed in a mixture of concentrated sulfuric acid and hydrogen peroxide (ratio 3:1) for 5-10 min to completely remove any remaining organic material form the slides. Slides were then thoroughly rinsed with and stored in deionized water (Milli-Q purified water kept at 25° C.). A POPC lipid monolayer was deposited on a quartz substrate by the Langmuir-Blodgett (LB) method using KSV minithrough. For the LB deposition, a POPC lipid solution in chloroform was spread on the subphase and allowed to evaporate chloroform for about 30 min, followed by monolayer compression to 32 mN/m. First layer was deposited by retrieving the slide from the subphase at a rate of 15 mm/min. The second layer of the bilayer was created by fusion. For this step, the monolayer on the slide was incubated with a solution of POPC vesicles (50 nm in diameter obtained by extrusion) mixed with the peptide solution at pH 4 (0.5 mM POPC and 10 μM peptide). The fusion occurred for about 6 hours in 100% humidity condition. Then, the excess vesicles were carefully removed and the slides were stack to make a pile filled with the peptide solution (5 μM) at pH 4. The bilayers with the peptide solution were allowed to equilibrate for about 6 hours. Measurements were taken at 3 steps during the process: when the monolayers were incubated with the excess of liposomes, soon after spaces between slides were filled with the peptide solution and 6 hours after the second measurement. 14 slides (28 bilayers) were assembled and OCD spectrum was recorded on a MOS-450 spectrometer with 2 s sampling time. All control measurements of the peptide between slides with and without supported bilayer and in presence of excess of POPC liposomes were carried out.

Stopped-Flow Fluorescence and Circular Dichroism Measurements

Stopped-flow fluorescence and CD measurements were carried out on a SFM-300 mixing apparatus connected to a MOS-450 spectrometer (Biologic, Inc.) under a temperature control. The FC-20 and TS-100/15 observation cuvettes were used for the fluorescence and CD measurements, respectively. All solutions were degassed several minutes under a vacuum before loading into the syringes to minimize air bubbles. pHLIP variants (7 μM) were pre-incubated with POPC (1.5 mM) at pH 8.0 to reach binding equilibrium and folding/insertion was induced by fast mixing (5 ms dead time) of equal volumes of pHLIP-POPC variants at pH 8.0 and appropriately diluted HCl, to obtain a drop of pH from 8 to desired value. In the unfolding experiments, pHLIP variants were pre-incubated with POPC at pH 8.0. Then HCl was added to lower the pH to 3.6, and time was allowed for equilibration (half an hour). Unfolding was induced by rapidly mixing equal volumes of pHLIP-POPC variants at pH 3.6 and diluted NaOH to increase the pH from 3.6 to desired value. In majority of cases, samples were collected after the stopped-flow shots and the steady-state fluorescence spectra were recorded on a PC1 spectrofluorometer. Changes of the pHLIP fluorescence signal were recorded through a 320 nm cutoff filter using an excitation wavelength of 295 nm. The fluorescence signal was corrected for the photobleaching. Each kinetic curve was recorded several times and then averaged, excluding the first 3-4 shots. Changes of the pHLIP CD signal where recorded at 225 nm. About 20 shots were performed and CD signals were averaged.

Probing pH Changes on Inner Leaflet of Lipid Bilayer by Changes of FITC Fluorescence To probe changes of pH on inner leaflet of lipid bilayer POPC liposomes containing 10 mol % of FITC-DHPE were used. FITC is a pH-sensitive fluorescent dye conjugated with headgroups of lipids, the dye absorbance and fluorescence decreases with decrease of pH from 9 to 4. The pH8-3.6 transition was induced by fast mixing (5 ms dead time) of 1.5 mM of POPC-FITC liposomes and HCl at 3:4 ratio. For the pH8—transition 1:1 mixing ratio was used. To raise the pH, fluorescent liposomes, which were pre-mixed with HCl and had pH4 equilibrated inside and outside the vesicles, were rapidly mixed with the diluted NaOH. 1:1 and 3:4 ratios were used to induce pH3.6-6 and pH3.6-8 transitions, respectively. The fluorescence changes of FITC signal were recorded at 515 nm emission wavelength at the excitation wavelength set at 492 nm. The fluorescence signal was corrected for the photobleaching. Each kinetic curve was recorded several times and then averaged, excluding the first 3-4 shots Data Analysis The kinetic equations were solved in Mathematica 7 (Wolfram Research). Nonlinear least squares curve fitting procedures were carried out in Origin 8.5 and MatLab 2009b (7.9.0.529 version).

Kinetic of pHLIP Interactions

The pHLIP peptide forms helix as a result of pH drop 1000 faster than it inserts into a lipid bilayer, and insertion occurs through several steps (intermediates). The time of insertion and nature of these intermediates might be explained by the presence of four protonatable groups at the C-terminus of the peptide, which have to cross membrane to complete the process of insertion. In order to cross the highly hydrophobic membrane core, these charged groups should be at least partially protonated. It was assumed that the number of protonatable groups at the C-terminus could correlate with the rates of insertion and exit, as well as the number of intermediate states along the insertion/exit pathways. To evaluate this idea, two truncated pHLIP variants: pHLIP-2 and pHLIP-1 were analyzed, where the number of protonatable groups (shown in red in FIG. 72A) was reduced to two and one, respectively. Additional Asp residues were placed to the N-terminus to preserve peptide solubility.

To get insights into the structural nature of intermediates along the insertion and exit pathways, three single-Trp variants of pHLIP-4 peptide (pHLIP-W1, pHLIP-W2 and pHLIP-W3) were examined, where Trp residue was positioned at the beginning, middle, and end of TM helix. See FIG. 72B.

To demonstrate that pHLIP variants preserve the unique pH dependent membrane-inserting properties, fluorescence and CD spectroscopic techniques were utilized. Previously, three major states of pHLIP peptide interaction with lipid bilayer of membrane were identified: the peptide in buffer at pH8 in absence (state I) and presence (state II) of liposomes and inserted in the lipid bilayer to form TM orientation at low pH (state III) (Reshetnyak Y K et al., 2007 Biophysical journal, 93:2363-2372). The transitions between the states can be monitored by the changes of peptide fluorescence and CD signals and TM orientation could be probed by OCD (Reshetnyak Y K et al., 2007 Biophysical journal, 93:2363-2372; Andreev O A et al., 2010 Proceedings of the National Academy of Sciences of the United States of America, 107:4081-4086).

Figure 21A:
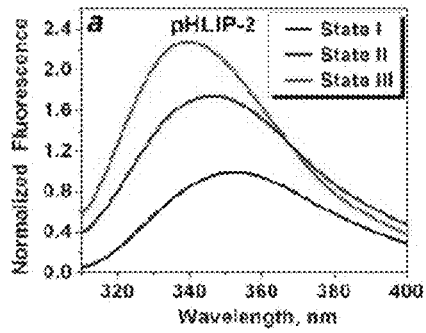
FIGS. 21A-F are a series of line graphs demonstrating the three states and pH-dependent insertion into membrane for pHLIP-2 and -1 variants. Three states of the pHLIP-2 and -1 variants monitored by the changes of the steady-state tryptophan fluorescence (A, D) and CD (B, E) spectroscopic signals are presented (state I corresponds to the peptide in solution at pH8; state II corresponds to the peptide in presence of POPC liposomes at pH8; state III corresponds to the peptide with POPC, when pH was dropped from 8 to 3.6 by addition of aliquot of HCl). OCD signals (green lines on the B, E) demonstrate transmembrane orientation of the helices at low pH. The pH-dependent insertion into the lipid bilayer of membrane for the pHLIP-2 and -1 is shown on C and F, respectively.
Figure 21D:
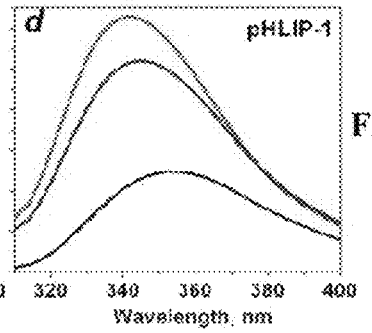
Figure 21B:
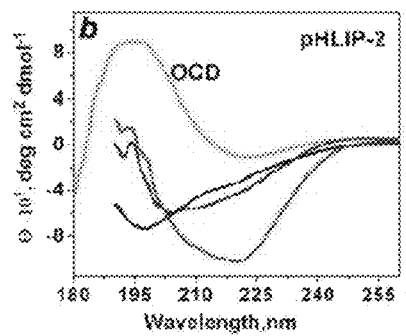
Figure 21E:
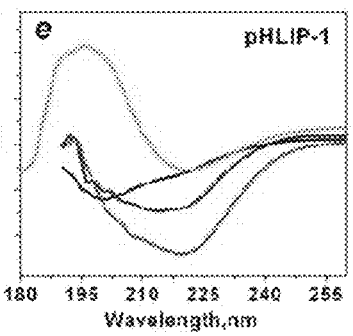
Figure 21C:
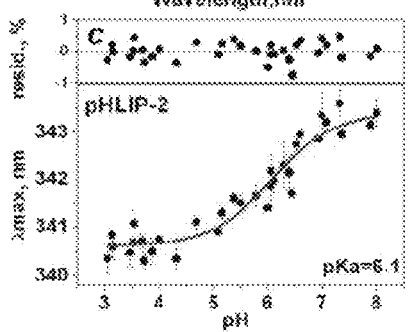
Figure 21F:
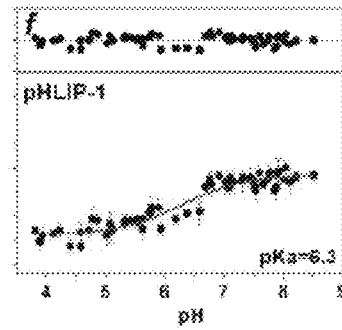
Figure 22A:
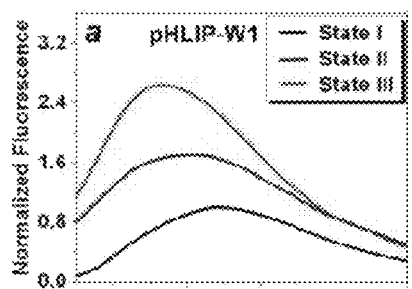
FIGS. 22A-F are a series of line graphs demonstrating the three states of single-Trp pHLIP variants. Three states of the single-Trp pHLIP variants (pHLIP-W1, -W2, -W3) monitored by the changes of the steady-state tryptophan fluorescence (A, C, E) and CD (B, D, F) spectroscopic signals are presented. OCD signals (green lines on the B, D, F) demonstrate transmembrane orientation of the helices at low pH.
Figure 22B:
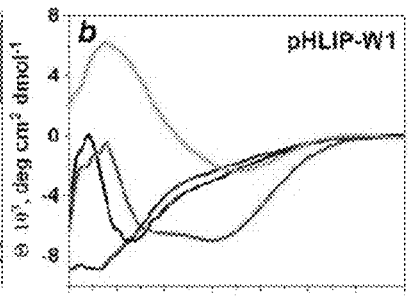
Figure 22C:
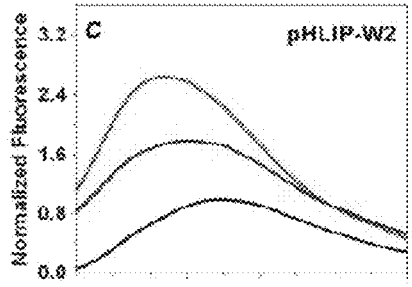
Figure 22D:
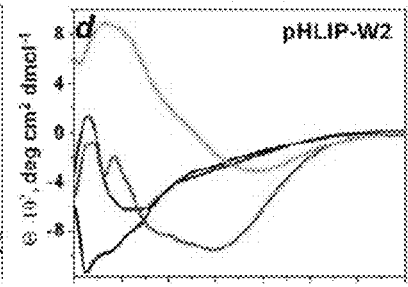
Figure 22E:
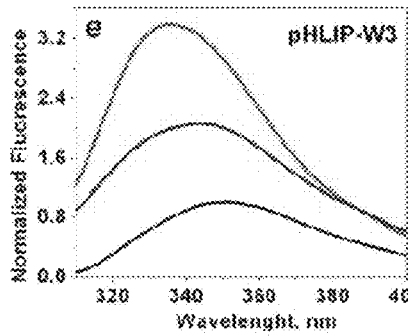
Figure 22F:
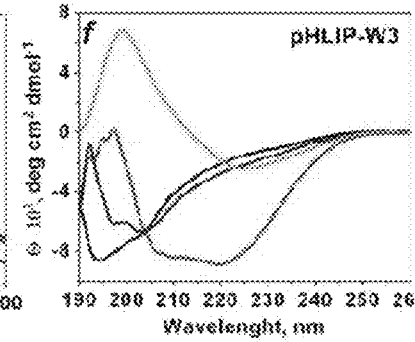

Fluorescence and CD spectra of the pHLIP variants at normal and low pH were recorded in absence and presence of POPC liposomes (FIGS. 21A-F and FIGS. 22A-F). At pH8 in absence of liposomes (state I) all pHLIP variants are unstructured (characteristic negative band on CD spectra at 195 nm) with tryptophan residues exposed to the aqueous solution (the maximum of fluorescence is at 348-350 nm). The addition of POPC liposomes at pH8 (state II) leads to the increase of fluorescence quantum yield along with the blue shift of the position of maximum of emission spectra, which reflects peptide attachment to the lipid bilayer and partial partition into it. The pHLIP-2 and pHLIP-1, which have less polar residues at the C-terminal end than pHLIP-4, demonstrate deeper partition into the lipid bilayer (higher increase of fluorescence and more short-wavelength shifted position of the fluorescence spectrum) and increase of helicity (appearance of negative CD signal at 222-225 nm) (FIGS. 21A-E). At pH4 (state III) further increase of fluorescence intensity and additional blue shift of emission spectra were observed for all pHLIP variants, which occurs when tryptophan residues become buried into the hydrophobic core of a membrane. Peptide partition into the membrane is accompanied by the formation of helical structure (minima at 208 and 222 nm on CD spectra). Single-Trp pHLIP variant with location of Trp residue at the C-terminal end of the helix (pHLIP-W3) demonstrates the highest increase of fluorescence in state III among the investigated peptides (FIG. 22E). To verify the transmembrane orientation of the helices, OCD measurements were performed at low pH. A characteristic OCD spectrum was obtained for each pHLIP variant with the positive and negative bands around 200 and 225 nm, respectively, indicating the transmembrane orientation (green lines on FIG. 21B, FIG. 21E and FIG. 22B, FIG. 22D, FIG. 22F). Since Asp residues were moved from the inserting C-terminus of the pHLIP-2 and -1 variants, pH-dependencies of the insertion into the membrane were carried out for these pHLIP variants. FIG. 21C and FIG. 21F demonstrate the shift of the position of maximum of tryptophan emission of pHLIP-2 and pHLIP-1 as a function of pH. The pKa of the transition was found by fitting of the curves with the Henderson-Hasselbalch equation (see Method section). pKa of membrane-insertion for the pHLIP-2 and pHLIP-1 is 6.1 and 6.3, respectively, which is very close to the pKa of insertion for the pHLIP-4. Some increase in pKa value for the pHLIP-1 might reflect slight shift of pKa of protonation of Asp/Glu residues due to the deeper positioning of the peptide into a lipid bilayer in the state II.

Figure 23A:
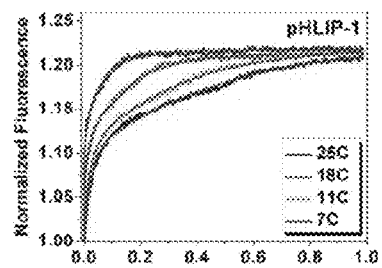
FIGS. 23A-D are a series of line graphs showing insertion and folding of pHLIP-4, -2 and -1 variants at different temperatures and Arrhenius plot. Kinetics of the fluorescence changes for the pHLIP-4, -2, -1 (A, B, C) recorded at various temperatures are presented. The fitting curves are colored in red. Arrhenius plots (D) are shown for the second and third rates of the pHLIP-2, -1 and 4. The data were fitted by the Arrhenius equation (7).
Figure 23B:
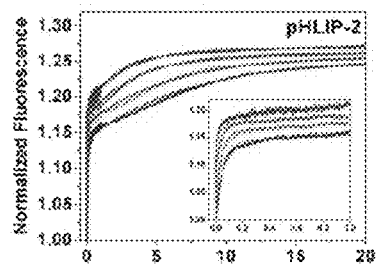
Figure 23C:
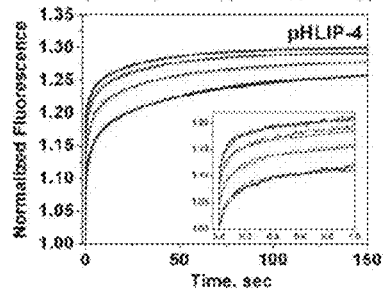

Since modifications of the pHLIP sequence do not alter pH-dependent ability of variants to interact with a lipid bilayer of membrane, kinetic studies with pHLIP variants were performed. In contrast to previous work, the excitation was set at 295 nm to exclude contribution of Tyr residues in the observed fluorescence signal and exclude possibilities of FRET from Tyr to Trp. First, insertion of pHLIP-4, -2, -1 peptides into the lipid bilayer triggered by drop of pH from 8 to 3.6 (induced by rapid mixing of pHLIP pre-incubated with POPC at pH8 with HCl) was monitored at various temperatures (7, 11, 18, 25° C.) (FIGS. 23A-C). Even without any mathematical treatment of the kinetics curves, it is clear that the process of the pHLIP-2 and pHLIP-1 insertion into the bilayer is completed approximately 10 and 100 times, respectively, faster than the insertion of the pHLIP-4. At the same time, the rate of the helical structure formation for all truncated variants is very similar to the rate of helix formation for the pHLIP-4 (about 100 ms for 85-90% of CD signal changes). Thus, the number of protonatable residues at the inserting end does not affect the formation of helical structure, but correlate with the time of peptide insertion into the lipid bilayer.

Previously, a pseudo-first order model was utilized to fit kinetic data and find rates and contributions of individual components. Only forward reactions were taken into consideration to simplify the mathematical model. Described herein is the processes taking into account both forward and backward reactions. Several models were considered: two-state (no intermediates):

$$A \underset{k_{\bar{1}}}{\overset{k_1}{\rightleftarrows}} B$$

three-state (single intermediate):

$$A \underset{k_{\bar{1}}}{\overset{k_1}{\rightleftarrows}} B \underset{k_{\bar{2}}}{\overset{k_2}{\rightleftarrows}} C$$

and four-state (two intermediates) models:

$$A \underset{k_{\bar{1}}}{\overset{k_1}{\rightleftarrows}} B \underset{k_{\bar{2}}}{\overset{k_2}{\rightleftarrows}} C \underset{k_{\bar{3}}}{\overset{k_3}{\rightleftarrows}} D$$

The transitions between states are described by the set of differential equations (see Appendix 1-3), which could be solved, but the obtained functions would be very complex and will contain a number of variable parameters increasing with the complexity of the applied model. It is not practical to perform fitting of the experimental data using such complex functions: the slight variation in input data dramatically affect the solution, thus making it unreliable. However, the solution could be presented in general form as a sum of the exponential functions:

$$F(t)=f_0+f_1\exp(-t/\tau_1) \text{ for the two-state model} \quad (1)$$

$$F(t)=f_0+f_1\exp(-t/\tau_2)+f_2\exp(-t/\tau_3) \text{ for the three-state model} \quad (2)$$

$$F(t)=f_0+f_1\exp(-t/\tau_1)+f_2\exp(-t/\tau_2)+f_3\exp(-t/\tau_3) \text{ for the four-state model} \quad (3)$$

where $\tau_i$ are the characteristics time for each transition or $v_i=1/\tau_i$ are the characteristic rate of the transitions, and $f_i$ are the characteristics contributions. Thus fitting of the measured curves could be performed by the exponential functions. However, the characteristic rates (or time) and contributions need to be related to the real rate constants ($k_i$) and contributions (the equations are given in Appendix 1-3). Due to the complexity of the problem, relations were established only between the characteristic rates and the real rate constants not considering the contributions. By making a number of assumptions simple approximate relations between k and v could be established (for the details see Appendix 1-3). For the two-state model:

$$k_1 \sim v_1, \quad (4)$$

for the three-state model:

$$k_1 \sim \frac{v_1}{1.1} - \frac{v_2}{12.21}, \quad k_2 \sim 1.0091 v_2 \quad (5)$$

and for the four-state model:

$$k_1 \sim v_1, \quad k_2 \sim \frac{v_2}{1.1} - \frac{v_3}{12.21}, \quad k_3 \sim 0.991 v_3 \quad (6)$$

The experimental kinetic curves were fitted by the single, double and three exponential functions (eqs. 1-3), which are general solutions for the two-, three- or four-state models, respectively. In each case, the solution with the minimal number of exponents that provide an adequate fit of the experimental data was selected. Global fitting was performed in all cases, when it was possible. Thus, some characteristic times were used as shared parameters in the fitting of kinetic curves obtained at different temperatures or different pHs. In Tables 1, 3-5, the characteristic times obtained in a result of fitting and the rate constants calculated according to the equations 4-6 are presented.

Figure 23D:
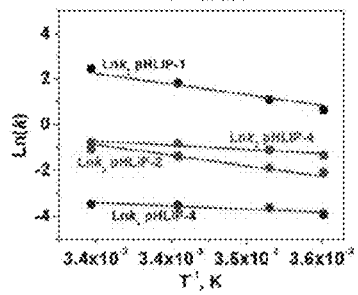

For the adequate description of the fluorescence insertion kinetics of the pHLIP-4 peptide, the four-state model has to be implicated. However, the process of pHLIP-2 and -1 insertion into the membrane could be described by the two-state model. The pHLIP-4 adopts TM configuration within 30-50 sec (at various temperatures), pHLIP-2—within 3-8 sec, and for the pHLIP-1 the process is completed within first 80-400 ms, which coincides with the time of helix formation (90-100 ms). Thus, the process of helix formation and peptide insertion occurs practically simultaneously, unless there are charges at the inserting tail, which should be at least partially protonated to insert across a bilayer. The higher the number of charged groups are at the inserting end, the lower is the probability of them to be protonated at the same time and be moved across a bilayer. Therefore, the process of insertion slows down and even additional intermediate states appear on the insertion pathway, which might be transient for the pHLIP-1 and -2. The first (fastest) component was calculated with less accuracy than the others, since it is within the range of dead time of our experimental set up. The characteristic time, r, was kept constant when the fitting of kinetics curves measured at different temperatures for all pHLIPs was carried out. The rate constant of the first component is twice less for the pHLIP-2 in comparison to the pHLIP-1, and twice less for the pHLIP-4 compared to the pHLIP-2 (Table 1). To establish activation energies ($E_a$) and frequency factors (A) for the transitions between states for each pHLIP variant the Arrhenius plots were constructed (FIG. 23D). The points were fitted by the Arrhenius equation (red lines on FIG. 23D):

$$\ln k = -E_a/RT + \ln A \quad (7)$$

The global fit was applied for the analysis of the second transition for the pHLIP-2 and -1, and the second and third transitions for the pHLIP-4. The thermodynamic activation parameters are shown in the Table 2. The activation energy barrier for the pHLIP-1 and -2 is 13.2 kcal/mol, the difference is in frequency factors. The frequency factor for the pHLIP-1 transition to the final state is an order of magnitude higher than the frequency factor for the pHLIP-2. This might reflect the lower probability of simultaneous protonation of both COO groups of Glu and C-terminus on the pHLIP-2, than the probability of protonation of single carboxyl terminus of the pHLIP-1. Insertion of helical structure of the pHLIP-4 into the lipid bilayer occurs by two steps with the activation barrier of about 4.6 kcal/mol each, but more than million times lower frequency factors than for the pHLIP-2 and -1. Especially low frequency factor (value of 80) was obtained for the transition to the final TM state for the pHLIP-4.

Figure 24A:
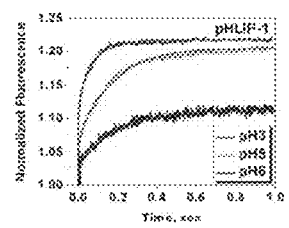
FIGS. 24A-H are a series of line graphs illustrating insertion and folding of pHLIP-4, -2 and -1 variants at different pHs. Kinetics of the fluorescence and CD changes recorded at different pH jump transitions (pH 8-6—blue line; pH 8-5 green line; and pH 8-3.6 black line) for pHLIP-1 (A), pHLIP-2 short time scale (B) and long timescale (E-F), pHLIP-4 short time scale (C) and long timescale (G-H) are presented. The representative kinetic of the CD changes for the pH8-3.6 transition is shown (D) (similar signal was obtained for all pHLIP variants). All fitting curves are colored in red.
Figure 24B:
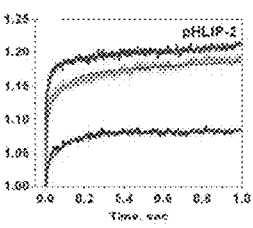
Figure 24C:
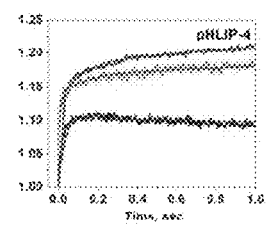
Figure 24D:
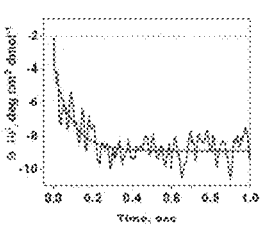
Figure 24E:
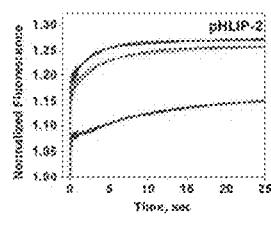
Figure 24F:
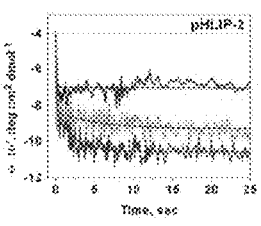
Figure 24G:
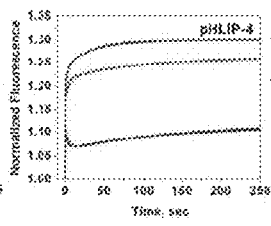
Figure 24H:
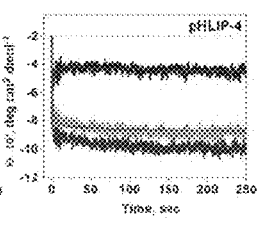
Figure 25:
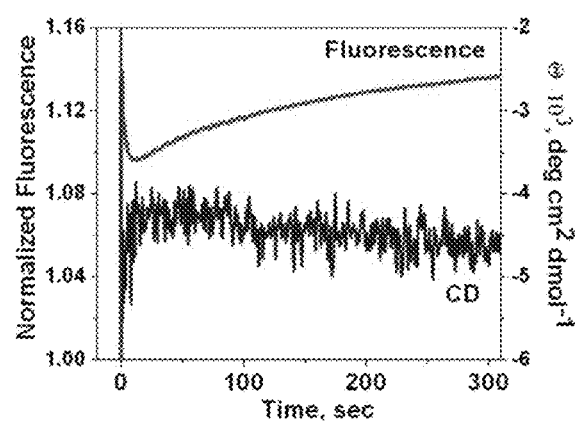
FIG. 25 is a line graph showing "Kink" on the fluorescence and CD kinetic curves. The CD (blue line) and fluorescence (red line) signal changes at the pH8-6 transition for the pHLIP-4 variant are shown.

To elucidate the nature of intermediate states, transitions from pH8 to 3.6 and intermediate pHs were examined. The fluorescence and CD kinetics were recorded for pH8-6, pH8-5 and pH8-3.6 transitions (FIGS. 24A-H). With reduction of pH jumps both processes of peptides folding and insertion into a bilayer slow down. The pHLIP-2 and pHLIP-1 insertion/folding could be described by the three-state model, while the four-state model is needed for the description of the insertion and folding of the pHLIP-4. The first (fast) rate of the insertion is very similar for all pHLIP variants (FIGS. 24A-C) and coincides with the rate of helix formation (FIG. 24D and Table 3). However, after the first 100-300 ms, behavior of pHLIP variants is significantly different. The pHLIP-1 forms helical structure and partitions into the lipid bilayer slightly slower, when pH was dropped from 8 to 6 in comparison to 8-3.6 pH jump (FIG. 24A). All processes are completed within first 200-300 ms for the pHLIP-1 at any pH jump. The absence of several protonatable groups at the inserting end makes peptide to be less dependent on changes of pH-jumps. In contrast, pHLIP-2 and pHLIP-4 insertion into the membrane more dependent on final pH of the transition (FIGS. 24E-F and G-H Thus, more protonatable groups are on the inserting end the slower process of insertion is at intermediate pH jumps. About 85% of CD signal changes for both peptides occur within first 80 ms for all pH-transitions (Table 3). The rate constants for the rest 15% of the CD signal changes correlate very well with the rate constant of the fluorescence changes at the final step of the insertion and depend on magnitude of pH-jump. This could indicate that the final adjustment of the content of helical structure occurs at the final stage of insertion, when peptides adopt TM orientation.

pHLIP-4 behavior at pH jump from 8 to 6, the "kink" in the fluorescence and CD kinetic curves was observed. After rapid (90-100 ms) increase of the fluorescence signal, it decreases within next 5-7 sec, and later on it increases again (FIG. 25). The similar pattern was observed for the changes of the CD signal: the molar ellipticity decreases, then increases and slowly drops again. The time scale of the fluorescence and CD signal changes coincide. The kinetic curves of the insertion and folding at pH8-6 jump were fitted by the three-exponential function with negative amplitudes for the second component (shown in red in Table 3). The monitored changes indicate that after drop of pH, pHLIP-4 partitions into lipid bilayer, which is accompanied with the formation of helical structure, while later, the peptide comes out from the membrane with the reduction of helical content, and finally it "dives" into the membrane slowly, which leads to the increase of helical content.

Figures 26A, 26B, 26C, 26D, 26E, 26F, 26G, 26H:
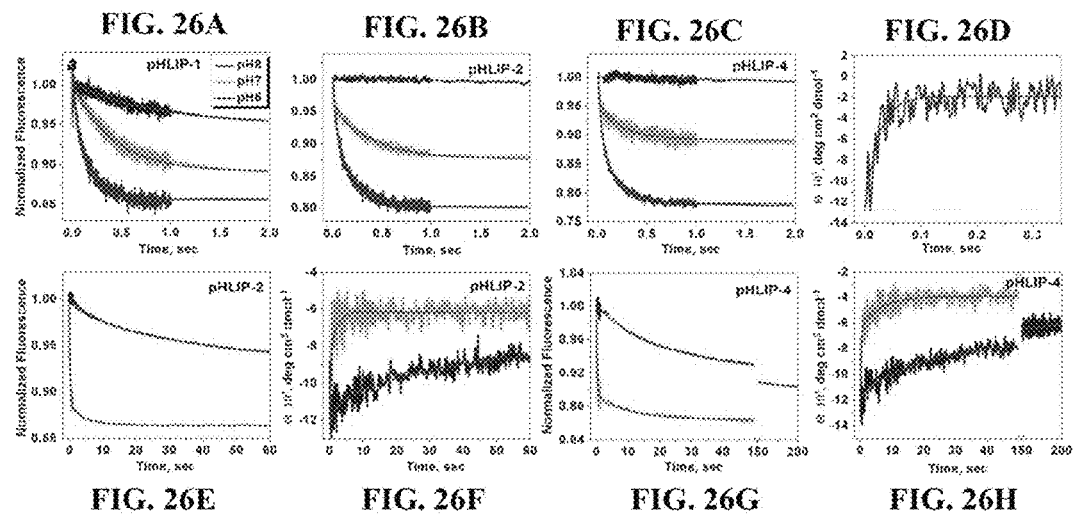
FIGS. 26A-H are a series of line graphs showing exit and unfolding of pHLIP-4, -2 and -1 variants at different pHs. Kinetics of the fluorescence and CD changes recorded at different pH jump transitions (pH 3.6-6—blue line; pH 3.6-7—green line; and pH 3.6-8—black line) for pHLIP-1 (A), pHLIP-2 short time scale (B) and long timescale (E-F), pHLIP-4 short time scale (C) and long timescale (G-H) are presented. The representative kinetic of the CD changes for the pH3.6-8 transition is shown (D) (similar signal was obtained for all pHLIP variants). All fitting curves are colored in red.

Next the processes of exit/unfolding of the pHLIP variants when pH was changed from 3.6 to 5, 6 and 8 was examined (FIG. 26 and Table 4). These transitions were induced by the addition of NaOH to the solution of the peptide pre-incubated with POPC at pH3.6. The CD and fluorescence data show very fast transitions for all variants when pH is raised up to 8 (FIGS. 26A-C). In this case, exit happens relatively fast within 50-150 ms. With reduction of pH jumps both processes of the peptides unfolding and exit from the bilayer slow down. Similar to the case of insertion/folding, pHLIP-1 demonstrates much less dependence on the magnitude of pH jumps than pHLIP-2 and -4. The process of the pHLIP-2 exit/unfolding slows down from 200 ms for pH3.6-8 jump to 60-80 sec for pH3.6-6 jump (FIGS. 26E-F). The dramatic changes were observed for the pHLIP-4 for different pH jumps: the exit/unfolding slows down from 200 ms to 150-170 sec (FIGS. 26G-H). To explain the obtained results, the pH changes inside a liposome need to be taken into account, e.g., the pH is equilibrated fast inside a liposome after pH jump. This experiment begins when the peptides are inserted into the lipid bilayer, and the pH is already equilibrated (the low pH is outside and inside of the bilayer). Thus, protonatable carboxyl groups transferred across the membrane are in their non-charged form inside the liposome. The stopped-flow experiment starts with a rapid injection of NaOH. First, de-protonation of the carboxyl residues located in TM part of a peptide would occur. As a result, TM state is destabilized and the peptide can unfold and exit bilayer. To exit the C-terminal tail of the peptide needs to cross the lipid bilayer. The peptide would exit fast if carboxyl groups would be in their non-charged (or at least partially charged) state, while the process would slow down if carboxyl groups would be in their charged de-protonated state. Thus, it was next determined how fast concentration of NaOH would be equilibrated inside liposomes, which leads to the de-protonation of the carboxyl groups.

To address this question, pH jump experiments were performed with liposomes containing 10% fluorescein (FITC) conjugated to the headgroups of phospholipids. FITC is a pH-sensitive dye, the absorbance and fluorescence of which increases with increase of pH. FITC, as well as other pH-sensitive dyes is encapsulated into liposomes to probe pH changes in liposomes. It was determined how fast pH would change on the inner and outer leaflets of the bilayer. The pH changes were monitored by changes of FITC fluorescence in a result of pH raise from 3.6 to pH 8 and pH 6 by addition of NaOH to the solution (which already contained many $H^+$ and Cl— ions to mimic our unfolding experiments). About 50-60% of the fluorescence increase of FITC occurs immediately (within the dead time of our experiment) and it is attributed to the pH increase in the vicinity of the outer leaflet of the bilayer. The characteristic time of the fluorescence increase, which reflects pH changes on inner leaflet of the bilayer was measured to be 1.3 sec for pH3.6-8 jump and 6.3 sec for pH3.6-6 jump. It was assumed that in a result of the jump, first the de-protonation of the carboxyl groups in TM part of the pHLIP peptides occurs, which leads to the helix destabilization. In case of the pH3.6-8 jump, the peptides exit and unfolding completed within 200 ms before the pH equilibrates inside liposome (1.3 sec), so the carboxyl groups at the C-terminal end of the peptides can transverse lipid bilayer in their non-charged form. However, for the pH3.6-6 jump, the pH inside liposome equilibrates before (6.3 sec) peptides exit (70 sec for pHLIP-2 and 170 sec for pHLIP-4) from the membrane. The equilibration of pH leads to the de-protonation of carboxyl groups at the C-terminus of peptides and reduces probability of their movement across a bilayer. Thus, the exit slows down for the pHLIP-2 and even in more significant degree for the pHLIP-4, since they have protonatable carboxyl groups on their C-terminus. However, there is no significant difference in characteristic time of exit from a bilayer for various pH jumps for the pHLIP-1, since there is just a single carboxyl terminus, which could be de-protonated.

Figure 27A:
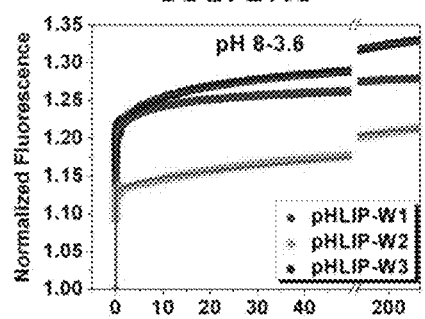
FIGS. 27A-D are a series of line graphs demonstrating insertion/exit of single-Trp pHLIP variants at different pHs. Kinetics of the fluorescence changes recorded at different pH jump transitions for pHLIP-W1 (black line), pHLIP-W2 (green line), and pHLIP-W3 (blue line) at pH 8-3.6 (A), at pH 8-6 (B), at pH3.6-8 (C) and pH 3.6-6 (D) transitions are presented. All fitting curves are colored in red.
Figure 27B:
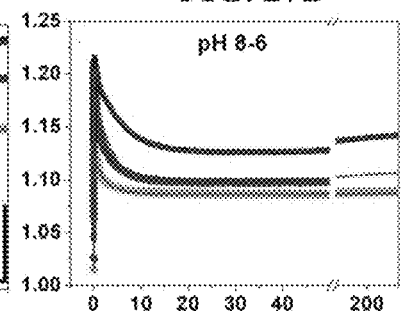

To reveal insides in a "structural" nature of intermediates insertion and exit of the single-tryptophan variants of pHLIP-4 peptide are examined, where Trp residue was located at the beginning (pHLIP-W1), middle (pHLIP-W2) and end (pHLIP-W3) of TM helix. It allows monitoring the propagation of different points of the pHLIP-4 into and out from a lipid bilayer. Changes of the fluorescence of the pHLIP-W1, -W2 and -W3 in a result of pH 8-3.6, 8-6, 3.6-8 and 3.6-6 were recorded (FIGS. 27A-D and Table 5). The characteristic times of transitions (Table 5) for the single-Trp variants are similar to the pHLIP-4, while twice more time is required for the pHLIP-W2 and -W3 to insert and adopt final TM configuration when pH is dropped from 8 to 3.6 (FIG. 27A). At pH8-6 transition, the similar to the pHLIP-4 "kink" is observed for the single-Trp variants within the same time scale of 4-7 sec. The most pronounced kink is observed for the pHLIP-W3, and less pronounced for the pHLIP-W1 and -W2 (FIG. 27B). As described above, the kink is associated with partial exit and unfolding of the pHLIP-4 peptide in a path to the inserted and folded state when pH is dropped from 8 to 6. Thus, it was concluded that the C-terminal end of the peptide, which has four protonatable groups, tends to exit bilayer in more significant degree than other parts of the peptide.

Figure 27C:
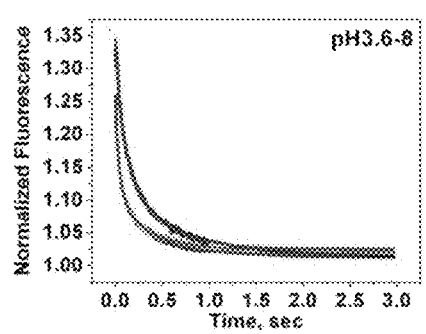
Figure 27D:
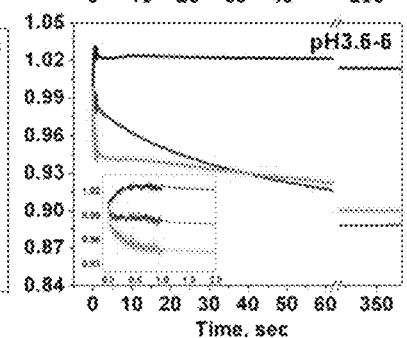

Exit and unfolding for pH3.6-8 transition happens fast for all single-Trp variants (within 350 ms). Unfolding and exit for intermediate transition of pH3.6-6 proceeds much slower compared to pH3.6-8 transition (FIGS. 27C-D). Very interesting changes of the signal were observed for the pHLIP-W3 in a result of pH increase from 3.6 to 6. The fluorescence decays for the pHLIP-W1 and -W2, while the pHLIP-W3 first demonstrates an increase of fluorescence, which later very slowly decays. It was assumed that it is related to the actual movement of Trp residue across a bilayer in the process of the peptide exit from the membrane, which is accompanied by the increase of quantum yield of emission of tryptophan fluorophore.

This study is a continuation of a recent investigation of the membrane-associated pHLIP folding/unfolding, where the rates of the formation of secondary structure were measured. It was demonstrated that the helix forms first on the surface of bilayer followed by slow insertion. Original pHLIP sequence (also known as pHLIP-4) has four protonatable carboxyl groups at the inserting C-terminus. It was assumed that slow insertion of the pHLIP helix is associated with low probability of simultaneous protonation of the C-terminal carboxyl groups, which need to cross a bilayer. Truncated versions of pHLIP-4 were investigated, where two (pHLIP-2) and one (pHLIP-1) protonatable groups were at the peptide inserting end (additional Asp residues were placed at the N-terminus to preserve peptide solubility). Also, single-Trp variants of the pHLIP-4 peptide, where Trp residues were placed at the beginning (pHLIP-W1), middle (pHLIP-W2) and end (pHLIP-W3) of the TM helix, were investigated to gain insights into the structural nature of intermediates on the folding and unfolding pathways. The steady-state fluorescence, CD and OCD data confirmed that all pHLIP variants preserve pH-dependent properties of interaction with membrane as pHLIP-4, and kinetic studies with the pHLIP variants were carried out.

Figure 28A:
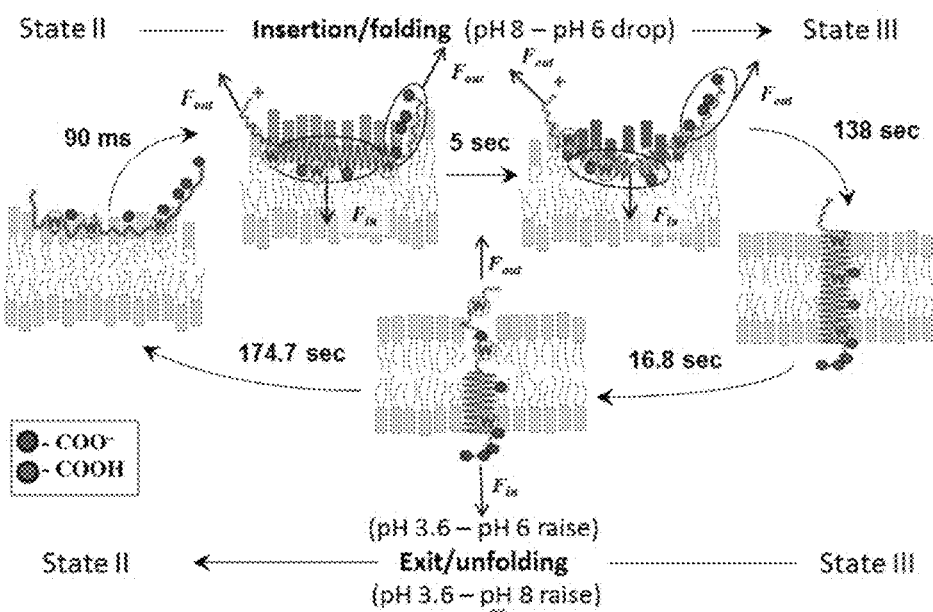
FIGS. 28A-B are schematics illustrating a model of membrane-associate folding and unfolding for pHLIP-4. The schematic presentation of insertion/folding and exit/unfolding of the pHLIP-4 in a result of pH jumps from 8 to 3.6 and vice versa (A) and intermediate pH jumps from 8 to 6 and from pH3.6 to pH8 (B). Letter "W" indicated approximate positions of Trp residues in the single-Trp pHLIP-4 variants. Circles represent approximate position of the protonatable carboxyl groups of Asp, Glu and C-terminus. Membrane distortion is shown by lipids with darker headgroups.
Figure 28B:
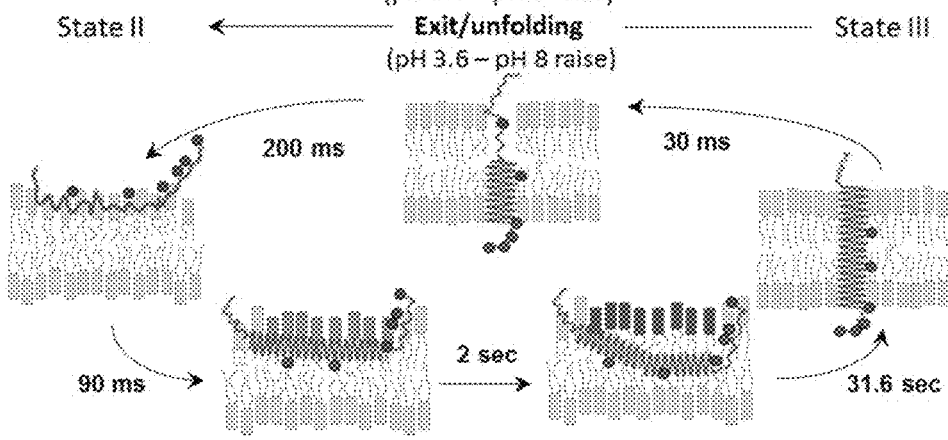
Figure 29:
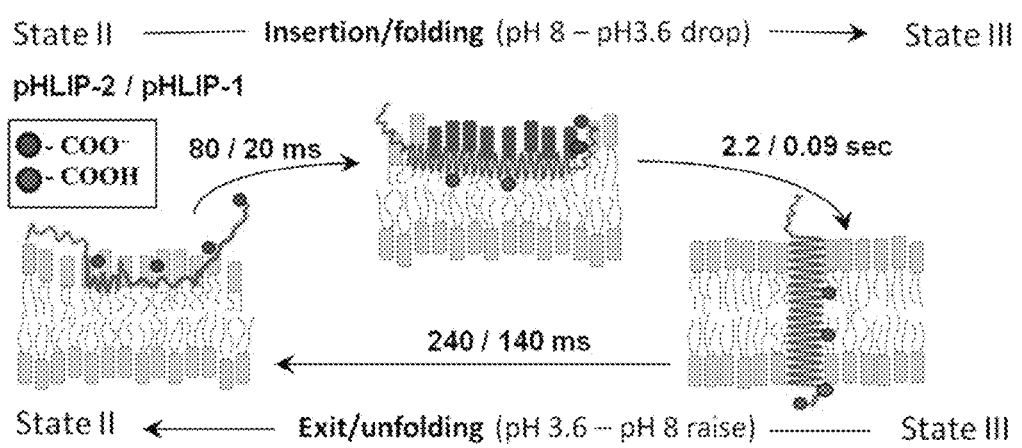
FIG. 29 is a schematic showing a model of membrane-associate folding and unfolding for pHLIP-2/pHLIP-1 variants. The schematic presentation of insertion/folding and exit/unfolding of the pHLIP-2 and -1 in a result of pH jumps from 8 to 3.6 and vice versa. Circles represent approximate position of the protonatable carboxyl groups of Asp, Glu and C-terminus. Membrane distortion is shown by lipids with darker headgroups.
Figure 30A:
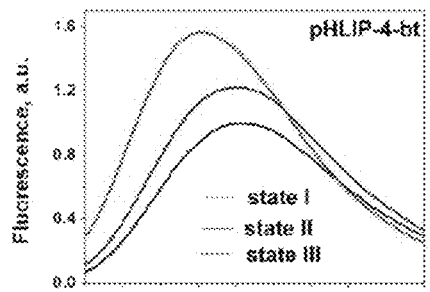
FIGS. 30A-F are a series of line graphs showing the three states monitored by the changes of fluorescence for pHLIP-cargo constructs. Three states of the pHLIP-4, -2 and -2E with biotin and biotingPeg cargoes monitored by the changes of the steady-state peptide fluorescence are presented (state I corresponds to the peptide-cargo in solution at pH8; state II corresponds to the peptide-cargo in presence of POPC liposomes at pH8; state III corresponds to the peptide-cargo with POPC, when pH was dropped from 8 to 3.6 by addition of aliquot of HCl).
Figure 30B:
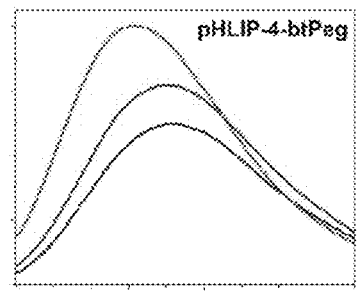
Figure 30C:
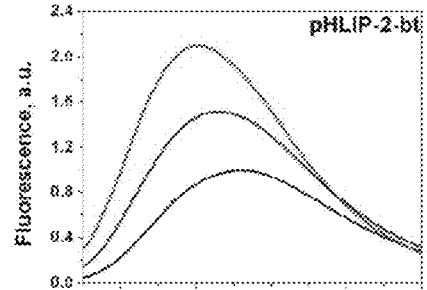
Figure 30D:
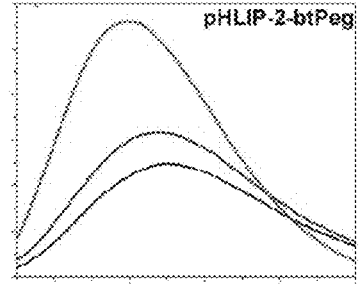
Figure 30E:
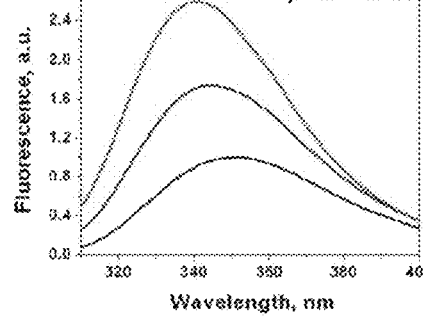
Figure 30F:
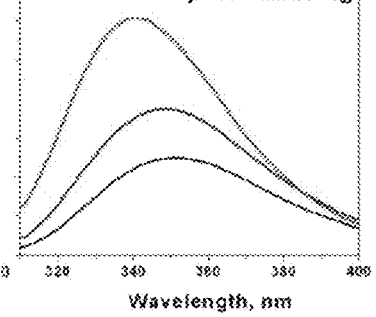
Figure 31A:
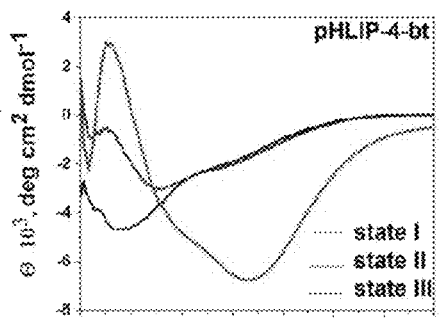
FIGS. 31A-F are a series of line graphs demonstrating the three states monitored by the changes of CD for pHLIP-cargo constructs. Three states of the pHLIP-4, -2 and -2E with biotin and biotingPeg cargoes monitored by the changes of the steady-state peptide CD are presented.
Figure 31B:
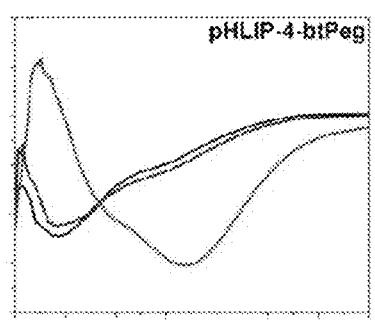
Figure 31C:
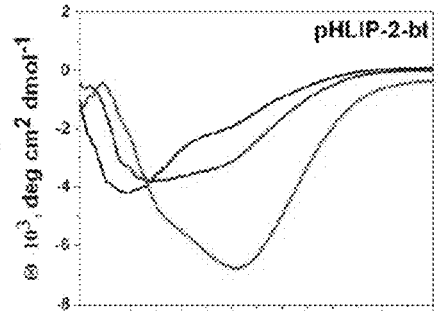
Figure 31D:
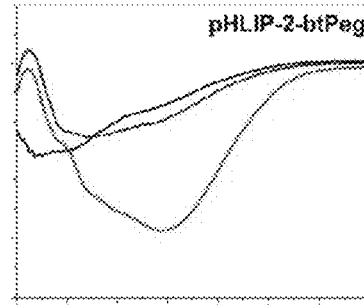
Figure 31E:
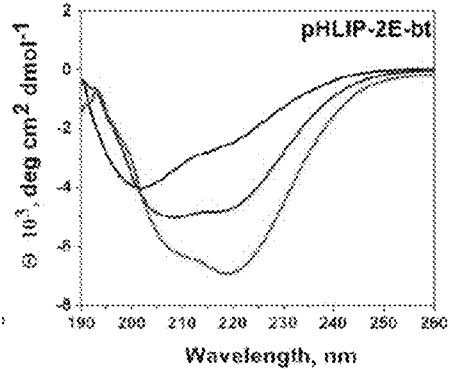
Figure 31F:
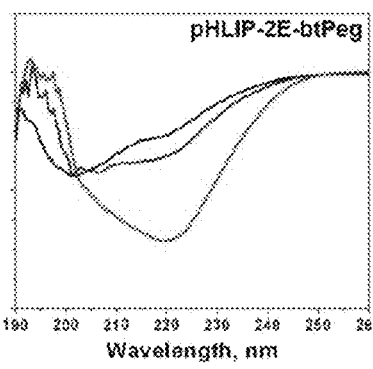

Described in detail below are models of membrane-associated folding/unfolding proposed based on the results presented herein. As described previously, sequential pathway was assumed for the processes of insertion and exit (FIGS. 28A-B and FIG. 29). Insertion starts for all variants with the state II where the peptide is bound to the surface of the lipid bilayer mostly in unstructured configurations. The pHLIP-2 and -1 are buried slightly deeper into the membrane with partial α-helical content due to the less number of charges at the C-terminus of the peptides at pH8. It was assumed, that the drop of pH leads, first, to the protonation (or partial protonation) of the carboxyl groups located in TM part of the peptide, which are positioned closer to the hydrophobic core of the bilayer and, most probably, have the highest values of pKa of protonation in the sequences. It is known that the $pK_a$ of protonation/deprotonation of residues depends on the dielectric properties of their environment. It was shown previously that Asp residues in TM part of bacteriorhodopisin of the C-helix (pHLIP is derived from the C-helix) have higher pKa of protonation, then the ones that are exposed to polar aqueous environment. The protonation of the carboxyl groups in the TM part of pHLIP peptides induces further partition of the peptide into membrane, which is accompanied by the formation of secondary structure within first 20-90 ms. As a result, the force directed toward a bilayer core ($\vec{F}_{in}$) is created at the center of TM part where the hydrophobic Leu and protonated Asp residues are located (FIG. 28A). On the other hand, at the negatively charged C-terminus (which hasn't been protonated yet) and positively charged N-terminus the "pulling" forces ($\vec{F}_{out}$) directed from the bilayer core are applied, which results in a pulling of the peptide out from the membrane core. The difference between pHLIP-4, -2 and -1 peptides is in the magnitude of the "pulling" force, which is the highest for the pHLIP-4 with four charged groups at the C-terminus and the smallest for the pHLIP-1, which has just C-terminal end. Thus, insertion of the pHLIP-2 and -1 into a lipid bilayer is completed 10 and 100 times faster compared to the insertion of the pHLIP-4 (FIG. 29). Moreover, existence of high pulling force at the C-terminus of the pHLIP-4 leads to the stabilization of an addition intermediate on the insertion pathway.

In the case of intermediate pH jump, the probability of protonation of the C-terminal carboxyl groups is even lower and the $\vec{F}_{out}$ force became more significant, which leads to the partial exit of the pHLIP-4 peptide from the bilayer and reduction of helical content ("kink" on the fluorescence and CD kinetic curves, FIG. 25). Experiments with single-Trp pHLIP-4 variants allowed for the demonstration that the C-terminal part of the TM helix exits in more significant degree than the N-terminal part, while middle of the TM helix does move much. At pH jump from 8 to 3.6 the probability of simultaneous protonation of four carboxyl groups at the C-terminus is much higher, and the final step on the folding pathway of the pHLIP-4 is much faster (31.6 s) compared to the final step at pH8-6 transition, which is about 138 s. The partial exit and unfolding of the pHLIP-2 at the intermediate pH jump less substantial than for the pHLIP-4 and no exit/unfolding is observed for the pHLIP-1 due to much weaker "pulling" force applied to the C-terminal inserting end of the peptide. Thus, formation of the secondary structure and insertion of the pHLIP-1 practically coincide. If it would be no charge at the peptide inserting end, then folding/insertion would proceed with no intermediate states as all-or-none first order phase transition from the unfolded surface-bound to the folded inserted state.

Prior to the invention described herein, the driving force for the interfacial helix insertion into bilayer to adopt TM orientation was unknown. It was assumed that the lipid distortion is the main driving force. When polypeptide forms rigid helical structure and propagates slightly deeper into the lipid bilayer, the membrane tension is created (the situation of an asymmetric inclusion into the one leaflet of bilayer compared to the tension created on a membrane by an unstructured flexible polypeptide. The stopped-flow SAXS data are analyzed to reveal what is happening with liposome and lipid bilayer during the peptide insertion/folding and exit/unfolding.

The results presented herein indicate that the activation energy of the transitions on folding pathway for the pHLIP-4, -2, and -1 is similar: it is ~13.2 kcal/mol for both truncated variants and -4.5 kcal/mol for each intermediate transition step on the insertion pathway of the pHLIP-4. The activation energy might reflect the existence of the hydrophobic bilayer of membrane, which is an energetic barrier a polypeptide needs to overcome to adopt TM configuration. The activation energy is similar for both pHLIP-2 and -1 for the transitions from the unfolded surface-bound to the folded inserted states, since the energetic barrier is the same for both peptides. At each step on the folding pathway, the pHLIP-4 peptide partitions dipper into a membrane, this reduces the activation energy barriers. The total energetic barrier could be the same for a polypeptide crossing bilayer, however the frequency of the transitions is very different for various pHLIP peptides: it is 10 orders of magnitude higher for the pHLIP-1 compared to the pHLIP-4. The frequency factor might reflect the probability of simultaneous protonation of the carboxyl groups at the C-terminus, which have to cross bilayer (most probably in their un-charged form). Thus, the pHLIP-4 has the lowest frequency factor by having four charged carboxyl groups at the C-terminal inserting end, while the pHLIP-1 has the highest frequency factor, which results in the fastest transition.

As in the case of folding/insertion, the process of unfolding/exit is induced by pH jump, which most probably leads to the de-protonation (or at least partial de-protonation) of Asp residues located in the TM part of peptides. It results of appearance of the "pulling" force $\vec{F}_{out}$ (FIG. 28A). The peptides exit from the bilayer is accompanied by the unfolding. The question is how the protonatable groups at the C-terminus might affect peptide unfolding and exit. First, the folding/insertion experiments, which are performed on liposomes, mimic real processes of a polypeptide interaction with cellular membranes. However, unfolding/exit experiments are more artificial, since the pH equilibrates at both sides of bilayer of liposome in contrast to cellular membranes, where intracellular pH is around 7.4, while extracellular pH in diseased tissue or pH inside lysosome is low. Exit starts for all pHLIP variants with the state III: a peptide inserted into a bilayer. The carboxyl groups translocated across a bilayer are in their non-charged form, since the pH is equilibrated inside liposomes. All pHLIP variants, regardless of number of protonatable groups at the C-terminus, exit and unfold at least 10 times faster (about 0.05-0.15 s) then pH equilibrates inside a liposome (1.3 s). At the intermediate pH jumps, pH inside liposome equilibrates faster (within 6 sec) then peptides exit. It leads to the protonation (or at least partial protonation) of the carboxyl groups at the inserted C-terminus, and as a result, the force directed inside a liposomes ($\vec{F}_{in}$) is created (FIG. 28A). More charges are at the C-terminus, the less probable is the process of the C-terminus translocation across a bilayer and more time it takes to exit and unfold. The results also confirm that the peptides exit on outside leaflet. Otherwise, if the peptides would be able to exit inside a liposome, then the exit rate would not be depended on the number of protonatable residues at the C-terminus, rather it would be affected by the N-terminus of the peptides and would be highest for the pHLIP-4 with less number of charged residues at the N-terminus.

The results presented herein shine light on the mechanism of membrane-associate folding/unfolding providing answers to the questions of formation of helical structures and existence of intermediates. It is evident that the intermediates might exist on the folding and unfolding pathways depending on a polypeptide end, which has to cross a bilayer. However, the intermediates are non-mandatory. In a simple case of non-charged and non-polar inserting end, the transition most probably would be all-or-none described by the two-state model. These experimental observations indicate that a polypeptide partitioning into a lipid bilayer is accompanied by the formation of the secondary structure, while a peptide exists from a membrane coincide with unfolding. Thus, if any intermediate states would exist on the folding pathway (due to the charges or polar cargo attached to the peptide inserting end), the interfacial helical intermediate would be mandatory and will occur before a peptide propagates into a hydrophobic core of membrane. The energetic cost of exposing of a polar backbone inside a bilayer is higher than the cost of membrane distortion created by an asymmetric inclusion of helices on the outer leaflet of membrane.

The results presented herein also provide important information for the main principles of design of drug delivery agents for the targeting of acidic diseased tissue and translocation of molecules across a bilayer. The speed of insertion and exit could be changed in range of two orders of magnitude.

Tables
Insertion at Different Temperatures.

Characteristic times ($\tau$, sec), obtained in a result of exponential fitting (eq. 1-3) of the fluorescence kinetics (transition from pH8 to 3.6) for pHLIP-1, -2, -4 at different temperatures. Fitting was performed in a global mode: the first characteristic time was shared for all fitting curves within different temperatures for the individual pHLIPs. The curves are shown on FIGS. 23A-C. The rate constants (k, $sec^{-1}$) calculated according to the eqs 4-6 are shown in brackets, these values were used to constructs the Arrhenius plots (FIG. 23D).

|  | 25° C. | 18° C. | 11° C. | 7° C. |
|---|---|---|---|---|
| pHLIP-1 | 0.02 s (44.4-45.3 $s^{-1}$ for various temperatures) | | | |
|  | 0.08 s (12.6 $s^{-1}$) | 0.15 s (6.72 $s^{-1}$) | 0.31 s (3.26 $s^{-1}$) | 0.48 s (2.10 $s^{-1}$) |
| pHLIP-2 | 0.04 s (22.70-22.72 $s^{-1}$ for various temperatures) | | | |
|  | 2.7 s (0.37 $s^{-1}$) | 3.7 s (0.27 $s^{-1}$) | 6.0 s (0.17 $s^{-1}$) | 7.5 s (0.13 $s^{-1}$) |
| pHLIP-4 | 0.09 s (11.1 $s^{-1}$) | | | |
|  | 2.0 s (0.45 $s^{-1}$) | 2.1 s (0.43 $s^{-1}$) | 2.8 s (0.32 $s^{-1}$) | 3.5 s (0.26 $s^{-1}$) |
|  | 31.6 s (0.031 $s^{-1}$) | 33 s (0.03 $s^{-1}$) | 38 s (0.026 $s^{-1}$) | 50 s (0.02 $s^{-1}$) |

The Activation Energies and Frequency Factors.

The activation energy, $E_a$, and frequency factor, A, was calculated by the fitting of the Arrhenius plots (FIG. 23D) by the Arrhenius equation (7).

|  | $E_a$, kcal/mol | A |
|---|---|---|
| pHLIP-1 | 13.2 | 4.2 * $10^{10}$ |
| pHLIP-2 | | 1.9 * $10^9$ |
| pHLIP-4 | 4.6 | 1.1 * $10^3$ |

Insertion and Folding at Different pH Transitions.

Characteristic times ($\tau$, sec), obtained in a result of exponential fitting of the fluorescence and CD kinetics (transitions from pH8 to 3.6, 5 and 6) for the pHLIP-1, -2, -4 (see FIGS. 24A-H). Fitting was performed in a global mode: the first characteristic time was shared for all fitting curves within pH transitions for individual pHLIPs. The components with negative contributions of the amplitude (signal changes occur in opposite direction) are shown in red in FIG. 73. The rate constants (k, $sec^{-1}$) calculated according to the eqs 4-6 are shown in brackets.

Exit and Unfolding at Different pH Transitions.

Characteristic times ($\tau$, sec), obtained in a result of exponential fitting of the fluorescence and CD kinetics (transitions from pH8 to 3.6, 5 and 6) for the pHLIP-1, -2, -4 (see FIGS. 26A-H). The rate constants (k, $sec^{-1}$) calculated according to the eqs 4-6 are shown in brackets.

|  | pH 3.6-8 | pH 3.6-7 | pH 3.6-6 |
|---|---|---|---|
| pHLIP-1 fluorescence | 0.14 s (7.14 $s^{-1}$) | 0.4 s (2.5 $s^{-1}$) | 0.85 s (1.18 $s^{-1}$) |
| pHLIP-1, CD |  | 0.02 s (50 $s^{-1}$) |  |
| pHLIP-2 fluorescence | 0.03 s (29.9 $s^{-1}$) 0.21 s (4.81 $s^{-1}$) | 0.3 s (3.01 $s^{-1}$) 4.8 s (0.21 $s^{-1}$) | 8.1 s (0.11 $s^{-1}$) 67.7 s (0.015 $s^{-1}$) |
| pHLIP-2 CD | 0.02 s (50 $s^{-1}$) | 0.3 s (3.01 $s^{-1}$) 3.9 s (0.26 $s^{-1}$) | 8.0 s (0.11 $s^{-1}$) 77.0 s (0.013 $s^{-1}$) |
| pHLIP-4 fluorescence | 0.03 s (29.9 $s^{-1}$) 0.2 s (5.05 $s^{-1}$) | 0.22 s (4.12 $s^{-1}$) 11 s (0.092 $s^{-1}$) | 16.8 s (0.054 $s^{-1}$) 174.7 s (0.0058 $s^{-1}$) |
| pHLIP-4 CD | 0.02 s (50 $s^{-1}$) | 0.22 s (4.12 $s^{-1}$) 6.5 s (0.16 $s^{-1}$) | 16.8 s (0.054 $s^{-1}$) 149 s (0.0068 $s^{-1}$) |

Insertion and Exit of Single-Trp pHLIP Variants at Various pH Transitions.

Characteristic times ($\tau$, sec), obtained in a result of exponential fitting of the fluorescence kinetics (transitions from pH8 to 3.6, 6 and transitions from pH3.6 to 6, 8) for the pHLIP-W1, -W2, -W3 (see FIGS. 27A-D). Fitting was performed in a global mode: two characteristic times were shared for all fitting curves for all pHLIP variants. The components with negative contributions of the amplitude (signal changes occur in opposite direction) are shown in red in FIG. 74. The rate constants (k, $sec^{-1}$) calculated according to the eqs 4-6 are shown in brackets.

Two-State Model

The two-state model is used to describe fast processes of folding of the pHLIP variants, kinetic curves of which are fitted well by the single-exponential function. This model doesn't assume existence of intermediate states.

$$A \rightleftharpoons B \quad (1.1)$$

The transition from the state A to B is described by the differential equation:

$$\frac{d[A]}{dt} = -k_1[A] + k_1^-[B] \quad (1.2)$$

$$[A] + [B] = 1 \quad (1.3)$$

The variables A and B designate relative populations of the corresponding states. $k_1$ and $k^-{}_1$ are the rates constant for the forward and backward reactions, respectively. We assume that initially all pHLIP molecules are in the state A and hence the initial conditions are:

$$A(0)=1, B(0)=0 \quad (1.4)$$

The exact solution of the differential equation 1.2 is the single-exponential function:

$$[A(t)] = \frac{k_1^-}{k_1 + k_1^-} + \left(\frac{k_1}{k_1 + k_1^-}\right)e^{-(k_1 + k_1^-)t} \quad (1.5)$$

The experimental kinetic curves could be fitted by the single-exponential function:

$$S_{exp} = g_0 + g_1 \exp(-v_1 t) \quad (1.6)$$

where the characteristic rate $v_1$ (or the characteristic time, $t_1 = 1/v_1$) expressed in a form of the rate constants:

$$v_1 = k_1 + k_1^- \quad (1.7)$$

If we assume that the equilibrium between the states A and B is strongly shifted to the right, meaning that $k_1 \gg k_1^-$ and the difference between the rate constants at least an order of magnitude:

$$\frac{k_1}{k_1^-} \approx 10 \quad (1.8)$$

then we can estimate the rate of the forward reaction from the characteristic rate obtained in the result of fitting of the experimental data by the single-exponential function:

$$k_1 \sim 0.91 v_1 \quad (1.9)$$

Three-State Model

In majority of cases it was not possible to get adequate fitting of the experimental data by the single-exponential function. Therefore we introduced three-state model, which assumes the existence of single intermediate:

$$A \underset{k_1^-}{\overset{k_1}{\rightleftarrows}} B \underset{k_2^-}{\overset{k_2}{\rightleftarrows}} C \quad (2.1)$$

The transitions from one state to another are described by the differential equations:

$$\frac{d[A]}{dt} = -k_1[A] + k_1^-[B] \quad (2.2)$$

$$\frac{d[B]}{dt} = k_1[A] - (k_1^- + k_2)[B] + k_2^-[C] \quad (2.3)$$

$$[A] + [B] + [C] = 1 \quad (2.4)$$

The variables A, B and C designate relative populations of the corresponding states. We assume that initially all pHLIP molecules are in the state A and hence the initial conditions are:

$$A(0)=1, B(0)=C(0)=0 \quad (2.5)$$

Finally the equilibrium will be reached and the equilibrium populations can be easily found by the graph technique known in the art, where arrows represent corresponding transitions in the scheme (2.1) and can be substituted with their rate constants:

$$A_0 = \frac{\leftarrow \leftarrow}{\leftarrow \leftarrow + \rightarrow \leftarrow + \rightarrow \rightarrow} = \frac{k_1^- k_2^-}{k_1^- k_2^- + k_1 k_2^- + k_1 k_2} \quad (2.6)$$

$$B_0 = \frac{\rightarrow \leftarrow}{\leftarrow \leftarrow + \rightarrow \leftarrow + \rightarrow \rightarrow} = \frac{k_1 k_2^-}{k_1^- k_2^- + k_1 k_2^- + k_1 k_2}$$

$$C_0 = \frac{\rightarrow \rightarrow}{\leftarrow \leftarrow + \rightarrow \leftarrow + \rightarrow \rightarrow} = \frac{k_1 k_2}{k_1^- k_2^- + k_1 k_2^- + k_1 k_2}$$

To obtain the time evolution of all states one can exclude B and C from the system (2.2-2.4) and obtain differential equation for A:

$$\frac{d^2[A]}{dt^2} + (k_1 + k_1^- + k_2 + k_2^-)\frac{d[A]}{dt} + \quad (2.7)$$
$$(k_1^- k_2^- + k_1 k_2 + k_1 k_2^-)A - k_1^- k_2^- = 0$$

In general form the solution of the equation 2.7 is given by the two-exponential function:

$$A(t) = A_0 + A_1 \exp(-v_1 t) + A_2 \exp(-v_2 t) \quad (2.8)$$

where the characteristic rates $v_1$ and $1'_2$ are expressed in a form of rate constants:

$$v_1 = \frac{1}{2}(k_1 + k_1^- + k_2 + k_2^-) + \quad (2.9)$$
$$\sqrt{\frac{1}{4}(k_1 + k_1^- + k_2 + k_2^-)^2 - (k_1^- k_2^- + k_1 k_2 + k_1 k_2^-)}$$

$$v_2 = \frac{1}{2}(k_1 + k_1^- + k_2 + k_2^-) - \quad (2.10)$$
$$\sqrt{\frac{1}{4}(k_1 + k_1^- + k_2 + k_2^-)^2 - (k_1^- k_2^- + k_1 k_2 + k_1 k_2^-)}$$

Population of the state B is found from the equation 2.2:

$$B = \frac{1}{k_1^-}\frac{dA}{dt} + \frac{k_1}{k_1^-}A = \quad (2.11)$$
$$\frac{1}{k_1^-}[k_1 A_0 + A_1(k_1 - v_1)\exp(-v_1 t) + A_2(k_1 - v_2)\exp(-v_2 t)]$$

and finally population of the state C is given:

$$C = 1 - A - B = 1 - \left(1 + \frac{k_1}{k_1^-}\right)A_0 - \quad (2.12)$$
$$\left[1 + \frac{k_1 - v_1}{k_1^-}\right]\exp(-v_1 t)A_1 - \left[1 + \frac{k_1 - v_2}{k_1^-}\right]\exp(-v_2 t)A_2$$

Thus, population of the states B and C can be expressed via $A_0$, $A_1$, and $A_2$. Taking into account that $A(0)=1$ and $B(0)=0$ we can obtain:

$$A_0 + A_1 + A_2 = 1 \quad (2.13)$$

$$\frac{1}{k_1^-}[k_1 A_0 + A_1(k_1 - v_1) + A_2(k_1 - v_2)] = 0 \quad (2.14)$$

Solving equations (2.13) and (2.14) one can find:

$$A_0 = \frac{k_1^- k_2^-}{k_1^- k_2^- + k_1 k_2^- + k_1 k_2} \tag{2.15}$$

$$A_1 = \frac{k_1 - v_1(1 - A_0)}{v_1 - v_2} \tag{2.16}$$

$$A_2 = \frac{-k_1 + v_1(1 - A_0)}{v_1 - v_2} \tag{2.17}$$

If transitions between the states B and C are much slower than between the states A and B, then equations 2.15-2.17 could be significantly simplified and the amplitudes $A_0$, $A_1$, and $A_2$ can be expressed via the rate constants $k_i$ in a closed form:

$$A_1 \approx \frac{k_1}{(k_1 + k_1^-)}\left[1 - \frac{2k_1^- k_2}{(k_1 + k_1^-)^2}\right] \tag{2.18}$$

$$A_2 \approx \frac{k_1}{(k_1 + k_1^-)} \frac{k_1 k_1^- k_2}{(k_1 k_2 + k_1 k_2^- + k_1^- k_2^-)}\left[1 - \frac{2k_1^- k_2}{(k_1 + k_1^-)^2}\right] \tag{2.19}$$

Let us designate the spectral (fluorescence of CD) signal of the different states A, B and C by $S_A$, $S_B$, $S_C$. Then the spectral signal of the whole system is:

$$S_{theor} = S_A A + S_B B + S_C C \tag{2.20}$$

Substituting here the expressions for the populations of the different states using equations 2.8; 2.11 and 2.12 one can obtain:

$$S_{theor} = S_C + A_0\left[S_A + \frac{S_B k_1}{k_1^-} - S_C\left(1 + \frac{k_1}{k_1^-}\right)\right] +$$
$$A_1 \exp(-v_1 t)\left[S_A + \frac{S_B(k_1 - v_1)}{k_1^-} - S_C\left(1 + \frac{k_1 - v_1}{k_1^-}\right)\right] +$$
$$A_2 \exp(-v_2 t)\left[S_A + \frac{S_B(k_1 - v_2)}{k_1^-} - S_C\left(1 + \frac{k_1 - v_2}{k_1^-}\right)\right] \tag{2.21}$$

Experimentally it was found that the most of the pHLIP-1 and -2 kinetic curves could be adequately fitted by the two-exponential function:

$$S_{exp} = g_0 + g_1 \exp(-v_1 t) + g_2 \exp(-v_2 t) \tag{2.22}$$

Therefore the experimental measurements $S_{exp}$ provide five parameters: two characteristic rate constants $v_1$ and $v_2$ and three characteristic fluorescence amplitudes $g_0$, $g_1$ and $g_2$. Comparing $S_{theor}$ and $S_{exp}$ we can find the relationships between the theoretical and experimental parameters:

$$g_0 = S_A A_0 + \frac{S_B k_1}{k_1^-} A_0 + S_c - S_c\left(1 + \frac{k_1}{k_1^-}\right) A_0 \tag{2.23}$$

$$g_1 = A_1\left[S_A + S_B \frac{k_1 - v_1}{k_1^-} - S_c\left(1 + \frac{k_1 - v_1}{k_1^-}\right)\right] \tag{2.24}$$

$$g_2 = A_2\left[S_A + S_B \frac{k_1 - v_1}{k_1^-} - S_c\left(1 + \frac{k_1 - v_2}{k_1^-}\right)\right] \tag{2.25}$$

And the rates are given by the equations 2.9 and 2.10. Unfortunately, theoretical description involves seven parameters: four rate constants $k_1$, $k_2$, $k_3$, and $k_4$ and three fluorescence/CD amplitudes $S_A$, $S_B$, $S_C$, against five experimental parameters, which make it impossible to find parameters unless we would make assumptions. First, we concentrate our attention only on the rate constants. Second, we noticed that $v_1 \gg v_2$, thus equations 2.9 and 2.10 can be expanded into series. The major terms in this expansion are:

$$v_1 \approx (k_1 + k_1^-) + \frac{k_1^- k_2}{(k_1 + k_1^-)} \tag{2.26}$$

$$v_2 \approx k_2^- + \frac{k_1 k_2}{(k_1 + k_1^-)} \tag{2.27}$$

If we assume that equilibrium between the states A, B and C is strongly shifted to the right, meaning that $k_1 \gg k_1^-$ and $k_2 \gg k_2^-$, and the difference between the rate constants at least an order of magnitude:

$$\frac{k_1}{k_1^-} \approx 10, \tag{2.28}$$

$$\frac{k_2}{k_2^-} \approx 10$$

then the rate of the forward reaction could be estimated from the characteristic rate obtained in the result of fitting of the experimental data by the single-exponential function:

$$k_1 \sim \frac{v_1}{1.1} - \frac{v_2}{12.21} \tag{2.29}$$

$$k_2 \sim 1.0091 v_2 \tag{2.30}$$

Four-State Model

The adequate fitting of the pHLIP-4 kinetic data was achieved only when three-exponential function was used. Therefore we introduced four-state model, which assumes existence of two intermediates:

$$A \rightleftharpoons B \rightleftharpoons C \rightleftharpoons D \tag{3.1}$$

The transitions in this system are described by the set of equations:

$$\frac{d[A]}{dt} = -k_1[A] + k_1^-[B] \tag{3.2}$$

$$\frac{d[B]}{dt} = k_1[A] - (k_1^- + k_2)[B] + k_2^-[C] \tag{3.3}$$

$$\frac{d[C]}{dt} = k_2[B] - (k_2^- + k_3)[C] + k_3^-[D] \tag{3.4}$$

$$[A] + [B] + [C] + [D] = 1 \tag{3.5}$$

The variables A, B, C and D designate relative populations of the corresponding states. We assume that initially all pHLIP molecules are in the state A and hence the initial conditions are:

$$A(0)=1, B(0)=C(0)=D(0)=0 \tag{3.6}$$

Finally the equilibrium will be reached and the equilibrium populations can be easily found by the graph technique:

$$A_0 = \frac{\overleftarrow{\phantom{x}}\overleftarrow{\phantom{x}}\overleftarrow{\phantom{x}}}{\overleftarrow{\phantom{x}}\overleftarrow{\phantom{x}}\overleftarrow{\phantom{x}}+\overrightarrow{\phantom{x}}\overleftarrow{\phantom{x}}\overleftarrow{\phantom{x}}+\overrightarrow{\phantom{x}}\overrightarrow{\phantom{x}}\overleftarrow{\phantom{x}}+\overrightarrow{\phantom{x}}\overrightarrow{\phantom{x}}\overrightarrow{\phantom{x}}} = \quad (3.7)$$

$$\frac{k_1^- k_2^- k_3^-}{k_1^- k_2^- k_3^- + k_1 k_2^- k_3^- + k_1 k_2 k_3^- + k_1 k_2 k_3}$$

$$B_0 = \frac{\overrightarrow{\phantom{x}}\overleftarrow{\phantom{x}}\overleftarrow{\phantom{x}}}{\overleftarrow{\phantom{x}}\overleftarrow{\phantom{x}}\overleftarrow{\phantom{x}}+\overrightarrow{\phantom{x}}\overleftarrow{\phantom{x}}\overleftarrow{\phantom{x}}+\overrightarrow{\phantom{x}}\overrightarrow{\phantom{x}}\overleftarrow{\phantom{x}}+\overrightarrow{\phantom{x}}\overrightarrow{\phantom{x}}\overrightarrow{\phantom{x}}} =$$

$$\frac{k_1 k_2^- k_3^-}{k_1^- k_2^- k_3^- + k_1 k_2^- k_3^- + k_1 k_2 k_3^- + k_1 k_2 k_3}$$

$$C_0 = \frac{\overrightarrow{\phantom{x}}\overrightarrow{\phantom{x}}\overleftarrow{\phantom{x}}}{\overleftarrow{\phantom{x}}\overleftarrow{\phantom{x}}\overleftarrow{\phantom{x}}+\overrightarrow{\phantom{x}}\overleftarrow{\phantom{x}}\overleftarrow{\phantom{x}}+\overrightarrow{\phantom{x}}\overrightarrow{\phantom{x}}\overleftarrow{\phantom{x}}+\overrightarrow{\phantom{x}}\overrightarrow{\phantom{x}}\overrightarrow{\phantom{x}}} =$$

$$\frac{k_1 k_2 k_3^-}{k_1^- k_2^- k_3^- + k_1 k_2^- k_3^- + k_1 k_2 k_3^- + k_1 k_2 k_3}$$

$$D_0 = \frac{\overrightarrow{\phantom{x}}\overrightarrow{\phantom{x}}\overrightarrow{\phantom{x}}}{\overleftarrow{\phantom{x}}\overleftarrow{\phantom{x}}\overleftarrow{\phantom{x}}+\overrightarrow{\phantom{x}}\overleftarrow{\phantom{x}}\overleftarrow{\phantom{x}}+\overrightarrow{\phantom{x}}\overrightarrow{\phantom{x}}\overleftarrow{\phantom{x}}+\overrightarrow{\phantom{x}}\overrightarrow{\phantom{x}}\overrightarrow{\phantom{x}}} =$$

$$\frac{k_1 k_2 k_3}{k_1^- k_2^- k_3^- + k_1 k_2^- k_3^- + k_1 k_2 k_3^- + k_1 k_2 k_3}$$

Solution of these equations is given by the three-exponential functions with the characteristic rates $v_1$, $v_2$, $v_3$ and it is rather cumbersome. We can assume that the first transition is very fast and the equilibrium is strongly shifted toward the state B, which means $k_1^- \approx 0$. Then $$v_1 \sim k_1, \quad (3.8)$$

and $$[A](t) = A_1 \exp(-v_1 t) = \exp(-k_1 t) \quad (3.9)$$

Remaining equations are:

$$\frac{d[B]}{dt} = k_1[A] - (k_1^- + k_2)[B] + k_2^-[C] \quad (3.10)$$

$$\frac{d[C]}{dt} = k_2[B] - (k_2^- + k_3)[C] + k_3^-[D] \quad (3.11)$$

$$[A] + [B] + [C] + [D] = 1 \quad (3.12)$$

To solve this set one can exclude D:

$$\frac{d[C]}{dt} = k_2[B] - (k_2^- + k_3)[C] + k_3^-(1 - [A] - [B] - [C]) \quad (3.13)$$

and then exclude C:

$$\frac{d^2[B]}{dt^2} + (k_2 + k_2^- + k_3 + k_3^-)\frac{d[B]}{dt} + (k_2^- k_3^- + (k_3 + k_3^-)k_2)[B] + [-(k_1 + k_2^- + k_3 + k_3^-)k_1 + k_2^- k_3^-]\exp(-k_1 t) - k_2^- k_3^- = 0 \quad (3.14)$$

Solution of this differential equation is given by $$B = B_0 + B_1 \exp(-v_1 t) + B_2 \exp(-v_2 t) + B_3 \exp(-v_3 t) \quad (3.15)$$

with similar expressions for C and D. The first characteristic rate $v_1$ is given by the equation 3.8, and $v_2$ and $v_3$ are determined by:

$$v_i = -0.5(k_2 + k_2^- + k_3 + k_3^-) \pm \quad (3.16)$$

$$\sqrt{0.25(k_2 + k_2^- + k_3 + k_3^-)^2 - k_2^- k_3^- - (k_3 + k_3^-)k_2} =$$

$$-0.5(k_2 + k_2^- + k_3 + k_3^-) \pm 0.5\sqrt{(k_2 + k_2^- - k_3 - k_3^-)^2 - 4k_2^- k_3^-}$$

If we assume that the rates of consequent stages significantly decrease, i.e. $k_2$, $k_2^- \gg k_3$, $k_3^-$, then one can expand expression 3.16 into series and find solution in a simple form:

$$v_2 \approx (k_2 + k_2^-) + \frac{k_2^- k_3}{(k_2 + k_2^-)} \quad (3.17)$$

$$v_3 \approx \frac{k_2 k_3 + k_2 k_3^- + k_2^- k_3^-}{(k_2 + k_2^-)} \quad (3.18)$$

We can reasonably assume that the equilibrium (3.1) between the states B, C and D is strongly shifted to the right, meaning that $k_2 \gg k_2^-$ and $k_3 \gg k_3^-$. The difference should be at least an order of magnitude:

$$\frac{k_2}{k_2^-} \approx 10, \quad \frac{k_3}{k_3^-} \approx 10 \quad (3.19)$$

and the rate constants are:

$$k_1 \sim v_1 \quad (3.20)$$

$$k_2 \sim \frac{v_2}{1.1} - \frac{v_3}{12.21} \quad (3.21)$$

$$k_3 \sim 0.991 v_3 \quad (3.22)$$

Example 13: Membrane-Associated Folding: Polar Cargo Translocation Across a Lipid Bilayer Described herein is the mechanism of cargo translocation across a membrane by the single molecule transporter, pHLIP® (pH (Low) Insertion Peptide). The main principle of this novel drug delivery approach is based on the phenomenon of a pH-dependent insertion and folding of moderately hydrophobic membrane peptides. Several pHLIP variants were used to probe delivery of cargoes of different polarity (biotin and biotin-Peg) attached to the peptide inserting end. It is confirmed that all pHLIP variants with attached cargo molecules preserve pH-dependent properties of interaction with membrane. While the equilibrium thermodynamics favor the binding and insertion of pHLIP-cargo constructs, kinetics was significantly slowed down. The presence of polar cargo at the peptide inserting end leads to the appearance of two additional intermediate states on the insertion pathway of the pHLIP-2E, which itself (when no cargo is attached) shows all-or-none transition from the membrane-surface partially unstructured to the inserted transmembrane states described very well by the two-state model. The findings are very valuable for the design of new delivery agents for the direct translocation of polar cargo across a membrane. To facilitate the different delivery needs for different applications the hydrophobicity of the cargo could be modified without affecting cargo's ability to bind to its cellular target (shown by us previously) and/or various peptides of the pHLIP family could be employed, which show different rates and pKa of the cargo translocation across cellular membranes.

Cargo Translocation Across a Bilayer

The transportation of molecules across a membrane is a vital property of a cell. Cells can transport molecules by various mechanisms. The number of molecules that can freely diffuse across a cellular membrane is very limited since the energetic barrier for transition across a hydrophobic lipid bilayer of a membrane is very high for polar molecules. The endocytotic mechanisms are very effective; however, there is a problem of escaping from endosomes, which is a main obstacle for delivery of drugs into cells.

It has been demonstrated that a moderately hydrophobic, water-soluble membrane peptide pHLIP (pH (Low) Insertion Peptide) can insert into membranes and translocate molecules in a pH-sensitive manner. The mechanism of membrane insertion and folding of pHLIP is based on the protonation of the carboxyl groups of Asp/Glu residues, which results in enhancement of the peptide hydrophobicity and increase the affinity for lipid bilayer, triggering peptide folding and subsequent membrane insertion. The energy of membrane associated-folding of about 2 kcal/mol could be used to move polar cell-impermeable cargo molecules attached to the inserting end of the pHLIP through the hydrophobic bilayer of membrane. Both, pH-targeting behavior and molecular translocation have been proven on cultured cells and in vivo. Among the successfully translocated into cytoplasm polar cargo molecules are fluorescent dyes, gene regulation agent—peptide nucleic acid, toxin-phalloidin conjugated with fluorescent dye rhodamine (Reshetnyak Y K et al., 2006 Proc. Natl. Acad. Sci. U.S.A, 103(17):6460-6465), cyclic peptides (Thevenin D et al., 2009 Chem. Biol., 16(7):754-762), phalloidin, when the facilitator group, rhodamine, was attached to the inserting end of pHLIP (An M et al., 2010 Proc. Natl. Acad. Sci. U.S.A, 107(47):20246-20250 (in eng)), phallacidin (another version of the toxin) with six carbon groups attached to it (Wijesinghe D D et al., Tuning hydrophobicity of phallacidin cargo for improved translocation across plasma membrane by pH (Low) Insertion Peptide. In preparation.). Thus, it opens an opportunity to develop a novel concept in drug delivery, which is based on the use of pH-sensitive single peptide molecular transporter.

The thermodynamic and kinetic studies provide understanding of the mechanism of pHLIP interaction with lipid bilayer of membrane. The results of the kinetic studies presented above indicate that the rate of the peptide insertion into membrane could be enhanced 10 and even 100 times if charged groups are removed from the inserting end of the peptide. The main goal of this study is to elucidate mechanism of cargo translocation across the bilayer by a family of pH-sensitive single peptide molecular transporters, pHLIPs. As a cargo, biotin and biotin-Peg, which were attached to the C-terminus of several pHLIP variants including truncated (fast) pHLIPs, were utilized.

Conjugation of Biotin and Biotin-Peg to the pHLIPs

The pHLIP peptides were prepared by solid-phase peptide synthesis at the W.M. Keck Foundation Biotechnology Resource Laboratory at Yale University. The lyophilized powder was soluble in 3 M urea or DMSO (dimethyl sulfoxide). When dissolved in urea the peptide was transferred to buffer using a G-10 size-exclusion spin column. The concentration of the peptide was determined spectrophotomericly by measuring absorbance at 280 nm ($\epsilon_{280}$=13,940 $M^{-1}cm^{-1}$). For conjugation with biotin and biotingPeg, pHLIP peptides were mixed with the biotin-maleimide or biotin-dPeg$_3$-maleimide (Quanta Biodesign Ltd) in DMSO in a ratio of 1:10 and incubated at room temperature for about 8 hrs and at 4° C. until the conjugation reaction was completed. The reaction progress was monitored by HPLC. The product was purified using reverse phase C18 HPLC, lyophilized and characterized by SELDI-TOF mass spectrometry.

Measurements of Water-Octanol Partition Coefficient

The polarity of biotin-maleimide and Peg-biotin-maleimide was determined by assessment of relative partitioning between aqueous and octanol liquid phases. The biotin and biotin-Peg was dissolved in 10 mM phosphate buffer pH8 (0.5 ml) at concentrations of 3 and 5 mM (for biotin), 10 and 50 mM (for biotin-Peg) followed by the addition of n-octanol (0.5 ml). The solutions were mixed by rotation for 24 hrs at room temperature and left for another 48 hrs to reach equilibrium. After phase separation, absorption at 300 nm was recorded. The molar extinction coefficients in n-octanol and phosphate buffer are assumed to be the same, and the ratio of the OD readings was used directly to calculate the partition coefficient, P=ODn–octanol/ODwater, and Log P values, which reflects the relative polarity of cargo.

Liposomes Preparation

Liposomes were prepared by extrusion: POPC (1-palmitoyl-2-oleoyl-sn-glycero-3-phosphocholine) (700 µl of 10 mg/ml in chloroform) was transferred to a 100 ml round bottom flask and a lipid layer was obtained by evaporating the chloroform in a rotary evaporator, followed by drying under high vacuum for 2 hrs. The lipid layer was resuspended in 10 mM phosphate buffer, pH8, and extruded 31 times through 50 or 100 nm membrane to obtain large unilamellar vesicles.

Steady State Fluorescence and CD Measurements

Protein fluorescence and circular dichroism (CD) spectra were measured on a PC1 ISS spectrofluorometer (ISS, Inc.) and a MOS-450 spectrometer (Bioligic, Inc.), respectively, under temperature control at 25° C. 7 µM of peptide and 1.5 mM of POPC in 10 mM phosphate buffer pH8 were pre-incubated overnight at 4° C. The three states were monitored by changes of fluorescence and CD. The fluorescence spectra of the pHLIP variant were recorded with the excitation at 280 nm and use of polarizers at excitation (magic angle) and emission (vertical) light paths. 280 nm excitation wavelength was chosen instead of 295 nm to reduce the absorbance of biotin centered at 300 nm. Peptide CD spectra were recorded from 190 nm to 260 nm at 0.5 nm increments using a sample cuvette with an optical path length of 0.5 cm.

Stopped-Flow Fluorescence Measurements

The stopped-flow fluorescence measurements at different temperatures were carried out using a SFM-300 mixing apparatus connected to a MOS-450 spectrometer. The FC-20 observation cuvette was used for the fluorescence measurements. All solutions were degassed several minutes under a vacuum before loading into the syringes to minimize air bubbles. pHLIP variants (7 µM) were pre-incubated with POPC (1.5 mM) at pH 8.0 to reach binding equilibrium and folding/insertion was induced by fast mixing (5 ms dead time) of equal volumes of pHLIP-POPC variants at pH 8.0 and appropriately diluted HCl, to obtain a drop of pH from 8 to 3.6. Changes of the pHLIP fluorescence signal were recorded through a 320 nm cutoff filter using an excitation wavelength of 280 nm. The fluorescence signal was corrected for the photobleaching. Each kinetic curve was recorded several times and then averaged, excluding the first 3-4 shots.

pH Dependence Study

Solutions of pHLIP-2-bt and pHLIP-2E-bt were mixed with POPC to obtain 200 µl of 3 µM of peptide and 2 mM POPC in phosphate buffer pH8. The pH of the peptide/lipid samples were dropped by addition of HCL and left for about 5 min for equilibration. pH was measured by a microelectrode probe (Orion 8220B). The fluorescence spectra at excitation of 280 nm were recorded at each pH value under the constant temperature. The spectra were analyzed by the decomposition algorithms (Burstein E A et al., 2001 Biophys J, 81(3): 1699-1709 (in eng)) using on-line PFAST toolkit (Protein Fluorescence And Structural Toolkit) (Shen C et al., 2001 Proteins: Struct., Funct., Bioinf., 71(4):1744-1754) to establish position of maximum. Finally, the position of maximum of fluorescence spectra ($\lambda_{max}$) versus pH was plotted and the Henderson-Hasselbalch equation was used to fit the data (using Origin 8.5 software):

$$\lambda_{max} = \lambda_{max}^2 + \frac{(\lambda_{max}^1 - \lambda_{max}^2)}{1 + 10^{n \cdot (pH - pKa)}}$$

where $\lambda^1_{max}$ and $\lambda^2_{max}$ are the beginning and end of the transition, n is the cooperativity parameter, and pKa—is the mid of transition, which was estimated.

Data Analysis

Nonlinear least squares curve fitting procedures were carried out in Origin 8.5.

Results

The molecular mechanism of pHLIP peptides interaction with lipid bilayer of membrane is described in detail below. Also described herein are results demonstrating that polar cell-impermeable cargo could be moved across a bilayer by the pHLIP in a pH-dependent manner. The main goal of this study was to gain mechanistic insights into the process of cargo translocation by various pHLIP variants. It was previously demonstrated that the removal of the protonatable carboxyl groups from the inserting C-terminus of the pHLIP significantly increases the rate of the peptides insertion into membrane. The pKa of the original pHLIP was shifted from 6.0 to 6.5 when Asp residue in the TM domain was replaced by Glu. For the cargo deliver applications higher pKa and rate of the peptide insertion are more appealing as the amount of cargo molecules translocated into cells are expected to be higher.

The pHLIP sequences that were selected for the investigation with cargo are shown in FIG. 75

The pHLIP-4 is an original pHLIP sequence used for the translocation of various cargo molecules. The pHLIP-2 is a truncated version of the pHLIP-4, containing just two carboxyl groups at the inserting end, which shows 10 times faster propagation into membrane in comparison to the pHLIP-4 in a result of pH drop from 8 to 3.6. The pHLIP-2E is a pHLIP-2 where two Asp residues were replaced by Glu to increase pKa of the peptide insertion into membrane. The Asp residues removed from the C-terminus were placed at the N-terminus to preserve the peptide solubility. All pHLIP variants had free SH group at the C-terminus for the conjugation with maleimide-cargo molecules. Biotin and biotin-Peg were used as cargo mainly due to their Log P values, the convenience of their conjugation to the peptide and low level of absorbance and no fluorescence in UV range (in contrast to fluorescent dyes). The measured Log P of biotin and biotin-Peg are −0.29 and −1.39, respectively (for the comparison Log P of phalloidin and phalloidin-rhodamine is −1.5 and −0.05, respectively, An et al., 2010). pHLIP-4 is capable of translocation of biotin-Peg, as well as other polar cargoes of similar polarity.

Fluorescence and CD spectroscopic techniques were utilized to probe pHLIPs-cargo interaction with the lipid bilayer of POPC liposomes. Three states were measured for the pHLIPs-biotin (pHLIP-bt) and pHLIPs-biotin-Peg (pHLIP-btPeg) as well as for the pHLIP-2E. The fluorescence and CD spectra of pHLIP variants with cargoes at normal and low pH in the absence and presence of POPC liposomes are shown on the FIGS. 30A-F and FIGS. 31A-F. The spectral parameters are summarized in the Table 1. All pHLIP-cargo constructs demonstrate characteristic three states. At pH8 in the absence of liposomes (state I) all pHLIP-cargo constructs are mostly unstructured (characteristic negative band on CD spectra at 195 nm) with fluorophores exposed to the aqueous solution (the maximum of fluorescence is at 350-352 nm). The addition of POPC liposomes at pH8 (state II) leads to the increase of fluorescence quantum yield along with the blue shift of the position of maximum of emission spectra, which reflects peptide-cargoes attachment to the lipid bilayer and partial partition into membrane. At low pH4 (state III) further increase of fluorescence intensity and additional blue shift of emission spectra were observed for all pHLIP-cargo constructs. The peptide-cargo partition into membrane is accompanied by the formation of helical structure (minima at 208 and 225 nm on CD spectra).

pHLIP variants with attached cargoes demonstrate less increase of fluorescence in the state II compared to the corresponding peptides with no cargo. The polarity of the cargo attached to the truncated pHLIP variants (-2 and 2E) correlates with the shift of the position of maximum of fluorescence to the longer-wavelengths in the state II, which is instructive about higher exposure of the emitting residues to solvent. A significant shift of the fluorescence was observed for the pHLIP-2E peptide, the position of maximum of emission spectra shifts from 341.3 nm (for pHLIP-2E) to 344.7 nm (for pHLIP-2E-bt) and 347.9 nm (for pHLIP-2E-btPeg). The emission is shifted from 345.6 nm (for pHLIP-2-bt) to 347.5 nm (for pHLIP-2-btPeg). Fluorescence of the pHLIP-4 and its cargo constructs is long-wavelength and positioned around 349 nm. The amount of helical structure presented in molar ellipticity ($\theta$) at 225 nm, which usually correlates with the peptide partition into membrane, is also reduced from −2.41 to −1.43 for the pHLIP-2-bt and -btPeg, and from −4.42 to −3.96 to −2.27 for the pHLIP-2E, -2E-bt and -2E-btPeg. The obtained data indicate that the peptides (especially pHLIP-2 and 2E, which are more hydrophobic and partition into membrane deeper and have higher helicity content at pH8 compared to pHLIP-4) are pulled up by the polar cargo molecules attached to their C-terminus. The higher is cargo polarity (negative Log P values) attached to the pHLIPs less is the partition of the constructs into membrane, which is accompanied with reduced helicity. The same tendency is observed for the state III. The quantum yield and content of helical structure is slightly reduced for the pHLIP variants with cargo compared to them without attached cargo. Despite on a fact that the obtained steady-state fluorescence and CD data could not provide quantitative measure of amount of cargo translocated across a lipid bilayer, however these data indicate that the attachment of a polar cargo reduces the number of peptide molecules reaching state III. Moreover, polarity of a cargo most probably correlates with the amount of its translocation across a bilayer.

Figure 32A:
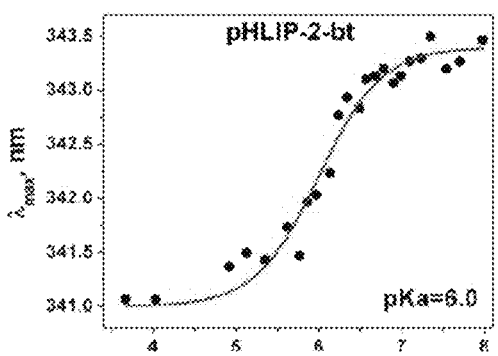
FIGS. 32A-B are a series of line graphs illustrating the pH-dependent insertion into lipid bilayer of membrane of the pHLIP-2-bt (A) and the pHLIP-2E-bt (B) is shown. The pKa of the transitions were found by the fitting of the curves with the Henderson-Hasselbalch equation. The fitting curves are colored in red.
Figure 32B:
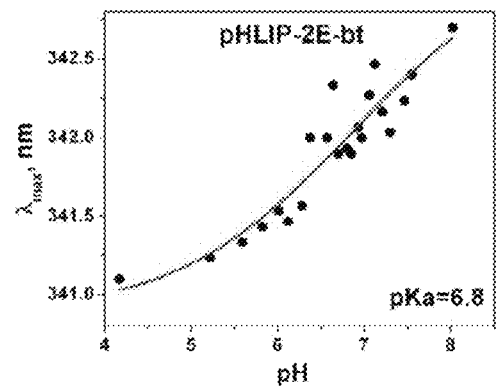

It was also investigated how the attachment of polar (not charged) cargo might affect pKa of the peptide-cargo construct insertion into a membrane. pH dependence experiments of the pHLIP-2-bt and pHLIP-2E-bt were performed. FIGS. 32A-B demonstrate shift of the position of maximum of emission of the pHLIP-2-bt and pHLIP-2E-bt as a function of pH. The pKa of the transition was found by the fitting of the curves with the Henderson-Hasselbalch equation (see Method section). The pKa of membrane-insertion for the pHLIP-2-bt and pHLIP-2E-bt is 6.0 and 6.8, respectively. The pKa of the pHLIP-2 was found to be 6.1 (Karabadzhak et al., submitted) and the pKa=6.5 for the original pHLIP (pHLIP-4), where a single Asp residue from the TM domain was replaced by Glu (Musial-Siwek et al, 2010). Slightly higher value of pKa for the pHLIP-2E-bt could be explained by the fact that two Asp residues were replaced by Glu, which have higher pKa of protonation.

Figures 33A, 33B:
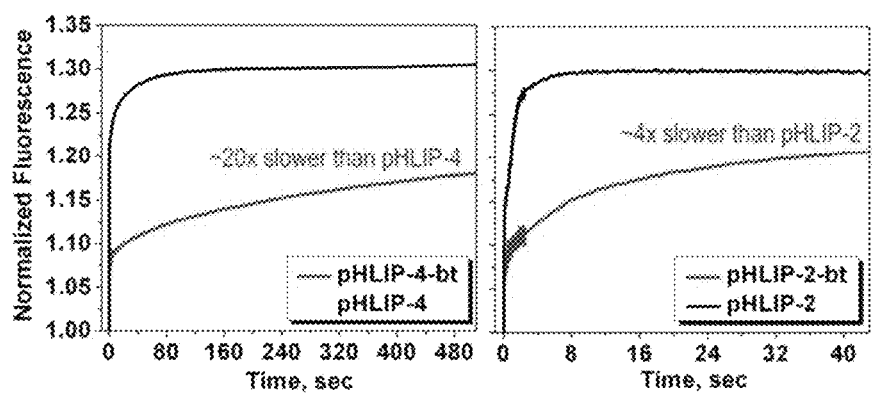
FIGS. 33A-B are a series of line graphs showing the insertion into membrane of the pHLIP-4 and -2 without and with biotin cargo attached to the C-terminus. Insertion of the pHLIP-4-bt and pHLIP-2-bt is about 20 and 4 times slower than the insertion of the pHLIP-4 and pHLIP-2 with no cargo, respectively.

Obtained results show that cargo does not affect much pH-dependent ability of pHLIPs to insert into membrane. The amount of inserted peptides correlate in some degree with cargo polarity: more polar cargo is, slightly less peptide insertion into membrane occurs. However, the changes are not dramatic. Next, the question of a cargo influence on the kinetics of pHLIPs insertion into membrane was examined. Fluorescent kinetics studies of the pHLIPs and pHLIP-cargo constructs insertion into membrane were performed. The pHLIP variants were pre-incubated with POPC liposomes at pH 8 to ensure equilibrium in the state II, and after a rapid mixing with HCl to reduce pH from 8 to 3.6, changes of the fluorescence were measured in real time. FIGS. 33A-B demonstrate that attachment of biotin cargo to peptides slows down the process of insertion of the pHLIP-4 and pHLIP-2 by 20 and 4 times, respectively. Note that the rate of insertion of the pHLIP-2 is 10 times higher compared to the pHLIP-4 (the details of the study could be found in the first manuscript of this series). Thus, cargo attachment in more significant degree affects kinetics of the peptide insertion rather than thermodynamics.

Figure 34A:
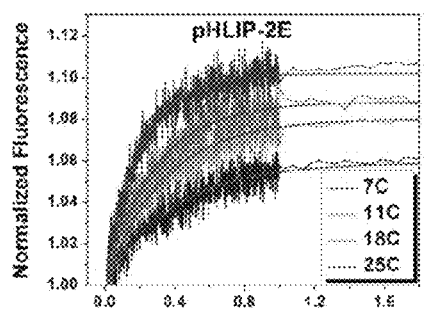
FIGS. 34A-D are a series of line graphs demonstrating the insertion into membrane of the pHLIP-2E, -2E-bt and pHLIP-2E-btPeg at different temperatures, the Arrhenius plot. Kinetics of the fluorescence changes for the pHLIP-2E, -2E-bt, -2E-btPeg recorded at various temperatures are presented. The Arrhenius plots are shown on (D). The data were fitted by the Arrhenius equation (5). The fitting curves are colored in red.
Figure 34B:
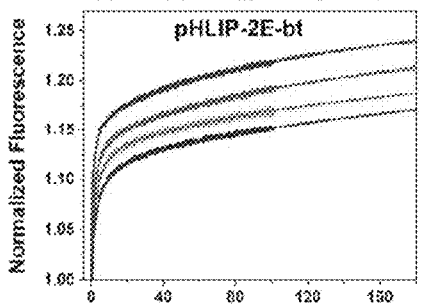
Figure 34C:
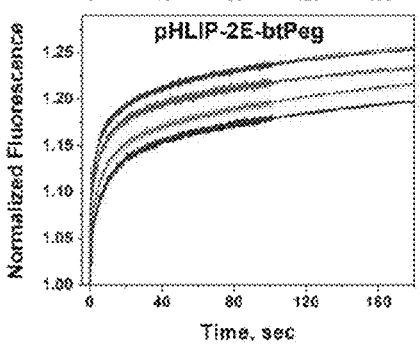

To gain more insights in the process of the peptide-cargo insertion into membrane kinetics of insertion for the pHLIP-2E, pHLIP-2E-bt and pHLIP-2E-btPeg were recorded at different temperatures. pHLIP-2E and cargoes attached to it was observed, since it is the most interesting pHLIP sequence from the point of view of cargo delivery to cytoplasm, and there are no kinetics data presented for this pHLIP variant in the previous study. Insertion of the pHLIP-2E without and with cargoes into the lipid bilayer was triggered by the drop of pH from 8 to 3.6, and the increase in fluorescence was monitored at different temperatures (25, 18, 11, 7° C.) (FIGS. 34A-C). The attachment of cargo slows the process of peptide insertion about 100 times.

To obtain rate constants, the mathematical formalism described above was utilized. The kinetic curves of the pHLIP-2E were adequately fitted by the single exponential function:

$$F(t)=f_0+f_1\exp(-t/\tau_1) \quad (1)$$

where $\tau_i$ are the characteristics time for each transition or $v_i=1/\tau_i$ are the characteristic rates of the transitions, and $f_i$ are the characteristics contributions. Single exponential function is a general solution for the two-state (no intermediates) model:

However, to describe the kinetic of the pHLIP-2E-bt and -btPeg three-exponential function was used:

$$F(t)=f_0+f_1\exp(-t/\tau_1)+f_2\exp(-t/\tau_2)+f_3\exp(-t/\tau_3) \quad (2)$$

which is a general solution of the four-state (two intermediates) model:

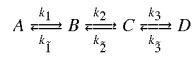

As described above, (see Appendix 1-3 in the Example above) by making a number of assumptions simple approximate relations between the rate constants k and the characteristic rates, v, obtained in a result of exponential fitting of the experimental data, could be established. For the two-state model:

$$k_1 \sim v_1, \quad (3)$$

and for the four-state model:

$$k_1 \sim v_1, \quad k_2 \sim \frac{v_2}{1.1} - \frac{v_3}{12.21}, \quad k_3 \sim 0.991 v_3 \quad (4)$$

The fitting of the kinetic curves of the pHLIP-2E-bt and -btPeg was performed with fixed characteristic times established by the fitting of the pHLIP-2E kinetic data. The characteristic times and rate constants are given in the Table 2. When cargo is attached to the inserting end of the peptide the process of insertion into membrane slows down from 200-400 ms (no cargo) to 80-130 sec (with cargo). There was no significant difference in the kinetic of insertion between pHLIP conjugated with biotin or biotin-Peg cargoes.

Figure 34D:
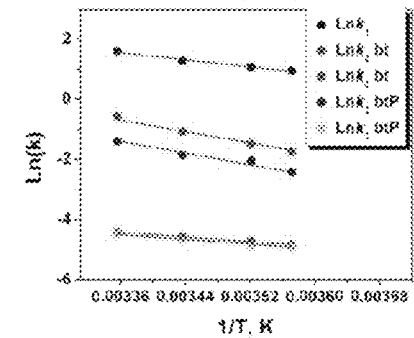

To establish activation energies ($E_a$) and frequency factors (A) for the transitions between states for the pHLIP-2E without and with cargoes, the Arrhenius plots were constructed (FIG. 34D). The points were fitted by the Arrhenius equation (red lines on FIG. 34D):

$$\ln k = -E_a/RT + \ln A \quad (5)$$

The global fit was applied for the analysis of the second transition of the pHLIP-2E-bt and -bt-Peg, and third transition for the same constructs. The thermodynamic activation parameters are shown in the Table 3. The activation energy barrier and frequency factor for the pHLIP-2E is 6 kcal/mol and $1.2 \times 10^5$, respectively. Two additional steps appear on the pathway of insertion for the pHLIP-2E-bt and -btPeg. The second and third transitions have activation energy barriers of 9.7 and 3.9 kcal/mol, respectively. The frequency factors for the pHLIP-cargo transition from the first intermediate to the second one are million times higher than the frequency factor for the transition to the final state. It might reflect the fact that at a final stage of the peptide propagation into a membrane to adopt TM orientation and move cargo across a bilayer, the process could be slowed down significantly.

Many approaches to targeted delivery are currently under development, each with its comparative advantages and disadvantages. In contrast to all known peptide-based delivery technologies, selective delivery of molecules across a membrane by pHLIP is achieved by pH-dependent folding of a peptide across the bilayer. pHLIP could be viewed as a single molecule transporter. The partition of pHLIP into the outer leaflet of lipid bilayer at neutral pH and the folding/insertion at low pH are accompanied by the release of energy. It was determined that the Gibbs Free Energy of binding to a POPC surface (state I-state II transition) at 37° C. is about −7 kcal/mol near neutral pH and the additional free energy of insertion and folding across a lipid bilayer at low pH (state II-state III transition) is nearly −2 kcal/mol. The energy difference between state II and state III is used to favor the equilibrium partitioning across the hydrophobic bilayer of a membrane. It was previously demonstrated that the pHLIP can translocate various polar molecules across a cellular membrane in a pH-dependent manner. This study was designed with main aim to gain understanding of mechanism of cargo translocation to be able to tune pHLIP properties and improve cargo delivery.

Biotin and biotin-Peg were utilized as polar cargo molecules of different polarity. The cargoes were attached to the inserting end of several pHLIP variants to probe pHLIP-cargo constructs interaction with membrane. Among the investigated pHLIP variants were pHLIP-4, pHLIP-2 and pHLIP-2E. The pHLIP-4 was used in all experiments for translocation of cargo. It has four protonatable residues at the inserting end. The pHLIP-2 and 2-E are truncated versions of the pHLIP-4, with two protonatable groups at the C-terminus. Two Asp residues were replaced by Glu in the pHLIP-2E to increase the pKa of protonation and peptide insertion into membrane.

The steady-state fluorescence and CD measurements indicate that the attachment of cargo does not affect the peptides ability to interact with lipid bilayer in a pH-dependent manner. The pHLIP-2-biotin has the similar pKa of insertion into membrane as the pHLIP-2. Thus, non-protonatable cargo does not change the pKa of insertion. At the same time, the pKa for the pHLIP-2E-bt was shifted to 6.8 due to the replacement of two Asp by Glu residues. The attachment of polar cargoes alters the state II of the peptides (peptide bound to the membrane at neutral and high pHs). The pHLIP-2 and, especially pHLIP-2E, demonstrated deeper positioning in the membrane compared to the pHLIP-4, due to the less number of charged groups at the C-terminus. Polar cargo attached to the C-terminus creates "pulling" force ($\vec{F}_{out}$) directed from the membrane core (FIGS. 35A-B) and, as a result the pHLIP-2 and -2E peptides adopt solvent more exposed position at the membrane surface. It was assumed that the affinity to membrane in the state II of the peptides with polar cargo is slightly lower compared to the affinity of the peptides with no cargo. The higher is polarity of cargo, less binding affinity might be observed. The spectral properties of the pHLIP-cargo constructs in the state III are just slightly different compared to those of the pHLIP peptides with no cargo, which might indicate that slightly less fraction of the peptide molecules are reaching TM state, when polar cargo is attached to the peptide inserting end.

Figure 35A:
FIGS. 35A-B are schematics illustrating a model of cargo translocation across a bilayer. The schematic presentation of the pHLIP-2E insertion into bilayer (A) and cargo translocation across a bilayer (B) in a result of pH jump from 8 to 3.6. Circles represent approximate position of the protonatable carboxyl groups. Membrane distortion is shown by lipids with darker headgroups.
Figure 35B:
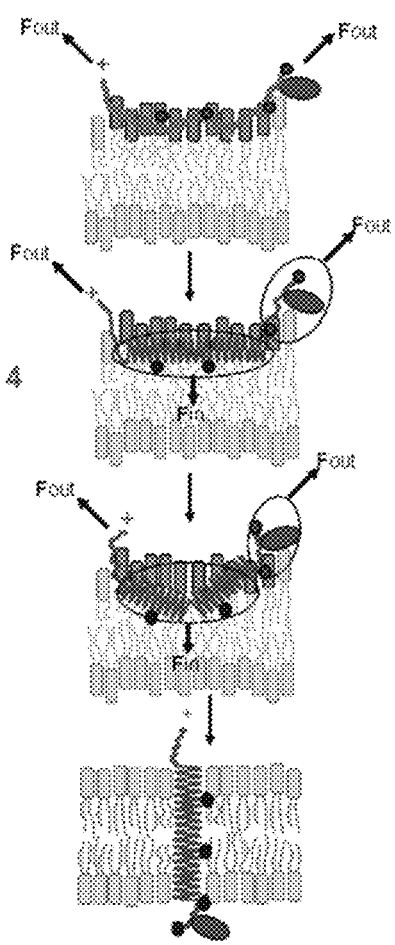
Figure 36A:
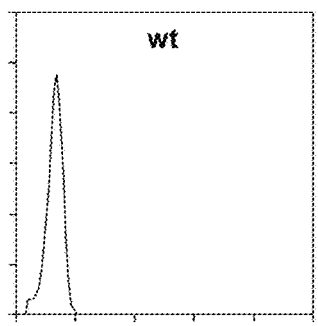
FIGS. 36A-F are line graphs showing sedimentation velocity of the different peptide variants. Apparent sedimentation coefficient distribution derived from sedimentation velocity profiles of the peptides in 5 mM phosphate buffer, pH 8, at 7 µM.
Figure 36B:
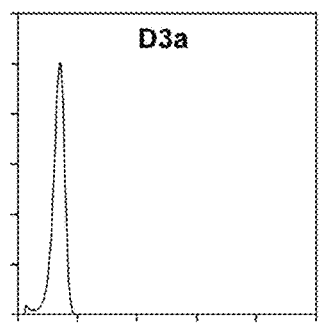
Figure 36C:
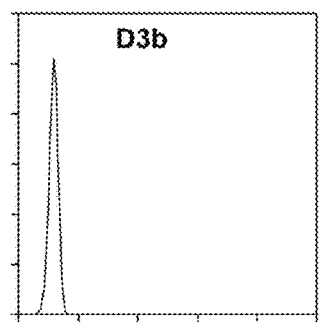
Figure 36D:
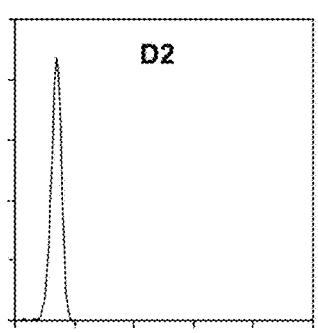
Figure 36E:
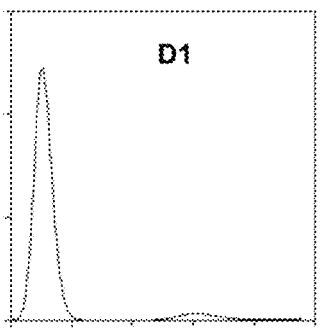
Figure 36F:
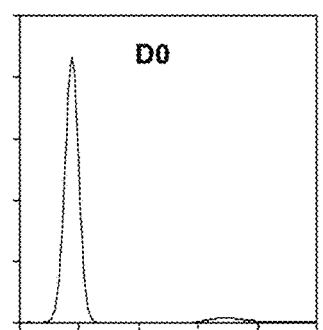
Figure 37A:
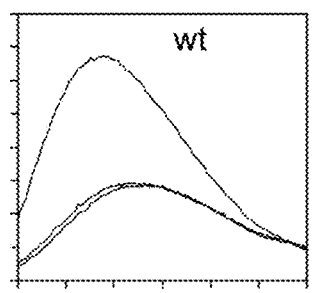
FIGS. 37A-F are a series of line graphs showing fluorescence spectra in buffer and POPC vesicles. Emission spectra of each variant were recorded under the following conditions: buffer at pH 7.5 (black lines), POPC at neutral pH (blue lines), and POPC pH 4 (red lines). The pH values for the different POPC samples at neutral pH were selected according to the midpoint and slope of the transitions shown in FIG. 41: wt, pH 7.5; D3a, pH 7.5; D3b, pH 7.1; D2, pH 6.5; D1, pH 6.2; D0, pH 8. Peptide concentration was 1.5 µM, and the lipid concentration 375 µM. Fluorescence intensity is given in arbitrary units (A. U.).
Figure 37B:
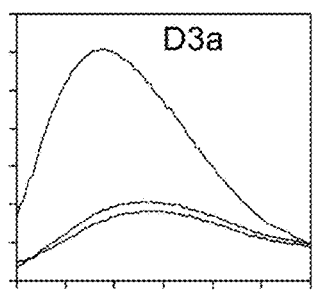
Figure 37C:
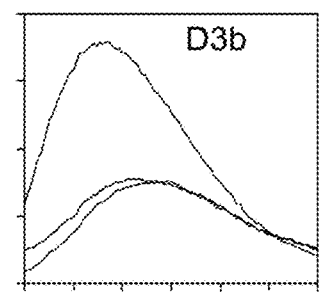
Figure 37D:
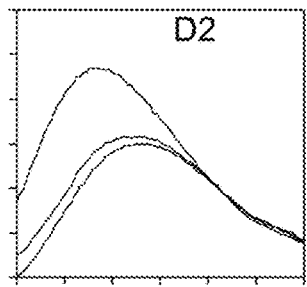
Figure 37E:
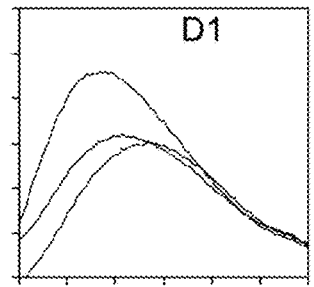
Figure 37F:
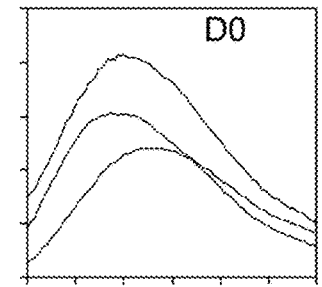
Figure 40A:
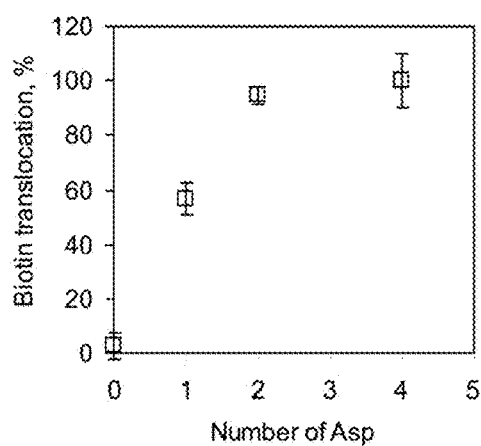
FIGS. 40A-B are box plots showing the quantification of the membrane insertion (biotin translocation) and reversibility. Data corresponding to the biotin translocation assay (open squares) and CD (black symbols) were plotted against the number of Asp residues in the TM and C-terminal regions. (A) Degree of normalized biotin translocation (open squares). For data normalization, the translocation level of wt pHLIP labeled with biotin at the C- and N-terminus were used as 100% and 0%, respectively. Results from D3a and D3b are not shown for the biotin translocation assay, as the biotin labeling for these peptides affected the interaction with lipids (data not shown). No adverse effects of the labeling were observed for the rest of the peptides tested. The averages and standard deviations are shown. (B) The percentage of reversibility of biotin translocation of the samples used in (A) is shown (open squares). For CD experiments, the degree of reversibility was determined monitoring the relative changes in ellipticity at 222 nm (black symbols). The averages and the standard deviations are shown. Data corresponding to D3b appears as a triangle, while the rest of the CD data appear as circles. All data points were used for a linear fitting ($R^2=0.95$).
Figure 40B:
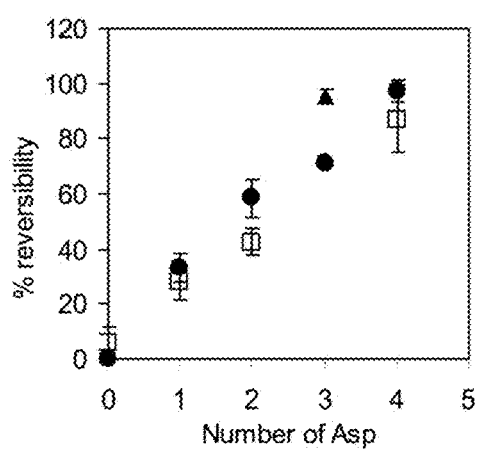
Figure 42A:
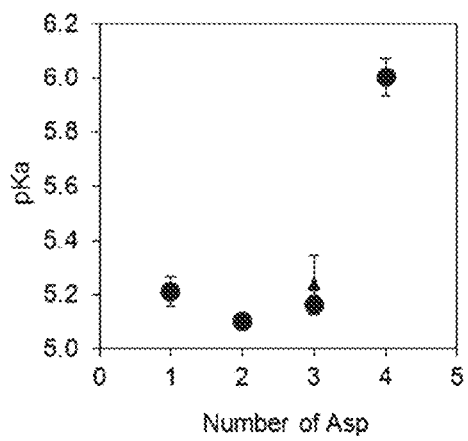
FIGS. 42A-B are a series of dot plots showing the parameters obtained from the fitting of the fluorescence pH transitions. The pKa (A) and m parameter (B) values obtained from the fitting of the data in FIG. 41 to Equation 1 are shown in black symbols. Data from the D3b variant is shown as triangles (to maintain the representation as in FIGS. 40A-B). The line corresponds to the fitting of all data points ($R^2=0.93$). Averages and standard deviations are shown.
Figure 42B:
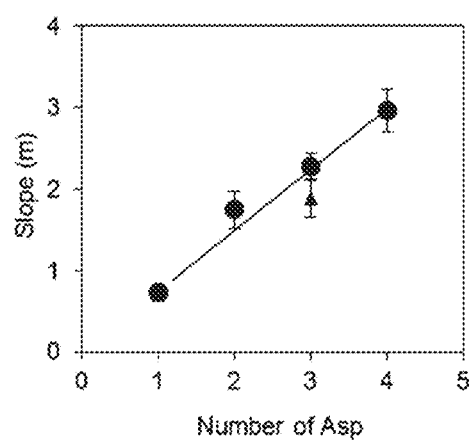
Figure 43:
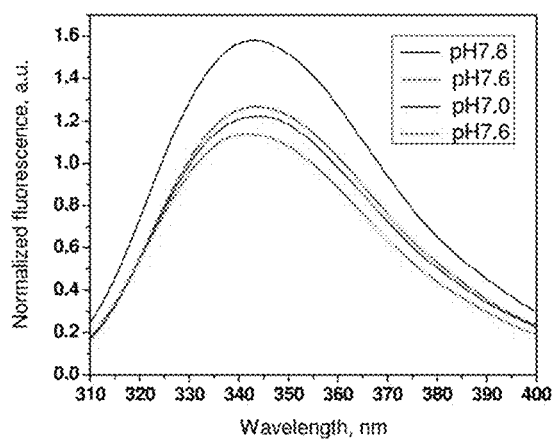
FIG. 43 is a line graph showing fluorescence of D2 in presence of POPC at various pHs.
Figure 44:
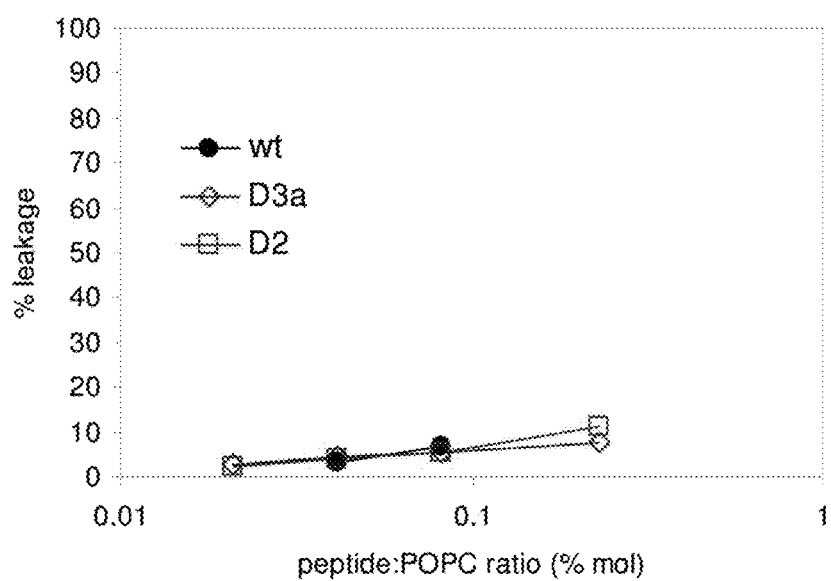
FIG. 44 is a line graph demonstrating leakage of encapsulated calcein. The release of calcein encapsulated in large unilamellar POPC liposomes was measured following the fluorescence at 515 nm in the presence of different concentrations of peptides. The level of 100% disruption of liposomes was determined after addition of 0.05% Triton X-100.
Figure 46A:
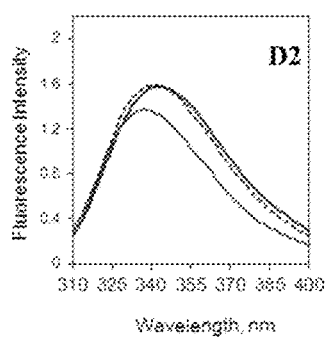
FIGS. 46A-C are a series of line graphs showing fluorescence studies of the reversibility of the membrane insertion for D2, D1 and D0. Spectra of the peptides in the presence of POPC at pH 4.1 (light grey lines) and 7.8 (dark grey lines). The pH of the samples at pH 4.1 was increased back to 7.8 (dashed blue lines) to study reversibility. For D2, where acidification caused TM helix formation occurs, the two blue lines have a good overlapping, suggesting a high degree of reversibility. For D1 and D0, a TM helix is not formed in a pH-dependent fashion, and then the interpretation of the reversibility data is less straightforward.
Figure 46B:
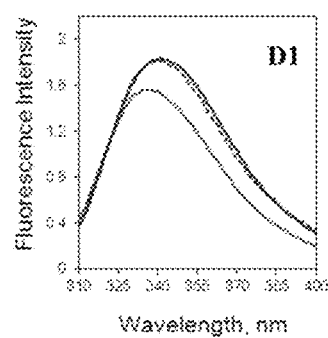
Figure 46C:
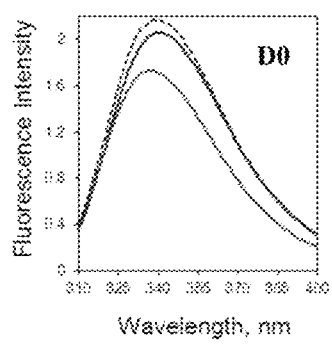

While the equilibrium thermodynamics favor the binding and insertion of pHLIP-cargo constructs, the slow kinetics could be limiting. Indeed, the most significant changes were observed in kinetics of the peptides insertion into a membrane when cargo was attached to the inserting end. The presence of polar cargo slows the rate of insertion several times, and intermediate states on the folding pathway are appeared, the similar changes were observed for the peptide with charged inserting end. The detailed investigation of the kinetics of insertion for the pHLIP-2E variant and it's conjugates were carried out with the biotin and biotin-Peg cargoes. First, kinetics of the pHLIP-2E insertion into lipid bilayer in a result of pH drop could be very well described by the two-state model with no intermediates. Thus, as predicted in the Example above, in a simple case, the process of a polypeptide insertion/folding is an all-or-none transition. The pHLIP-2E is an excellent example of such case. When the polar cargo such as biotin or biotin-Peg is attached to the C-terminus of the pHLIP-2E, the process of insertion slows down about 400 times, and two intermediates appear on the folding pathway. It was assumed that the drop of pH leads, first, to the protonation (or partial protonation) of the Glu residues, as a result, the force directed toward a bilayer core ($\vec{F}_{in}$) is created (FIGS. 35A-B). On the other hand, positively charged N-terminus and polar cargo at the C-terminus create "pulling" forces ($\vec{F}_{out}$) directed from the bilayer core, which prevent propagation of the peptide into membrane. It was assumed that more polar cargo would be the higher would be the strength of the pulling force. The difference in kinetics of insertion for the pHLIP-2E-bt and -btPeg is not significant. The slight difference is in the frequency factor, which is about two times lower for the pHLIP-2E-btPeg compared to the pHLIP-2E-bt for the transition to the second intermediate on the folding pathway.

The findings are very valuable for the design of new delivery agents for the direct translocation of polar cargo across a membrane. There are several important conclusions:

the simple case of the two-state folding model (insertion with no intermediates) is demonstrated in the case of the pHLIP-2E peptide;

a polar cargo creates "pulling" force, which might lead to the reduced affinity of a polypeptide-cargo to the membrane already at neutral pH, thus reduces the effective concentration of a cargo near membrane surface;

it takes a significantly longer time for a polypeptide to adopt final TM configuration, when a polar cargo is attached to the inserting end;

a polypeptide with cargo could be trapped in intermediates on the insertion/folding pathway;

there is no significant difference in the kinetics of a polypeptide insertion when cargoes of different polarity (Log P of −1.5 or −0.05) are attached to the peptide inserting end.

Finally, it is concluded that the pHLIP peptides with protonatable charged groups at the inserting end are suited very well for the delivery of very toxic cargo molecules to have minimum efficiency of translocation at neutral pH. This is due to the fact that at normal pH charged residues stays unprotonated and preventing peptide insertion across cell membrane. However, the slow kinetics could be even more limiting for in vivo use, since blood flow is very fast, and there is no enough time for the equilibration. Moreover, the 'trapping' in the intermediate state might occur and no cargo translocation would happen. Therefore, if it is necessary to move across a cellular membrane as many cargo molecules as possible in the mild-acidic environment, then truncated pHLIP peptides with Glu protonatable residues could be much better fit. They would demonstrate high rate and pKa of insertion. Thus, to facilitate the different delivery needs for the different applications i) various peptides of the pHLIP family could be employed, and/or ii) the hydrophobicity of cargo could be tuned without affecting cargo's ability to bind to its cellular target.

Tables

Three States of the pHLIP-Cargo Constructs.

The spectral parameters of the pHLIP-4, -2 and 2E conjugated to biotin and biotin-Peg cargoes in the states I, II and III are presented. The parameters were obtained in a result of analysis of the fluorescence and CD spectra shown on the FIGS. 30A-F and FIGS. 31A-F, respectively: the maximum position of fluorescence spectrum $\lambda_{max}$, S—the normalized area under the spectra (normalization was done on the area under the spectrum in the state I); $\theta_{225} \times 10^3$, deg cm$^2$ dmol$^{-1}$ the molar ellipticity at 225 nm.

|  | | State I | State II | State III |
|---|---|---|---|---|
| Increase of A. for pHLIP-4 is 1.54 and 2.15 in states II and III | | | | |
| pHLIP-4-bt | $\lambda_{max}$ | 351.3 nm | 349.5 nm | 340.9 nm |
| | S | 1.0 | 1.23 | 1.48 |
| | $\theta_{225}$ | −1.43 | −1.56 | −6.05 |
| pHLIP-4-btPeg | $\lambda_{max}$ | 351.5 nm | 349.7 nm | 341.3 nm |
| | S | 1.0 | 1.24 | 1.53 |
| | $\theta_{225}$ | −1.44 | −1.76 | −6.04 |
| Increase of A. for pHLIP-4 is 1.86 and 2.20 in states II and III | | | | |
| pHLIP-2-bt | $\lambda_{max}$ | 351.5 nm | 345.6 nm | 340.0 nm |
| | S | 1.0 | 1.51 | 1.96 |
| | $\theta_{225}$ | −1.39 | −2.41 | −6.33 |
| pHLIP-2-btPeg | $\lambda_{max}$ | 350.3 nm | 347.5 nm | 338.6 nm |
| | S | 1.0 | 1.28 | 1.99 |
| | $\theta_{225}$ | −0.99 | −1.43 | −5.05 |
| Increase of A. for pHLIP-4 is 2.54 and 2.64 in states II and III | | | | |
| pHLIP-2E | $\lambda_{max}$ | 351.2 nm | 341.3 nm | 339.2 nm |
| | S | 1.0 | 2.54 | 2.64 |
| | $\theta_{225}$ | −1.10 | −4.42 | −6.36 |
| pHLIP-2E-bt | $\lambda_{max}$ | 350.7 nm | 344.7 nm | 340.1 nm |
| | S | 1.0 | 1.71 | 2.41 |
| | $\theta_{225}$ | −1.89 | −3.96 | −6.09 |
| pHLIP-2E-btPeg | $\lambda_{max}$ | 350.9 nm | 347.9 nm | 340.1 nm |
| | S | 1.0 | 1.50 | 2.26 |
| | $\theta_{225}$ | −1.61 | −2.27 | −5.05 |

Insertion at Different Temperatures.

Characteristic times ($\tau$, sec), obtained in a result of exponential fitting (eq. 1-2) of the fluorescence kinetics (transition from pH8 to 3.6) of the pHLIP peptides without and with cargo at different temperatures are presented. The rate constants (k, sec$^{-1}$) were calculated according to the eqs 3-4, these values were used to constructs the Arrhenius plots (FIG. 34D).

| | pHLIP-2E pHLIP-2E-bt pHLIP-2E-btPeg | pHLIP-2E-bt | | pHLIP-2E-btPeg | |
|---|---|---|---|---|---|
| Temperature | $t_1$, s/$k_1$, s$^{-1}$ | $t_2$, s/$k_2$ s$^{-1}$ | $t_3$, s/$k_3$ s$^{-1}$ | $t_2$, s/$k_2$ s$^{-1}$ | $t_3$, s/$k_3$ s$^{-1}$ |
| 25° C. | 0.20/5.00 | 1.59/0.57 | 82.4/0.0120 | 3.7/0.24 | 86.0/0.0115 |
| 18° C. | 0.28/3.57 | 2.67/0.34 | 95.0/0.0104 | 5.8/0.16 | 103.9/0.0095 |
| 11° C. | 0.34/2.94 | 4.04/0.22 | 110.0/0.0090 | 7.0/0.13 | 125.0/0.0079 |
| 7° C. | 0.39/2.56 | 5.21/0.17 | 124.4/0.0080 | 10.0/0.09 | 133.3/0.0074 |

The Activation Energies and Frequency Factors.

The activation energy. $E_a$, and frequency factor, A, was calculated by fitting of the Arrhenius plots (FIG. 34D) by the Arrhenius equation (5).

| | $E_a$, kcal/mol | A |
|---|---|---|
| pHLIP-2E | 6.0 | 1.2 × 10$^5$ |
| pHLIP-2E-bt | 6.0 | 1.2 × 10$^5$ |
| | 9.72 | 6.3 × 10$^6$ |
| | 3.9 | 9.2 |
| pHLIP-2E-btPeg | 6.0 | 1.2 × 10$^5$ |
| | 9.72 | 3.1 × 10$^6$ |
| | 3.9 | 8.4 |

Example 14: Amino Acid Sequence Variation and pH-Driven Membrane Insertion of pHLIP Peptide The pH (low) insertion peptide (pHLIP) binds to the surface of lipid bilayers at neutral pH, and when the pH is lowered it inserts across the membrane to form a transmembrane helix. Peptide insertion is reversed when the pH is raised above the characteristic pKa (6.0). A key event in the membrane insertion is the protonation of aspartic (Asp) and/or glutamic (Glu) acid residues, since at neutral pH their negatively charged side chains hinder membrane insertion. In order to gain mechanistic understanding, membrane insertion and exit of a series of pHLIP variants in which the four Asp residues of SEQ ID NO:5 ("WT-Cys1 in Table 1) were sequentially mutated and studied. A correlation was established between number and location of protonatable groups with peptides ability to insert into and exit from the lipid bilayer of membrane in a pH-dependent manner and is useful to improve or customize targeting of acidic diseased tissue by pHLIP peptides.

The following abbreviations are used herein. CD, circular dichroism; HPLC, high performance liquid chromatography: MALDI-TOF, Matrix-assisted laser desorption/ionization-time of flight; OCD, oriented circular dichroism; POPC, 1-palmitoyl-2-oleoyl-sn-glycero-3-phosphocholine; TM, transmembrane.

pHLIP is monomeric at low concentrations, with a mostly unstructured conformation in neutral and basic solutions (state I; see FIGS. 37A-F). However, if lipid vesicles are present at neutral pH, pHLIP binds to their external surfaces with an energy of 6-7 kcal/mol (state II; see FIGS. 37A-F). In the membrane-attached state, pHLIP remains largely unstructured. However, if the solution pH is lowered, pHLIP inserts into lipid bilayers forming a transmembrane (TM) alpha helix (state III; FIGS. 37A-F). The insertion is fully reversible and unidirectional, with the C-terminus being translocated across the membrane. The pKa of peptide insertion into lipid bilayers is 6.0, and the energy difference between the attached and inserted states is 1.8 kcal/mol at 37° C.

The pHLIP sequence is relatively rich in acidic residues (see Table below). At neutral pH, the combined negative charges of these residues constitute a large energetic barrier for pHLIP insertion into the membrane. The reason for this is that the estimated energetic cost of transfer of a single aspartic acid residue from water to the hydrophobic core of the membrane is unfavorable by 3.6 kcal/mol for the unprotonated (negatively charged) state, while for the protonated (non-charged) state it is of only 0.4 kcal/mol. At equilibrium, four charged Asp and one Glu residues would simultaneously be in the membrane at about one part in 10. Thus, for pHLIP to be able to insert into membranes, protonation of a large fraction of the acidic residues is expected, and knowledge of the protonation pattern of the acidic residues of pHLIP is an essential part of understanding the molecular mechanism of the membrane insertion process. Two classes of carboxyl groups are of interest: those that remain buried in the membrane after pHLIP is inserted into membrane, and those that traverse the hydrophobic core of the membrane during insertion. Accordingly, both the pH-driven membrane insertion and the exit process were studied.

The following materials and methods were used to generated the data described in this example.

Peptide synthesis and assessment of monomeric state. Peptides were made by solid-phase synthesis using standard 9-fluorenylmethyloxycarbonyl chemistry and purified by reverse phase chromatography (C18 column, using a water/acetonitrile gradient in 0.01% trifluoroacetic acid). Purity was checked by MALDI-TOF mass spectrometry. Peptides were quantified by absorbance spectroscopy, using a molar extinction coefficient of 13940 $M^{-1}cm^{-1}$. Some peptides contain a single Cys residue in the C-terminus, and thus have the potential to form intermolecular disulfide bonds, leading to the formation of dimers. To rule out the possibility that this might be occurring in the experimental conditions, HPLC was run on peptide samples incubated (at room temperature for 3 h) at concentrations higher than those used in experiments and in the absence and presence of POPC. No dimer band was detected, and concentrations in the range of 0.1 mM peptide and ON incubation were required to detect a significant amount of dimer (~10%). Peptides listed in the table above in this example were used, except for some experiments with D2-D0, where a Cys-less version was employed (similar results were obtained for both results).

Analytical ultracentrifugation. Sedimentation velocity experiments were performed at 25° C. in a Beckman Optima XL-I at 35.000 rpm. Peptides were dissolved in 5 mM phosphate buffer, pH 8, at a concentration of 7 μM after 1 hour incubation at root temperature. Absorbance at 280 nm was used to monitor the centrifugation, and analysis was performed using SEDFIT.

Liposome preparation. The required amount of chloroform-dissolved POPC (1-palmitoyl-2-oleoyl-sn-glycero-3-phosphocholine) (Avanti Polar Lipids) was placed in a glass tube and dried with argon and then held under vacuum overnight. The dried film was resuspended in water or 10 mM phosphate buffer pH8 and vortexed. Extrusion was performed using a Mini-Extruder (Avanti Polar Lipids), with Nuclepore polycarbonate membranes of 0.1 or 0.05 μm pore sizes (Whatman). Depending on the lipid concentration, 15-25 extrusion steps were performed to obtain the final large unilamellar vesicles.

Fluorescence spectroscopy. Peptides were dissolved in 5 or 10 mM phosphate buffer, pH 8, and incubated with POPC vesicles prepared in water, resulting in a molar lipid to peptide ratio of 250:1. Time of incubation with POPC liposomes was varied from 90 min to 18 hours. The pH of the samples was adjusted with a 10 mM concentration of the following buffers for the indicated pH ranges: $H_3PO_4$, pH 1.0-3.5; sodium acetate, pH 3.5-5.5; $Na_2HPO_4/NaH_2PO_4$, pH 5.5-8.0; sodium borate, pH 8.0-10.5 or by addition of concentrated HCl. The final peptide concentration was varied from 1.5 to 5 μM in different experiments. Emission spectra were measured in a SLM-Aminco 8000C and PC2, ISS spectrofluorimeters at room temperature (controlled temperature) with excitation at 295 nm. The appropriate blanks were subtracted in all cases.

For the determination of the spectral maxima we used the FCAT mode of the PFAST software, which fits the experimental spectra to log-normal components. The spectral maxima value thus obtained for each point of the pH curve were plotted, and analyzed according to:

$$F = \frac{(F_a + F_b 10^{m(pH-pKa)})}{(1 + 10^{m(pH-pKa)})} \quad \text{(Equation 1)}$$

where $F_a=(f_A+S_A \text{ pH})$ and $F_b=(f_B+S_B \text{ pH})$; $f_A$ and $f_B$ are the spectral maxima for the acid and basic forms, respectively, and $S_A$ and $S_B$ are the slopes of the acid and basic baselines, m is the cooperativity parameter. Fitting by nonlinear least squares analysis was carried out with Origin.

Circular Dichroism. Samples were prepared as in the fluorescence experiments, but the final molar lipid to peptide ratio was 300:1, with a final peptide concentration varied from 2 to 5 μM. CD spectra were recorded in a Jasco J-810 and MOS450 Biologic spectropolarimeters interfaced with a Peltier system. Spectra were recorded at 25° C. using 2 or 5 mm cuvettes, the scan rate was 50 nm/min and 10-30 averaging steps were performed. Raw data was converted to mean residue ellipticity (MRE) according to:

$$[\Theta]=\Theta/(10l\ cN)$$

where $\Theta$ is the measured ellipticity, l is the pathlength of the cell, c is the protein concentration, and N is the number of amino acids. (Kelly et al., 2000, Current Protein and Peptide Letters 1, 349-384).

For the study of membrane attachment, insertion and its reversibility, the typical procedure was as follows: samples were incubated with POPC vesicles at pH 8 for 90 minutes and spectra recorded; then the pH was lowered to 4.0 and after 30 min measurements were performed. Finally, the pH of the sample was increased with sodium borate buffer, pH 10.2 to a final pH of 7.5 and after 30 minutes spectra were recorded. The degree of reversibility was established from the recovery of the signal at 222 nm. The final buffer concentration for the different experiments was in the 3-15 mM range. Appropriate blanks were subtracted in all cases.

OCD measurements. For oriented circular dichroism measurements we prepared the supported bilayer on quartz slides with spacers of 0.2 mm thickness on one side with special polish for far UV measurements (Starna). Slides were cleaned by sonication for 10 min in cuvette cleaner solution (Decon Contrad70, 5% in water), 2-propanol, acetone, 2-propanol and rinsed with deionized water. Then the slides were immersed in a mixture of concentrated sulfuric acid and hydrogen peroxide (ratio 3:1) for 5-10 min to completely remove any remaining organic material form the slides. Slides were then thoroughly rinsed with and stored in deionized water (Milli-Q purified water kept at 25° C.). A POPC lipid monolayer was deposited on a quartz substrate by the Langmuir-Blodgett (LB) method using (KSV minitrough). For the LB deposition, a cleaned slide was vertically immersed into the clean subphase (Milli-Q purified water kept at 25° C.) of a Langmuir-Blodgett through. A POPC lipid solution in chloroform was spread on the subphase and chloroform allowed to evaporate for about 30 min, followed by monolayer compression to 32 mN/m. First later was deposited by retrieving the slide from the subphase at a rate of 15 mm/min. The second layer of the bilayer was created by fusion. For this step, the monolayer on the slide was incubated with a solution of POPC vesicles (50 nm in diameter obtained by extrusion) mixed with peptide solution at the required pH (0.5 mM POPC and 10 μM peptide). The fusion occurred for about 6 hours in 100% humidity condition. Then, excess vesicles were carefully removed and the slides were stack to make a pile while filling up the spaces between them with a peptide solution (5 μM) at the required pH. Then the bilayers with the peptide solution were allowed to equilibrate for about 6 hours. Measurements were taken at 3 steps during the process: when the monolayers were incubated with excess of liposomes, soon after spaces between bilayers were filled with peptide solution, 6 hours after the second measurement. 14 slides (28 bilayers) were assembled and OCD spectrum was recorded on a MOS-450 spectrometer with 2 s sampling time.

Biotin translocation assay. The HABA dye (4'-hydroxyazobenzene-2-carboxylic acid) binds to avidin with a 1 to 1 stoichiometry, and it absorbs at 510 nm only in the avidin-bound state. This interaction is strongly displaced by the binding of biotin to avidin, resulting in a quantitative reduction in HABA absorbance. This property was used to study the location of the C-terminus of different peptides with regard to the liposome (inside or outside). The C-terminus of each of the peptide variants was labeled with biotin (see below). The rationale for the assay is that pH-driven insertion of the C-terminus would result in biotin translocation inside the liposome, causing shielding of the biotin from the medium outside the liposome, where a preformed HABA/avidin complex (Thermo Scientific) is added. Accordingly, no change in absorbance would be expected for these conditions. On the other hand, if pHLIP lies at the surface of the liposome, the C-terminal biotin would remain accessible to the solution outside the liposome (as the biotin group is polar, it is expected not be protected by the membrane), and would be able to bind to avidin and displace the HABA/avidin complex, with a consequent reduction in absorbance at 510 nm. Liposomes were prepared in 150 mM NaCl, and the ionic strength was carefully maintained during all steps to avoid liposome osmotic shock. Biotin-labeled peptides were incubated in the presence of POPC at pH 8 for 2 h at room temperature (150:1 lipid to peptide ratio). For study of the translocation, acetate buffer was added to the samples, resulting in a final pH of 4.3 prior to 1 hour incubation with the peptide. Only after the final conditions were established is the HABA/avidin complex was added to the solution. The final peptide concentration for the measurement conditions was 3 µM.

Peptides were labeled at the C-terminal Cys residues using the membrane-impermeable compound maleimide-$PEG_2$-biotin (Thermo Scientific), which has a long polar spacer arm of 29.1 Å that allows adequate biotin binding to avidin. The synthesis reaction was performed in 10 mM phosphate buffer, pH 7.5 (overnight incubation at 4° C.). Reaction products were purified by HPLC, and the mass of the biotin-labeled peptides checked by MALDI-TOF mass spectrometry. The octanol/water partition coefficient of maleimide-$PEG_2$-biotin was determined experimentally by measuring the absorbance at 300 nm in the aqueous and octanol (previously pre-equilibrated with water) phases after a 2 h vortexing. A log P value of −1.07±0.02 was obtained. As this value does not take into account the chemical changes of the crosslinking reaction (formation of a thio-ether bond between the maleimide moiety and the Cys side chain), the QikProp 3.0 software was employed to predict the log P value of the reacted form, resulting in a value of −1.4. (Kuyper et al., 2006, J. Am. Chem. Soc. 128(10), 3233-40).

pHLIP Amino Acid Sequence and Mechanisms of Lipid Bilayer Binding and Insertion

Sequence variations in the transmembrane region of pHLIP influence the delicate balance that preserves its water solubility. For example, a simultaneous change of the two aspartic acid residues at positions 14 and 25 to the homologous glutamic acid (Asp14/25Glu) resulted in a loss of pH-dependent membrane insertion due to aggregation of the peptide in aqueous solution (pHLIP variants have been developed with several Glu residues, which preserve pH-dependent properties). In order to reduce the likelihood that the introduced variations in the peptides cause aggregation, a dual strategy was implemented to increase their water-solubility: (i) an Asp-tag was added to the N-terminus (the non-inserting end) to increase the number of charges in the molecule, which improves the solubility of hydrophobic peptides. This addition resulted in the replacement of the N-terminal sequence AAEQ (SEQ ID NO: 305) with DDDED (SEQ ID NO: 306); and (ii) the TANGO algorithm (Fernandez-Escamilla et al., 2004, Nat. Biotechnol. 22, 1302-1306) to define the region of the pHLIP sequence with the highest aggregation tendency, and found this to be the stretch from residue 21 to 30 (coinciding with the most hydrophobic region of the peptide). Leu26 was mutated to Gly, which greatly reduced the predicted aggregation tendency.

These modifications were incorporated into a series of pHLIP variants, where four aspartic acid residues were sequentially mutated to non-acidic polar residues. The aspartic acid residues at the C-terminus of the peptide that transitorily traverse the core of membrane upon insertion (Asp31 and Asp33) were replaced with the non-charged homologue asparagine residues. On the other hand, for the Asp residues that are located at the core of the membrane after the insertion (in the positions 14 and 25), histidine was chosen as the replacement residue, as it is expected to be partially charged at neutral pH, thus improving water-solubility, while being only slightly polar in its uncharged state (the transfer energies from water to the bilayer interior are 0.43 and 0.11 kcal/mol for the neutral forms of Asp and His5, respectively), so that the insertion properties of pHLIP may not be altered. The peptides were named D0-D3 according to the number of aspartic acid residues present in the regions of interest (TM and C-terminus, as the positively charged N-terminus is not expected to interact with the membrane). For the variants with three aspartic acids, two alternatives were studied, one that kept Asp14 (D3a peptide) and the other Asp25 (D3b peptide).

Experiments were conducted to test the state of the variants in solution, where pHLIP is largely found as an unstructured monomer. Sedimentation velocity experiments were conducted to determine the oligomerization state of the different peptide variants in aqueous buffer. Previous analysis of wt pHLIP (at 7 µM in 10 mM phosphate buffer, 100 mM NaCl, pH 8) showed that pHLIP is mostly monomeric, but a small oligomer population is observed (~6%). Sedimentation velocity experiments were performed under the same conditions, but with no NaCl in the solution. For each peptide, a peak with a sedimentation coefficient of 0.72±0.12 S (Table (Parameters describing the studied peptides) and FIG. 1), which corresponds to a molecular weight of 3.4±0.8 kDa, was observed. This is in agreement with the expected monomer mass of the different peptides: 4126 Da for wt and ~4300 Da for the different variants. In the case of D1 and D0 a minor peak was also observed, with a sedimentation coefficient of 3.3±0.3 S. This component represents 5±2% of the total population, and its sedimentation coefficient corresponds to a molecular weight of 43 kDa (consistent with the presence of an octameric or decameric particle). The results indicate that the presence of oligomers is reduced at lower ionic strength. For the particular case of the D1 and D0 peptides, they seem to have a slightly higher oligomerization tendency in solution, but they are still 95% monomeric. The results suggest that all the peptide variants remain soluble and are essentially monomeric. For the rest of experiments, lower peptide concentrations (1.5-5 µM) than that used for sedimentation analysis (7 µM), and thus the level of oligomers present for D1 and D0 is expected to be lower.

Fluorescence spectra of the peptides in aqueous solution at neutral pH showed that in all cases the emission maximum was centered around 347-349 nm (FIG. 2, black lines and Table (studied peptides). This indicates that the two tryptophan residues of the peptides are largely exposed to aqueous solution, such as in fully unfolded proteins. This represents an improvement over the previously studied Asp14/25Glu mutant peptide, where peptide aggregation shifts the emission maximum to 342 nm in buffer at pH 87. A similar fluorescence maximum was also observed for the Asp14/25Asn mutant under the same conditions. The presence of mostly unstructured species in aqueous solution for each of the studied peptides was confirmed by circular dichroism (CD) experiments, since the observed CD spectra were characterized by a minimum at 203 nm (FIG. 3A-B, black lines), as observed for pHLIP in state I.

The two lipid-interacting states of the pHLIP variants were then examined: state II, where wt pHLIP is mostly unstructured and attached at the bilayer surface and state III, where wt pHLIP forms a TM helix at low pH1.6. Fluorescence experiments in the presence of POPC liposomes revealed that for the two D3 variants, the characteristic fluorescence signatures for states II and III were evident: (i) in the presence of liposomes at neutral pH (FIG. 2, blue lines), the fluorescence emission maxima of the peptides was slightly shifted from $348.7 \pm 1.0$ nm to $346.2 \pm 1.2$ nm, accompanied by a small fluorescence increase (Table (studied peptides); and (ii) when the pH was lowered to pH 4, a large fluorescence increase and spectral blue shift to $336.2 \pm 1.1$ nm occurred (red lines), which are typically observed when the Trp side chain is buried in the membrane hydrophobic core. To complement the fluorescence data, circular dichroism experiments were performed under the same conditions (FIG. 3A-B). The CD signature of the pHLIP membrane insertion process consists of the appearance of the characteristic signals associated with the formation of alpha helix: minima at 208 and 222 nm and positive ellipticity at 190 nm. Both D3 variants showed very similar spectral changes as it was observed for wt upon acidification. The results indicated that replacement of one of the Asp residues in the TM region of the peptide does not lead to the changes of the peptide ability to interact with the membrane in a pH-dependent manner.

The D2 variant, where both Asp were replaced by His residues, also demonstrates a pH-dependent membrane interaction. However, the spectral pattern was slightly different than for wt and D3 variants: the fluorescence intensity of D2 in presence of POPC decreased in the pH range 8-6 with no significant changes of spectral maximum at pH 8-7 and small shift to lower wavelengths at pH6. The amount of helical structure of D2 at neutral pH was slightly higher than wt and D3 (FIG. 2 and Table (studied peptides)), while it does not change in the pH range 8-6. D2 partitions into the lipid bilayer of membrane slightly deeper than wt and D3 at neutral pHs, since His residues are expected to be partially charged at neutral pHs, which enhances the hydrophobicity of the peptide TM and its affinity for the lipid bilayer. The decrease of fluorescence signal in the pH range 8-6 might be attributed to the partial quenching of emission of at least one of the Trp residues by one of the partially protonated His residues. At the same time at neutral pHs the peptide C-terminus containing four negative charges (2 Asp, 1 Glu and C-terminus) does not partition into the membrane, keeping peptide the at the membrane surface. Further drop of pH till 3-4 is associated with fluorescence spectral maximum blue shift some increase of fluorescence intensity (FIG. 2) and appearance of more pronounced negative band at 225 nm on CD spectra (FIG. 3A-B), which is usually indication of peptide insertion into bilayer1. Reduction of pH leads to the protonation of negatively charged groups at the C-terminus, and peptide insertion into membrane. At the same time, we expect that protonation of His residues at low pH should occur, which might lead to the peptide exit from the lipid bilayer or, alternatively, formation of a pore channel in the lipid bilayer, where positively charged His residues would be pointed toward the channel. Calcein encapsulation control experiments were performed that rule out the formation of pores in the membrane by the D2 and D3 peptides. Thus, most probably, the pKa of His protonation embedded into lipid bilayer was shifted toward very low pHs. We carried out fluorescence pH titrations to compare behavior of D2 and wt peptides at pHs lower than 3.5. While for wt no fluorescence change was detected at acid pH values, for D2 we observed that an additional process was present, with an apparent pKa of 2.5, characterized by a fluorescence decrease and a red-shift of the spectral maximum, which might be associated with peptide exit from the lipid bilayer. To establish the orientation of the helix in the membrane we performed OCD measurements. The data indicates that D2 adopts a TM orientation at pH 3.5-4.5, while increasing the pH leads to the peptide exit and appearance of a membrane-surface orientation of helix (FIG. 4A-D). The OCD spectrum at pH 1.9 does not correspond to a TM helix. Thus, we concluded that the pKa of both or at least one of the His residues is significantly shifted from 6.3-6.915 to a lower value (2.5) due to their location at the bilayer interface in state II, emphasizing the important influence of bilayer surface properties on interacting peptides. A similar trend was previously observed for peptides that insert into membranes via the deprotonation of His residues 16,17, although the magnitude of the pKa shift was smaller. However, large changes in pKa are typically observed when the side chains are in different environments, as the protonation of titrable amino acids depends on the dielectric properties of their environment. A fitting example of large pKa changes is found in the native environment of pHLIP, bacteriorhodopisin, where Asp14 and Asp25 have pKa values of 7.5 and higher than 9, respectively, significantly higher than the 3.7-4.0 pKa value found for fully solvated aspartic acid side chains.

D1 has one less Asp residue at the C-terminus than D2. The observed slightly larger blue-shift of fluorescence emission (FIG. 2) and higher content of helicity in presence of POPC at neutral pHs (FIGS. 3A-B) could be associated with a even deeper position of the peptide in the membrane. Slight changes of spectral signal occur upon acidification, which might indicate protonation of Asp33, Glu34 and C-terminus and peptide insertion into lipid bilayer. OCD spectrum obtained for D1 at pH3.3 (FIG. 4A-D) does not show clear TM orientation of the helix, while some decrease of ellipticity at 205-225 nm is observed, which might indicate existence of a mixture of TM and surface-parallel orientations of helices or appearance of significantly tilted TM helix.

D0, in contrast to all other pHLIP variants described above, has a blue-shifted maximum of fluorescence emission (FIG. 2) at neutral pHs in presence of POPC with high content of helical structure (FIGS. 3A-B). Practically no changes of spectral signal occur for D0 upon acidification (FIGS. 2 and 3A-B). OCD data show mostly surface orientation of helix at low pHs (FIGS. 4A-D), as expected for a peptide with no aspartic acids.

A biotin-avidin binding assay was used to study the magnitude and directionality of the membrane insertion of the peptides. A biotin moiety was attached to the peptides C-termini. The level of binding to avidin was measured, and the sequestration of the biotin molecule was determined by the translocation of the peptide C-terminus into the liposome interior. The biotin moiety was linked to the C-terminal Cys of the peptides via a long, polar PEG linker. The linker has a double purpose, facilitating biotin access to the avidin binding site, but more critical to our experiments, helping to delineate between the intra- and extra-liposomal location of the biotin, since the polarity of the moiety makes a location inside the bilayer unlikely. For this purpose, the amount of biotin available to bind to avidin molecules present exclusively outside the liposomes was quantified. Avidin binding to biotin was not detected for the D2 peptide at low pH (FIG. 5A) due to the biotin translocation across a membrane, which complements our data about complete insertion of these peptides into lipid bilayer and confirms that directionality of insertion is the same as for wt. Only partial and no translocation of biotin across the membrane were monitored for D1 and D0, respectively (FIG. 5A). This observation correlates with results indicating partial (or tilted) and no insertion into lipid bilayer of D1 and D0, respectively. Additionally, the translocation of the biotin (which represents a cargo) across the membrane does not appear to significantly hinder the membrane insertion of the peptides. This might be explained by its small size (526 Da) and its moderate polarity (log P=−1.4; see Materials and Methods for details), which are both well within the range of cargo properties that pHLIP effectively translocates.

To complement these findings, pH-induced changes were monitored in the position of the maximum of fluorescence emission of the peptides in presence of POPC, which provides details about peptide insertion into the lipid bilayer (FIGS. 6A-C). The plot of the position of spectral maxima followed a sigmoid behavior as a function of pH, corresponding to the transition between the interfacial and inserted states for all variants (except for D0). The fitting of the experimental data provided the two main parameters that describe the insertion process: the pKa and the cooperatively (m parameter). The pKa of membrane insertion obtained for wt pHLIP is 5.94±0.09. For the different variants, shifts of the pKa to lower values (~5.2) were detected (FIG. 7A). The reason for this observation might be related to the lower number of aspartic acid residues or the presence of histidines in the TM region of the pHLIP variants. In contrast to a similar pKa value for the variants, a gradual decrease in the cooperativity of the insertion process (m parameter) was observed for peptides with fewer Asp residues, as the titration occurred progressively over a wider pH range (~1 pH unit for wt, and ~2 pH units for D1) (FIGS. 6A-C and FIG. 7B). The data indicate that the cooperativity of insertion is linked to the number of protonatable residues. Cooperativity and pKa also might reflect position of protonatable groups in peptide sequence and their proximity to each other. When pHLIP is at the surface of the vesicle and the pH is lowered, the protonation of one Asp residue might facilitate the protonation of other protonatable residues shifting their pKa values. The protonation of the first Asp residue might induce partial insertion of the peptide into membrane. In this scenario, the protonation of the neighboring Asp residues would be energetically favored to shield the negative charge (i.e. the pKa value of the neighboring Asp is shifted to higher values in a more hydrophobic environment) and then a positive feedback would be established, triggering membrane insertion.

The role of the number and location of Asp residues on peptide exit from the membrane was also examined. The CD and fluorescence changes associated to pHLIP lipid insertion at acid pH are completely reversible. Changes of CD and fluorescence signals and reversibility of biotin translocation across membrane were monitored. The ellipticity increase associated with the peptide insertion into membrane was essentially reversible for wt and D3b (FIGS. 3A-B, dashed blue lines overlap with continuous blue lines) while for D3a, D2 and D1, the reversibility was only partial. Since changes of CD signal upon acidification for D2-D0 is less pronounced that for wt and D3, the reversibility of D2-D0 membrane insertion was also assessed by changes of fluorescence signal. Different levels of reversibility of the two D3 peptides were noted: the insertion process is significantly more reversible in D3b (90%) than in D3a (70%) (FIG. 5B). An overall, linear relationship was observed between the number of aspartic acid residues that interact with the membrane and the degree of alpha helix formation reversibility (FIG. 5B). The results obtained for the reversibility of the biotin translocation (exit process) also in agreement (FIG. 5B).

To address the question of reversibility and the time of equilibration of pH inside liposomes, the membrane-impermeable fluorescent probe 5(6)-carboxy-2',7'-dichlorofluorescein was encapsulated in POPC liposomes. The fluorescence of the probe is pH-sensitive, with a pKa of 5.1. When the pH of the solution outside the liposomes was lowered, the fluorescence of the encapsulated probe changed in a sigmoid fashion, with an apparent pKa of 5.05. A relative high proton permeation through unilamellar POPC liposomes in the minute time-scale has been observed. On the other hand, the kinetics data suggest that the time of wt peptide exit (with 2 TM and 4 C-terminal protonatable groups) is in the range of milliseconds. Thus, peptides exit from the lipid bilayer much faster that pH is equilibrated inside liposome, and most probably, C-terminal residues cross the membrane in their non-charged form.

For the peptide exit from the lipid bilayer to take place, the deprotonation of Asp residues must energetically destabilize the inserted state. Destabilization of the inserted state occurs mostly, when protonatable groups deeply buried into the hydrophobic core of membrane became charged. Therefore, exit of wt and D3b, which have two or one Asp in the hydrophobic core of membrane, is fully reversible. The reason for the difference in peptide insertion reversibility for D3a and D3b might be related to the presence of an arginine residue at position. Accordingly, the deprotonation of Asp25 in D3b would strongly destabilize the membrane-inserted state due to the presence of a negative charge in the hydrophobic core of the membrane, favoring the exit process. However, the negative charge of Asp14 in D3a might be forming a salt bridge with the neighboring side chain of Arg11, which would result in a weaker destabilization of the inserted state. Another potential explanation is an altered position of the TM domain, which was mentioned above. There is a possibility that the TM domain in variants is shifted toward C-terminal residues, which would lead to more significant exposure to aqueous environment of the amino acid in position 14 (with His in D3a) and shift to hydrophobic core of amino acids at positions 31 and 33. As a result, de-protonation of His14 in D3a might be associated with less destabilization of helix than de-protonation of His25 in D3b. The side chains of Asp31 and Asp33 most probably are interacting with the headgroup region of bilayer. The destabilization energy associated with their deprotonation is not enough to cause a complete exit from the membrane. The results indicate that the deprotonation of acidic residues located in the hydrophobic core of membrane ensure complete exit of the peptide.

The results show that all the studied peptides were soluble in solution, being essentially monomeric. This observation suggests that the addition of a D-tag at the N-terminus and the L26G mutation favors peptide solubility. Spectral data obtained with D3-D0 peptides indicate that the lower is number of negatively charged groups in the peptide sequence the deeper the peptide partitions into lipid bilayers, which is accompanied with formation of helical structure. At the same time, TM orientation (at least for D3-D2 peptides) is achieved as a result of protonation of Asp/Glu residues at the C-terminus, which can readily go across a membrane in its non-charged form. Transmembrane Asp residues are not essential for peptide insertion, and interestingly, membrane insertion upon acidification occurs in peptides having the presence of two His residues in the predicted TM region. Histidines have been used in the past to drive the insertion of peptides into membranes at neutral pHs. However, in these examples acidic residues were completely absent in the sequence. The establishment of states II and III is driven by acidic residues. Since the protonated (charged) state of the side chains of His14 and His25 in the hydrophobic core of the membrane would be energetically very unfavorable, in the peptides their pKa values are expected to shift to lower values in the membrane-inserted state (favoring this way the unprotonated state). Further acidification eventually causes their protonation, resulting in a strong destabilization of the inserted TM helix and peptide exit. In order to preserve the pH-dependent ability of peptide to interact with the membrane, negatively charged residues needs to be located in TM or C-terminal inserting end. These residues act as switches for pHLIP membrane insertion, as the negative charges of their side chains block membrane insertion. Acidification causes the protonation of these side chains, and it results in an increase in the overall hydrophobicity of the peptide, which leads to the TM helix formation to shield the hydrophobic residues of pHLIP from water molecules. When the pH is raised to near neutrality, the negatively charged state of the Asp/Glu side chains is again favored. This decreases the peptide hydrophobicity, resulting in exit from the transmembrane position. The complete peptide exit from the lipid bilayer is completed when deprotonation of Asp/Glu residues located in hydrophobic core of membrane occurs and destabilization of TM helix happens.

The knowledge gained from these studies is useful as a guide to customize and/or improve the imaging and therapeutic properties of pHLIP. For the specific case of cancer, pHLIP characteristics can be finely tuned to the extracellular pH (pHe) of different tumor types or to a particular tumor of the patient to be treated in a personalized medicine approach. For example, tumor targeting by wt pHLIP conjugated to Cu64-DOTA chelate for PET (positron emission tomography) imaging correlates with extracellular pH of tumors. Contrast index was higher in case of targeting of LNCaP tumors (pHe=6.78±0.29), than in case of targeting of PC-3 tumors (pHe=7.23±0.1020). Thus, pHLIP variants, where Asp14/25 were replaced by Glu, with a higher pKa (pKa=6.5)7, can be more effective for targeting of tumors with higher values of extracellular pH. The results indicate that the number of Asp residues in the TM region can modulate the pKa value. Thus, a peptide containing an extra Asp in the TM region is characterized by a higher pKa, and can be directed to certain tumors more effectively. Another important factor to be considered is the broadness of the pH-transition of the peptide, which is dictated by the cooperativity of the transition. On the one hand, for the case where the peptide pKa is lower than the tumor pHe, but the transition is broad (m value is low), a significant part of the pH-transition could intercept with the pHe value, resulting in a significant pHLIP tumor insertion. The pHLIP peptides described herein are characterized by a high differentiation between the amount of inserted and non-inserted peptides forms in a narrow range of pHs. This attribute is especially important for tumor targeting, since the difference in pH between normal and cancerous tissue is on the order of 0.5-0.7 units.

Example 15: Var7 pHLIP for Imaging

Var7 (also called "Short-3") is a lead compound for SPECT/PET imaging. The pHLIP sequence: Chelate-ACE-EQNPWARYLEWLFPTETLLLEL (SEQ ID NO: 249) consisted of D-amino acids. To transfer peptide to lower pHs, the peptide first was dissolved in buffer of pH8.0 and the slowly transferred to buffer of low pH.

Large unilamellar vesicles (LUVs) were prepared by extrusion. 1 ml of 25 mg POPC (1-Palmitoyl-2-Oleoyl-sn-Glycero-3-Phosphocholine, Avanti Polar Lipids, Inc.) in chloroform was desolvated on a rotary evaporator and dried under vacuum for several hours. The phospholipid film was rehydrated in phosphate buffer, vortexed for 2 hours, and repeatedly extruded 15-20 times through a 50 or 100 nm membrane.

Steady-state fluorescence measurements were carried out on a PC1 spectrofluorometer (ISS, Inc.) under temperature control. Peptide fluorescence spectra were recorded from 310 nm to 400 nm with the spectral widths of excitation and emission slits set at 2 nm and 2 nm, respectively, using an excitation wavelength of 295 nm. The polarizers in the excitation and emission paths were set at the "magic" angle (54.7° from the vertical orientation) and vertically (0°), respectively, in order to reduce Wood's anomalies from the reflecting holographic grating.

Steady-state CD measurements were carried out on a MOS-450 spectrometer (Bio-Logic, Inc.) under temperature control. The CD spectra were recorded from 190 nm to 270 nm. All measurements were performed at 22° C.

Peptide and POPC vesicle concentration in steady-state measurements was 7 µM and 1.5 mM, respectively. Peptide was mixed with liposomes at pH8.0 and kept overnight for final equilibration. To reduce pH several microliters of HCl acid was added to the solutions, and time was given for final equilibration. pH dependence measurements and titration experiments were carried out as described above. Stopped-flow fluorescence measurements were carried out using known methods.

Changes of intrinsic peptide fluorescence (increase of quantum yield and shift of the position of maximum to the short wavelengths) indicate that tryprophan residues propagate into lipid bilayer in a result of drop of pH. Changes of CD signal of peptide during its interaction with lipid bilayer of liposomes after drop of pH in presence of lipids indicated formation of helical structure in lipid bilayer at low pH. pH-dependence was monitored by changes of position of maximum of fluorescence spectra. The mid of transition of the peptide insertion into lipid bilayer (pKa) in a result of drop of pH is at pH=5.4. Binding/insertion of the peptide with lipid bilayer was monitored by increasing of fluorescence signal at increasing of POPC concentrations; equilibrium was achieved at low concentration of lipids in solution at low pH, when the peptide inserts into membrane. The affinity constant for the peptide to lipid bilayer (at high concentration of lipids) at pH4.5 is 20 times higher than the affinity constant at pH8.0, which results in 1.68 kcal/mol of free Gibbs energy difference of peptide interaction with membrane at pHs 8.0 and 4.5.

The kinetics of peptide propagation into lipid bilayer induced by drop of pH from 8 to 4.5-4.0 was studied. The peptide belongs to the class of fast peptides (which has no D or E on the C-terminus), which propagates into lipid bilayer within first 5 seconds. It is interesting, that 3E peptides demonstrate "kink" at 500-600 ms. It means that first, peptide "dives" into bilayer in a result of drop of pH (rapid increase of fluorescence), then comes out from the bilayer (increase of fluorescence) and propagates into membrane again to reach the final state.

Figure 52A:
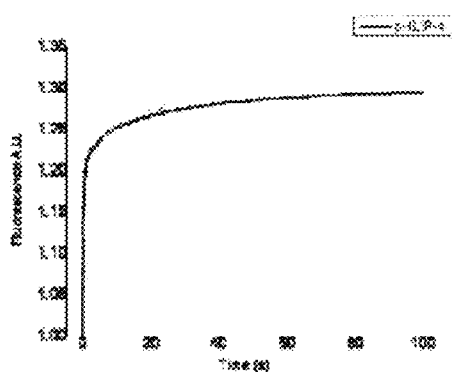
FIGS. 52A-C are a series of line graphs showing the results of kinetics experiments performed with pHLIP-4, pHLIP-2, and pHLIP-1.
Figure 52B:
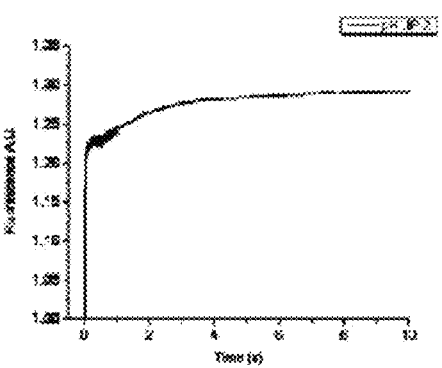
Figure 52C:
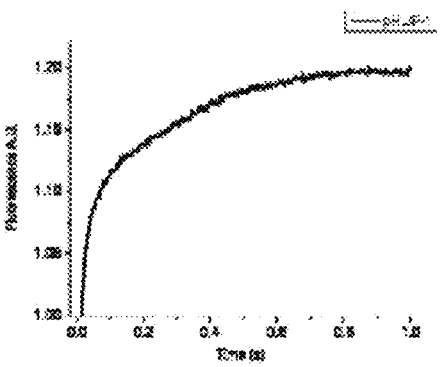

Example 16: Modulation of the Activation Barrier for pHLIP Insertion into Membrane Kinetics Studies with pHLIP Variants pHLIP-4:
(SEQ ID NO: 250)
AEQNPIY WARYADWLFTTPLLLLDLALLV DADEGT-COOH pHLIP-2:
(SEQ ID NO: 251)
AKEDQNPY WARYADWLFTTPLLLLDLALLV DG-COOH pHLIP-1:
(SEQ ID NO: 252)
AKEDQNDPY WARYADWLFTTPLLLLDLALLV G-COOH Described herein is the analysis of pHLIP-4, pHLIP-2 and pHLIP-1. Each peptide contains 4, 2 and 1 protonatable groups at the C-terminus, which goes across the membrane. Kinetics experiments were performed with 3 pHLIPs: peptides were mixed with POPC liposomes at pH8 and equilibrated. pH was dropped from 8 to 4 by mixing of peptide-POPC pH8 with solution of acid in the stopped-flow apparatus. Changes of Trp fluorescence and CD signals were monitored in real time. The alpha-helix was formed within first second, while propagation of the peptides into lipid bilayer were monitored by changes of Trp fluorescence. pHLIP-2 and pHLIP-1 propagates into membrane occurs 10 and 100 times faster than propagation of pHLIP-4 (FIGS. 52A-C).

Figure 53:
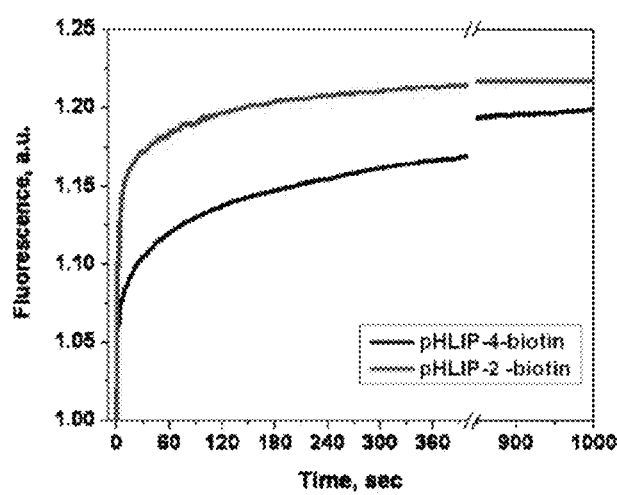
FIG. 53 is a line graph showing the effect of biotin on peptide insertion into the membrane.
Figure 54A:
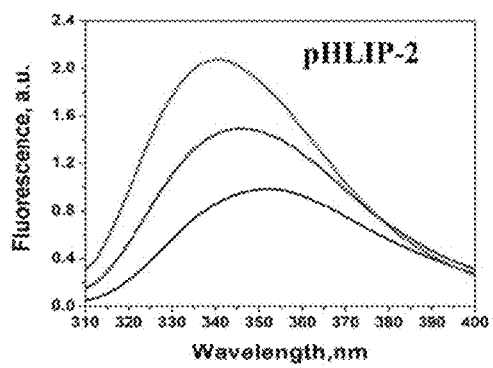
FIGS. 54A-D are a series of line graphs showing the effect of replacement of Asp residues with Glu in pHLIP variants. Fluorescence (A) and CD (B) spectra of three states of pHLIP-2 and pHLIP-2E. Black—State 1, Blue—State II, Red—State III.
Figure 54B:
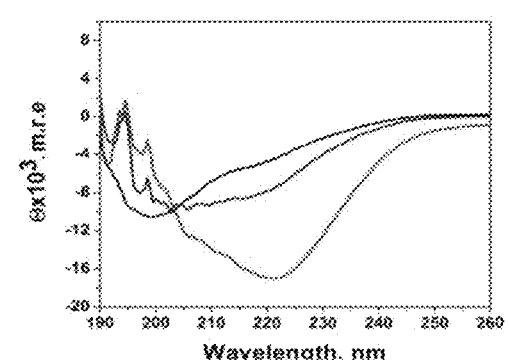
Figure 54C:
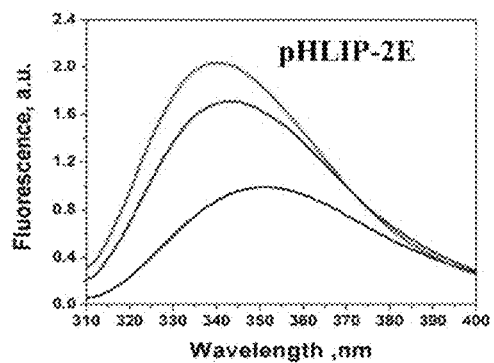
Figure 54D:
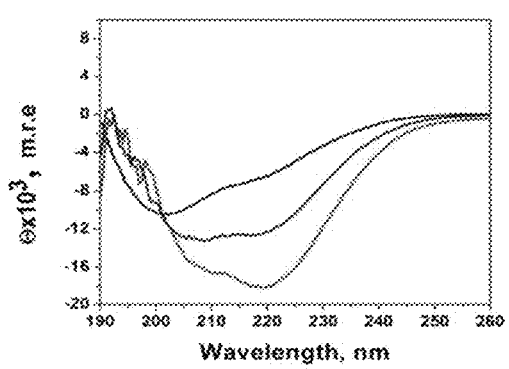

Modulation of pKa of pHLIP Insertion into Membrane with Biotin-Cargo Attached to the C-Terminus pHLIP-4:
(SEQ ID NO: 253)
AEQNPI YWARYADWLFTTPLLLLDLALLV DADEGC-Biotin-T-COOH pHLIP-2:
(SEQ ID NO: 254)
AEDQNP YWARYADWLFTTPLLLLDLALLV DC-Biotin-G-COOH pHLIP-2E:
(SEQ ID NO: 255)
AEDQNP YWARYADWLFTTPLLLLELALLV EC-Biotin-G-COOH To study how cargo might affect kinetics of peptide insertion into membrane, small molecule biotin (MW 244 Da, Log P ~-0.3) was covalently attached to Cys residue at the C terminus of several pHLIP variants. The attachment of biotin cargo slows down the process of peptides insertion into membrane. Insertion of pHLIPs-biotin into the lipid bilayer monitored by changes of Trp fluorescence signal is shown in FIG. 53.

Mathematical Model for Kinetics Data

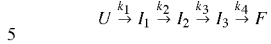

It was assumed that the rates of the backward reactions is much slower in comparison with the rates of forward reactions ($k_1$, $k_2$, $k_3$, $k_4$). Therefore, the backward reactions were ignored. The differential equations were solved in Mathematica and the solution was used to fit experimental data. The contribution into changes of spectral signals from the transition of one intermediate to other denoted as $f_1$, $f_2$, $f_3$, $f_4$.

$$g(t) = f_1 e^{-k_1 t} + f_2 e^{-k_1 t} \frac{k_1(e^{(k_1-k_2)t} - 1)}{k_1 - k_2} +$$

$$f_3 e^{-k_1 t} \frac{k_1 k_2 (e^{(k_1-k_3)t}(k_1-k_2) + e^{(k_1-k_2)t}(k_3-k_1) + (k_2-k_3))}{(k_1-k_2)(k_1-k_3)(k_2-k_3)} +$$

$$f_4 e^{-k_1 t} \frac{k_1 k_2 k_3}{(k_2-k_1)(k_2-k_3)(k_3-k_1)(k_2-k_4)(k_3-k_4)(k_4-k_1)} \times$$

$$\begin{pmatrix} e^{(k_1-k_3)t}(k_1-k_2)(k_1-k_4)(k_2-k_4) - \\ e^{(k_1-k_4)t}(k_1-k_2)(k_1-k_3)(k_2-k_3) - \\ e^{(k_1-k_2)t}(k_1-k_3)(k_1-k_4)(k_3-k_4) + (k_2-k_3)(k_2-k_4)(k_3-k_4) \end{pmatrix} +$$

$$f_5 e^{-k_1 t} \frac{1}{(k_2-k_1)(k_2-k_3)(k_3-k_1)(k_2-k_4)(k_3-k_4)(k_4-k_1)} \times$$

$$\begin{pmatrix} e^{(k_1-k_4)t} k_1 k_2 k_3 (k_1-k_2)(k_1-k_3)(k_2-k_3) - \\ e^{k_1 t}(k_1-k_2)(k_1-k_3)(k_2-k_3)(k_1-k_4)(k_2-k_4)(k_3-k_4) - \\ e^{(k_1-k_3)t} k_1 k_2 k_4 (k_1-k_2)(k_1-k_4)(k_2-k_4) + \\ e^{(k_1-k_2)t} k_1 k_3 k_4 (k_1-k_3)(k_1-k_4)(k_3-k_4) - \\ k_2 k_3 k_4 (k_2-k_3)(k_2-k_4)(k_3-k_4) \end{pmatrix}$$

$$-\frac{d[U]}{dt} = k_1[U]$$

$$-\frac{d[I_1]}{dt} = k_2[I_1] - k_1[U]$$

$$-\frac{d[I_2]}{dt} = k_3[I_2] - k_2[I_1]$$

$$-\frac{d[I_3]}{dt} = k_4[I_3] - k_3[I_2]$$

$$-\frac{d[F]}{dt} = -k_4[I_3]$$

| Peptide | $t_1$, ms (f, %) | $t_1$, s (f, %) | $t_1$, s (f, %) | $t_1$, s (f, %) |
|---|---|---|---|---|
| pHLIP-4 | 25.1 (20.5) | 0.47 (9.5) | 32.0 (28.2) | 651.6 (41.2) |
| pHLIP-2 | 7.5 (53.8) | 0.07 (11.3) | 4.1 (21.6) | 109.1 (13.2) |

Figure 55A:
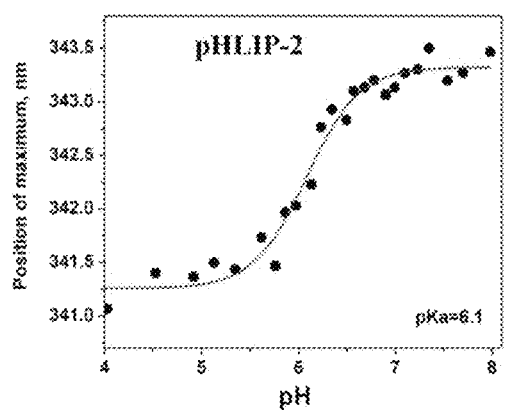
FIGS. 55A-B are a series of line graphs showing the pH-dependences of insertion into membrane of pHLIP-2 and pHLIP-2E.
Figure 55B:
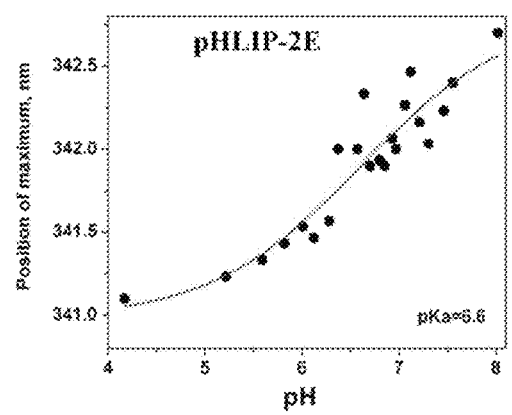

Replacement of Asp residues by Glu (compare pHLIP-2 and pHLIP-2E variants) resulted in a shift of pKa of insertion from 6.1 to 6.6. At the same time pHLIP-2E variant preserves all pHLIP-like properties (FIGS. 55A-B and FIG. 56).

Example 17: Summary of Amino Acid Sequence Variations

In addition to the pHLIP peptide sequences described above, additional sequences/variants are described in this example. The peptide variants comprise the defining characteristics of pHLIP (pH-dependency of activity, monomeric nature, membrane association, membrane insertion/spanning of lipid bilayer structures such as eukaryotic cell membranes, retention in cell membrane after insertion, and/or ability to translocate cargo from outside of a lipid bilayer structure such as a cell to the inside of the structure/cell) but differ in the length of the peptide (number of amino acids), pK of insertion (from 4.5 to 6.5), binding affinity to membrane, time of insertion into lipid bilayer or membrane, time of exit from lipid bilayer or membrane, blood clearance, tumor targeting ability, and ability to move cargo molecules across a lipid bilayer membrane.

Additional animal studies were carried out on the following pHLIP peptides.

See FIG. 76.

All variants demonstrated pH-dependent insertion into lipid bilayer of membrane. However, the affinity of variants to membrane varied. For example, short variants (especially Var12 and 13) had lower affinity to membrane than long variants. Shorter variants (such as Var3 and 4) that are truncated at the C-terminus (relative to the WT) demonstrated a stronger affinity to a lipid bilayer membrane at high pH (pH8) than WT and other variants. In terms of kinetics, all short versions demonstrated very fast insertion in comparison with WT and Reverse sequence (Var14).

Retention time (acetonitrile %) on HPLC runs for all variants with and without Alexa correlated with peptide size and hydrophobicity. Shorter peptides have shorter retention times. All E-versions (sequences designated with an "E" in the previous table have longer retention times in comparison with corresponding D-variants. Variants 1-16 were further characterized with regard to tumor/organ. Twenty-four hours after administration, pHLIP peptides were retained in the tumor while being cleared from other organs such as kidney, skin, heart, lungs, liver, spleen, bladder, stomach, intestine, muscle, and brain. Lack of nephrotoxicity (as demonstrated by these data) is another important advantage of these peptides, compositions, and methods. In some cases, e.g., Var3, Var7, the peptides were also retained in the kidney after 24 hours. In those situations, nephrotoxicity is minimized or eliminated by administration to the subject of a bicarbonate solution or the administration of a decoy peptide to bind and eliminate circulating pHLIP peptide.

A summary of amino acid sequence variations of wild type pHLIP described herein is presented in the tables below. Exemplary comments about each sequence include sequence name, design, pKa value, insertion reversibility, pH solubility, etc.

The check marks [✓] in the grids presented below illustrate the various substitutions that were made in the wild type pHLIP sequence. The wild type pHLIP membrane-inserting sequence, along with flanking sequences is presented in the first row of each grid. The first column of each grid represents the various amino acid substitutions that were introduced in the wild type pHLIP sequence. The check marks [✓] present in various boxes indicate that a variant pHLIP sequence was generated to substitute a specified amino acid for the amino acid in the wild type pHLIP sequence. Sequences with inserted amino acids and truncated sequences are also provided. Multiple check marks [✓] in each row may, but do not necessarily represent a single variant pHLIP sequence with various amino acid substitutions. Rather, each check mark [✓] represents that at least one variant pHLIP sequence has the specified substation at the indicated position. For example, a check mark [✓] in column D25, row L indicates that the amino acid "D" at position 25 in the wild type pHLIP sequence was substituted with an "L" amino acid. Similarly, a check mark [✓] in column L26, row D indicates that the amino acid "L" at position 26 in the wild type pHLIP sequence was substituted with a "D" amino acid. An exemplary amino acid with both of these substitutions is named "D25Down," and appears in the description below.

The tables below disclose the following sequences: page 173 discloses the "pHLIP WT" base sequence as SEQ ID NO: 307 and the illustrative consensus peptide as SEQ ID NO: 308; page 174 discloses the "pHLIP WT" base sequence as SEQ ID NO: 307 and the illustrative consensus peptide as SEQ ID NO: 309; page 175 discloses the "pHLIP WT" base sequence as SEQ ID NO: 307; page 176 discloses the "pHLIP WT" base sequence as SEQ ID NO: 307 and the illustrative consensus peptide as SEQ ID NO: 308; page 177 discloses the "pHLIP WT" base sequence as SEQ ID NO: 307 and the illustrative consensus peptide as SEQ ID NO: 309; page 178 discloses the "pHLIP WT" base sequence as SEQ ID NO: 310 and the illustrative consensus peptide as SEQ ID NO: 311; page 179 discloses the "pHLIP WT" base sequence as SEQ ID NO: 310 and the illustrative consensus peptide as SEQ ID NO: 312; pages 200 and 221 disclose the "EFTK(rhodamine)C(phalloidin)G" sequence as SEQ ID NO: 198.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

SEQUENCE LISTING

<160> NUMBER OF SEQ ID NOS: 314

<210> SEQ ID NO 1

```
<211> LENGTH: 39
<212> TYPE: PRT
<213> ORGANISM: Unknown
<220> FEATURE:
<223> OTHER INFORMATION: Description of Unknown: pH-sensitive membrane
      polypeptide

<400> SEQUENCE: 1

Ala Ala Glu Gln Asn Pro Ile Tyr Trp Trp Ala Arg Tyr Ala Asp Trp
1               5                   10                  15

Leu Phe Thr Thr Pro Leu Leu Leu Leu Asp Leu Ala Leu Leu Val Asp
            20                  25                  30

Ala Asp Glu Gly Thr Cys Gly
        35

<210> SEQ ID NO 2
<211> LENGTH: 35
<212> TYPE: PRT
<213> ORGANISM: Unknown
<220> FEATURE:
<223> OTHER INFORMATION: Description of Unknown: Wild-type pH-sensitive
      membrane polypeptide

<400> SEQUENCE: 2

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35

<210> SEQ ID NO 3
<211> LENGTH: 36
<212> TYPE: PRT
<213> ORGANISM: Unknown
<220> FEATURE:
<223> OTHER INFORMATION: Description of Unknown: Wild-type pH-sensitive
      membrane polypeptide

<400> SEQUENCE: 3

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 4
<211> LENGTH: 35
<212> TYPE: PRT
<213> ORGANISM: Unknown
<220> FEATURE:
<223> OTHER INFORMATION: Description of Unknown: Wild-type pH-sensitive
      membrane polypeptide

<400> SEQUENCE: 4

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35
```

```
<210> SEQ ID NO 5
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 6
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly
        35

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35
```

<210> SEQ ID NO 9
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Lys Cys Gly
        35

<210> SEQ ID NO 11
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Cys Thr
        35

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Cys Glu Gln Asn Pro Ile Tyr Trp Ala Arg Tyr Ala Asn Trp Leu
1               5                   10                  15

Phe Thr Thr Pro Leu Leu Leu Leu Asn Leu Ala Leu Leu Val Asp Ala
            20                  25                  30

Asp Glu Gly Thr Gly
        35

<210> SEQ ID NO 13
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Cys Glu Gln Asn Pro Ile Tyr Trp Ala Arg Tyr Ala Lys Trp Leu
1               5                   10                  15

Phe Thr Thr Pro Leu Leu Leu Leu Lys Leu Ala Leu Leu Val Asp Ala
            20                  25                  30

Asp Glu Gly Thr Gly
        35

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
            20                  25                  30

Asn Gln Gly Thr
        35

<210> SEQ ID NO 15
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Ala Glu Gln Asn Pro Ile Tyr Trp Ala Arg Tyr Ala Asp Trp Leu
1               5                   10                  15

Phe Thr Thr Pro Leu Leu Leu Leu Ala Leu Ala Leu Leu Val Asp Ala
            20                  25                  30

Asp Glu Gly Thr
        35

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Ala Glu Gln Asn Pro Ile Tyr Trp Ala Arg Tyr Ala Asp Trp Leu
1               5                   10                  15

Phe Thr Thr Ala Leu Leu Leu Leu Asp Leu Ala Leu Leu Val Asp Ala
            20                  25                  30

Asp Glu Gly Thr
        35

<210> SEQ ID NO 18
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
            20                  25                  30

Asp Glu Gly Thr
        35

<210> SEQ ID NO 19
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Ala Glu Gln Asn Pro Ile Tyr Trp Ala Arg Tyr Ala Glu Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 20
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Ala Glu Gln Asn Pro Ile Ile Tyr Trp Ala Arg Tyr Ala Asp Trp
1               5                   10                  15

Leu Phe Thr Asp Leu Pro Leu Leu Leu Asp Leu Leu Ala Leu Leu
            20                  25                  30

Val Asp Ala Asp Glu Gly Thr
             35

<210> SEQ ID NO 21
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Glu Gln Asn Pro Ile Tyr Trp Ala Gln Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr Cys Gly
            35

<210> SEQ ID NO 22
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Leu Ala Leu Leu Val Asp Ala
            20                  25                  30

Asp Glu Gly Thr Cys Gly
            35

<210> SEQ ID NO 23
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Ala Leu Leu Val Asp Ala
            20                  25                  30

Asp Glu Gly Thr Cys Gly
            35

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 25
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Gly Glu Gln Asn Pro Ile Tyr Trp Ala Arg Tyr Ala Trp Asp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 26
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Ala Glu Gln Asn Pro Ile Tyr Trp Ala Arg Tyr Ala Asp Trp Leu
1               5                   10                  15

Phe Thr Thr Gly Leu Leu Leu Asp Leu Ala Leu Leu Val Asp Ala
            20                  25                  30

Asp Glu Gly Thr
        35

<210> SEQ ID NO 27
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Asp Asp Glu Asp Asn Pro Ile Tyr Trp Ala Arg Tyr Ala Asp Trp
1               5                   10                  15

Leu Phe Thr Thr Pro Leu Leu Leu His Gly Ala Leu Leu Val Asp
            20                  25                  30

Ala Asp Glu Cys Thr
        35

<210> SEQ ID NO 28
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp

-continued

```
                    20                  25                  30

Ala Asp Glu Gly Cys Thr
            35

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
            35

<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
            35

<210> SEQ ID NO 31
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Glu Gln Asn Pro Ile Tyr Trp Ala Arg Tyr Ala Asp Phe Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 32
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ala Glu Gln Asn Pro Ile Tyr Phe Ala Arg Tyr Ala Asp Trp Leu Phe
1               5                   10                  15

Thr Thr Pro Leu Leu Leu Leu Asp Leu Ala Leu Leu Val Asp Ala Asp
```

```
                    20                  25                  30

Glu Gly Thr
        35

<210> SEQ ID NO 33
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Glu Gln Asn Pro Ile Tyr Phe Ala Arg Tyr Ala Asp Phe Leu Phe
1               5                   10                  15

Thr Thr Pro Leu Leu Leu Leu Asp Leu Ala Leu Leu Trp Asp Ala Asp
            20                  25                  30

Glu Thr

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ala Lys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ala Cys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ala Glu Asp Gln Asn Pro Tyr Trp Ala Arg Tyr Ala Asp Trp Leu Phe
1               5                   10                  15

Thr Thr Pro Leu Leu Leu Leu Asp Leu Ala Leu Leu Val Asp Cys Gly
            20                  25                  30

<210> SEQ ID NO 37
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 37

Ala Glu Asp Gln Asn Pro Tyr Trp Ala Arg Tyr Ala Asp Trp Leu Phe
1               5                   10                  15

Thr Thr Pro Leu Leu Leu Glu Leu Ala Leu Leu Val Glu Cys Gly
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Lys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala Cys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30

<210> SEQ ID NO 40
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp
            20                  25

<210> SEQ ID NO 41
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Thr Glu Asp Ala Asp Val Leu Leu Ala Leu Asp Leu Leu Leu Leu Pro
1               5                   10                  15

Thr Thr Phe Leu Trp Asp Ala Tyr Arg Ala Trp Tyr Pro Asn Gln Glu
```

Cys Ala

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Glu Gln Asn Pro Ile Tyr Trp Ala Arg Tyr Ala Asp Trp Leu Phe
1               5                   10                  15

Thr Thr Pro Leu
            20

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Glu Gln Asn Pro Ile Tyr Trp Ala Arg Tyr Ala Asp Trp Leu Phe
1               5                   10                  15

Thr Thr Pro Cys Leu
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Cys Glu Gln Asn Pro Ile Tyr Trp Ala Arg Tyr Ala Asp Trp Leu
1               5                   10                  15

Phe Thr Thr Pro Leu
            20

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Glu Gln Asn Pro Ile Tyr Phe Ala Arg Tyr Ala Asp Trp Leu Phe
1               5                   10                  15

Thr Thr Pro Leu
            20

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic

```
                                 peptide

<400> SEQUENCE: 46

Lys Glu Asp Gln Asn Pro Trp Ala Arg Tyr Ala Asp Leu Leu Phe Pro
1               5                   10                  15

Thr Thr Leu Ala Trp
            20

<210> SEQ ID NO 47
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Cys Glu Asp Gln Asn Pro Trp Ala Arg Tyr Ala Asp Leu Leu Phe
1               5                   10                  15

Pro Thr Thr Leu Ala Trp
            20

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Cys Glu Asp Gln Asn Pro Trp Ala Arg Tyr Ala Asp Trp Leu Phe
1               5                   10                  15

Pro Thr Thr Leu Leu Leu Leu Asp
            20

<210> SEQ ID NO 49
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Cys Glu Glu Gln Asn Pro Trp Ala Arg Tyr Ala Glu Leu Leu Phe
1               5                   10                  15

Pro Thr Thr Leu Ala Trp
            20

<210> SEQ ID NO 50
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Cys Glu Glu Gln Asn Pro Trp Ala Arg Tyr Ala Glu Trp Leu Phe
1               5                   10                  15

Pro Thr Thr Leu Leu Leu Leu Glu
            20
```

<210> SEQ ID NO 51
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Ala Cys Glu Glu Gln Asn Pro Trp Ala Arg Tyr Leu Glu Trp Leu Phe
1               5                   10                  15

Pro Thr Glu Thr Leu Leu Leu Glu Leu
            20                  25

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 53
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Thr
        35

<210> SEQ ID NO 54
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 55
<211> LENGTH: 36

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Cys Thr
            35

<210> SEQ ID NO 56
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
            35

<210> SEQ ID NO 57
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
            35

<210> SEQ ID NO 58
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
            35

<210> SEQ ID NO 59
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Cys Thr
        35

<210> SEQ ID NO 60
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Ala Ala Glu Gln Asn Pro Ile Tyr Trp Ala Arg Tyr Ala Asp Trp Leu
1               5                   10                  15

Phe Thr Thr Ala Leu Leu Leu Leu Asp Leu Ala Leu Leu Val Asp Ala
            20                  25                  30

Asp Glu Gly Thr
        35

<210> SEQ ID NO 61
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ala Cys Ala Glu Gln Asn Pro Ile Tyr Trp Ala Arg Tyr Ala Asp Trp
1               5                   10                  15

Leu Phe Thr Thr Gly Leu Leu Leu Leu Asp Leu Ala Leu Leu Val Asp
            20                  25                  30

Ala Asp Glu Gly Thr
        35

<210> SEQ ID NO 62
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ala Glu Gln Asn Pro Ile Tyr Trp Ala Arg Tyr Ala Asp Phe Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 63
```

```
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Ala Glu Gln Asn Pro Ile Tyr Phe Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35

<210> SEQ ID NO 64
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ala Glu Gln Asn Pro Ile Tyr Phe Ala Arg Tyr Ala Asp Phe Leu Phe
1               5                   10                  15

Thr Thr Pro Leu Leu Leu Leu Asp Leu Ala Leu Leu Trp Asp Ala Asp
            20                  25                  30

Glu Thr

<210> SEQ ID NO 65
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Ala Lys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ala Cys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30

<210> SEQ ID NO 67
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 67

Ala Glu Asp Gln Asn Pro Tyr Trp Ala Arg Tyr Ala Asp Trp Leu Phe
1               5                   10                  15

Thr Thr Pro Leu Leu Leu Leu Asp Leu Ala Leu Leu Val Asp Gly
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Glu Cys Gly
            20                  25                  30

<210> SEQ ID NO 69
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Lys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30

<210> SEQ ID NO 70
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ala Cys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ala Lys Glu Asp Gln Asn Asp Pro Tyr Trp Ala Arg Tyr Ala Asp Trp
1               5                   10                  15

Leu Phe Thr Thr Pro Leu Leu Leu Asp Leu Ala Leu Leu Val Gly
            20                  25                  30

<210> SEQ ID NO 72
```

```
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Thr Glu Asp Ala Asp Val Leu Leu Ala Leu Asp Leu Leu Leu Pro
1               5                  10                  15

Thr Thr Phe Leu Trp Asp Ala Tyr Arg Ala Trp Tyr Pro Asn Gln Glu
            20                  25                  30

Cys Ala

<210> SEQ ID NO 73
<211> LENGTH: 36
<212> TYPE: PRT
<213> ORGANISM: Unknown
<220> FEATURE:
<223> OTHER INFORMATION: Description of Unknown: Wild-type pH-sensitive
      membrane polypeptide

<400> SEQUENCE: 73

Gly Gly Glu Gln Asn Pro Ile Tyr Trp Ala Arg Tyr Ala Asp Trp Leu
1               5                  10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Glu Gln Asn Pro Ile Tyr Trp Ala Arg Tyr Ala Asp Trp Leu Phe
1               5                  10                  15

Thr Thr Pro Leu
            20

<210> SEQ ID NO 75
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Glu Gln Asn Pro Ile Tyr Trp Ala Arg Tyr Ala Asp Trp Leu Phe
1               5                  10                  15

Thr Thr Pro Cys Leu
            20

<210> SEQ ID NO 76
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 76

Ala Cys Glu Gln Asn Pro Ile Tyr Trp Ala Arg Tyr Ala Asp Trp Leu
1               5                   10                  15

Phe Thr Thr Pro Leu
            20

<210> SEQ ID NO 77
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Cys Glu Gln Asn Pro Ile Tyr Phe Ala Arg Tyr Ala Asp Trp Leu
1               5                   10                  15

Phe Thr Thr Pro Leu
            20

<210> SEQ ID NO 78
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp
            20                  25

<210> SEQ ID NO 79
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Cys Glu Glu Gln Asn Pro Trp Arg Ala Tyr Leu Glu Leu Leu Phe
1               5                   10                  15

Pro Thr Glu Thr Leu Leu Leu Glu Leu Leu Trp
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Cys Asp Asp Gln Asn Pro Trp Ala Arg Tyr Leu Asp Trp Leu Phe
1               5                   10                  15

Pro Thr Asp Thr Leu Leu Leu Asp Leu
            20                  25

<210> SEQ ID NO 81
```

```
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Asp Asn Asn Asn Pro Trp Arg Ala Tyr Leu Asp Leu Leu Phe Pro
1               5                   10                  15

Thr Asp Thr Leu Leu Leu Asp Trp
            20

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Cys Glu Glu Gln Asn Pro Trp Ala Arg Tyr Leu Glu Trp Leu Phe
1               5                   10                  15

Pro Thr Glu Thr Leu Leu Leu Glu Leu
            20                  25

<210> SEQ ID NO 83
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Cys Glu Asp Gln Asn Pro Trp Ala Arg Tyr Ala Asp Trp Leu Phe
1               5                   10                  15

Pro Thr Thr Leu Leu Leu Leu Asp
            20

<210> SEQ ID NO 84
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Cys Glu Glu Gln Asn Pro Trp Ala Arg Tyr Ala Glu Trp Leu Phe
1               5                   10                  15

Pro Thr Thr Leu Leu Leu Leu Glu
            20

<210> SEQ ID NO 85
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Cys Glu Asp Gln Asn Pro Trp Ala Arg Tyr Ala Asp Leu Leu Phe
1               5                   10                  15
```

Pro Thr Thr Leu Ala Trp
            20

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Cys Glu Asp Gln Asn Pro Trp Ala Arg Tyr Ala Glu Leu Leu Phe
1               5                   10                  15

Pro Thr Thr Leu Trp
            20

<210> SEQ ID NO 87
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Lys Glu Asp Gln Asn Pro Trp Ala Arg Tyr Ala Asp Leu Leu Phe Pro
1               5                   10                  15

Thr Thr Leu Trp
            20

<210> SEQ ID NO 88
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 89
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Asp Asp Glu Asp Asn Pro Ile Tyr Trp Ala Arg Tyr Ala His Trp
1               5                   10                  15

Leu Phe Thr Thr Pro Leu Leu Leu Leu Asp Gly Ala Leu Leu Val Asp
            20                  25                  30

Ala Asp Glu Cys Thr
        35

```
<210> SEQ ID NO 90
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asn
            20                  25                  30

Ala Asp Glu Cys Thr
        35

<210> SEQ ID NO 91
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asn
            20                  25                  30

Ala Asn Glu Cys Thr
        35

<210> SEQ ID NO 92
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Asp Asp Glu Asp Asn Pro Ile Tyr Trp Ala Arg Tyr Ala Asp Trp
1               5                   10                  15

Leu Phe Thr Thr Pro Leu Leu Leu His Gly Ala Leu Leu Val Asp
            20                  25                  30

Ala Asp Glu Cys Thr
        35

<210> SEQ ID NO 93
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Ala Cys Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Gly
        35
```

-continued

<210> SEQ ID NO 94
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Thr
        35

<210> SEQ ID NO 95
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 96
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Leu Ala Leu Leu Val Asp Ala
            20                  25                  30

Asp Glu Gly Thr Cys Gly
        35

<210> SEQ ID NO 97
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Ala Leu Leu Val Asp Ala
            20                  25                  30

Asp Glu Gly Thr Cys Gly
        35

<210> SEQ ID NO 98
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gly Gly Glu Gln Asn Pro Ile Tyr Trp Ala Arg Tyr Ala Trp Asp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 99
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Ala Ala Glu Gln Asn Pro Ile Tyr Trp Ala Arg Tyr Ala Glu Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 100
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ala Ala Glu Gln Asn Pro Ile Tyr Trp Ala Arg Tyr Ala Glu Trp Leu
1               5                   10                  15

Phe Thr Thr Pro Leu Leu Leu Leu Glu Leu Ala Leu Leu Val Asp Ala
            20                  25                  30

Asp Glu Gly Thr Cys Gly
        35

<210> SEQ ID NO 101
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly

```
<210> SEQ ID NO 102
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gly Gly Glu Gln Asn Pro Ile Tyr Trp Ala Gln Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 103
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Gly Glu Gln Asn Pro Ile Tyr Trp Ala Gln Asp Tyr Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 104
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 105
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ala Cys Glu Gln Asn Pro Ile Tyr Trp Ala Arg Tyr Ala Asn Trp Leu
1               5                   10                  15

Phe Thr Thr Pro Leu Leu Leu Leu Asn Leu Ala Leu Leu Val Asp Ala
            20                  25                  30
```

Asp Glu Gly Thr Gly
        35

<210> SEQ ID NO 106
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asn
            20                  25                  30

Ala Asn Glu Cys Thr
        35

<210> SEQ ID NO 107
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asn
            20                  25                  30

Ala Asp Glu Cys Thr
        35

<210> SEQ ID NO 108
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Asp Asp Glu Asp Asn Pro Ile Tyr Trp Ala Arg Tyr Ala Asp Trp
1               5                   10                  15

Leu Phe Thr Thr Pro Leu Leu Leu His Gly Ala Leu Leu Val Asp
            20                  25                  30

Ala Asp Glu Cys Thr
        35

<210> SEQ ID NO 109
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asp
            20                  25                  30

Ala Asp Glu Cys Thr
        35

<210> SEQ ID NO 110
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Asp Asp Glu Asp Asn Pro Ile Tyr Trp Ala Arg Tyr Ala His Trp
1               5                   10                  15

Leu Phe Thr Thr Pro Leu Leu Leu Leu Asp Gly Ala Leu Leu Val Asp
                20                  25                  30

Ala Asp Glu Cys Thr
        35

<210> SEQ ID NO 111
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
                20                  25                  30

Asn Gln Gly Thr
        35

<210> SEQ ID NO 112
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
                20                  25                  30

Asp Glu Gly Thr Cys Gly
        35

<210> SEQ ID NO 113
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Ala Ala Glu Gln Asn Pro Ile Tyr Trp Ala Arg Tyr Ala Glu Trp Leu
1               5                   10                  15

Phe Thr Thr Pro Leu Leu Leu Leu Glu Leu Ala Leu Leu Val Asp Ala

-continued

```
                 20                  25                  30

Asp Glu Gly Thr Cys Gly
        35

<210> SEQ ID NO 114
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ala Ala Glu Gln Asn Pro Ile Tyr Trp Ala Arg Tyr Ala Asp Trp Leu
1               5                   10                  15

Phe Thr Thr Pro Leu Leu Leu Glu Leu Ala Leu Leu Val Asp Ala
                 20                  25                  30

Asp Glu Gly Thr Lys Cys Gly
        35

<210> SEQ ID NO 115
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gly Gly Glu Gln Asn Pro Ile Tyr Trp Ala Gln Tyr Ala Asp Trp Leu
1               5                   10                  15

Phe Thr Thr Pro Leu Leu Leu Asp Leu Ala Leu Leu Val Asp Ala
                 20                  25                  30

Asp Glu Gly Thr Cys Gly
        35

<210> SEQ ID NO 116
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gly Gly Glu Gln Asn Pro Ile Tyr Trp Ala Gln Tyr Asp Ala Trp Leu
1               5                   10                  15

Phe Thr Thr Pro Leu Leu Leu Asp Leu Ala Leu Leu Val Asp Ala
                 20                  25                  30

Asp Glu Gly Thr Cys Gly
        35

<210> SEQ ID NO 117
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gly Gly Glu Gln Asn Pro Ile Tyr Trp Ala Gln Asp Tyr Ala Trp Leu
1               5                   10                  15
```

```
Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 118
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
            20                  25                  30

Asn Gln Gly Thr
        35

<210> SEQ ID NO 119
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
        35

<210> SEQ ID NO 120
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
        35

<210> SEQ ID NO 121
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ala Cys Glu Gln Asn Pro Ile Tyr Trp Ala Arg Tyr Ala Lys Trp Leu
1               5                   10                  15
```

```
Phe Thr Thr Pro Leu Leu Leu Lys Leu Ala Leu Leu Val Asp Ala
            20                  25                  30

Asp Glu Gly Thr Gly
        35

<210> SEQ ID NO 122
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gly Gly Glu Gln Asn Pro Ile Tyr Trp Ala Gln Asp Tyr Ala Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 123
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gly Gly Glu Gln Asn Pro Ile Tyr Trp Ala Gln Tyr Asp Ala Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 124
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gly Gly Glu Gln Asn Pro Ile Tyr Trp Ala Gln Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 125
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ala Ala Glu Gln Asn Pro Ile Tyr Trp Ala Arg Tyr Ala Ala Trp Leu
```

```
                1               5                  10                  15
Phe Thr Thr Pro Leu Leu Leu Leu Asp Leu Ala Leu Leu Val Asp Ala
                20                  25                  30

Asp Glu Gly Thr Cys Gly
                35

<210> SEQ ID NO 126
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Ala Ala Glu Gln Asn Pro Ile Tyr Trp Ala Arg Tyr Ala Asp Trp Leu
1               5                   10                  15

Phe Thr Asp Leu Pro Leu Leu Leu Asp Leu Leu Ala Leu Leu Val
                20                  25                  30

Asp Ala Asp Glu Gly Thr
                35

<210> SEQ ID NO 127
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Ala Leu Leu Val Asp Ala
                20                  25                  30

Asp Glu Gly Thr Cys Gly
                35

<210> SEQ ID NO 128
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Leu Ala Leu Leu Val Asp Ala
                20                  25                  30

Asp Glu Gly Thr Cys Gly
                35

<210> SEQ ID NO 129
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129
```

```
Ala Ala Glu Gln Asn Pro Ile Tyr Trp Ala Arg Tyr Ala Asp Trp Leu
1               5                   10                  15

Phe Thr Thr Gly Leu Leu Leu Asp Leu Ala Leu Leu Val Asp Ala
            20                  25                  30

Asp Glu Gly Thr
        35

<210> SEQ ID NO 130
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ala Ala Glu Gln Asn Pro Ile Tyr Trp Ala Arg Tyr Ala Ala Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 131
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gly Gly Glu Gln Asn Pro Ile Tyr Trp Ala Gln Tyr Asp Ala Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 132
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gly Gly Glu Gln Asn Pro Ile Tyr Trp Ala Gln Asp Tyr Ala Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 133
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133
```

```
Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 134
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Ala Ala Glu Gln Asn Pro Ile Tyr Trp Ala Arg Tyr Ala Asp Trp Leu
1               5                   10                  15

Phe Thr Thr Pro Leu Leu Leu Leu Ala Leu Ala Leu Leu Val Asp Ala
                20                  25                  30

Asp Glu Gly Thr Cys Gly
            35

<210> SEQ ID NO 135
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 135

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr Lys Cys Gly
            35

<210> SEQ ID NO 136
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 136

Ala Ala Glu Gln Asn Pro Ile Tyr Trp Ala Arg Tyr Ala Asp Trp Leu
1               5                   10                  15
```

Phe Thr Thr Pro Leu Leu Leu Glu Leu Ala Leu Leu Val Asp Ala
            20                  25                  30

Asp Glu Gly Thr Lys Cys Gly
        35

<210> SEQ ID NO 137
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Cys(phalloidin)

<400> SEQUENCE: 137

Ala Ala Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 138
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Cys(phalloidin)

<400> SEQUENCE: 138

Ala Ala Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 139
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 140
<211> LENGTH: 35
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 140

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Thr
        35

<210> SEQ ID NO 141
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly
        35

<210> SEQ ID NO 142
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 143
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
            20                  25                  30

Asn Gln Gly Thr
        35

<210> SEQ ID NO 144
<211> LENGTH: 37

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
        35

<210> SEQ ID NO 145
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
        35

<210> SEQ ID NO 146
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 147
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Cys(phalloidin)

<400> SEQUENCE: 147

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
```

<210> SEQ ID NO 148
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 148

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
            20                  25                  30

Asp Glu Gly Thr Lys Cys Gly
        35

<210> SEQ ID NO 149
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 149

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Lys Cys Gly
        35

<210> SEQ ID NO 150
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Cys Thr
        35

```
<210> SEQ ID NO 151
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Asp Asp Asp Glu Asp Asn Pro Ile Tyr Trp Ala Arg Tyr Ala His Trp
1               5                   10                  15

Leu Phe Thr Thr Pro Leu Leu Leu Leu Asp Gly Ala Leu Leu Val Asp
            20                  25                  30

Ala Asp Glu Cys Thr
        35

<210> SEQ ID NO 152
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
        35

<210> SEQ ID NO 153
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
        35

<210> SEQ ID NO 154
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Cys Thr
        35
```

<210> SEQ ID NO 155
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 156
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Asp Asp Glu Asp Asn Pro Ile Tyr Trp Ala Arg Tyr Ala His Trp
1               5                   10                  15

Leu Phe Thr Thr Pro Leu Leu Leu Leu Asp Gly Ala Leu Leu Val Asp
            20                  25                  30

Ala Asp Glu Cys Thr
        35

<210> SEQ ID NO 157
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 158
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
        35

<210> SEQ ID NO 159
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
        35

<210> SEQ ID NO 160
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
        35

<210> SEQ ID NO 161
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
        35

<210> SEQ ID NO 162
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Cys Thr

<210> SEQ ID NO 163
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 164
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Asp Asp Asp Glu Asp Asn Pro Ile Tyr Trp Ala Arg Tyr Ala His Trp
1               5                   10                  15

Leu Phe Thr Thr Pro Leu Leu Leu Leu Asp Gly Ala Leu Leu Val Asp
            20                  25                  30

Ala Asp Glu Cys Thr
        35

<210> SEQ ID NO 165
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
            20                  25                  30

Asn Gln Gly Thr
        35

<210> SEQ ID NO 166
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

```
Ala Asp Glu Cys Thr
        35

<210> SEQ ID NO 167
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Asp Asp Glu Asp Asn Pro Ile Tyr Trp Ala Arg Tyr Ala Asp Trp
1               5                   10                  15

Leu Phe Thr Thr Pro Leu Leu Leu His Gly Ala Leu Leu Val Asp
            20                  25                  30

Ala Asp Glu Cys Thr
        35

<210> SEQ ID NO 168
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asp
            20                  25                  30

Ala Asp Glu Cys Thr
        35

<210> SEQ ID NO 169
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Asp Asp Glu Asp Asn Pro Ile Tyr Trp Ala Arg Tyr Ala His Trp
1               5                   10                  15

Leu Phe Thr Thr Pro Leu Leu Leu Asp Gly Ala Leu Leu Val Asp
            20                  25                  30

Ala Asp Glu Cys Thr
        35

<210> SEQ ID NO 170
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asn
            20                  25                  30
```

```
Ala Asn Glu Cys Thr
        35

<210> SEQ ID NO 171
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Asp Asp Asp Glu Asp Asn Pro Ile Tyr Trp Ala Arg Tyr Ala His Trp
1               5                   10                  15

Leu Phe Thr Thr Pro Leu Leu Leu Leu Asp Gly Ala Leu Leu Val Asp
            20                  25                  30

Ala Asp Glu Cys Thr
        35

<210> SEQ ID NO 172
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 173
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 174
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
```

20                  25                  30

Ala Asp Glu Cys Thr
            35

<210> SEQ ID NO 175
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
                    20                  25                  30

Ala Asn Glu Cys Thr
            35

<210> SEQ ID NO 176
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Ala Ala Glu Gln Asn Pro Ile Tyr Trp Ala Arg Tyr Ala Asp Trp Leu
1               5                   10                  15

Phe Thr Thr Gly Leu Leu Leu Leu Asp Leu Ala Leu Leu Val Asp Ala
                    20                  25                  30

Asp Glu Gly Thr
            35

<210> SEQ ID NO 177
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gly Gly Glu Gln Asn Pro Ile Tyr Trp Ala Arg Tyr Ala Trp Asp Leu
1               5                   10                  15

Phe Thr Thr Pro Leu Leu Leu Leu Asp Leu Ala Leu Leu Val Asp Ala
                    20                  25                  30

Asp Glu Gly Thr Cys Gly
            35

<210> SEQ ID NO 178
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 179
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gly Gly Glu Gln Asn Pro Ile Tyr Trp Ala Gln Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 180
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gly Gly Glu Gln Asn Pro Ile Tyr Trp Ala Gln Asp Tyr Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 181
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 182
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gly Gly Glu Gln Asn Pro Ile Tyr Trp Ala Arg Tyr Ala Asp Trp Leu
1               5                   10                  15

```
Phe Thr Thr Pro Leu Leu Leu Leu Asp Ala Leu Leu Val Asp Ala
            20                  25                  30

Asp Glu Gly Thr Cys Gly
        35

<210> SEQ ID NO 183
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Leu Ala Leu Leu Val Asp Ala
            20                  25                  30

Asp Glu Gly Thr Cys Gly
        35

<210> SEQ ID NO 184
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Leu Ala Leu Leu Val Asp Ala
            20                  25                  30

Asp Glu Gly Thr Cys Gly
        35

<210> SEQ ID NO 185
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gly Gly Glu Gln Asn Pro Ile Tyr Trp Ala Arg Tyr Ala Asp Trp Leu
1               5                   10                  15

Phe Thr Thr Pro Leu Leu Leu Leu Leu Asp Ala Leu Leu Val Asp Ala
            20                  25                  30

Asp Glu Gly Thr Cys Gly
        35

<210> SEQ ID NO 186
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Gly Gly Glu Gln Asn Pro Ile Tyr Trp Ala Gln Tyr Ala Asp Trp Leu
```

-continued

```
                1               5                  10                  15
Phe Thr Thr Pro Leu Leu Leu Leu Asp Leu Ala Leu Leu Val Asp Ala
                20                  25                  30
Asp Glu Gly Thr Cys Gly
        35

<210> SEQ ID NO 187
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Gly Gly Glu Gln Asn Pro Ile Tyr Trp Ala Gln Tyr Asp Ala Trp Leu
1               5                  10                  15

Phe Thr Thr Pro Leu Leu Leu Leu Asp Leu Ala Leu Leu Val Asp Ala
                20                  25                  30

Asp Glu Gly Thr Cys Gly
        35

<210> SEQ ID NO 188
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Gly Gly Glu Gln Asn Pro Ile Tyr Trp Ala Gln Asp Tyr Ala Trp Leu
1               5                  10                  15

Phe Thr Thr Pro Leu Leu Leu Leu Asp Leu Ala Leu Leu Val Asp Ala
                20                  25                  30

Asp Glu Gly Thr Cys Gly
        35

<210> SEQ ID NO 189
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gly Gly Glu Gln Asn Pro Ile Tyr Trp Ala Gln Tyr Asp Ala Trp Leu
1               5                  10                  15

Phe Thr Thr Pro Leu Leu Leu Leu Asp Leu Ala Leu Leu Val Asp Ala
                20                  25                  30

Asp Glu Gly Thr Cys Gly
        35

<210> SEQ ID NO 190
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190
```

```
Gly Gly Glu Gln Asn Pro Ile Tyr Trp Ala Gln Asp Tyr Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 191
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gly Gly Glu Gln Asn Pro Ile Tyr Trp Ala Gln Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 192
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 193
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gly Gly Glu Gln Asn Pro Ile Tyr Trp Ala Gln Asp Tyr Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 194
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194
```

Gly Gly Glu Gln Asn Pro Ile Tyr Trp Ala Gln Tyr Asp Ala Trp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 195
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Gly Gly Glu Gln Asn Pro Ile Tyr Trp Ala Gln Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 196
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 197
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
                20                  25                  30

Asp Glu Gly Thr Lys Cys Gly
            35

<210> SEQ ID NO 198
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (4)..(4)
<223> OTHER INFORMATION: Lys(rhodamine)
<220> FEATURE:
<221> NAME/KEY: MOD_RES
<222> LOCATION: (5)..(5)
<223> OTHER INFORMATION: Cys(phalloidin)

<400> SEQUENCE: 198

Glu Gly Thr Lys Cys Gly
1               5

<210> SEQ ID NO 199
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 199

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr Lys Cys Gly
                35

<210> SEQ ID NO 200
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr Gly
                35

<210> SEQ ID NO 201
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Cys(phalloidin)

<400> SEQUENCE: 201

Ala Ala Glu Gln Asn Pro Ile Tyr Trp Ala Arg Tyr Ala Asp Trp Leu
1               5                   10                  15
```

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 202
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 202

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Lys Cys Gly
        35

<210> SEQ ID NO 203
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 203

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
            20                  25                  30

Asp Glu Gly Thr Lys Cys Gly
        35

<210> SEQ ID NO 204
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Ala Ala Glu Gln Asn Pro Ile Tyr Trp Ala Arg Tyr Ala Asp Trp Leu
1               5                   10                  15

Phe Thr Asp Leu Pro Leu Leu Leu Asp Leu Leu Ala Leu Leu Val
            20                  25                  30

Asp Ala Asp Glu Gly Thr
        35

<210> SEQ ID NO 205
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 206
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Gly Gly Glu Gln Asn Pro Ile Tyr Trp Ala Gln Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 207
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Gly Gly Glu Gln Asn Pro Ile Tyr Trp Ala Gln Asp Tyr Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 208
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 209
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Ala Ala Glu Gln Asn Pro Ile Tyr Trp Ala Arg Tyr Ala Glu Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 210
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Ala Ala Glu Gln Asn Pro Ile Tyr Trp Ala Arg Tyr Ala Glu Trp Leu
1               5                   10                  15

Phe Thr Thr Pro Leu Leu Leu Leu Glu Leu Ala Leu Leu Val Asp Ala
            20                  25                  30

Asp Glu Gly Thr Cys Gly
        35

<210> SEQ ID NO 211
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Ala Ala Glu Gln Asn Pro Ile Tyr Trp Ala Arg Tyr Ala Asp Trp Leu
1               5                   10                  15

Phe Thr Thr Pro Leu Leu Leu Leu Ala Leu Ala Leu Leu Val Asp Ala
            20                  25                  30

Asp Glu Gly Thr Cys Gly
        35

<210> SEQ ID NO 212
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala

Asp Glu Gly Thr Cys Gly
        35

<210> SEQ ID NO 213
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Ala Ala Glu Gln Asn Pro Ile Tyr Trp Ala Arg Tyr Ala Glu Trp Leu
1               5                   10                  15

Phe Thr Thr Pro Leu Leu Leu Leu Glu Leu Ala Leu Leu Val Asp Ala
            20                  25                  30

Asp Glu Gly Thr Cys Gly
        35

<210> SEQ ID NO 214
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 214

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
            20                  25                  30

Asp Glu Gly Thr Lys Cys Gly
        35

<210> SEQ ID NO 215
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Ala Cys Glu Gln Asn Pro Ile Tyr Trp Ala Arg Tyr Ala Lys Trp Leu
1               5                   10                  15

Phe Thr Thr Pro Leu Leu Leu Leu Lys Leu Ala Leu Leu Val Asp Ala
            20                  25                  30

Asp Glu Gly Thr Gly
        35

<210> SEQ ID NO 216
<211> LENGTH: 37
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 216

Ala Cys Glu Gln Asn Pro Ile Tyr Trp Ala Arg Tyr Ala Asn Trp Leu
1               5                   10                  15

Phe Thr Thr Pro Leu Leu Leu Asn Leu Ala Leu Leu Val Asp Ala
            20                  25                  30

Asp Glu Gly Thr Gly
        35

<210> SEQ ID NO 217
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Ala Ala Glu Gln Asn Pro Ile Tyr Trp Ala Arg Tyr Ala Asp Trp Leu
1               5                   10                  15

Phe Thr Thr Ala Leu Leu Leu Leu Asp Leu Ala Leu Leu Val Asp Ala
            20                  25                  30

Asp Glu Gly Thr
        35

<210> SEQ ID NO 218
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ala Glu Gln Asn Pro Ile Tyr Phe Ala Arg Tyr Ala Asp Leu Leu Phe
1               5                   10                  15

Pro Thr Thr Leu Ala Trp
            20

<210> SEQ ID NO 219
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ala Glu Gln Asn Pro Ile Tyr Trp Ala Arg Tyr Ala Asp Leu Leu Phe
1               5                   10                  15

Pro Thr Thr Leu Ala Phe
            20

<210> SEQ ID NO 220
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ala Glu Gln Asn Pro Ile Tyr Trp Ala Arg Tyr Ala Asp Leu Leu Phe
1               5                   10                  15

Pro Thr Thr Leu Ala Trp
            20

<210> SEQ ID NO 221
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Ala Cys Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Thr
        35

<210> SEQ ID NO 222

<400> SEQUENCE: 222

000

<210> SEQ ID NO 223
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr
        35

<210> SEQ ID NO 224
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Ala Ala Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 225
<211> LENGTH: 39
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 225

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Lys Cys Gly
        35

<210> SEQ ID NO 226
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Cys Thr
        35

<210> SEQ ID NO 227
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 227
cctcttacct cagttaca                                                 18

<210> SEQ ID NO 228
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 228
cctcttacct cagttaca                                                 18

<210> SEQ ID NO 229
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
```

<223> OTHER INFORMATION: Peptide nucleic acid

<400> SEQUENCE: 229
cctcttacct cagttaca                                                    18

<210> SEQ ID NO 230
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 230
cctcttacct cagttaca                                                    18

<210> SEQ ID NO 231
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 231
cctctgacct catttaca                                                    18

<210> SEQ ID NO 232
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 232
cctcttacct cagttaca                                                    18

<210> SEQ ID NO 233
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 233
cctctgacct catttaca                                                    18

<210> SEQ ID NO 234
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 234
cctcttacct cagttaca                                                 18

<210> SEQ ID NO 235
<211> LENGTH: 38
<212> TYPE: PRT
<213> ORGANISM: Unknown
<220> FEATURE:
<223> OTHER INFORMATION: Description of Unknown: pH-sensitive membrane
      polypeptide

<400> SEQUENCE: 235

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 236
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Ala Glu Asp Gln Asn Pro Tyr Trp Ala Arg Tyr Asp Trp Leu Phe Thr
1               5                   10                  15

Thr Pro Leu Leu Leu Leu Asp Leu Ala Leu Leu Val Asp Cys Gly
            20                  25                  30

<210> SEQ ID NO 237
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Glu Cys Gly
            20                  25                  30

<210> SEQ ID NO 238
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Ala Glu Gln Asn Pro Ile Tyr Trp Ala Arg Tyr Ala Asp Trp Leu Phe
1               5                   10                  15

```
Thr Thr Pro Leu Leu Leu Leu Asp Leu Ala Leu Leu Val Asp Ala Asp
            20                  25                  30

Glu Gly Cys Thr
        35

<210> SEQ ID NO 239
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Thr
        35

<210> SEQ ID NO 240
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35

<210> SEQ ID NO 241
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Ala Glu Asp Gln Asn Pro Tyr Trp Ala Arg Tyr Ala Asp Trp Leu Phe
1               5                   10                  15

Thr Thr Pro Leu Leu Leu Leu Asp Leu Ala Leu Leu Val Asp Gly
            20                  25                  30

<210> SEQ ID NO 242
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Ala Glu Asp Gln Asn Asp Pro Tyr Trp Ala Arg Tyr Ala Asp Trp Leu
1               5                   10                  15

Phe Thr Thr Pro Leu Leu Leu Leu Asp Leu Ala Leu Leu Val Gly
```

20                  25                  30

<210> SEQ ID NO 243
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Ala Glu Gln Asn Pro Ile Tyr Trp Ala Arg Tyr Ala Asp Phe Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 244
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Ala Glu Gln Asn Pro Ile Tyr Phe Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 245
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Ala Glu Gln Asn Pro Ile Tyr Phe Ala Arg Tyr Ala Asp Phe Leu Phe
1               5                   10                  15

Thr Thr Pro Leu Leu Leu Leu Asp Leu Ala Leu Leu Trp Asp Ala Asp
            20                  25                  30

Glu Thr

<210> SEQ ID NO 246
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Cys Thr
            35

```
<210> SEQ ID NO 247
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Ala Glu Asp Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Cys
            20                  25                  30

Gly Thr

<210> SEQ ID NO 248
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Ala Glu Asp Gln Asn Asp Pro Ile Tyr Trp Ala Arg Tyr Ala Asp Trp
1               5                   10                  15

Leu Phe Thr Thr Pro Leu Leu Leu Leu Glu Leu Ala Leu Leu Val Glu
            20                  25                  30

Cys Gly Thr
        35

<210> SEQ ID NO 249
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ala Cys Glu Glu Gln Asn Pro Trp Ala Arg Tyr Leu Glu Trp Leu Phe
1               5                   10                  15

Pro Thr Glu Thr Leu Leu Leu Glu Leu
            20                  25

<210> SEQ ID NO 250
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35

<210> SEQ ID NO 251
<211> LENGTH: 32
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Ala Lys Glu Asp Gln Asn Pro Tyr Trp Ala Arg Tyr Ala Asp Trp Leu
1               5                   10                  15
Phe Thr Thr Pro Leu Leu Leu Leu Asp Leu Ala Leu Leu Val Asp Gly
            20                  25                  30

<210> SEQ ID NO 252
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Ala Lys Glu Asp Gln Asn Asp Pro Tyr Trp Ala Arg Tyr Ala Asp Trp
1               5                   10                  15
Leu Phe Thr Thr Pro Leu Leu Leu Leu Asp Leu Ala Leu Leu Val Gly
            20                  25                  30

<210> SEQ ID NO 253
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Ala Glu Gln Asn Pro Ile Tyr Trp Ala Arg Tyr Ala Asp Trp Leu Phe
1               5                   10                  15
Thr Thr Pro Leu Leu Leu Leu Asp Leu Ala Leu Leu Val Asp Ala Asp
            20                  25                  30
Glu Gly Cys
        35

<210> SEQ ID NO 254
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Ala Glu Asp Gln Asn Pro Tyr Trp Ala Arg Tyr Ala Asp Trp Leu Phe
1               5                   10                  15
Thr Thr Pro Leu Leu Leu Leu Asp Leu Ala Leu Leu Val Asp Cys
            20                  25                  30

<210> SEQ ID NO 255
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

```
Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Glu Cys
            20                  25                  30
```

<210> SEQ ID NO 256
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

```
Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr
            35
```

<210> SEQ ID NO 257
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

```
Ala Cys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
                20                  25                  30
```

<210> SEQ ID NO 258
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

```
Ala Cys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30
```

<210> SEQ ID NO 259
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

```
Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp
            20                  25
```

<210> SEQ ID NO 260

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Ala Cys Glu Glu Gln Asn Pro Trp Arg Ala Tyr Leu Glu Leu Leu Phe
1               5                  10                  15

Pro Thr Glu Thr Leu Leu Leu Glu Leu Leu Trp
            20                  25

<210> SEQ ID NO 261
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ala Cys Asp Asp Gln Asn Pro Trp Ala Arg Tyr Leu Asp Trp Leu Phe
1               5                  10                  15

Pro Thr Asp Thr Leu Leu Leu Asp Leu
            20                  25

<210> SEQ ID NO 262
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Cys Asp Asn Asn Asn Pro Trp Arg Ala Tyr Leu Asp Leu Leu Phe Pro
1               5                  10                  15

Thr Asp Thr Leu Leu Leu Asp Trp
            20

<210> SEQ ID NO 263
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ala Cys Glu Glu Gln Asn Pro Trp Ala Arg Tyr Leu Glu Trp Leu Phe
1               5                  10                  15

Pro Thr Glu Thr Leu Leu Leu Glu Leu
            20                  25

<210> SEQ ID NO 264
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Cys Glu Glu Gln Gln Pro Trp Ala Gln Tyr Leu Glu Leu Leu Phe Pro
1               5                  10                  15
```

```
Thr Glu Thr Leu Leu Leu Glu Trp
            20

<210> SEQ ID NO 265
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Cys Glu Glu Gln Gln Pro Trp Arg Ala Tyr Leu Glu Leu Leu Phe Pro
1               5                   10                  15

Thr Glu Thr Leu Leu Leu Glu Trp
            20

<210> SEQ ID NO 266
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ala Cys Glu Asp Gln Asn Pro Trp Ala Arg Tyr Ala Asp Trp Leu Phe
1               5                   10                  15

Pro Thr Thr Leu Leu Leu Leu Asp
            20

<210> SEQ ID NO 267
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ala Cys Glu Glu Gln Asn Pro Trp Ala Arg Tyr Ala Glu Trp Leu Phe
1               5                   10                  15

Pro Thr Thr Leu Leu Leu Leu Glu
            20

<210> SEQ ID NO 268
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ala Cys Glu Asp Gln Asn Pro Trp Ala Arg Tyr Ala Asp Leu Leu Phe
1               5                   10                  15

Pro Thr Thr Leu Ala Trp
            20

<210> SEQ ID NO 269
<211> LENGTH: 22
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 269

Ala Cys Glu Glu Gln Asn Pro Trp Ala Arg Tyr Ala Glu Leu Leu Phe
1               5                   10                  15
Pro Thr Thr Leu Ala Trp
            20

<210> SEQ ID NO 270
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Thr Glu Asp Ala Asp Val Leu Leu Ala Leu Asp Leu Leu Leu Pro
1               5                   10                  15
Thr Thr Phe Leu Trp Asp Ala Tyr Arg Ala Trp Tyr Pro Asn Gln Glu
            20                  25                  30
Cys Ala

<210> SEQ ID NO 271
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Cys Asp Asp Asp Asp Asn Pro Asn Tyr Trp Ala Arg Tyr Ala Asn
1               5                   10                  15
Trp Leu Phe Thr Thr Pro Leu Leu Leu Asn Gly Ala Leu Leu Val
            20                  25                  30
Glu Ala Glu Glu Thr
        35

<210> SEQ ID NO 272
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Cys Asp Asp Asp Asp Asn Pro Asn Tyr Trp Ala Arg Tyr Ala Pro
1               5                   10                  15
Trp Leu Phe Thr Thr Pro Leu Leu Leu Pro Gly Ala Leu Leu Val
            20                  25                  30
Glu Ala Glu Glu Thr
        35

<210> SEQ ID NO 273

<400> SEQUENCE: 273

000

<210> SEQ ID NO 274
<211> LENGTH: 36

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Cys Thr
        35

<210> SEQ ID NO 275
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly
        35

<210> SEQ ID NO 276
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Ala Cys Glu Gln Asn Pro Ile Tyr Trp Ala Arg Tyr Ala Asn Trp Leu
1               5                   10                  15

Phe Thr Thr Pro Leu Leu Leu Leu Asn Leu Ala Leu Leu Val Asp Ala
            20                  25                  30

Asp Glu Gly Thr
        35

<210> SEQ ID NO 277
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Thr
        35

<210> SEQ ID NO 278
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Thr
        35

<210> SEQ ID NO 279
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Cys Asp Asp Asp Glu Asp Asn Pro Ile Tyr Trp Ala Arg Tyr Ala His
1               5                   10                  15

Trp Leu Phe Thr Thr Pro Leu Leu Leu Leu His Gly Ala Leu Leu Val
            20                  25                  30

Asp Ala Asp Glu Thr
        35

<210> SEQ ID NO 280
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Gly Thr
        35

<210> SEQ ID NO 281
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Gly Thr
        35
```

<210> SEQ ID NO 282
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Gly Thr
        35

<210> SEQ ID NO 283
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Ala Lys Glu Asp Gln Asn Asp Pro Tyr Trp Ala Arg Tyr Ala Asp Trp
1               5                   10                  15

Leu Phe Thr Thr Pro Leu Leu Leu Leu Asp Leu Ala Leu Leu Val Gly
            20                  25                  30

<210> SEQ ID NO 284
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Cys Gly
            20                  25                  30

<210> SEQ ID NO 285
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ala Lys Asp Asp Gln Asn Pro Trp Arg Ala Tyr Leu Asp Leu Leu Phe
1               5                   10                  15

Pro Thr Asp Thr Leu Leu Leu Asp Leu Leu Trp Cys
            20                  25

<210> SEQ ID NO 286
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 286

Ala Cys Glu Glu Gln Asn Pro Trp Arg Ala Tyr Leu Glu Leu Leu Phe
1               5                   10                  15

Pro Thr Glu Thr Leu Leu Leu Glu Leu Leu Trp
            20                  25

<210> SEQ ID NO 287
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ala Cys Asp Asp Gln Asn Pro Trp Ala Arg Tyr Leu Asp Trp Leu Phe
1               5                   10                  15

Pro Thr Asp Thr Leu Leu Leu Asp Leu
            20                  25

<210> SEQ ID NO 288
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Cys Asp Asn Asn Asn Pro Trp Arg Ala Tyr Leu Asp Leu Leu Phe Pro
1               5                   10                  15

Thr Asp Thr Leu Leu Leu Asp Trp
            20

<210> SEQ ID NO 289
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Cys Glu Glu Gln Gln Pro Trp Ala Gln Tyr Leu Glu Leu Leu Phe Pro
1               5                   10                  15

Thr Glu Thr Leu Leu Leu Glu Trp
            20

<210> SEQ ID NO 290
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Cys Glu Glu Gln Gln Pro Trp Arg Ala Tyr Leu Glu Leu Leu Phe Pro
1               5                   10                  15

Thr Glu Thr Leu Leu Leu Glu Trp
            20

<210> SEQ ID NO 291
<211> LENGTH: 37
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Cys Asp Asp Asp Asp Asn Pro Asn Tyr Trp Ala Arg Tyr Ala Asn
1               5                   10                  15

Trp Leu Phe Thr Thr Pro Leu Leu Leu Asn Gly Ala Leu Leu Val
            20                  25                  30

Glu Ala Glu Glu Thr
            35

<210> SEQ ID NO 292
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Cys Asp Asp Asp Asp Asn Pro Asn Tyr Trp Ala Arg Tyr Ala Pro
1               5                   10                  15

Trp Leu Phe Thr Thr Pro Leu Leu Leu Pro Gly Ala Leu Leu Val
            20                  25                  30

Glu Ala Glu Glu
            35

<210> SEQ ID NO 293
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ala Glu Gln Asn Pro Ile Tyr Phe Ala Arg Tyr Ala Asp Leu Leu Phe
1               5                   10                  15

Pro Thr Thr Leu Ala Trp
            20

<210> SEQ ID NO 294
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ala Glu Gln Asn Pro Ile Tyr Trp Ala Arg Tyr Ala Asp Leu Leu Phe
1               5                   10                  15

Pro Thr Thr Leu Ala Phe
            20

<210> SEQ ID NO 295
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 295

Ala Glu Gln Asn Pro Ile Tyr Trp Ala Arg Tyr Ala Asp Leu Leu Phe
1               5                   10                  15

Pro Thr Thr Leu Ala Trp
            20

<210> SEQ ID NO 296
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Lys Glu Asp Gln Asn Pro Trp Ala Arg Tyr Ala Asp Leu Leu Phe Pro
1               5                   10                  15

Thr Thr Leu Trp
            20

<210> SEQ ID NO 297
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Ala Cys Glu Glu Gln Asn Pro Gln Ala Glu Tyr Ala Glu Trp Leu Phe
1               5                   10                  15

Pro Thr Thr Leu Leu Leu Leu Glu
            20

<210> SEQ ID NO 298
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Ala Ala Glu Glu Gln Asn Pro Trp Ala Arg Tyr Leu Glu Trp Leu Phe
1               5                   10                  15

Pro Thr Gly Thr Leu Leu Leu Glu Leu
            20                  25

<210> SEQ ID NO 299
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Ala Lys Glu Glu Gln Asn Pro Trp Ala Arg Tyr Leu Glu Trp Leu Phe
1               5                   10                  15

Pro Thr Glu Thr Leu Leu Leu Glu Leu
            20                  25

<210> SEQ ID NO 300

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 300

Trp Leu Xaa Leu Leu
1               5

<210> SEQ ID NO 301
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 301

Ala Gly Trp Leu Xaa Leu Leu Ala Gly Trp Leu Gly Leu Leu
1               5                   10

<210> SEQ ID NO 302
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 302

Trp Ile Xaa Leu Leu
1               5

<210> SEQ ID NO 303
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 303

Gly Gly Xaa Gly Gly
1               5

<210> SEQ ID NO 304
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 304

His His His His His His
1               5

<210> SEQ ID NO 305
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ala Ala Glu Gln
1

<210> SEQ ID NO 306
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Asp Asp Asp Glu Asp
1               5

<210> SEQ ID NO 307
<211> LENGTH: 38
<212> TYPE: PRT
<213> ORGANISM: Unknown
<220> FEATURE:
<223> OTHER INFORMATION: Description of Unknown: Wild-type pH-sensitive
      membrane polypeptide

<400> SEQUENCE: 307

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly Gly
        35

<210> SEQ ID NO 308
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ala or Asp
<220> FEATURE:
<221> NAME/KEY: MOD_RES
<222> LOCATION: (2)..(2)
<223> OTHER INFORMATION: Ala, Asp or Cys
<220> FEATURE:
<221> NAME/KEY: MOD_RES
<222> LOCATION: (4)..(4)
<223> OTHER INFORMATION: Gln or Asp
<220> FEATURE:
<221> NAME/KEY: MOD_RES
<222> LOCATION: (11)..(11)
<223> OTHER INFORMATION: Arg or Gln
<220> FEATURE:
<221> NAME/KEY: MOD_RES
```

```
<222> LOCATION: (12)..(12)
<223> OTHER INFORMATION: Tyr or Asp
<220> FEATURE:
<221> NAME/KEY: MOD_RES
<222> LOCATION: (13)..(13)
<223> OTHER INFORMATION: Ala, Asp or Tyr
<220> FEATURE:
<221> NAME/KEY: MOD_RES
<222> LOCATION: (14)..(14)
<223> OTHER INFORMATION: Asp, Asn, Glu, His, Lys, Ala or Trp
<220> FEATURE:
<221> NAME/KEY: MOD_RES
<222> LOCATION: (15)..(15)
<223> OTHER INFORMATION: Trp or Asp
<220> FEATURE:
<221> NAME/KEY: MOD_RES
<222> LOCATION: (19)..(19)
<223> OTHER INFORMATION: Thr or Asp
<220> FEATURE:
<221> NAME/KEY: MOD_RES
<222> LOCATION: (20)..(20)
<223> OTHER INFORMATION: Pro, Gly or Ala
<220> FEATURE:
<221> NAME/KEY: MOD_RES
<222> LOCATION: (24)..(24)
<223> OTHER INFORMATION: Leu or Asp
<220> FEATURE:
<221> NAME/KEY: MOD_RES
<222> LOCATION: (25)..(25)
<223> OTHER INFORMATION: Asp, Leu, Asn, Glu, His, Lys or Ala
<220> FEATURE:
<221> NAME/KEY: MOD_RES
<222> LOCATION: (26)..(26)
<223> OTHER INFORMATION: Leu, Asp or Gly
<220> FEATURE:
<221> NAME/KEY: MOD_RES
<222> LOCATION: (31)..(31)
<223> OTHER INFORMATION: Asp or Asn
<220> FEATURE:
<221> NAME/KEY: MOD_RES
<222> LOCATION: (33)..(33)
<223> OTHER INFORMATION: Asp or Asn
<220> FEATURE:
<221> NAME/KEY: MOD_RES
<222> LOCATION: (34)..(34)
<223> OTHER INFORMATION: Glu or Gln
<220> FEATURE:
<221> NAME/KEY: MOD_RES
<222> LOCATION: (35)..(35)
<223> OTHER INFORMATION: Gly or Cys
<220> FEATURE:
<221> NAME/KEY: MOD_RES
<222> LOCATION: (37)..(37)
<223> OTHER INFORMATION: Gly or Cys

<400> SEQUENCE: 308

Xaa Xaa Glu Xaa Asn Pro Ile Tyr Trp Ala Xaa Xaa Xaa Xaa Xaa Leu
1               5                   10                  15

Phe Thr Xaa Xaa Leu Leu Leu Xaa Xaa Xaa Ala Leu Leu Val Xaa Ala
            20                  25                  30

Xaa Xaa Xaa Thr Xaa Gly
        35

<210> SEQ ID NO 309
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present
<220> FEATURE:
```

```
<221> NAME/KEY: MOD_RES
<222> LOCATION: (21)..(21)
<223> OTHER INFORMATION: May or may not be present
<220> FEATURE:
<221> NAME/KEY: MOD_RES
<222> LOCATION: (29)..(29)
<223> OTHER INFORMATION: May or may not be present
<220> FEATURE:
<221> NAME/KEY: MOD_RES
<222> LOCATION: (40)..(40)
<223> OTHER INFORMATION: May or may not be present

<400> SEQUENCE: 309

Asp Ala Ala Glu Gln Asn Pro Ile Tyr Trp Ala Arg Tyr Ala Asp Trp
1               5                   10                  15

Leu Phe Thr Thr Leu Pro Leu Leu Leu Asp Leu Ala Leu Leu
            20                  25                  30

Val Asp Ala Asp Glu Gly Thr Lys Gly Gly
        35                  40

<210> SEQ ID NO 310
<211> LENGTH: 38
<212> TYPE: PRT
<213> ORGANISM: Unknown
<220> FEATURE:
<223> OTHER INFORMATION: Description of Unknown: Wild-type pH-sensitive
      membrane polypeptide

<400> SEQUENCE: 310

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Gly Gly
        35

<210> SEQ ID NO 311
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gly, Asp or Ala
<220> FEATURE:
<221> NAME/KEY: MOD_RES
<222> LOCATION: (2)..(2)
<223> OTHER INFORMATION: Gly, Asp or Cys
<220> FEATURE:
<221> NAME/KEY: MOD_RES
<222> LOCATION: (4)..(4)
<223> OTHER INFORMATION: Gln or Asp
<220> FEATURE:
<221> NAME/KEY: MOD_RES
<222> LOCATION: (11)..(11)
<223> OTHER INFORMATION: Arg or Gln
<220> FEATURE:
<221> NAME/KEY: MOD_RES
<222> LOCATION: (12)..(12)
<223> OTHER INFORMATION: Tyr or Asp
<220> FEATURE:
<221> NAME/KEY: MOD_RES
<222> LOCATION: (13)..(13)
<223> OTHER INFORMATION: Ala, Asp or Tyr
<220> FEATURE:
<221> NAME/KEY: MOD_RES
<222> LOCATION: (14)..(14)
<223> OTHER INFORMATION: Asp, Asn, Glu, His, Lys, Ala or Trp
```

```
<220> FEATURE:
<221> NAME/KEY: MOD_RES
<222> LOCATION: (15)..(15)
<223> OTHER INFORMATION: Trp or Asp
<220> FEATURE:
<221> NAME/KEY: MOD_RES
<222> LOCATION: (19)..(19)
<223> OTHER INFORMATION: Thr or Asp
<220> FEATURE:
<221> NAME/KEY: MOD_RES
<222> LOCATION: (20)..(20)
<223> OTHER INFORMATION: Pro, Gly or Ala
<220> FEATURE:
<221> NAME/KEY: MOD_RES
<222> LOCATION: (24)..(24)
<223> OTHER INFORMATION: Leu or Asp
<220> FEATURE:
<221> NAME/KEY: MOD_RES
<222> LOCATION: (25)..(25)
<223> OTHER INFORMATION: Asp, Leu, Asn, Glu, His, Lys or Ala
<220> FEATURE:
<221> NAME/KEY: MOD_RES
<222> LOCATION: (26)..(26)
<223> OTHER INFORMATION: Leu, Asp or Gly
<220> FEATURE:
<221> NAME/KEY: MOD_RES
<222> LOCATION: (31)..(31)
<223> OTHER INFORMATION: Asp or Asn
<220> FEATURE:
<221> NAME/KEY: MOD_RES
<222> LOCATION: (33)..(33)
<223> OTHER INFORMATION: Asp or Asn
<220> FEATURE:
<221> NAME/KEY: MOD_RES
<222> LOCATION: (34)..(34)
<223> OTHER INFORMATION: Glu or Gln
<220> FEATURE:
<221> NAME/KEY: MOD_RES
<222> LOCATION: (35)..(35)
<223> OTHER INFORMATION: Gly or Cys

<400> SEQUENCE: 311

Xaa Xaa Glu Xaa Asn Pro Ile Tyr Trp Ala Xaa Xaa Xaa Xaa Xaa Leu
1               5                   10                  15

Phe Thr Xaa Xaa Leu Leu Leu Xaa Xaa Xaa Ala Leu Leu Val Xaa Ala
            20                  25                  30

Xaa Xaa Xaa Thr Gly Gly
        35

<210> SEQ ID NO 312
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (7)..(7)
<223> OTHER INFORMATION: May or may not be present
<220> FEATURE:
<221> NAME/KEY: MOD_RES
<222> LOCATION: (22)..(22)
<223> OTHER INFORMATION: May or may not be present
<220> FEATURE:
<221> NAME/KEY: MOD_RES
<222> LOCATION: (30)..(30)
<223> OTHER INFORMATION: May or may not be present
<220> FEATURE:
<221> NAME/KEY: MOD_RES
<222> LOCATION: (40)..(40)
```

-continued

```
<223> OTHER INFORMATION: May or may not be present
<220> FEATURE:
<221> NAME/KEY: MOD_RES
<222> LOCATION: (42)..(42)
<223> OTHER INFORMATION: Lys, Cys or absent

<400> SEQUENCE: 312

Asp Gly Gly Glu Gln Asn Asp Pro Ile Tyr Trp Ala Arg Tyr Ala Asp
1               5                   10                  15

Trp Leu Phe Thr Thr Leu Pro Leu Leu Leu Leu Asp Leu Leu Ala Leu
            20                  25                  30

Leu Val Asp Ala Asp Glu Gly Cys Thr Xaa Gly Gly
        35                  40

<210> SEQ ID NO 313
<211> LENGTH: 38
<212> TYPE: PRT
<213> ORGANISM: Artificial Sequence
<220> FEATURE:
<223> OTHER INFORMATION: Synthetic polypeptide,which is modified at the
      CYS, residue 37 of the peptide, with a S-S-linker attached to the
      nitrogen of amino-phalloidin

<400> SEQUENCE: 313

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 314
<211> LENGTH: 31
<212> TYPE: PRT
<213> ORGANISM: Artificial Sequence
<220> FEATURE:
<223> OTHER INFORMATION: modification of Cys residue 30 with a S-S
      linker attached to 2-amino phalloidin, Lys residue 29 modified
      with an alkyl linker attached to rhodamine, and Alanine residue 1
      modified with a COCH3 group.

<400> SEQUENCE: 314

Ala Glu Asp Gln Asn Pro Tyr Trp Ala Arg Tyr Asp Trp Leu Phe Thr
1               5                   10                  15

Thr Pro Leu Leu Leu Leu Asp Leu Ala Leu Leu Val Asp Cys Gly
            20                  25                  30
```

What is claimed is:

1. An environmentally sensitive composition comprising a pH-triggered membrane peptide comprising (a) at least 8 contiguous amino acids of SEQ ID NO:40, 285, 287, or 288, wherein, (b) at least 6 of the contiguous 8 amino acids of said membrane peptide are non-polar, (c) at least one of the at least 8 amino acids of said membrane peptide is protonatable, and (d) the peptide has a higher affinity to a membrane lipid bilayer at pH 5.0 compared to at pH 8.0.

2. The composition of claim 1, further comprising a single flanking domain at an N-terminus or at a C-terminus of said membrane peptide.

3. The composition of claim 2, further comprising a first flanking domain at said C-terminus and a second flanking domain at said N-terminus.

4. The composition of claim 3, further comprising a cargo attached to one of said flanking domains, wherein said cargo is selected from a therapeutic, diagnostic, radiation-enhancing, radiation-sensitizing, imaging, gene regulation, cytotoxic, apoptotic, or research reagent.

5. The composition of claim 4, wherein said cargo is attached to said flanking region via a thiol linkage.

6. The composition of claim 1, wherein one or more atoms are replaced by a radioactive isotope or a stable isotope.

7. The composition of claim 1, wherein one or more of the amino acid side chains are chemically modified to render them radioactive or detectable by probing radiation.

8. The composition of claim 1, comprising one or more cargoes attached to said peptide used as a therapeutic, diagnostic, imaging, immune activation, gene regulation or cell function regulation agent, radiation-enhancing agent, radiation-sensitizing agent, or as a research tool.

9. The composition of claim 1, for use as an agent to deliver a functional cargo across cell membranes to cells in a diseased tissue with a naturally acidic extracellular environment or in a tissue with an artificially induced acidic extracellular environment relative to normal physiological pH.

10. The composition of claim 9, wherein said diseased tissue is selected from the group consisting of inflamed tissue, ischemic tissue, arthritic tissue, tissue infected with a microorganism, and atherosclerotic tissue.

11. The composition of claim 1, for use as an agent to deliver a functional cargo to cell surfaces in a diseased tissue with a naturally acidic extracellular environment or in a tissue with an artificially induced acidic extracellular environment relative to normal physiological pH.

12. The composition of claim 4, wherein said cargo comprises phalloidin, phallo toxin, amanitin toxin, a DNA intercalator, or a peptide nucleic acid.

13. The composition of claim 1, wherein said sequence comprises residues 15-22 of SEQ ID NO: 40.

14. The composition of claim 4, wherein said cargo comprises a dye, a fluorescent protein, a nanoparticle, or a radioactive isotope.

15. The composition of claim 14, wherein the dye is a fluorescent dye.

16. The composition of claim 14,
   (a) comprising a dye selected from the group consisting of rhodamine, Alexa750, or Cy5.5;
   (b) comprising a fluorescent protein, wherein the fluorescent protein is green fluorescent protein;
   (c) comprising a nanoparticle that comprises gold; or
   (d) comprising a radioactive isotope selected from the group consisting of Fluorine-18, Copper-64, Thallium-201, Iodine-123, Gallium-67, Strontium-82, Cadmium-113, Tellurium-123, Cobalt-60, or Technetium-99m.

17. The composition of claim 8, comprising a magnetic resonance, positron emission tomography, single photon emission computed tomography, or fluorescence imaging agent.

18. The composition of claim 8, comprising a positron emission tomography agent.

19. The composition of claim 18, wherein said positron emission tomography agent comprises a Copper-64 or Fluorine-18 radioactive isotope.

20. A diagnostic conjugate comprising the composition of claim 1 and a pharmaceutically acceptable detectable marker linked thereto.

21. The conjugate of claim 20, wherein said detectable marker comprises a dye.

22. The conjugate of claim 21, wherein the dye comprises a fluorescent dye.

23. The conjugate of claim 20, wherein said detectable marker comprises a nanoparticle.

24. A therapeutic conjugate comprising the composition of claim 1, further comprising a first cargo comprising a cytotoxic agent and a second cargo comprising a hydrophobicity-balancing cargo.

25. The conjugate of claim 24, wherein said cytotoxic agent is selected from the group consisting of phalloidin, phallo toxin, amanitin toxin, a boron-containing compound, and a DNA intercalator.

26. A method of guiding surgical tumor excision, comprising administering to an anatomical site comprising a tumor the conjugate of claim 4, removing a primary tumor from said site, detecting residual tumor cells by binding of said conjugate to said residual tumor cells, and excising said residual tumor cells.

27. A method of determining the aggressiveness of a primary tumor, comprising contacting said tumor with the composition of claim 1, wherein an increased level of binding of said composition compared to a control level of binding indicates an increased risk of metastasis from said primary tumor.

28. A method of preferentially inhibiting proliferation of tumor cells, comprising administering to a subject suffering from a tumor the composition of claim 1, wherein tumor cells are preferentially inhibited compared to normal non-tumor cells.

* * * * *